(12) United States Patent
Johnson et al.

(10) Patent No.: US 12,048,814 B2
(45) Date of Patent: Jul. 30, 2024

(54) PATIENT INTERFACE

(71) Applicant: Fisher & Paykel Healthcare Limited, Auckland (NZ)

(72) Inventors: Chelsea Erin Johnson, Auckland (NZ); Robert Andrew David Milne, Auckland (NZ); Riki Zane Shearer, Auckland (NZ); Michael Paul Ronayne, Auckland (NZ); Daniel Charles Wilson, Auckland (NZ); Leon Tyler Stanley, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 198 days.

(21) Appl. No.: 17/304,233

(22) Filed: Jun. 16, 2021

(65) Prior Publication Data
US 2021/0379314 A1 Dec. 9, 2021

Related U.S. Application Data

(63) Continuation of application No. 15/512,498, filed as application No. PCT/NZ2015/050156 on Sep. 18, 2015, now Pat. No. 11,058,841.

(Continued)

(51) Int. Cl.
*A61M 16/06* (2006.01)

(52) U.S. Cl.
CPC .... *A61M 16/0688* (2014.02); *A61M 16/0672* (2014.02); *A61M 2205/0216* (2013.01); *A61M 2207/00* (2013.01)

(58) Field of Classification Search
CPC .......... A51M 16/0672; A51M 16/0666; A51M 16/0677; A51M 16/0683; A51M 16/0685;
(Continued)

(56) References Cited

U.S. PATENT DOCUMENTS 2,693,800 A  4/1951  Caldwell
3,513,844 A  5/1970  Smith
(Continued)

FOREIGN PATENT DOCUMENTS

AU  2007278766  1/2008
CA  2814601  4/2013
(Continued)

OTHER PUBLICATIONS

China National Intellectual Property Administration, Second Office Action, Application No. 201580060077.0, dated Oct. 18, 2019, in 29 pages.
(Continued)

*Primary Examiner* — Michael R Reid
*Assistant Examiner* — Nathan M Le
(74) *Attorney, Agent, or Firm* — Knobbe Martens Olson & Bear LLP

(57) ABSTRACT

A patient interface, such as a nasal cannula is described. The patient interface has a body portion to be located, in-use upon a face of a user. The body portion has at least one side arm that extends laterally from a central bridge portion to be located about a user's septum region, where each side arm is connected to a resilient, or relatively more rigid, bridge portion element. The interface has at least one, and preferably a pair of, nasal prong(s). The body portion has at least one fluid passageway connected to the nasal prong(s) for supply of a gas to the nare(s) of the user's nose. A cross section of the passageway varies along the length of the body portion to regions of varying flexibility along the body portion. The bridge portion element defines a substantially predetermined spatial relationship for outlet(s) of a gas delivery system supplying gas via each side arm to the outlet(s) from which, for example, the nasal prong(s) may be provided in fluid connection. Each side arm may comprise (Continued)

one or more predefined or predisposed points or localised compensation regions (or sites) positioned along the side arm, or a side arm element, to accommodate or facilitate a compensation of the patient interface in or at one or more of the compensation regions (or sites).

18 Claims, 61 Drawing Sheets

Related U.S. Application Data

(60) Provisional application No. 62/198,851, filed on Jul. 30, 2015, provisional application No. 62/183,099, filed on Jun. 22, 2015, provisional application No. 62/121,144, filed on Feb. 26, 2015, provisional application No. 62/064,106, filed on Oct. 15, 2014, provisional application No. 62/052,980, filed on Sep. 19, 2014.

(58) Field of Classification Search
CPC .......... A61M 16/0688; A61M 16/0672; A61M 16/0666; A61M 16/06; A61M 16/00
See application file for complete search history.

(56) References Cited

U.S. PATENT DOCUMENTS

| | | | |
|---|---|---|---|
| 3,726,275 A | 4/1973 | Jackson et al. | |
| 3,754,552 A | 8/1973 | King | |
| 4,106,505 A | 8/1978 | Salter et al. | |
| 4,278,082 A | 7/1981 | Blackmer | |
| 4,742,824 A | 5/1988 | Payton | |
| 4,753,233 A | 6/1988 | Grimes | |
| 5,269,296 A | 12/1993 | Landis | |
| 5,687,715 A | 11/1997 | Landis | |
| 6,298,850 B1 | 10/2001 | Argraves | |
| 7,406,966 B2 | 8/2008 | Wondka | |
| 7,614,401 B2 | 11/2009 | Thompson | |
| 8,025,058 B2 | 9/2011 | Chandran et al. | |
| 8,136,527 B2 | 3/2012 | Wondka | |
| 11,058,841 B2 | 7/2021 | Johnson et al. | |
| 11,110,242 B2 | 9/2021 | Ronayne et al. | |
| 2001/0029954 A1 | 10/2001 | Palmer | |
| 2002/0046755 A1 | 4/2002 | De Voss | |
| 2003/0079749 A1 | 5/2003 | Strickland et al. | |
| 2003/0116163 A1 | 6/2003 | Wood | |
| 2003/0126724 A1 | 7/2003 | Kono et al. | |
| 2003/0135192 A1 | 7/2003 | Guralski et al. | |
| 2004/0226566 A1 | 11/2004 | Gunaratnam et al. | |
| 2004/0261797 A1 | 12/2004 | White et al. | |
| 2005/0028822 A1 | 2/2005 | Sleeper et al. | |
| 2005/0033247 A1 | 2/2005 | Thompson | |
| 2005/0066976 A1 | 3/2005 | Wondka | |
| 2006/0107958 A1 | 5/2006 | Sleeper | |
| 2006/0180151 A1 | 8/2006 | Rinaldi | |
| 2007/0283957 A1 | 12/2007 | Schobel et al. | |
| 2008/0060649 A1 | 3/2008 | Veliss et al. | |
| 2008/0142019 A1* | 6/2008 | Lewis ................... | A61B 5/0205 128/207.18 |
| 2008/0190436 A1 | 8/2008 | Jaffe et al. | |
| 2009/0056711 A1 | 3/2009 | Richards et al. | |
| 2009/0095303 A1 | 4/2009 | Sher et al. | |
| 2009/0151729 A1 | 6/2009 | Judson et al. | |
| 2009/0173349 A1 | 7/2009 | Hernandez et al. | |
| 2009/0183739 A1 | 7/2009 | Wondka | |
| 2010/0000534 A1* | 1/2010 | Kooij ................... | A61M 16/0616 128/207.13 |
| 2010/0018534 A1* | 1/2010 | Veliss ................... | A61M 16/0622 128/206.24 |
| 2010/0113955 A1 | 5/2010 | Colman et al. | |
| 2010/0192957 A1 | 8/2010 | Hobson et al. | |
| 2010/0224196 A1 | 9/2010 | Jablons | |
| 2010/0252037 A1 | 10/2010 | Wondka et al. | |
| 2011/0067704 A1* | 3/2011 | Kooij ................ | A61M 16/0858 128/207.18 |
| 2011/0126841 A1* | 6/2011 | Matula, Jr. ........ | A61M 16/0816 128/207.18 |
| 2011/0214676 A1 | 9/2011 | Allum et al. | |
| 2011/0247619 A1 | 10/2011 | Formica et al. | |
| 2012/0060845 A1 | 3/2012 | McKinnon et al. | |
| 2012/0111332 A1 | 5/2012 | Gusky et al. | |
| 2012/0132209 A1 | 5/2012 | Rummery et al. | |
| 2014/0000626 A1 | 1/2014 | O'Connor et al. | |
| 2014/0130805 A1* | 5/2014 | Tiep .................. | A61M 16/0683 128/207.18 |
| 2014/0158127 A1 | 6/2014 | Boucher et al. | |
| 2014/0332007 A1 | 11/2014 | Znamenskiy et al. | |
| 2016/0235937 A1 | 8/2016 | Ronayne et al. | |
| 2017/0348500 A1 | 12/2017 | Johnson et al. | |
| 2021/0379313 A1 | 12/2021 | Ronayne et al. | |

FOREIGN PATENT DOCUMENTS

| | | |
|---|---|---|
| CN | 1905917 A | 1/2007 |
| CN | 101653632 A | 2/2010 |
| CN | 101977656 A | 2/2011 |
| CN | 101389369 A | 3/2013 |
| EP | 2130563 | 12/2009 |
| EP | 1481702 | 9/2012 |
| EP | 2022528 | 3/2016 |
| EP | 3057638 | 8/2016 |
| JP | 2007/506480 | 3/2007 |
| JP | 2009-291615 | 12/2009 |
| JP | 2009-544371 | 12/2009 |
| JP | 2011/5002229 | 1/2011 |
| JP | 2011/509762 | 3/2011 |
| JP | 2011/510707 | 4/2011 |
| JP | 2012-515562 | 7/2012 |
| JP | 2012/522608 | 9/2012 |
| JP | 2013-503720 | 2/2013 |
| JP | 2013-540037 | 10/2013 |
| WO | WO 2004/073778 | 9/2004 |
| WO | WO 2005/010608 | 2/2005 |
| WO | WO 2005/018524 | 3/2005 |
| WO | WO 2006/130903 | 12/2006 |
| WO | WO 2008/011682 | 1/2008 |
| WO | WO 2008/060587 | 5/2008 |
| WO | WO 2008/070929 | 6/2008 |
| WO | WO 2009/052560 | 4/2009 |
| WO | WO 2009/109005 | 9/2009 |
| WO | WO 2011/062510 | 5/2011 |
| WO | WO 2012/053910 | 4/2012 |
| WO | WO 2013/014581 | 1/2013 |
| WO | WO 2014/142681 A1 | 9/2014 |
| WO | WO 2015/057083 | 4/2015 |
| WO | WO 2016/157103 | 10/2016 |

OTHER PUBLICATIONS

Australian Government, Examination Report No. 1 for Standard Patent Application, Application No. 2015318732, dated Aug. 9, 2019, in 4 pages.
Examination Report dated Jun. 18, 2018 for Australian Application No. 2014335018 in 5 pages.
Extended European Search Report, PCT/NZ2015/050156; dated Feb. 20, 2018; 8 pages.
International Search Report, PCT/NZ2015/050156, dated Nov. 10, 2015, in 5 pages.
Extended European Search Report dated May 15, 2017 in EP Appl. No. 1485791.2 in 7 pages.
International Search Report and Written Opinion; PCT/NZ2014/000217; date Jan. 12, 2015; 21 pages.
Japanese Office Action in 8 pages dated Aug. 13, 2018 in Japanese Application No. 2016-524416.
Chinese Exam report in 10 pages dated Jun. 28, 2017 in Chinese Application No. 201480069093.1.
European Examination Report dated Jan. 25, 2019 in EP Appl. No. 1485791.2 in 3 pages.
Chinese exam report in 11 pages dated Oct. 17, 2018 in Chinese Application No. 201480069093.1.

(56) References Cited

OTHER PUBLICATIONS

Chinese Office Action dated Jan. 29, 2019 for Chinese Application No. 201580060077.0 in 20 pages.
Japanese Examination Report dated Mar. 6, 2019, Japanese Patent Application 2016-524416 in 9 pages.
Japanese Examination Report, Japanese Application No. 20177-515742, dated Jun. 18, 2019 in 12 pages.
UK Examination Report for Patent Application No. GB2014636.1 dated Nov. 9, 2020, in 8 pages.
UK Examination Report for Patent Application No. GB2012226.3 dated Nov. 6, 2020, in 8 pages.
Japanese Examination Report for Patent Application 2017-515742, dated Nov. 16, 2020, 4 pages.
Japanese Patent Office, Notice of Reasons for Refusal (Office Action), Japanese Patent Application No. 2016-524416, dated Jan. 4, 2021, in 7 pages.
Canadian Patent Office, Examiner's Report, Application No. 2,927,088, dated Jan. 14, 2021, in 4 pages.
Notification of Reexamination for Chinese Application No. 201480069093.1, dated Jan. 20, 2020 in 16 pages.
European Examination Report for European Patent Application 15841985.3 dated Jul. 8, 2020, 6 pages.
Australian Examination Report No. 1 for Standard Patent Application for Application No. 2019203650, dated Aug. 3, 2020, in 8 pages.
Japanese Examination Report for Japanese Patent Application 2016-524416, dated Nov. 7, 2019 in 5 pages.
Notice of Reasons for Refusal for Japanese Application No. 2017-515742, dated Apr. 14, 2020, in 8 pages.
Examination Cover Letter and Examination Report for Patent Application No. GB1606325.7 dated Apr. 21, 2020, in 4 pages.
Chinese Examination Report and English Translation for Chinese Application No. 201580060077.0, dated May 15, 2020, 8 pages.
Australian Examination Report No. 2 for Standard Patent Application, Application No. 2015318732, dated Jun. 18, 2020, in 5 pages.
Japanese PreAppeal Review Report for Japanese Patent Application 2016-524416, 7 pages.

* cited by examiner

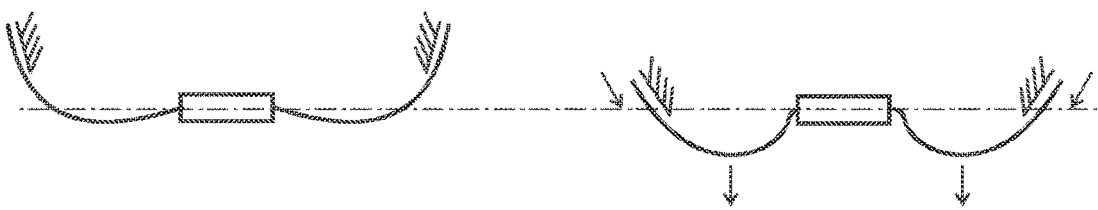
*FIGURE 2F*  *FIGURE 2G*
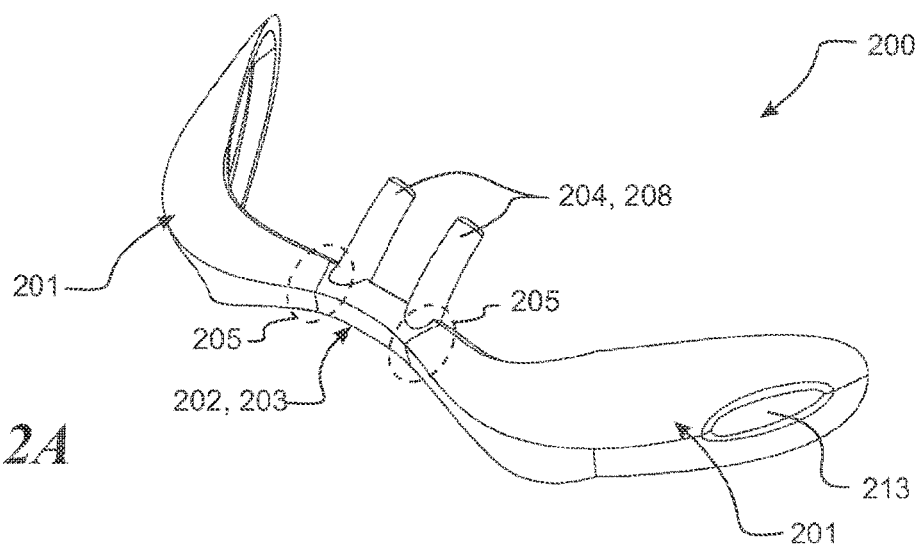
*FIGURE 2A*
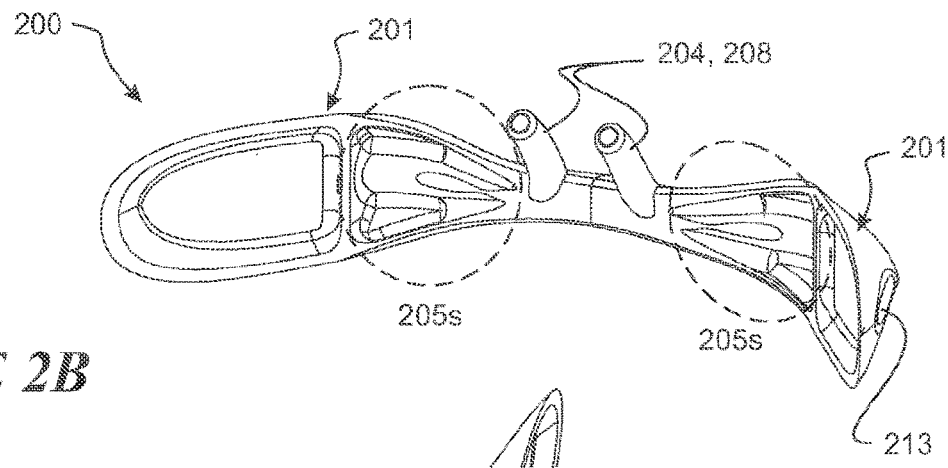
*FIGURE 2B*
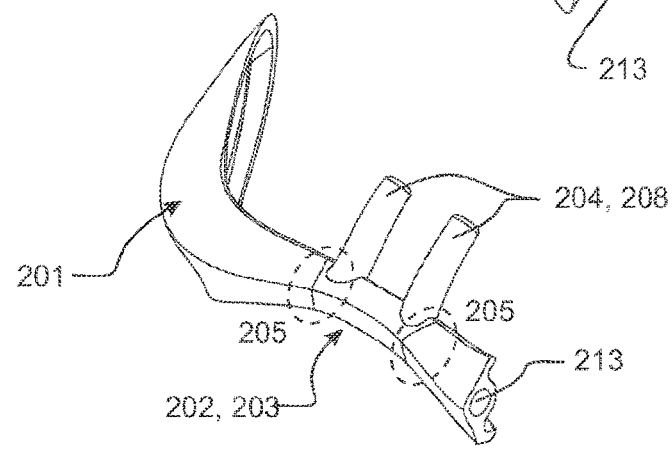
*FIGURE 2C*

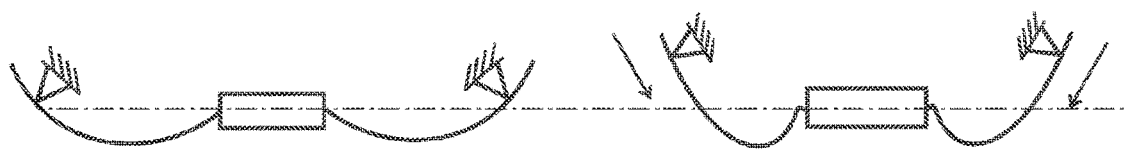
*FIGURE 3D*  *FIGURE 3E*
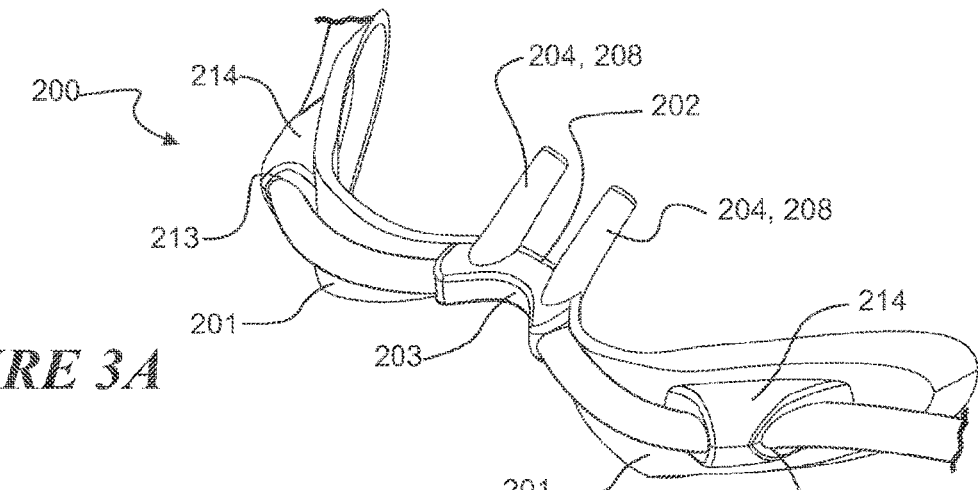
*FIGURE 3A*
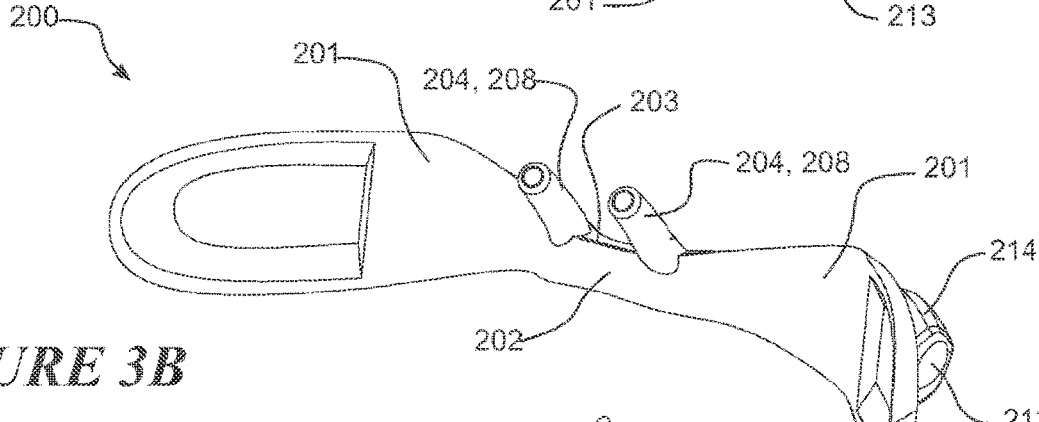
*FIGURE 3B*
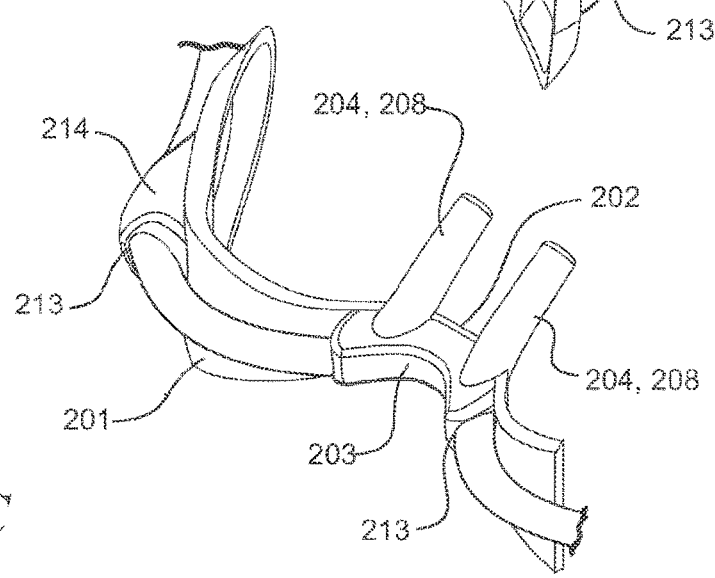
*FIGURE 3C*

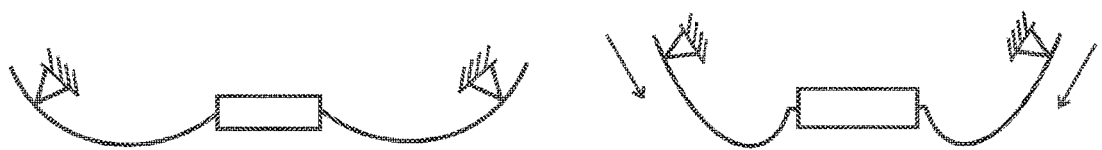
*FIGURE 4D*  *FIGURE 4E*
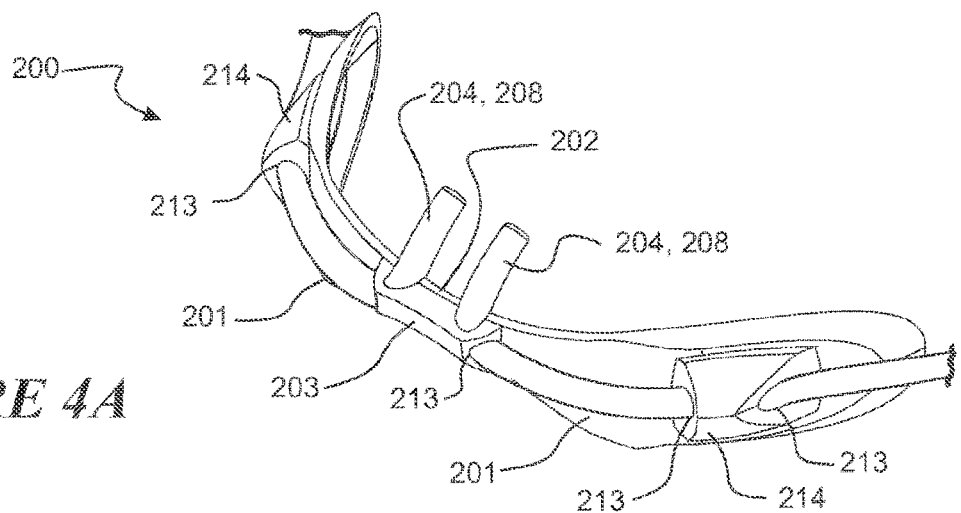
*FIGURE 4A*
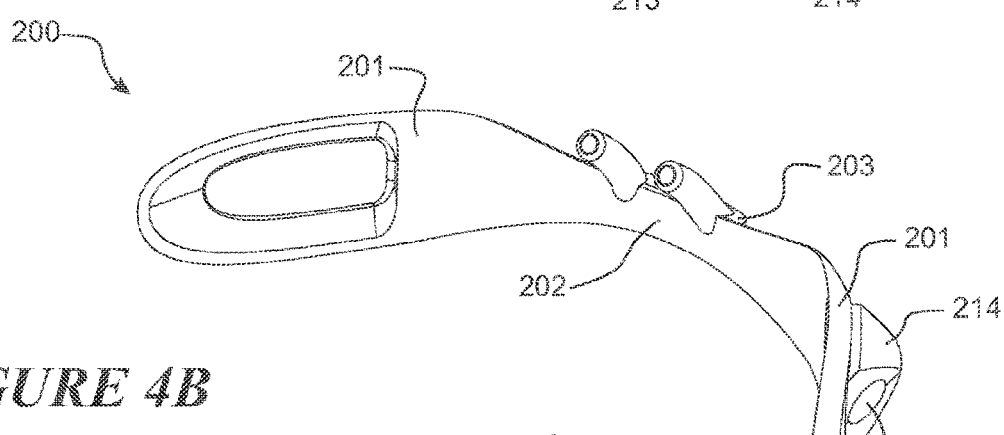
*FIGURE 4B*
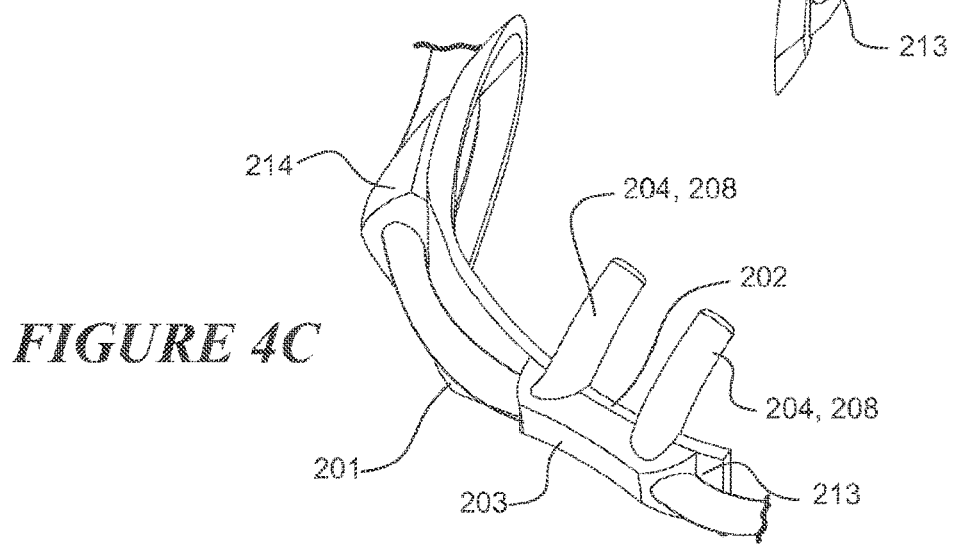
*FIGURE 4C*

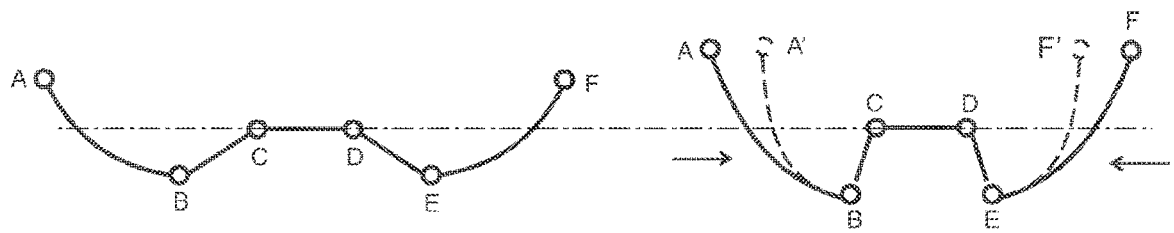
FIGURE 5F
FIGURE 5G
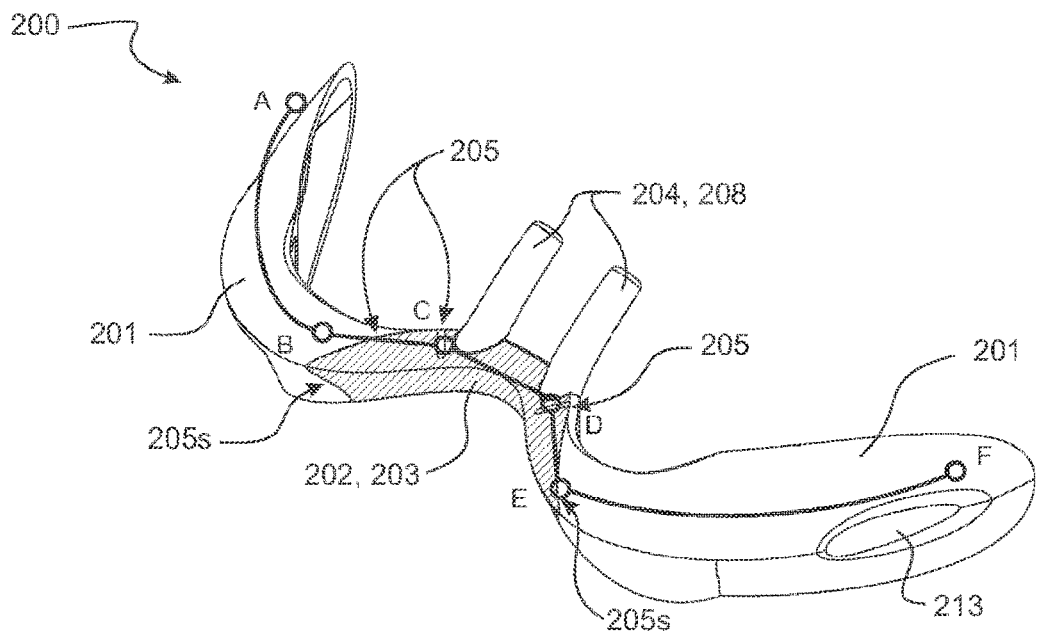
FIGURE 5A
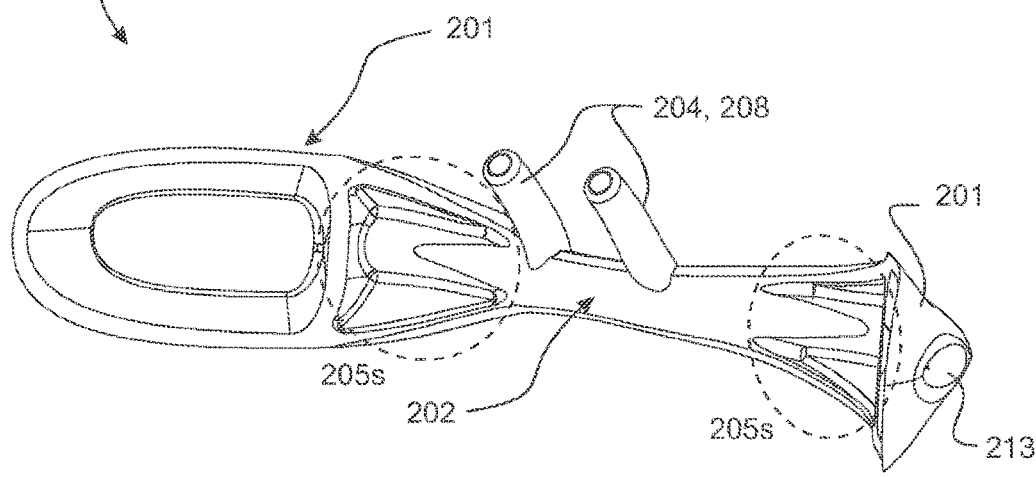
FIGURE 5B

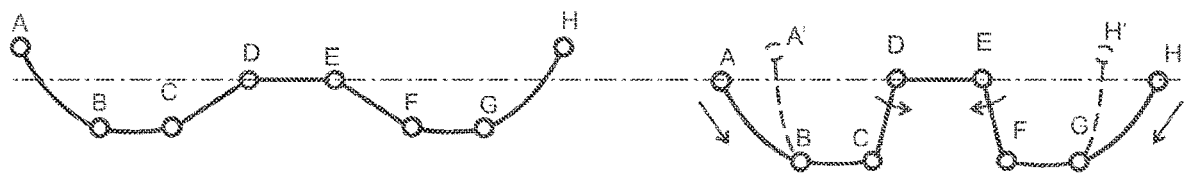
*FIGURE 6F*
*FIGURE 6G*
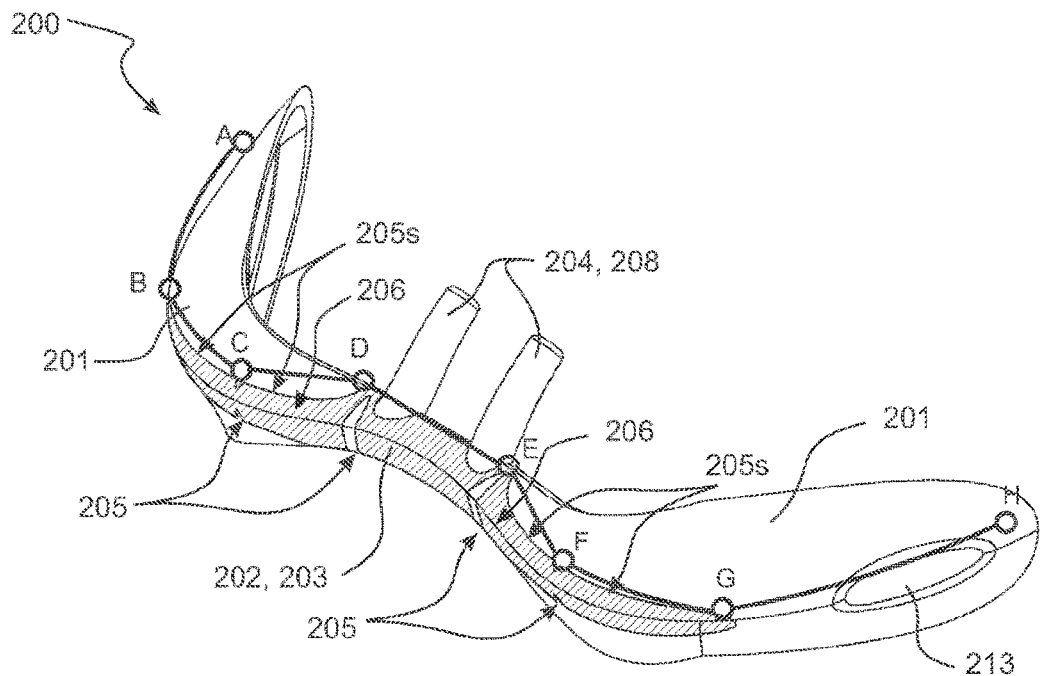
*FIGURE 6A*
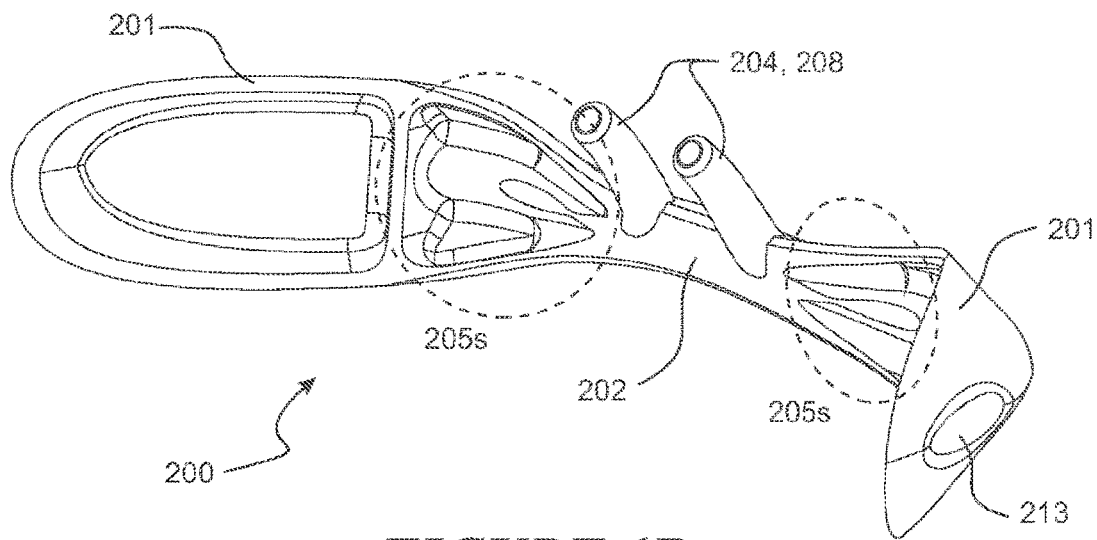
*FIGURE 6B*

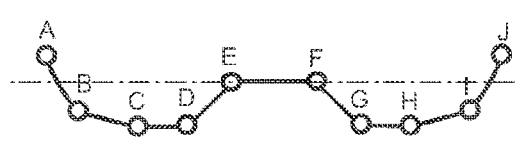
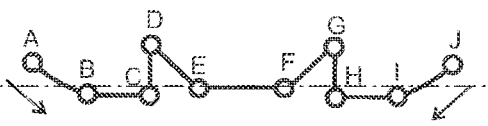
*FIGURE 7F*   *FIGURE 7G*
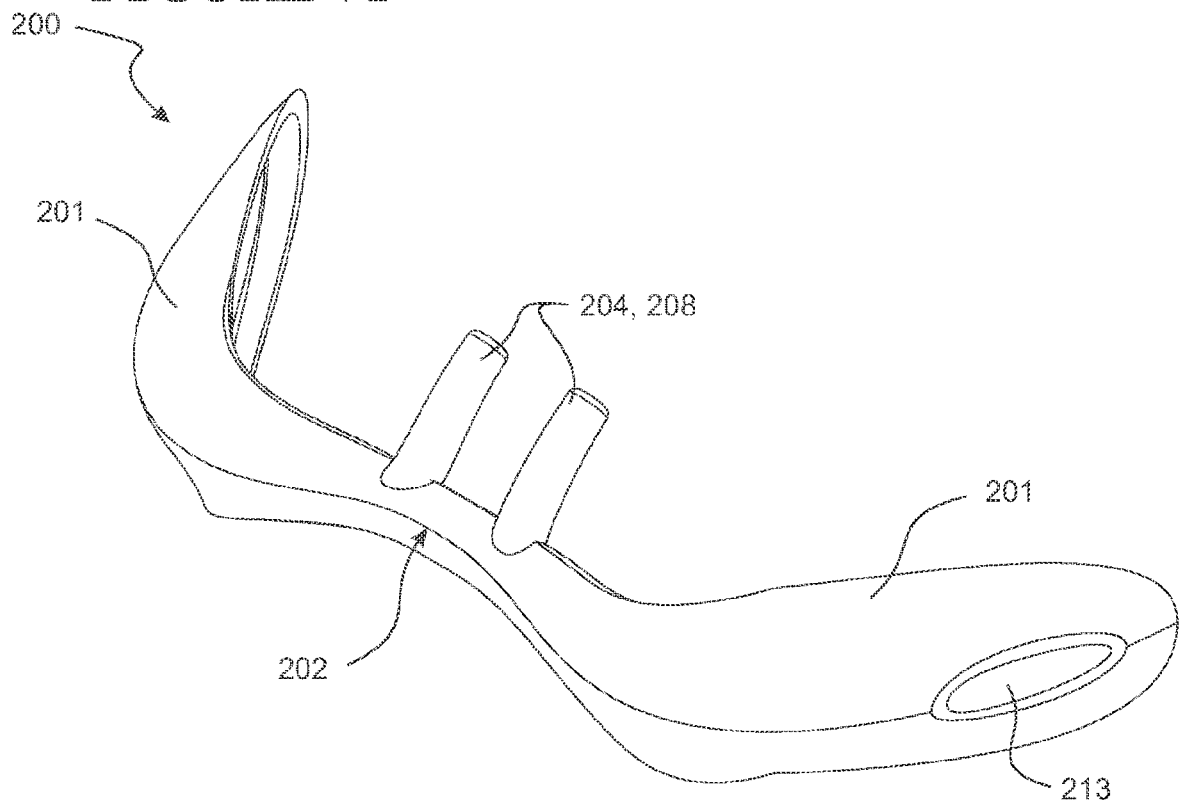
*FIGURE 7A*
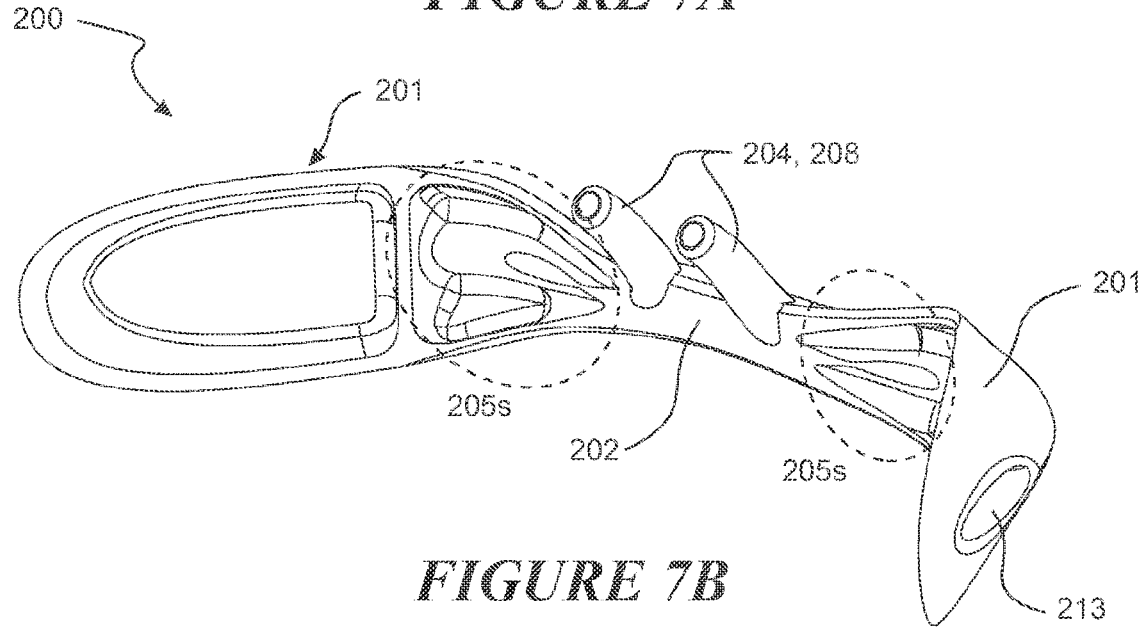
*FIGURE 7B*

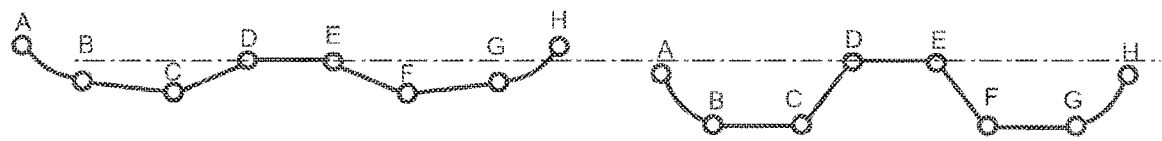
*FIGURE 8F*     *FIGURE 8G*
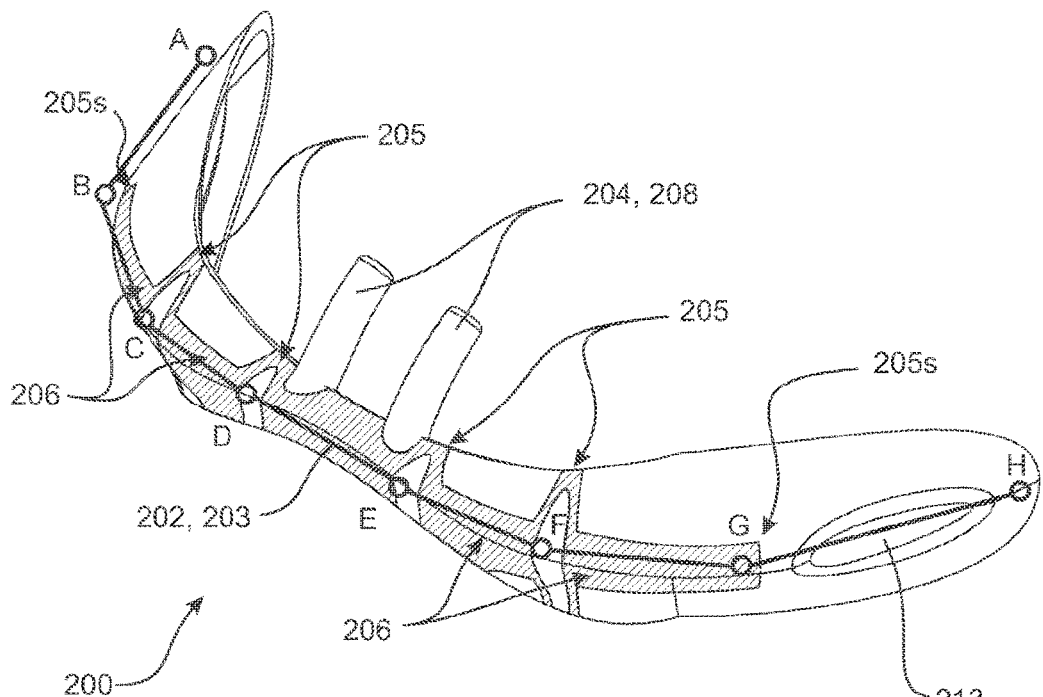
*FIGURE 8A*
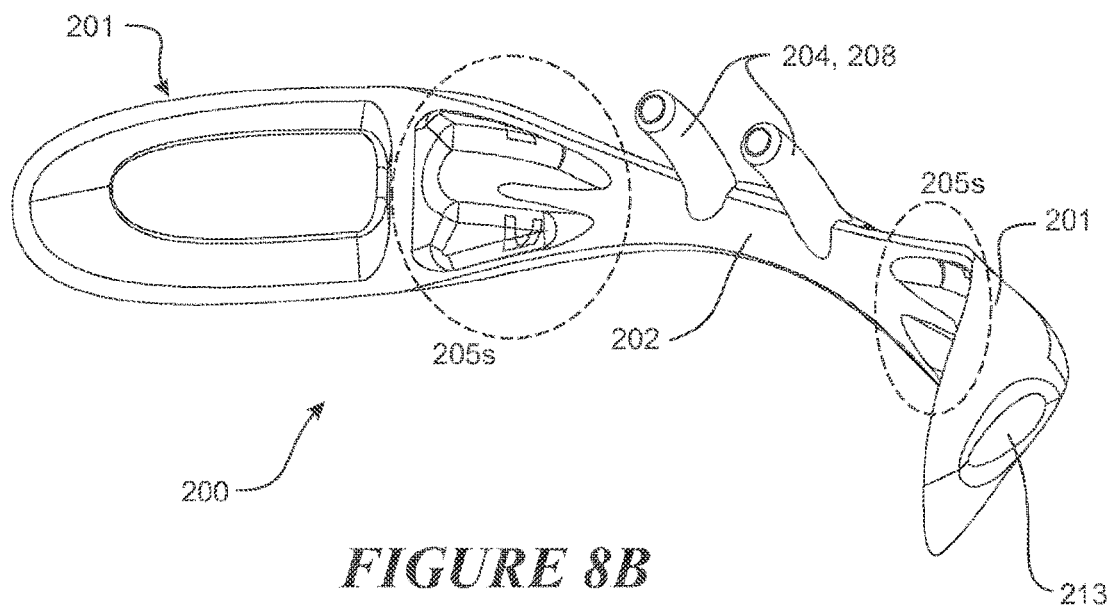
*FIGURE 8B*

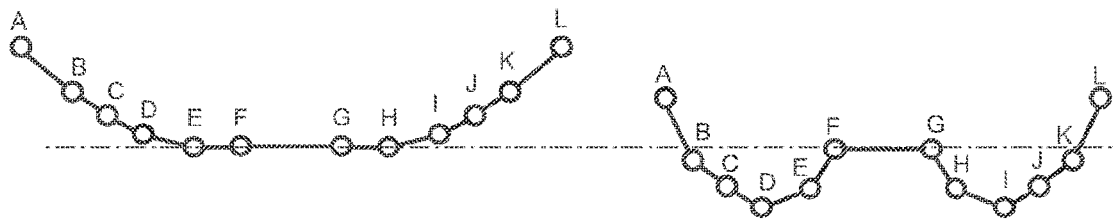
FIGURE 9F  FIGURE 9G
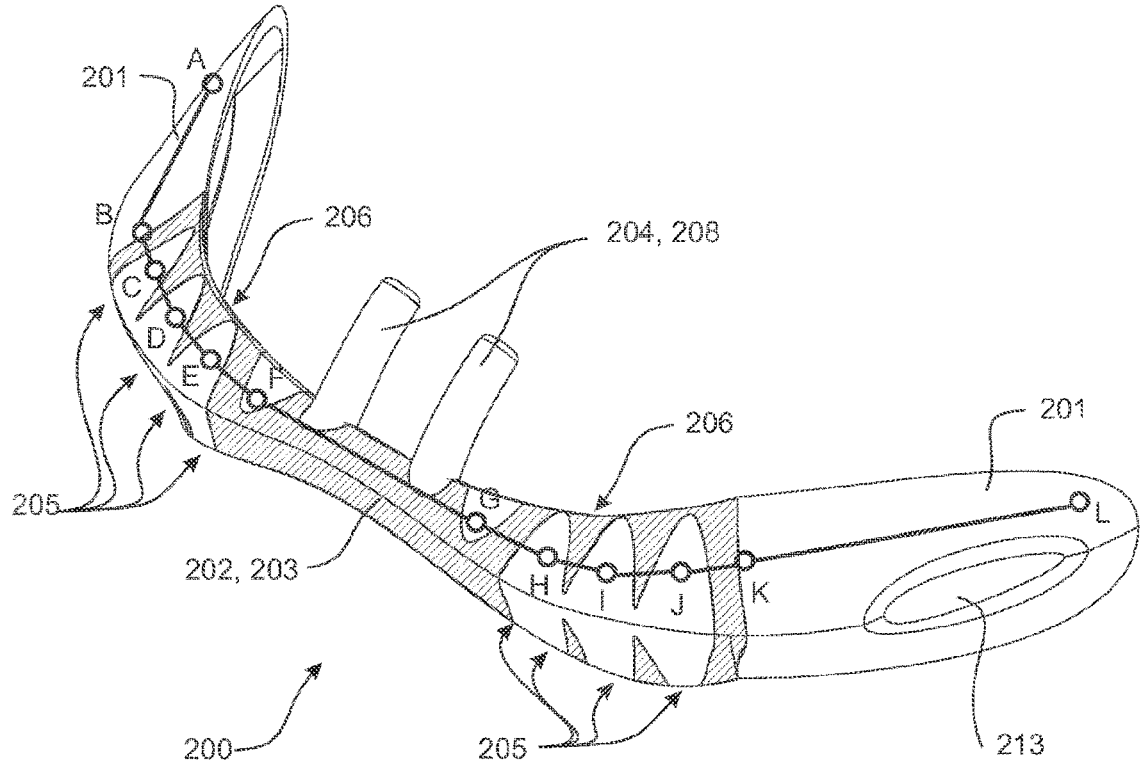
FIGURE 9A
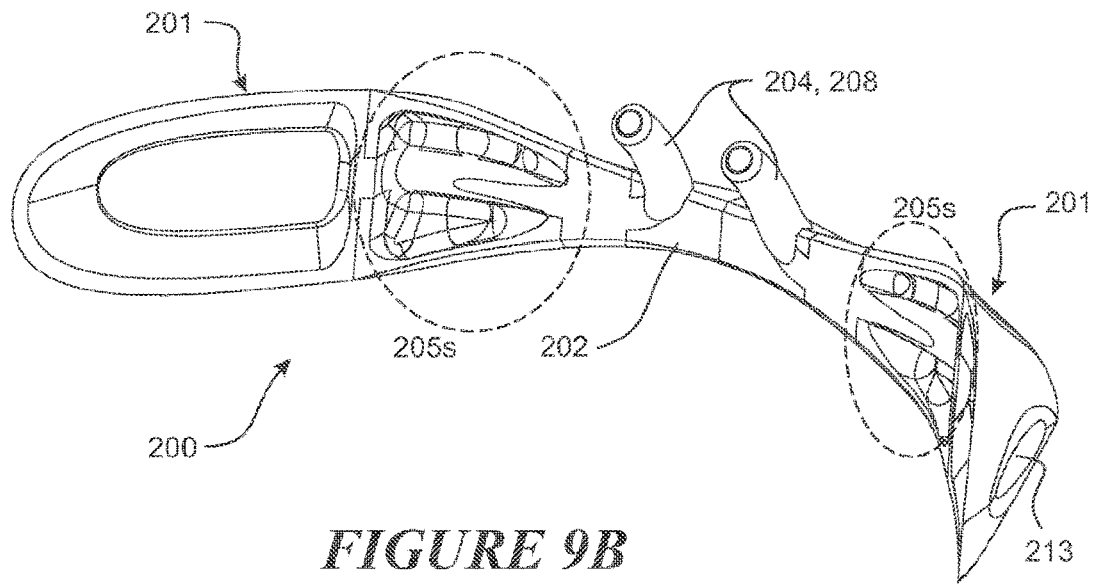
FIGURE 9B

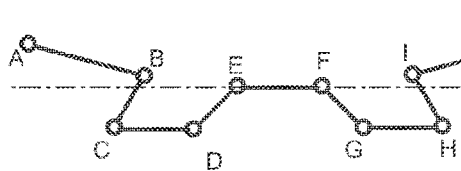
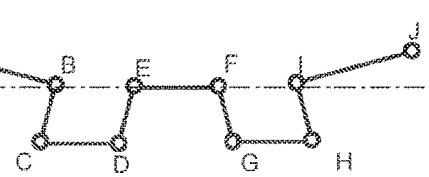
FIGURE 14F             FIGURE 14G
FIGURE 14C
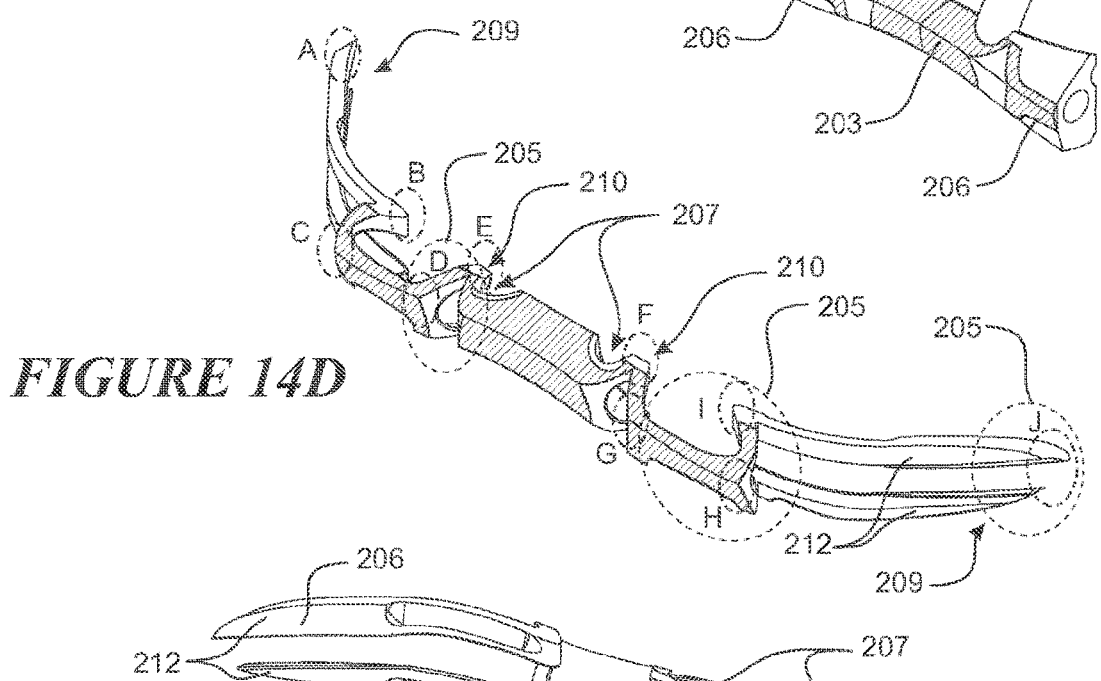
FIGURE 14D
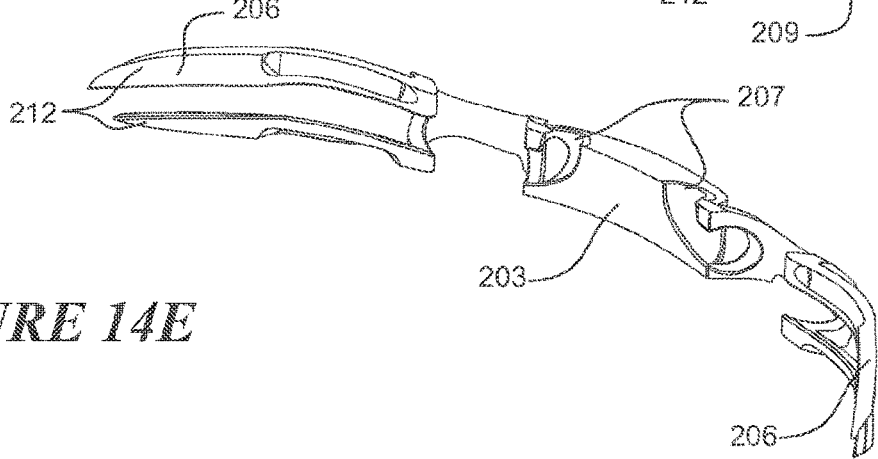
FIGURE 14E

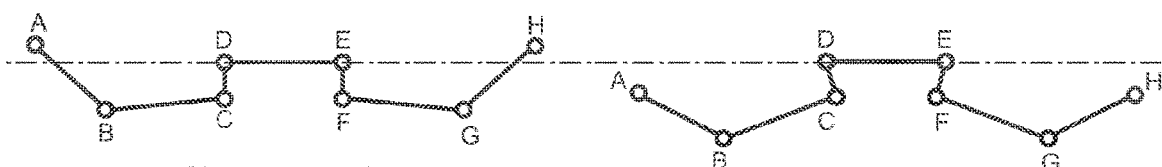
*FIGURE 15F*    *FIGURE 15G*
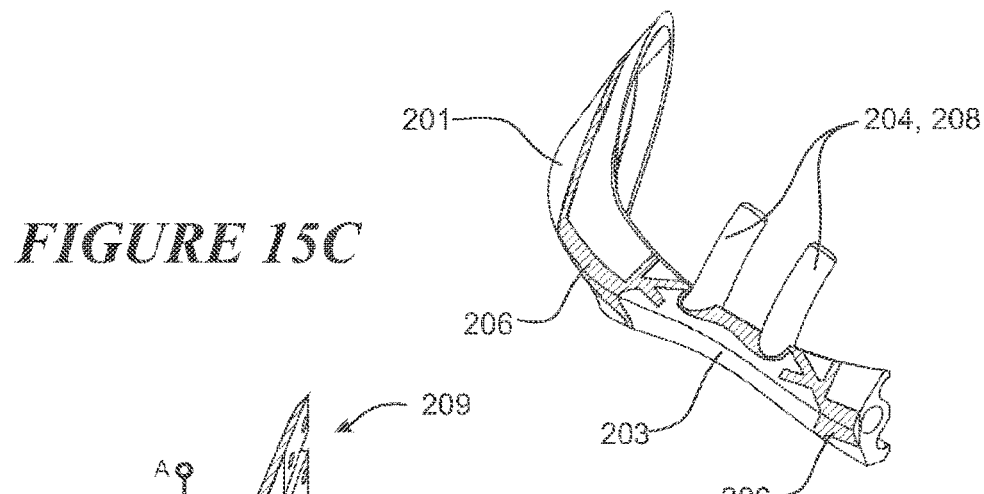
*FIGURE 15C*
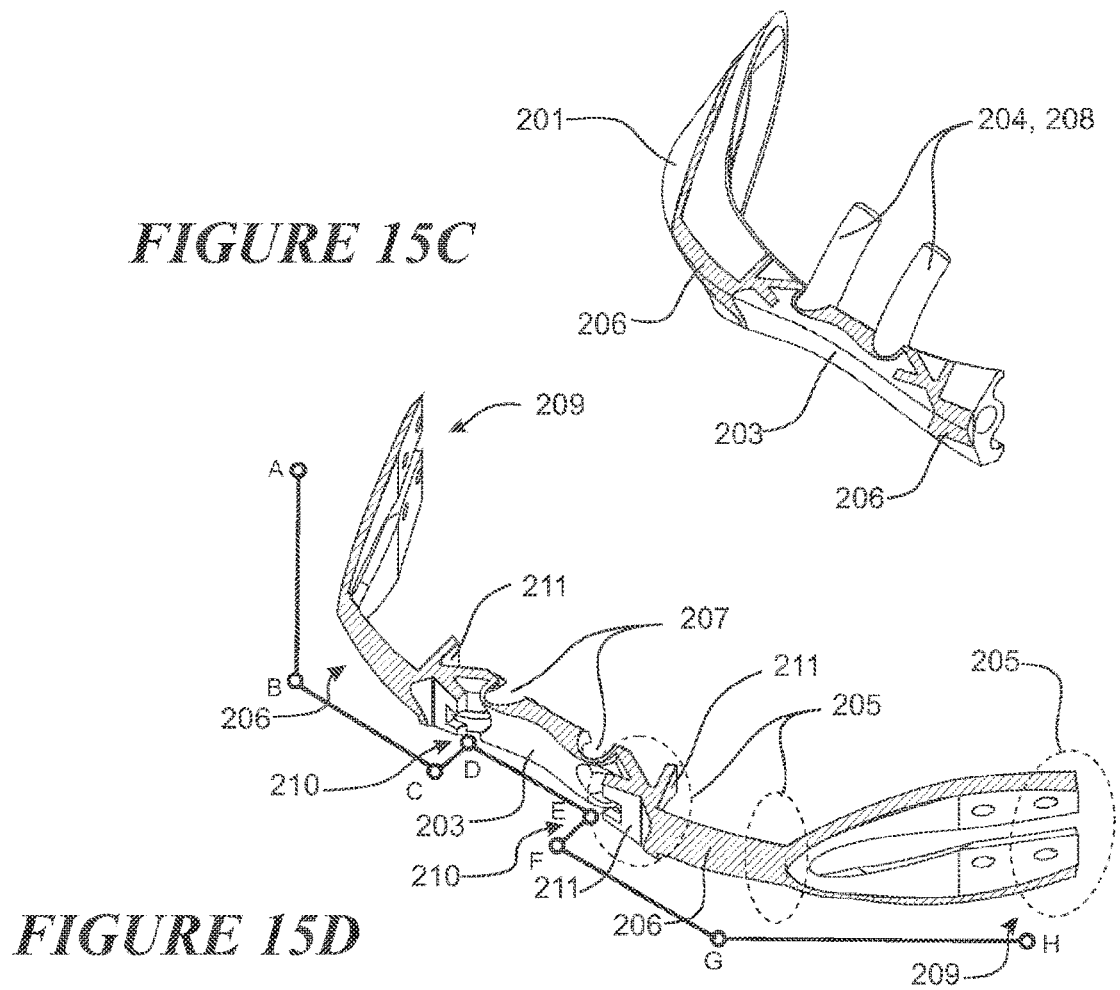
*FIGURE 15D*
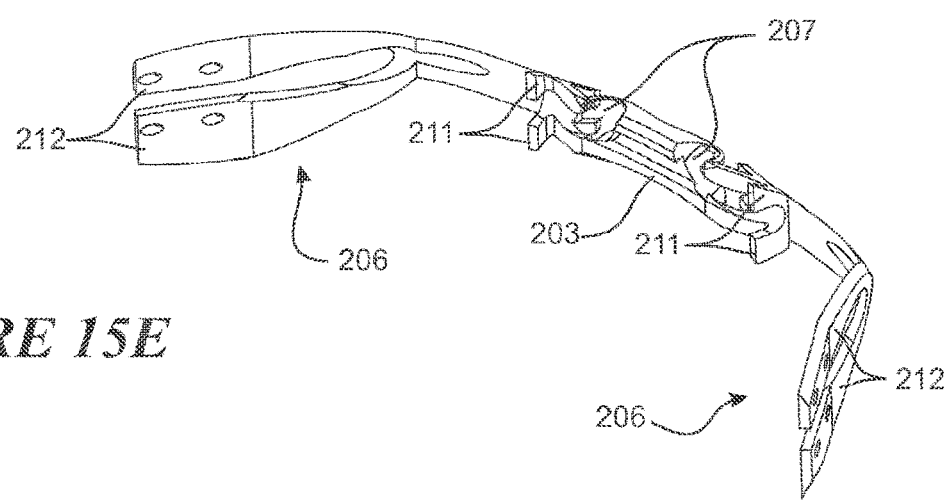
*FIGURE 15E*

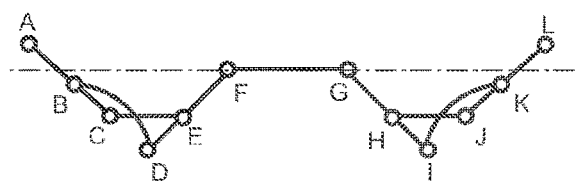
FIGURE 16F
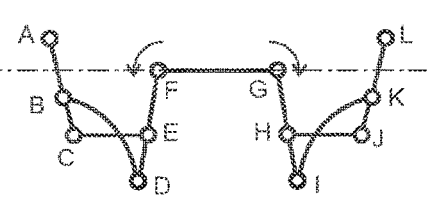
FIGURE 16G
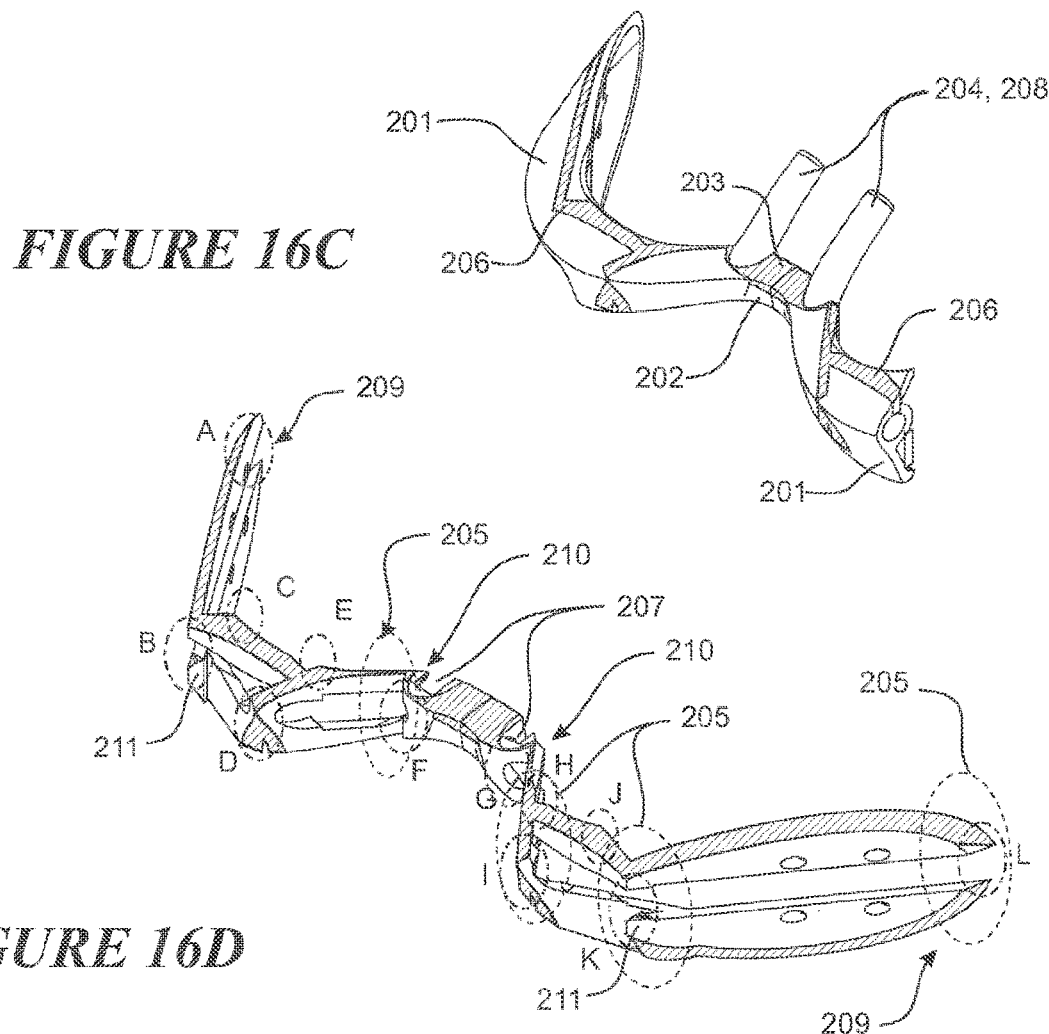
FIGURE 16C
FIGURE 16D
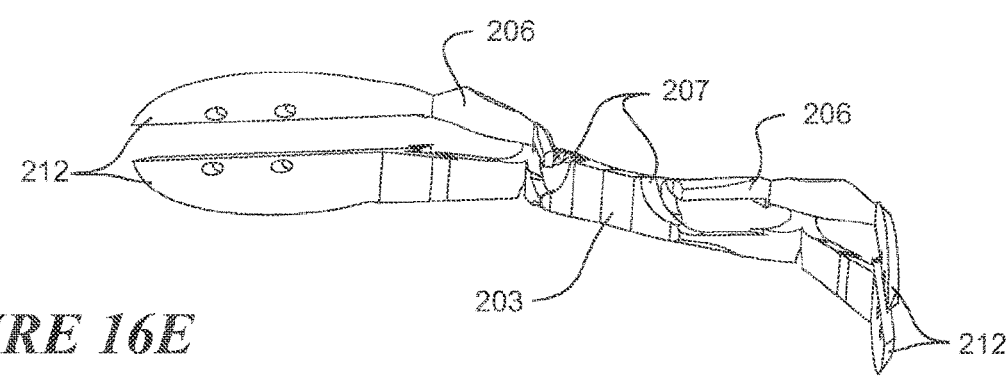
FIGURE 16E

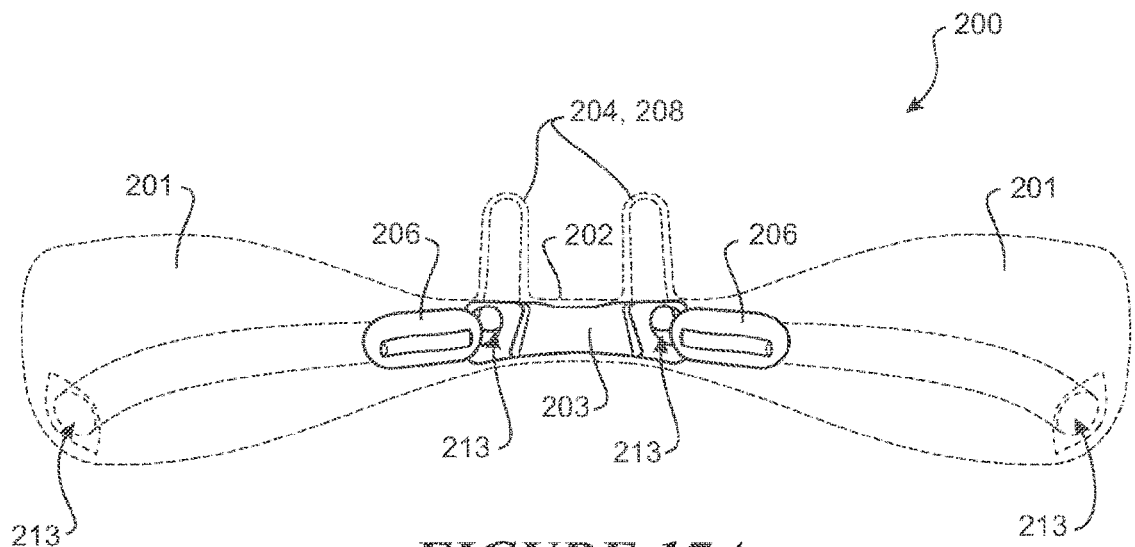
*FIGURE 17A*
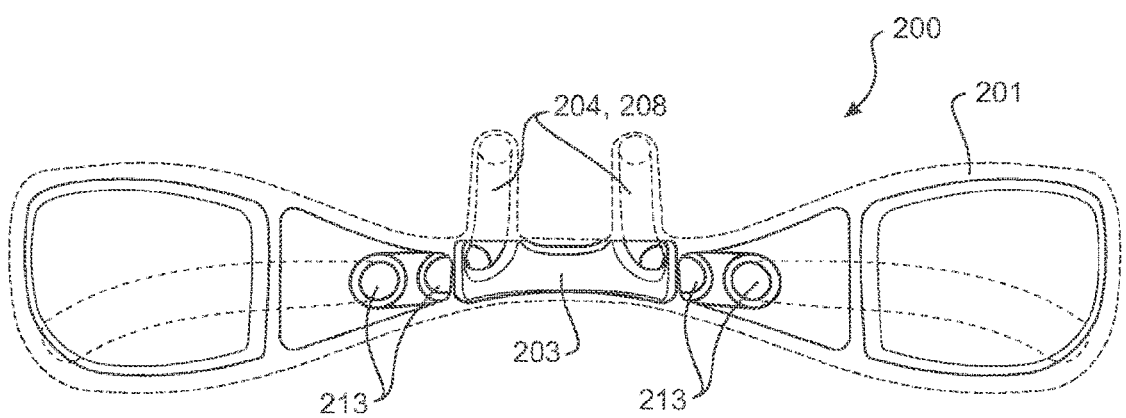
*FIGURE 17B*
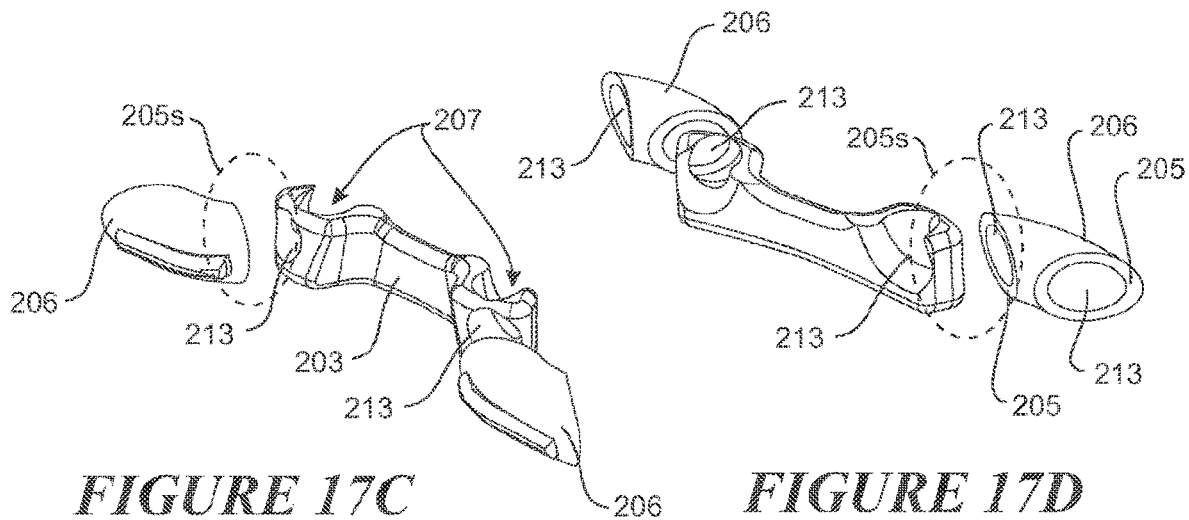
*FIGURE 17C*     *FIGURE 17D*

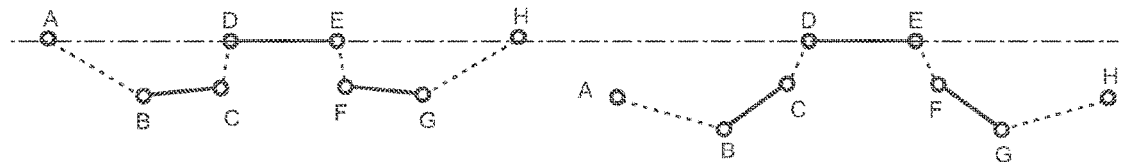
*FIGURE 17F*     *FIGURE 17G*
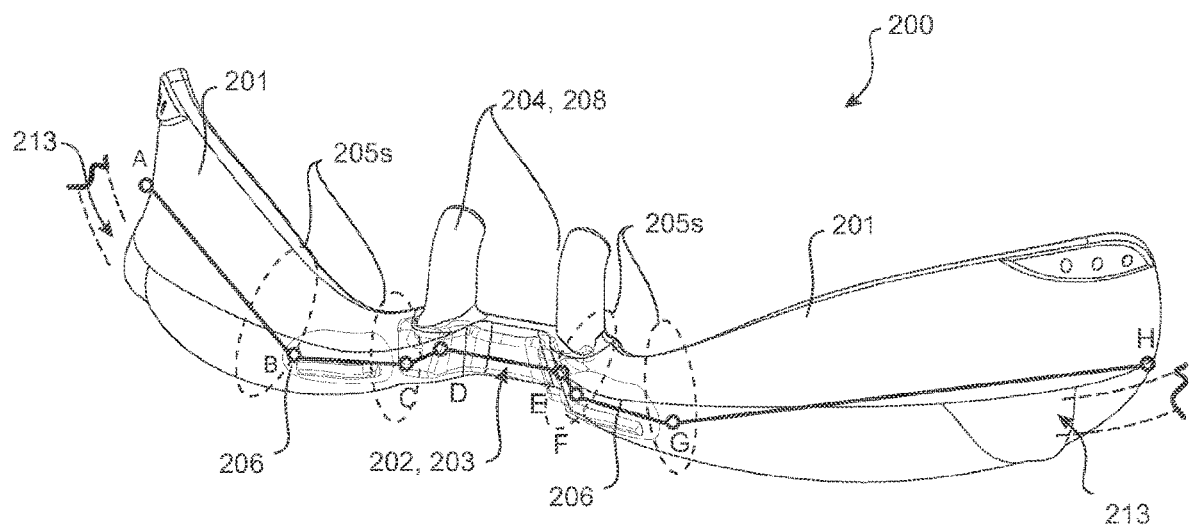
*FIGURE 17E*

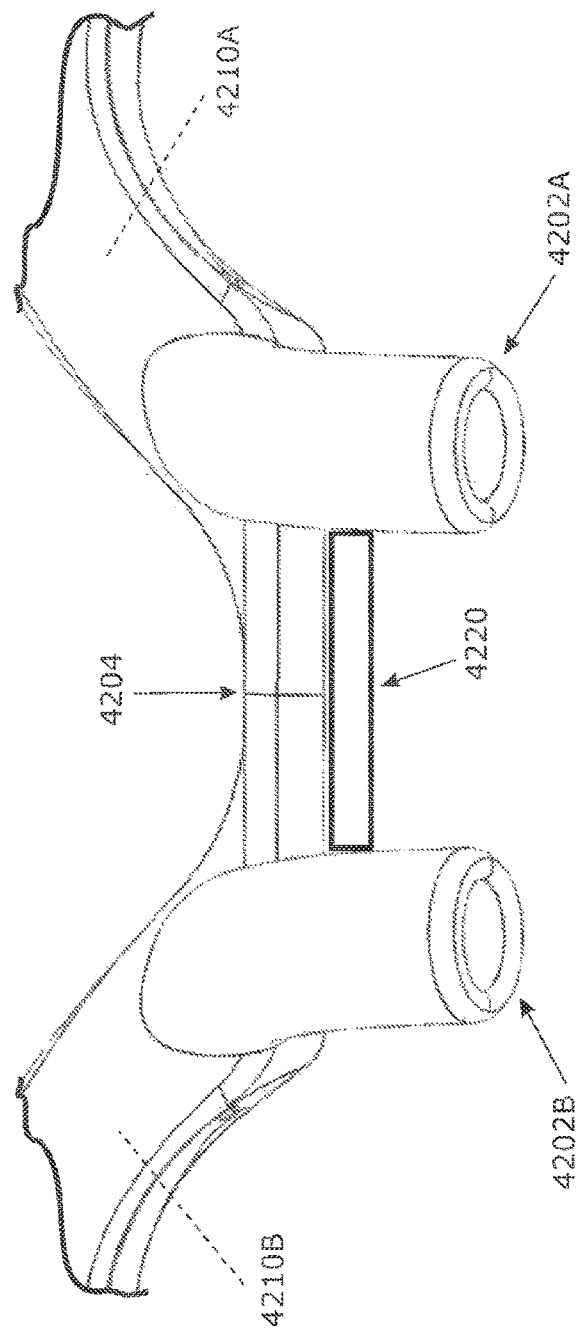
FIGURE 22A
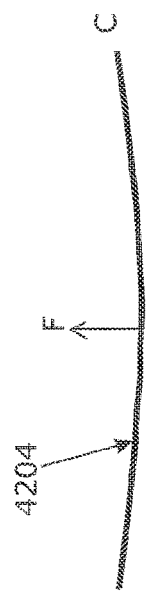
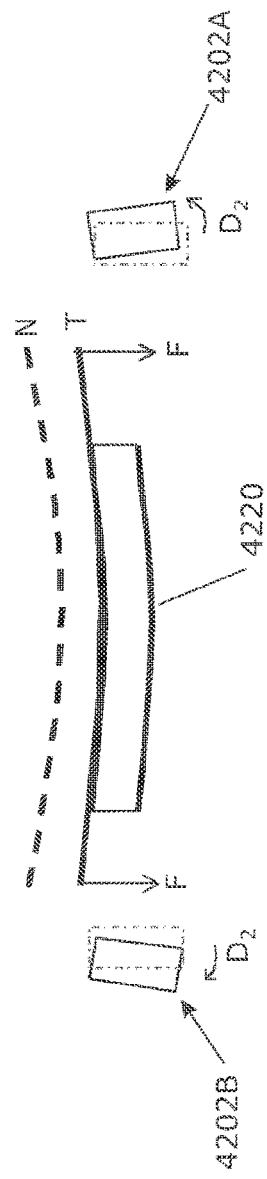
FIGURE 22B

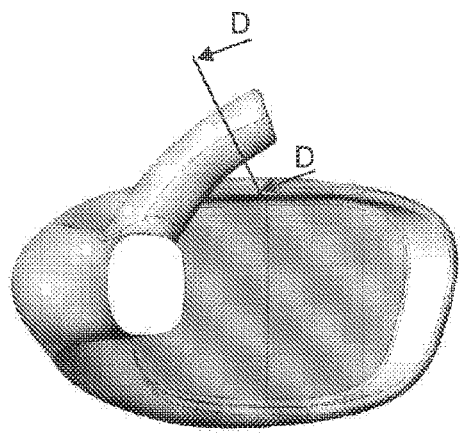
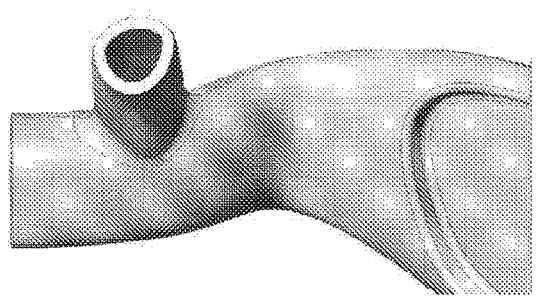
FIGURE 42A      FIGURE 42B
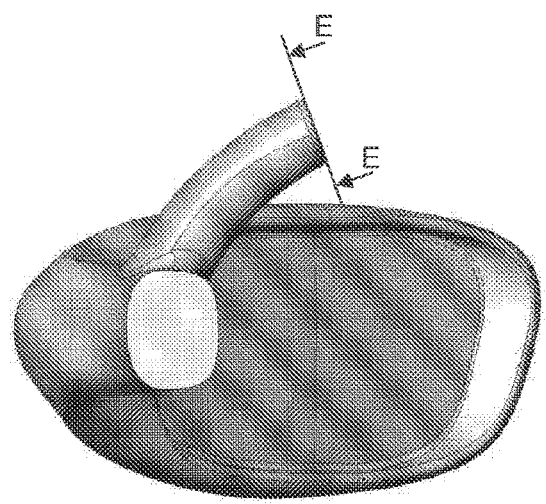
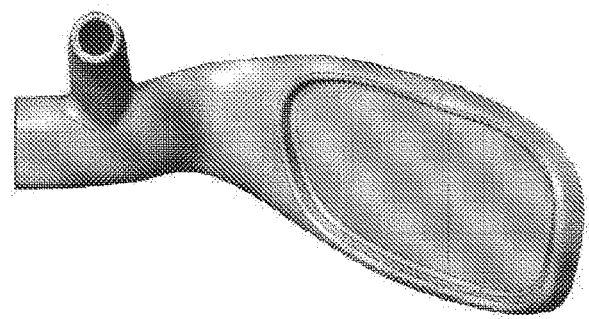
FIGURE 43A      FIGURE 43B

PATIENT INTERFACE

INCORPORATION BY REFERENCE TO ANY PRIORITY APPLICATIONS

Any and all applications for which a foreign or domestic priority claim is identified in connection with the present application are hereby incorporated by reference herein and made a part of the present disclosure. The present application is a continuation of U.S. patent application Ser. No. 15/512,498, filed Mar. 17, 2017, which is a U.S. National Phase of PCT Application No. PCT/NZ2015/050156, filed Sep. 18, 2015, which claims the priority benefit of U.S. Provisional Application No. 62/198,851, filed Jul. 30, 2015, U.S. Provisional Application No. 62/183,099, filed Jun. 22, 2015, U.S. Provisional Application No. 62/121,144, filed Feb. 26, 2015, U.S. Provisional Application No. 62/064,106, filed Oct. 15, 2014, and U.S. Provisional Application No. 62/052,980, filed Sep. 19, 2014, the entireties of which are hereby incorporated by reference herein.

FIELD

The present disclosure relates to a patient interface for delivering gases to a user, more particularly, though not solely, to patient interfaces for delivering a flow of gases to a user which compensate or accommodate for movements or forces applied or translated to the interface from destabilising the interface from a therapy delivery positioning upon a user during use or alternatively to patient interfaces that deliver gases to a user's nares or nasal passages.

BACKGROUND

There are many forms of patient interfaces for delivery of gases to a user, such as for example full face masks, oro-nasal masks, nasal masks and nasal cannula. It is desirable to provide for a patient interface in a manner that conforms to a user's changing facial geometry or which is configured in a manner to maintain a stable position upon the user or to at least help improve the maintenance of stability when external forces are applied to such a patient interface.

There are a significant variety of patient interfaces available to users, each of which may have their own stability issues.

Stability of an interface upon a user is of importance for at least the reasons of comfort and maintenance of a desired therapy delivery to the user. In achieving one or both of these outcomes, or yet other outcomes, the provision of alternative patient interfaces with improved stability and/or performance on the face of the user would be useful.

Instability of an interface may lead to dislodgment of an interface or components of the interface which may affect the desired delivery or integrity of therapy for the user.

In various modes, instability of an interface upon a user may be, for example, the result of loading such as by a user speaking and changing the geometry of their face to which the interface is positioned. Facial geometry, such as that of humans, varies greatly due to a large range of factors. These factors may include, but are not limited to, gender, age, or particular medical conditions. Incorrect sizing and geometry of an interface to a particular user may also adversely affect the stability and usability of certain patient interfaces.

In terms of facial movement, when a user speaks, eats, cries or has their facial features distorted or exaggerated, such movement can affect the stability of a patient interface or components of the interface on a user, for example such as a nasal prong or a pair of such prongs of a nasal cannula which may inadvertently come out of a gas delivery position for delivering gas to the nare(s) of a user's nose. More prolonged changes to facial features can also arise from aspects such as a user's position, for example while sleeping. Long term changes in geometry can also occur from user growth and injury recovery.

In relation to the above, it will be appreciated that either due to changes in geometry of a user to which the patient interface is located, or for example by yet other forces, such as by a user pulling on a tube or the interface or other components attached to these, forces or movements can be transmitted to the interface and components thereof. The application of such forces can pose problems of stability, comfort and operational use of the patient interface for a user.

Further aspects and advantages of the present invention will become apparent from the ensuing description which is given by way of example only.

SUMMARY

It is therefore an object of certain embodiments disclosed herein to provide a patient interface or at least portions of a patient interface which when implemented into a patient interface will go at least some way towards addressing the foregoing problems or which will at least provide the industry/public with a useful choice.

In accordance with at least one of the aspects disclosed herein there is provided a patient interface, such as a nasal cannula, comprising:
  a. a body portion to be located, in-use upon a face of a user, the body portion having one side arm or preferably a pair of said side arms extending laterally from a substantially central bridge portion to be located, in-use, in or about a user's septum region,
  b. at least one, and preferably a pair of, nasal prong(s) extending from the bridge portion to be inserted into, or to direct a flow of gas into, a nare or the nares of the user's nose in an operational position,
  c. the body portion having at least one fluid passageway connected to the nasal prong(s) for supply of a gas to the nare(s) of the user's nose,
  d. wherein, a cross section of the passageway varies along the length of the body portion to provide regions of varying flexibility along the body portion.

In some embodiments, the or each said side arm comprises one or more predefined or predisposed points or localised compensation regions (or sites) positioned along the side arm to accommodate or facilitate a compensation of the patient interface in or at one or more of the compensation regions (or sites), and wherein when a force applied to the patient interface is experienced by a side arm or side arms of the interface, the compensation regions (or sites) of the side arm or the side arm element, or both, accommodate the force by way of a flexure or bending or hinging or other displacement of the side arm or the side arm element, or both.

In some embodiments, one or more of the compensation regions (or sites) are a region or site of bending or hinging region though or about at least two different (non-parallel) planes passing through the interface.

In some embodiments, the bridge portion comprises a bridge portion element and the bridge portion, the bridge portion element, or both the bridge portion and bridge portion element is/are substantially isolated from forces applied or to, or experienced by, the patient interface.

In some embodiments, the bridge portion element and the side arm element or elements are separate parts that can be assembled to form a unitary structure.

In some embodiments, the bridge portion element is of a dimension sufficient to span the width of a user's septum region, or is a distance or the width between gas outlets, or is defined by a maximum distance substantially spanning from one nasolabial fold to another nasolabial fold of a user, and the side arm element is dimensioned to extend at least a part away along the length of the side arm.

In some embodiments, the bridge portion element includes one or a pair of cut-outs or shaped portions to locate, position or house at least one, or a pair of, outlet(s) for a gas delivery system supplying gas to a user's airway.

In some embodiments, the bridge portion element is or comprises a textile material and is positioned on the outer surface of the bridge portion, wherein the bridge portion element adds to the stiffness of the bridge portion in order to maintain the distance between the prongs.

In some embodiments, the or each said side arm comprises at least one substantially resilient, or relatively more rigid, side arm element, the side arm element defining at least in part a form or curvature of the or each side arm and having one or more predefined or predisposed points or localised compensation regions (or sites) positioned along the or each side arm and/or the or each side arm element to accommodate a compensation of the patient interface in or at one or more of compensation regions (or sites), and wherein the side arm or arms are patient interface stabilisers.

In some embodiments, the side arm element comprises one or more cut-outs to allow flexing of the side arm element such that the side arm portion can flex in response to an application of forces.

In some embodiments, the interface is overmoulded onto the bridge portion element and the side arm element.

In accordance with at least one of the aspects disclosed herein there is provided a patient interface comprising:
a. a body portion to be located, in-use upon a face of a user, the body portion having left and right side arms and a bridge portion between the left and right side arms,
b. at least one nasal prong extending from the bridge portion to be inserted into, or to direct a flow of gas into, a nare or the nares of the user's nose in an operational position,
c. the body portion having at least one fluid passageway connected to the nasal prong(s) for supply of a gas to the nare(s) of the user's nose,
d. wherein, a cross section of the passageway varies along the length of the body portion to provide regions of varying flexibility along the body portion.

In some embodiments, the cross section of the passageway varies in shape along at least a portion of the length of the body portion and varies from a substantially circular cross section at or near an outer end for connection with (either releasably or permanently) a breathing tube or conduit, to an elongated cross section, the elongated cross section having a longer axis arranged substantially vertically (parallel to a user's face).

In some embodiments, the elongated cross section is provided in or forms a bending region or hinging portion of the body portion, the elongated cross section providing greater flexibility for bending of the body portion towards or away from the user's face in a direction of a shorter axis of the elongated cross section.

In some embodiments, the at least one nasal prong comprises a pair of nasal prongs, and the bridge region comprises a solid section between the prongs so that the bridge region is more rigid than the bending regions, and the bridge region has a height or vertical dimension that is sufficient to provide torsional stability and prevent twisting of the bridge region in use.

In some embodiments, the bridge portion comprises wall sections that are thicker than wall sections of the bending regions so that the bridge portion is more rigid than the bending regions.

In some embodiments, the bridge portion comprises a further more rigid material to provide rigidity to the bridge region, the bridge portion being formed from a rigid material that is different to the material forming the remainder of the patient interface.

In some embodiments, the side arms comprise one or more side arm elements that are provided to or within the side arms of the interface, the side arm elements being formed from a rigid material to provide rigidity to the side arms/portions, the side arm element further comprising one or more cut outs or notches to allow the side arms to flex/hinge in response to forces applied to or experienced by the side arms.

In some embodiments, the bridge portion transitions into the left and right side arms by extending outwardly in a flared or curved manner away from a user's face side of the bridge portion, the left and right side arms curving away from the bridge portion rearwardly from a front extent of the body portion, the curvature(s) of the user's face side of the bridge portion and/or transition regions between the bridge portion and the left and right side arms has a relatively large radius (or radiuses) so that pressure from the bridge and/or the transition regions on the user's face is spread over the user's philtrum or upper lip region.

In some embodiments, the body portion comprises a U-shaped region between the at least one nasal prong and the adjacent left or right side arms when the body portion is viewed from above, an inside of the U-shaped region facing the user's face in use, each U-shaped region forms or is provided in a bending region where the body portion preferentially bends when the left or right portion of the body portion is flexed towards or away from the user's face, and the bending region tends to bend in a valley of the U-shaped region.

In some embodiments, an internal angle of the U-shaped region is less than about 130 degrees, or 120 degrees, or 110 degree, or 105 degrees.

In some embodiments, the patient interface is a single integrally formed component formed from a single material in a single moulding operation, wherein the patient interface is formed from a thermoplastic or silicone material with a Shore A hardness of approximately 5 to 60.

In some embodiments, a cross section of the passageway at a base of at least one nasal prong is an asymmetric cross section, one side of the cross section being flatter than an opposite side of the cross section and a passageway extending along at least one nasal prong changes in shape from the asymmetric cross section at or near the base of at least one nasal prong to a circular cross section at or near a tip of at least one nasal prong.

In some embodiments, the cross sectional area at least one nasal prong reduces from the base to the tip of the prong and the flatter side of at least one nasal prong is positioned towards a forward side of the patient interface (facing away from the user's face).

In some embodiments, at least one nasal prong has a base that is integrally formed with the bridge portion of the body portion of the patient interface, and wherein the base of at least one nasal prong comprises a fillet between a wall of the prong and the bridge portion, the fillet extending around the perimeter of at least one nasal prong, and wherein a radius of the fillet varies around the perimeter of at least one nasal prong.

In some embodiments, the patient interface comprises at least one pad of a retention system for retaining the interface in position when being worn in-use by a user, the pads attached to at least one of the left and right side arms of the body portion, the pad being substantially symmetrical about a central approximately vertical axis that divides the pad into left and right sides so that the same shaped pad may be applied to both the left and right side arms of the body portion, optionally each pad of the one pad is attached to the respective left or right portion by overmoulding with an overmoulding material, whether attached by the interface being moulded integrally with the pad or the pad or subsequently attached to the interface by an overmoulding of the interface and pad.

In some embodiments, the retention system comprises a two-part releasable attachment (or connection) arrangement, the arrangement comprises:
 a. a dermal patch and a user interface patch,
 b. the dermal patch having a patient side and an interface side,
 c. the patient side of the dermal patch being attachable to the skin of a user, (e.g. by an adhesive, generally being of a dermatologically sensitive adhesive such as a hydrocolloid),
 d. the interface side of the dermal patch being provided with the first part of a two-part releasable attachment or connection system, and
 e. the user interface patch having a interface side and patient side,
 f. the patient side of the user interface patch being provided with the complimentary second part of the two-part releasable attachment or connection system,
 g. the interface side of the user interface patch being attachable (or connectable) to the user interface and/or the component associated with the user interface (e.g. a tube or tubing).

In some embodiments, the body portion, or at least the left or right side arms are co-moulded or overmoulded with the retention system such that the pad is retained on or within the side arm portions of the interface.

In some embodiments, each of the left and right side arms comprise one or more predefined or predisposed points or localised compensation regions (or sites) positioned along the or each side arm to accommodate a compensation of the patient interface in or at one or more of compensation regions (or sites), configured to accommodate a force by way of flexure or bending or hinging or other displacement.

In some embodiments, one or more of the compensation regions (or sites) are a region or site of bending or hinging region though or about at least two different (non-parallel) planes passing through the interface.

In some embodiments, the bridge portion comprises a bridge portion element and the bridge portion, the bridge portion element, or both the bridge portion and bridge portion element is/are substantially isolated from forces applied or to, or experienced by, the patient interface.

In accordance with at least one of the aspects disclosed herein there is provided a patient interface comprising:
 a. one side arm or preferably a pair of said side arms extending laterally from a substantially central bridge portion to be located, in-use, in or about a user's septum region, b. wherein the or each said side arm is connected to a substantially resilient, or relatively more rigid, bridge portion element, the bridge portion element defining a substantially predetermined spatial relationship for an outlet or outlets of a gas delivery system with the or each said side arm.

In accordance with at least one of the aspects disclosed herein there is provided a patient interface comprising:
 a. one side arm or preferably a pair of said side arms extending laterally from a substantially central bridge portion to be located, in-use, in or about a user's septum region,
 b. the or each said side arm comprising one or more predefined or predisposed points or localised compensation regions (or sites) positioned along the side arm to accommodate or facilitate a compensation of the patient interface in or at one or more of the compensation regions (or sites), and
 c. wherein the or each said side arm is connected to a substantially resilient, or relatively more rigid, bridge portion element, the bridge portion element defining a substantially predetermined spatial relationship for an outlet or outlets of a gas delivery system with the or each said side arm.

In accordance with at least one of the aspects disclosed herein there is provided a patient interface comprising:
 a. one side arm or preferably a pair of said side arms extending laterally from a substantially central bridge portion to be located, in-use, in or about a user's septum region,
 b. the or each said side arm comprising at least one substantially resilient, or relatively more rigid, side arm element, the side arm element defining at least in part a form or curvature of the or each side arm and having one or more predefined or predisposed points or localised compensation regions (or sites) positioned along the or each side arm and/or the or each side arm element to accommodate a compensation of the patient interface in or at one or more of compensation regions (or sites), and
 c. wherein the or each said side arm element is connected, or is inter-connected via a connecting material, to a substantially resilient, or relatively more rigid, bridge portion element, the bridge portion element defining a substantially predetermined spatial relationship for an outlet or outlets of a gas delivery system with the or each said side arm.

According to one or more of the aspects above, one or more of the following additional embodiments may be provided.

In some embodiments, the bridge portion or bridge portion element (or both) is/are substantially isolated from forces as may be applied or to, or may be experienced by, the patient interface.

In some embodiments, a force applied to the patient interface may be experienced by a side arm or side arms of the interface, the compensation regions (or sites) of the side arm or the side arm element, or both, accommodate the force by way of a flexure or bending or hinging or other displacement of the side arm or the side arm element, or both.

In some embodiments, the side arm or arms are patient interface stabilisers.

In some embodiments, the bridge portion element and the side arm element or elements are separate parts assembled to form a unitary component.

In some embodiments, the bridge portion element and the side arm element or elements is a single component, or at least the bridge portion and at least one side arm element is a single component.

In some embodiments, the bridge portion element and the side arm element or elements are integrally formed as a single component, or at least the bridge portion element and at least one side arm element is integrally formed as a single component.

In some embodiments, the bridge portion element and the side arm element or elements is formed as an integral component.

In some embodiments, the bridge portion element and at least one of the side arm element or elements are separate components, each of which may be substantially interconnected, or provided in an interconnected relationship with each other by a material of the patient interface, such as of a side arm or side arms.

In some embodiments, the bridge portion element is a component discontinuous with one or more side arm elements.

In some embodiments, a side arm comprises one or more separate side arm elements, each of said one or more separate side arm elements being spaced apart through, or along a length of, a said side arm.

In some embodiments, each of the one or more separate side arm elements are spaced apart as an array through or along the length of one or each said side arm.

In some embodiments, the bridge portion element and the side arm element or elements are separate parts provided in connection, or are inter-connected, with each other, via one or a pair of associated side arm(s) and optionally the bridge portion, an associated side arm comprising of one or more associated side arm elements.

In some embodiments, each separate side arm element provides for a relatively resilient portion, a material of the side arm interposed between each, or adjacent to each, separate side arm element, the material of the side arm providing for a compensation region (or site).

In some embodiments, the patient interface comprises a bridge portion element, and at least one separate side arm element located in each one of a pair of side arms.

In some embodiments, the bridge portion is disposed intermediate of a pair of side arms.

In some embodiments, the bridge portion element is disposed intermediate of the side arm elements of a pair of side arms.

In some embodiments, the bridge portion element is of a dimension (sufficient) to span the width of a user's septum region, or is a distance or the width between gas outlets, or is defined by a maximum distance substantially spanning from one nasolabial fold to another nasolabial fold of a user.

In some embodiments, the bridge portion element includes one or a pair of cut-outs or shaped portions to locate, position or house at least one, or a pair of, outlet(s) for a gas delivery system supplying gas to a user's airway.

In some embodiments, the bridge portion element includes one or a pair of cut-outs or shaped portions to locate, position or house one nasal prong or a pair of nasal prongs as the outlet or outlets for a gas delivery system supplying gas to a user's nare or nares.

In some embodiments, one or more of the compensation regions (or sites) facilitates a flexure or bending or hinging or localised displacement and/or elastic deformation.

In some embodiments, one or more of the compensation regions (or sites) is a region or site of bending or hinging region though or about at least one plane passing through the interface.

In some embodiments, one or more of the compensation regions (or sites) is a region or site of bending or hinging region though or about a plurality of parallel planes passing through the interface.

In some embodiments, one or more of the compensation regions (or sites) is a region or site of bending or hinging region though or about at least two different (non-parallel) planes passing through the interface.

In some embodiments, one or more of the compensation regions (or sites) is a region or site of bending or hinging region though or about at least two different (orthogonal) planes passing through the interface.

In some embodiments, the one or more compensation regions (or sites) flex or bend (or are hinged or may locally displace or elastically deform or move) more preferentially in a, or one or more first direction(s), or first set of directions and less preferentially in another direction or another set of directions.

In some embodiments, the one or more compensation regions (or sites) are configured or adapted to substantially resist flexure or bending (or hinging or local displacement or elastic deformation) in a less preferential direction or set of directions.

In some embodiments, the first direction or first set or directions is/are in a substantially transverse plane.

In some embodiments, the first direction or first set of directions is/are in a substantially transverse plane in a ventral direction or a dorsal direction, or may be both in the ventral direction and the dorsal direction.

In some embodiments, the first direction or first set of directions is/are in one or more of: a substantially transverse plane, a substantially sagittal plane and/or in a substantially coronal plane.

In some embodiments, the first direction or the first set of directions is in a direction or directions which substantially facilitate the side arm element moving or bending relative to the bridge portion element.

In some embodiments, the side arm element is formed of a substantially resilient material or is configured or adapted to provide substantial resilience to flexure or bending (or to hinging or local displacement or elastic deformation) in the side arm element regions selected from one or more of the following:
  a. provided between a single compensation region (or site) positioned laterally outward from the bridge portion element and an outer end of the side arm element,
  b. provided between an outer-more compensation region (or site) of the side arm element and an outer end of the side arm element,
  c. provided between each of a series of compensation regions (or sites) of the side arm element,
  d. provided between two compensation regions (or sites) positioned laterally outward from the bridge portion element, and between an outer-more compensation region (or site) of the side arm element and an outer end of the side arm element.

In some embodiments, each side arm element comprises a single compensation region (or site).

In some embodiments, each side arm element comprises two compensation regions (or sites).

In some embodiments, each side arm element comprises three compensation regions (or sites).

In some embodiments, each side arm element comprises a plurality of compensation regions (or sites).

In some embodiments, at least one compensation region (or site) is located at an inner-more end of a side arm element in a connection with the bridge portion element.

In some embodiments, at least one of the compensation regions (or sites) is located at a junction or connection between a side arm element and the bridge portion element.

In some embodiments, at least one of the compensation regions (or sites) is located in or at a zone of the bridge portion element defined substantially by a peripheral, or laterally outer, edge of a user's septum region.

In some embodiments, wherein the or each side arm element is/are configured to flex or bend (or are hinged or locally displaces or may elastically deform or move) relative to the bridge portion element.

In some embodiments, wherein a side arm element further comprises one or more minor projections.

In some embodiments, wherein the one or more minor projections are engageable, or provided to be of a shape or configuration to be associated, with a material of the side arm.

In some embodiments, wherein Interaction or engagement of the minor projection with the material of the side arm provides for a resistance to flexure or bending (or hinging or elastic deformation) of a side arm element.

In some embodiments, wherein the material of the side arm is at least partially compressible (or may be substantially incompressible or partially compressible), such that the minor projection(s) can translate a force or movement experienced by a side arm element as a compression of the material of the side arm (or can translate a force or movement experienced by a side arm element as an extension of the material when the material is placed under tension by the minor projection(s)).

In some embodiments, wherein the material of the side arm encapsulates or envelops the at least one side arm element.

In some embodiments, a side arm partially encapsulates or partially envelops at least one side arm element.

In some embodiments, the side arm wholly encapsulates or envelops at least one side arm element.

In some embodiments, a material of the side arm fills one or more voids between the side arm element and the side arm.

In some embodiments, a material of the side arm surrounds the side arm element, locating a side arm element in, or at, or adjacent to, the one or more predefined or predisposed points or localised compensation regions (or sites).

In some embodiments, when a pair of side arms is provided, each of the side arms extend laterally from the bridge portion, one side arm of the pair of side arms provided to extend substantially about a left side of a user's face and the other side arm of the pair of side arms provided to extend substantially about a right side of a user's face.

In some embodiments, the or each side arm extends substantially about a user's face, optionally along at least a part of a user's cheek.

In some embodiments, the or each side arm extends substantially laterally away from or outwardly from a user's sagittal plane.

In some embodiments, the or each side arm element extends at least a portion of a length or a substantial length of or along or through each such side arm comprising said side arm element.

In some embodiments, the or each side arm element comprises of a plurality of side arm element limbs.

In some embodiments, a side arm element limb comprises or includes one or more minor projections.

In some embodiments, the or each side arm or side arm element, or both, forms or is formed to provide at least a part of a passageway for receiving of a gas supply to be delivered to a user via the outlet or outlets or for receiving of a conduit for delivering a gas to a user via the outlet or outlets.

In some embodiments, the side arm forms the passageway.

In some embodiments, the side arm element(s) form the passageway.

In some embodiments, the portion of the passageway formed at least in part by the side arm element(s) is at least 50% of a wall circumference or wall perimeter (for example of a unit length section) of the passageway so formed.

In some embodiments, the portion of the passageway formed at least in part by the side arm is a remainder of the wall circumference or wall perimeter (for example of a unit length section) that is otherwise formed by the side arm element(s).

In some embodiments, the passageway is a void space or cavity or recess in or through the side arm(s) or side arm element(s), or both, through which gas may be directed or supplied for delivery to the outlet or outlets.

In some embodiments, the passageway, is defined at least in part by the side arm and at least in part the side arm element.

In some embodiments, a side arm comprises a port for accessing a passageway that extends to the gas outlet(s) for delivery of a gas to the gas outlet(s).

In some embodiments, each side arm of a pair of side arms comprises a port for accessing a passageway that extends through each side arm to an associated gas outlet.

In some embodiments, each side arm provides for a separate passageway for separate delivery of gas to an associated gas outlet.

In some embodiments, the side arm or arms is/are to be positioned, in-use, upon a user's face.

In some embodiments, the side arm or arms is/are to be positioned, in-use, upon a user's facial cheeks.

In some embodiments, the interface is a nasal cannula comprising a pair of nasal prongs as the outlets, and wherein a headgear or retention system is attachable to a pair of side arms for retaining the nasal cannula in position when being worn in-use by a user.

In some embodiments, the retention system comprises a releasable connection system for releasably connecting the patient interface, such as at least a rear of each side arm, to a user's face (for example the releasable connection system may comprises of hook and loop or hook and hook type connectors for such a releasable system)

In some embodiments, the releasable connection system comprises at least one pad attached to a user's face upon which the patient interface may be releasably engageable thereto.

In some embodiments, the bridge portion element is, or comprises, a polymeric material.

In some embodiments, the or each side arm element is, or comprises, a polymeric material.

In some embodiments, the polymeric material is one or a combination of any one or more of: thermoplastic elastomer(s), polypropylene based elastomer(s), liquid silicone rubber(s), or breathable thermoplastic polyurethane(s), or breathable polyamides, more preferably polymers may be those such as, but not limited to, polyolefins, thermoplastic elastomers, or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A hardness of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

Nasal cannula can be used as patient interfaces in high flow therapy systems. When fitted, gases are channeled through nasal delivery elements (for example, tubular prongs) of the nasal cannula, which rest in the nares of a patient. In some patients, and particularly for neonates or infant patients, when the face contorts due to compressive forces exerted by another object (for example, when resting the face against a pillow or bed frame) or due to the expression of emotions (for example, when crying or frowning), forces exerted on the nasal cannula can cause the nasal delivery elements to be urged out of the nares. Although the nasal cannula may be constructed such that many such forces will have a reduced tendency to cause the nasal delivery elements to be dislodged from the nares (see, for example, commonly-owned PCT/NZ2014/000217, commonly-owned U.S. 61/891,697, commonly-owned U.S. 61/919,579, commonly-owned U.S. 62/052,980, or commonly-owned U.S. 62/064,106, the disclosures of each of which are hereby incorporated into this application in their entireties), in some cases the nasal delivery elements may still splay apart from one another when such forces are applied. Solutions to the above difficulties are sought.

In some embodiments, the patient interface comprises: a first side arm adapted to located on or adjacent a first portion of a face of a user; a second side arm adapted to located on or adjacent a second portion of the face of the user; a bridge extending between and linking the first and second side arms; and a supporting structure positioned over at least a part of the bridge.

In some embodiments the supporting structure extends over the entire bridge. In some configurations, the supporting structure is positioned over at least a part of a user facing portion of the bridge. In some configurations, the supporting structure is positioned over a part of a non-user facing portion of the bridge. In some configurations, the supporting structure is positioned over the entirety of the non-user facing portion of the bridge. In some configurations the user facing portion of the bridge is adapted to rest on or adjacent the philtrum of the user. In some configurations the supporting structure is configured to resist tension forces. In some configurations the supporting structure is configured to resist compression forces. In some configurations the supporting structure is configured to resist shear forces. In some configurations the supporting structure, in use, changes the neutral axis of the bridge to reduce or resist bending within the bridge section.

In some embodiments, the supporting structure is at least in part formed from a textile material. In some such configurations, the textile material is a woven, non-woven or knitted textile material.

In some embodiments, the supporting structure is a sheet. In some configurations, the supporting structure comprises a rigid material. In some configurations, the supporting structure comprises a semi-rigid material.

In some embodiments, the supporting structure is formed from a polymer material. In some configurations the supporting structure and the bridge are formed at least in part from the same polymer material. In some configurations the polymer material comprises a malleable and flexible polymer. In some configurations the polymer material comprises a rigid polymer. In some configurations the supporting structure being formed from a material that is more rigid than the material forming the bridge.

In some configurations, the first body is adapted to rest on a cheek of the user.

In some embodiments, the first and second side arms are adapted to rest on opposing cheeks of the user.

In some embodiments, the first and/or second side arms comprise one or more nasal delivery elements or prongs adapted to rest in one or more nares of the user. In some such configurations, the one or more nasal delivery elements are configured to allow for ambient gases outside of the patient interface to pass through the nares. In other words, the nasal delivery elements may be unsealingly positioned in the nares. In some such configurations, the one or more nasal delivery elements are shaped or angled such that they extend inwards towards a septum of the user. In some such configurations, the one or more nasal delivery elements are shaped or angled such that tips of the one or more nasal delivery elements point, in use, towards a back of the user's head. In some such configurations, the first and/or second side arms comprise one or more gas delivery lumen in pneumatic communication with the one or more nasal delivery elements. In some such configurations, one or more gas delivery conduits may be in pneumatic communication with the one or more gas delivery lumen. In other configurations, the one or more nasal delivery elements may be configured to be sealingly positioned in the nares.

In some embodiments, the supporting structure extends along the first and/or second side arms. In some such configurations, the supporting structure extends along user facing portions of the first and/or second side arms. In some such configurations, the supporting structure extends only along user facing portions of the first and/or second side arms. In some such configurations, at least a portion of the supporting structure present on the user facing portions of the first and/or second side arms is adapted to interface with one or more fixation structures secured to the face to fasten the patient interface to the face. In some configurations the supporting structure extends along a non-user facing portion of the first and/or second side arms.

In some embodiments, the patient interface is shaped so as to match contours of the face of the user. In some configurations the first side arm and/or second side arm comprise one or more hinging or pivoting joints, allowing for movement of the first and/or second side arm relative to each other and/or relative to the bridge.

In some embodiments, the first and/or second side arms comprise one or more regions of reduced thickness relative to adjacent regions of the first and/or second side arms. In some such configurations, the one or more regions of reduced thickness are positioned on portions of the first and/or second side arms that rest on one or more cheeks of the user. In some such configurations, the one or more regions of reduced thickness are positioned on outer edges of the first and/or second side arms. In some configurations, the one or more regions of reduced thickness are only positioned on outer edges of the first and/or second side arms.

In some embodiments, the patient interface comprises one or more attachment structures secured to user facing portions of the first and/or second side arms, the one or more attachment structures adapted to interface with one or more fixation structures secured to the face to fasten the patient interface to the face.

In accordance with at least one of the aspects disclosed herein there is provided a nasal cannula comprising: first and second side arms adapted to locate on or adjacent opposing cheeks of a user; at least one nasal delivery element extending from the first and/or second side arms adapted to nonsealingly rest in one or more nares of the user; a bridge linking the first and second side arms; and a stiffening structure positioned over at least a part of the bridge.

In other embodiments, the at least one nasal delivery element may be adapted to sealingly rest in one or more nares of the user.

In some embodiments, the stiffening structure is positioned only over a part of the bridge. In some configurations, the stiffening structure is positioned over at least a part of a user facing portion of the bridge. In some such configurations, the stiffening structure is positioned only on a part of or all of a user facing portion of the bridge. In some configurations the stiffening structure is configured to resist compression forces. In some configurations the stiffening structure is configured to resist tension forces. In some configurations the stiffening structure is configured to resist shear forces. In some configurations the stiffening structure is configured to resist bending, in use, by shifting the neutral axis of the bridge.

In some embodiments, the stiffening structure is at least in part formed from a textile material. In some such configurations, the textile material is a woven, non-woven or knitted textile material.

In some embodiments, the stiffening structure is a sheet. In some configurations, the stiffening structure comprises a rigid material. In some configurations, the stiffening structure comprises a semi-rigid material.

In some embodiments, the stiffening structure and bridge are formed at least in part from the same polymer material. In some configurations the polymer material comprises a malleable and flexible polymer. In some configurations the polymer material comprises a rigid polymer. In some configurations the stiffening structure comprises a material that is more rigid than the material forming the bridge.

In some embodiments, the at least one nasal delivery element is shaped or angled such that it extends inwardly towards a septum of the user.

In some embodiments, the at least one nasal delivery element is shaped or angled such that a tip of the at least one nasal delivery element points, in use, towards a back of the user's head.

In some embodiments, the first and/or second side arms comprise one or more gas delivery lumen in pneumatic communication with the at least one nasal delivery element. In some such configurations, the nasal cannula further comprises one or more gas delivery conduits in pneumatic communication with the one or more gas delivery lumen.

In some embodiments, the stiffening structure extends along the first and/or second side arms. In some such configurations, the stiffening structure extends along user facing portions of the first and/or second side arms. In some such configurations, the stiffening structure extends only along user facing portions of the first and/or second side arms. In some such configurations, at least a portion of the stiffening structure present on the user facing portions of the first and/or second side arms is adapted to interface one or more fixation structures secured to the face to fasten the nasal cannula to the face. In some configurations the stiffening structure extends across non-user facing portions of the first and/or second side arms. In some configurations the stiffening structure is positioned on a non-user facing portion of the bridge. In some configurations the user facing portion of the bridge is adapted to rest on or adjacent the philtrum of the user.

In some embodiments, the nasal cannula is shaped so as to match contours of the face of the user.

In some embodiments, the first and/or second side arms comprise one or more regions of reduced thickness relative to adjacent regions of the first and/or second side arms. In some such configurations, the regions of reduced thickness are positioned on outer edges of the first and/or second side arms. In some such configurations, the regions of reduced thickness are positioned only on outer edges of the first and/or second side arms.

In some embodiments, the nasal cannula further comprises one or more attachment structures secured to user facing portions of the first and/or second side arms, the one or more attachment structures adapted to interface with one or more fixation structures secured to the face to fasten the nasal cannula to the face.

In accordance with at least one of the aspects disclosed herein a nasal cannula is disclosed. The nasal cannula comprises: a first side arm adapted to rest on a first portion of a face of a user; a second side arm adapted to rest on a second portion of the face of the user; and at least one nasal delivery element extending from the first and/or second side arms adapted to nonsealingly rest in one or more nares of the user; wherein the first and/or second side arms comprise one or more regions of reduced thickness relative to adjacent regions of the first and/or second side arms.

In some embodiments, the first and second side arms are adapted to rest on opposing cheeks of the user.

In some embodiments, the one or more regions of reduced thickness are positioned on portions of the first and/or second side arms that rest on one or more cheeks of the user.

In some embodiments, the one or more regions of reduced thickness are positioned on outer edges of the first and/or second side arms. In some such configurations, the one or more regions of reduced thickness are positioned only on outer edges of the first and/or second side arms.

In some embodiments, the nasal cannula further comprises a bridge linking the first and second side arms.

In accordance with at least one of the aspects disclosed herein a patient interface, such as a nasal cannula, comprises:
a. a pair of respective left and right side arms, to be located, in-use upon a face of a user,
b. at least one, and preferably a pair of, nasal prong(s) to be inserted into, or to direct a flow of gas into, a nare or the nares of the user's nose, and
c. a bridge attached to and extending from a connection point with the left side arm to a connection point with the right side arm, one or each of the respective connection points comprising a primary moveable joint, such as a hinged or pivoting joint, allowing for a primary movement of the bridge relative to a respective side arm.

In some embodiments, the primary moveable joint enables relative rotation between the end of the bridge and the respective side arm about at least one axis.

In some embodiments, the primary movement joint is one or a combination of: an articulating joint, a pin-and-barrel type joint, a ball and socket type joint.

In some embodiments, each side arm comprises a facial pad contoured to engage a region of the user's face.

In some embodiments, the at least one, and preferably the pair of, nasal prong(s) extend from one, or each, of the inner-more ends of the respective left and/or right side arms, or from a region of one or both of the respective side arms substantially adjacent to the inner-more ends and wherein the bridge is a bar extending over or adjacent said nasal prong(s).

In some embodiments, the interface further comprises a mounting attached to a respective side arm to facilitate the connection point for the bar, the mounting comprising a secondary moveable joint, such as a hinged or pivoting joint, allowing for a secondary movement of the mount relative to the respective side arm to which it is attached, with the bar attached to the mounting via the primary moveable joint.

In some embodiments, the mounting is slidably attached to the respective side arm to enable adjustment of the relative position along the side arm to thereby adjust the distance between the prongs.

In some embodiments, a displacement of the position of one or both of the left and/or right side arms, when the patient interface is in-situ upon a user's face, is transmitted to the bar via the connection point(s) or the mounting(s) and the respective primary and/or secondary moveable joints in a manner so as to minimise movement of the prong or prongs in relation to the user's nare(s).

In some embodiments, the primary and secondary moveable joints are aligned for allowing movement of attached components in substantially the same orientation.

In some embodiments, the primary and secondary moveable joints are non-aligned for allowing movement in dissimilar orientations.

In some embodiments, the bar comprises one or more additional moveable joints.

In some embodiments, the left and right side arms, including the nasal prongs, are relatively flexible or conformable relative to the bar and/or mounting(s).

In some embodiments, the connection point or the mounting(s) Include a finger extending outwardly therefrom upon which the primary moveable joint is located for connection to the bar.

In some embodiments, the bar is an over-centre component of the patient interface, with the connection points or mounting(s) positioned symmetrically upon each of the respective side arm(s).

In some embodiments, the secondary moveable joint is one or a combination of: an articulating joint, a pin-and-barrel type joint, and a ball and socket type joint.

In some embodiments, the bridge includes the at least one, and preferably the pair, of nasal prong(s).

In some embodiments, each primary moveable joint is provided between an end of the bridge and an inner end of the respective side arm.

In some embodiments, the primary moveable joint enables relative rotation between the end of the bridge and the respective side arm about three substantially orthogonal axes.

In some embodiments, the primary moveable joint comprises a ball and socket type joint.

In some embodiments, a pair of primary moveable joint is provided between each end of the bridge and an inner end of the respective left and right side arms.

In some embodiments, a displacement of the position of one or both of the left and/or right side arms, when the patient interface is in-situ upon a user's face, is transmitted to one or each primary moveable joint in a manner so as to minimise displacement of the bridge and the prong or prongs in relation to the user's nare(s).

In accordance with at least one of the aspects disclosed herein a patient interface, such as a nasal cannula, comprises:

a. a body portion to be located, in-use upon a face of a user, and
b. at least one, and preferably a pair of, nasal prong(s) extending from the body portion to be inserted into, or to direct a flow of gas into, a nare or the nares of the user's nose in an operational position,
c. the body having at least one hollow region having a fluid passage connected to the nasal prong(s)) for supply of a gas to the nare(s) of the user's nose, and
d. wherein, during supply of fluid through the fluid passage, the hollow region substantially resists transmittal of a displacement force from one or more regions of the body portion to the nasal prong(s) and maintains the operational position of the prongs.

In some embodiments, the body portion comprises a substantially rigid frame and at least one relatively soft hollow region extending from the rigid frame.

In some embodiments, the at least one hollow region is inflatable to expand in a direction of extension of the nasal prong or nasal prongs.

In some embodiments, the hollow region is coupled to the nasal prong(s) and inflatable during supply of a gas to the nare(s) of the user's nose, the hollow region locating against a user's philtrum or upper lip region in at least the inflated state to substantially maintain the nasal prong(s) in the operational position.

In some embodiments, in the inflated state, the hollow region is substantially deeper than a depth of a frame of the body portion adjacent the hollow region.

In some embodiments, either end of the body portion comprises a user facial contacting surface contoured to engage the user's facial cheek region in use.

In some embodiments, the body portion or at least either end of the body portion is shaped or curved to substantially complement a user's facial structure in use.

In some embodiments, the body portion comprises a pair of respective left and right body segments or side arms.

In some embodiments, the left and right body segments or side arms are substantially flexible.

In some embodiments, the nasal prong(s) extend from one, or each, of the inner-more ends of the respective left and/or right body segments or side arms, or from a region of one or both of the respective body portions or side arms substantially adjacent to the inner-more ends.

In some embodiments, a bridge portion connects the inner-more ends of the respective left and right side arms.

In some embodiments, the bridge portion is substantially rigid relative to the left and right body segments.

In some embodiments, at least one, and preferably both, left and/or right body segments comprise a hollow region, each having a fluid passage for delivering a supply of a gas to the respective nasal prong.

In some embodiments, the interface further comprises one or more internal support columns extending between opposing internal surfaces of the hollow region to maintain an open fluid passage.

In some embodiments, the one or more internal support columns comprise a plurality of support columns spatially distributed within the hollow region.

In accordance with at least one of the aspects disclosed herein a patient interface, such as a nasal cannula, comprises:

a. a body portion, to be located, in-use, upon a face of a user,
b. a bridge portion extending away from the body portion, and c. at least one, and preferably a pair of, nasal prong(s) extending from the bridge portion to be inserted into, or to direct a flow of gas into, a nare or the nares of the user's nose in an operational position, d. wherein the body portion actively adjusts using potential from the system or stored in the cannula.

In some embodiments, the body portion is located, in-use, upon one facial cheek of a user and the other facial cheek of the user is free from the interface.

In accordance with at least one of the aspects disclosed herein, a patient interface, such as a nasal cannula, comprises:

a. a body portion to be located, in-use upon a face of a user, and b. at least one, and preferably a pair of, nasal prong(s) extending from the body portion to be inserted into, or to direct a flow of gas into, a nare or the nares of the user's nose in an operational position, c. the patient interface having a non-use configuration in which the body portion is substantially planar or at least either end of the body portion is substantially planar and co-planar with the other end of the body portion and the at least one, and preferably a pair of, nasal prong(s) extend(s) in a direction outwardly away from a central plane of the body portion, d. and an in-use configuration in which the body portion, or at least either end of the body portion, is/are shaped or curved to substantially complement a user's facial structure in use and the nasal prong(s) extend(s) in a direction substantially parallel to a central plane of the body portion.

In some embodiments, the body portion is a single, integrally formed component.

In some embodiments, the body portion and the at least one, and preferably a pair of, nasal prong(s) are a single, integrally formed component.

In some embodiments, the ends of the body portion are to be positioned, in-use, upon a user's face.

In some embodiments, the ends of the body portion are to be positioned, in-use, upon a user's facial cheeks.

In some embodiments, the interface further comprises a bridge portion with a cavity that is concave when viewed in a direction opposite to that of a user.

In some embodiments, the or each cavity is filled or at least partially filled with a relatively soft and/or flexible material, or filled with a relatively more stiff material or a stiffening material.

In some embodiments, the interface further comprises arcuate transitions between the bridge and adjacent portions of the body.

In some embodiments, the arcuate transitions are spaced outwardly from the prongs.

In some embodiments, the centre of each of the arcuate transitions is positioned outwardly relatively to a midline or longitudinal axis of the adjacent prong to reduce movement of the prongs in use.

In some embodiments, the thickness of the body portion is relatively thin to reduce the elastic/spring force experienced by the user on their philtrum.

In some embodiments, the portions of the patient interface that flex may have ridges, corrugations, or cut outs to minimise or eliminate kinking of the patient interface.

In some embodiments, the prongs in the non-use configuration may be angled outwards from each other at an angle of about 32°.

In some embodiments, the area of patient interface intended to be in contact with a user's philtrum has a comfort enhancing surface finish.

In some embodiments, the interface further comprises loop material for releasably connecting the patient interface to a user's face.

In some embodiments, the interface is a nasal cannula comprising a pair of nasal prongs as the outlets, and wherein a headgear or retention system is attachable to the cannula for retaining the nasal cannula in position when being worn in-use by a user.

In some embodiments, the retention system comprises a releasable connection system for releasably connecting the patient to a user's face (for example the releasable connection system may comprises of hook and loop or hook and hook type connectors for such a releasable system)

In some embodiments, one part of the releasable connection system is provided on the patient interface.

In some embodiments, the part of the releasable connection system provided on the patient interface is provided in connection with the interface by an overmoulding or an overmoulding connection of the interface to or about the part. By overmoulding of a portion of the interface to the part of the releasable connection system, a more durable or robust attachment or engagement of the part to the interface may be achieved. The material used to form or be moulded into the interface can be simultaneously allowed to flow about or onto a part of the releasable connection system, such as a pad or patch comprising loops (or alternatively hooks). This can allow for a more integrated part comprising such loops or hooks into the patient interface.

In some embodiments, the overmoulding or overmoulding connection of the interface to or about the part extends at least about a perimeter of the part, and may optionally extend partially or wholly across a face of the part from which a component of the releasable connection system may extend.

For example, in some embodiments, where the part provides for a hook or a loop, or another type of a two-part releasable connection system, the overmoulding may extend about the perimeter of such a part or may extend across partially or wholly the face from which the hook or the loop, or the another type of a two-part releasable connection system may extend therefrom.

Alternative embodiments are also provided in which the part to be attached to the patient interface may be done so in a manner once the interface has been first moulded or formed (or manufactured). For example, using a moulded or formed (or manufactured) Interface, a subsequent or additional over-moulding step or stage may be conducted to provided for an over-moulding which connected or attaches each of the part and the interface together through an overmoulding connection. As discussed above, the moulding material may be allowed to flow to extend about the perimeter of such a part or may extend across partially or wholly the face of the part.

In some embodiments, the releasable connection system comprises at least one pad attached to a user's face upon which the patient interface may be releasably engageable thereto.

In some embodiments, the body portion, or at least either end of the body portion, comprise(s) a resilient material.

In some embodiments, the body portion, or at least either end of the body portion, comprise(s) a flexible material.

In some embodiments, the interface is, or comprises, a polymeric material.

In some embodiments, the polymeric material is one or a combination of any one or more of: thermoplastic elastomer(s), polypropylene based elastomer(s), liquid silicone rubber(s), or breathable thermoplastic polyurethane(s), or breathable polyamides, more preferably polymers may be those such as, but not limited to, polyolefins, thermoplastic elastomers, or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A hardness of less than about 30, or about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

In accordance with at least one of the aspects disclosed herein a patient interface, such as a nasal cannula, comprises: an elongate body to be to be located, in-use, upon a face of a user, the body comprising at least one, and preferably a pair of, nasal prong(s) to be inserted into, or to direct a flow of gas into, a nare or the nares of the user's nose, and at least one, and preferably a pair of, facial contacting surface(s) movably coupled to the body to respond to force(s) or movement(s), or both, experienced by facial contacting surface(s) and at least partially alleviate the transfer of such force(s) and/or movement(s) to the body and to the nasal prong(s).

In some embodiments, each facial contacting surface is movably coupled to an end portion of the body.

In some embodiments, each facial contacting surface is slidably coupled to the body.

In some embodiments, each facial contacting surface has a hollow guide associated therewith for slidably receiving a portion of the body there through.

In some embodiments, the patient interface further comprises a resilient member associated with each facial contacting surface.

In some embodiments, the resilient member is coupled between the facial contacting portion and the body.

In some embodiments, the resilient member biases the facial contacting surface towards a centre of the body.

In some embodiments, the resilient member comprises a compression spring.

In some embodiments, the body comprises a bridge portion from which the nasal prong(s) extend(s). In some embodiments, the bridge portion is inwardly curved to extend towards the user's septum in situ.

In some embodiments, the body is substantially rigid.

In some embodiments, the body is substantially hollow and fluidly coupled to the nasal prong(s) to enable the flow of gases there through.

In some embodiments, at least one end, and preferably both ends, of the body are configured to fluidly couple a gases flow path of a breathing circuit.

In some embodiments, each facial contacting surface is contoured to engage a facial cheek of the user.

In accordance with at least one of the aspects disclosed herein, a patient interface, such as a nasal cannula, comprises: a body to be located, in-use upon a face of a user, the body including at least one, and preferably a pair of, nasal prong(s) to be inserted into, or to direct a flow of gas into, a nare or the nares of the user's nose in an operational position, and at least one, and preferably a pair of, active element(s) each configured to activate in response to input energy to move at least one other region of the body to retain the nasal prong(s) in the operational position.

In some embodiments, the input energy is non-mechanical energy.

In some embodiments, at least one active element is configured to convert the input energy into mechanical energy to move the at least one other region of the body.

In some embodiments, each active element comprises at least one, and preferably a pair of, expansion element(s) configured to expand in response to the input energy to move at least one other region adjacent the nasal prong(s) to retain the nasal prong or prongs in the operational position.

In some embodiments, the expansion element(s) is/are located on a user engaging side of the body.

In some embodiments, the expansion element(s) is/are configured to locate adjacent a facial cheek of the user in situ.

In some embodiments, the patient interface further comprises one or more hinges, pivots or articulated joints, or any combination thereof operable in response to activation of one or more of the active element(s).

In some embodiments, there are one or more hinges at a bridge portion of the body from which the nasal prong(s) extend.

In some embodiments, wherein the expansion element(s) is/are configured to expand in response to the input energy to move a bridge portion of the body from which the nasal prong(s) extend towards and/or against the philtrum of the user in situ.

In some embodiments, the body is flexible in at least one or more regions to deform in response to expansion of the expansion element(s) and cause the bridge portion to move towards the philtrum in situ.

In some embodiments, the bridge portion comprises the one or more hinges.

In some embodiments, the at least one active element is an electromechanical element configured to receive electrical activation energy to move at least one other region of the body.

In some embodiments, the electromechanical element is coupled to an electrical circuit and is activated in response to an electrical activation signal generated by a change in voltage, resistance or current or any combination in the electrical circuit.

In some embodiments, a movement, or force, or both, experienced by one or more regions of the body generates the electrical activation signal.

In some embodiments, movement of the one or more regions of the body causes electrical contacts of the circuit to engage and generate the electrical activation signal.

In some embodiments, movement of the one or more regions of the body causes a change in electrical resistance in the circuit to generate the electrical activation signal.

In some embodiments, the electromechanical element comprises a conductive polymer, or bimetallic strips, or any combination thereof.

In some embodiments, the electromechanical element comprises a pair of electromagnets.

In some embodiments, the input energy is exhibited through a change in humidity at one or more regions of the body and at least one active element is configured to activate in response to a threshold humidity, or a change in humidity, or both, to move the at least one other region of the body to retain the nasal prong(s) in the operational position.

In some embodiments, the active element is configured to absorb water and expand in response to a threshold humidity, or a change in humidity, or both, to thereby move the at least one other region of the body.

In some embodiments, the active element, or at least part of the active element, is located adjacent a base of an associated nasal prong and is configured to engage the philtrum in situ, and wherein expansion of the active element or the part of the active element causes the nasal prong to pivot towards the back of the user's respective nare to retain the nasal prong in the operational position.

In some embodiments, the at least one active element comprises a polymeric material configured to expand with increasing humidity.

In some embodiments, the at least one active element forms at least a portion of the body.

In some embodiments, the body comprises a left body portion or side arm and a separate right body portion or side arm, each of left and right body portions or side arms having an active element and a nasal prong associated therewith.

In some embodiments, the patient interface further comprises a bridge portion bridging over the active elements of the left and right side arms respectively to retain the elements against the user's philtrum in situ.

In some embodiments, the patient interface further comprises at least one, and preferably a pair of facial contacting pads configured to engage a user's face in use, wherein an end or either end of the bridge portion is coupled to the facial contacting pad or the facial contacting pads respectively.

In accordance with at least one of the embodiments disclosed herein a patient interface, such as a nasal cannula, comprises:
  a. a body portion to be located, in-use upon a face of a user, the body portion having left and right side arms and a bridge portion in between the left and right side arms,
  b. at least one, and preferably a pair of, nasal prong(s) extending from the bridge portion to be inserted into, or to direct a flow of gas into, a nare or the nares of the user's nose in an operational position,
  c. the body portion having at least one fluid passageway connected to the nasal prong(s) for supply of a gas to the nare(s) of the user's nose,
  d. wherein, a cross section of the passageway varies along the length of the body portion to provide regions of varying flexibility along the body portion.

In some embodiments, the cross section of the passageway varies in shape along at least a portion of the length of the body portion.

In some embodiments, the cross section varies from a substantially circular cross section at or near an outer end for connection with (either releasably or permanently) a breathing tube or conduit, to an elongated cross section, the elongated cross section having a longer axis arranged substantially vertically (parallel to a user's face).

In some embodiments, the elongated cross section is provided in or forms a bending region or hinging portion of the body portion, the elongated cross section providing greater flexibility for bending of the body portion towards or away from the user's face in a direction of a shorter axis of the elongated cross section.

In some embodiments, the elongated cross section is adjacent to the bridge portion of the body portion between a said prong and an inlet to the passageway at which a breathing tube or conduit is attached.

In some embodiments, the body portion preferentially bends towards and away from the user's face in the bending regions of the body portion.

In some embodiments, a cross sectional area of the passageway is substantially constant along the portion of the length of the body portion.

In some embodiments, the bridge portion is relatively stiff compared to other portions of the patient interface.

In some embodiments, the bridge portion transitions into the left and right side arms by extending outwardly in a flared or curved manner away from a user's face side of the bridge portion, the left and right side arms curving away from the bridge portion rearwardly from a front extent of the body portion.

In some embodiments, curvature(s) of the user's face side of the bridge portion and/or transition regions between the bridge portion and the left and right side arms has a relatively large radius (or radiuses) so that pressure from the bridge and/or the transition regions on the user's face is spread over the user's philtrum or upper lip region.

In some embodiments, the body portion extends forwardly from each side of the bridge portion to a position forward of the bridge portion, and then extends rearwardly so that distal ends of the left and right side arms are positioned rearward of the bridge portion at least in an in-use position.

In some embodiments, the body portion comprises a U-shaped region between each nasal prong and the left and right side arms when the body portion is viewed from above, an inside of the U-shaped region facing the user's face in use.

In some embodiments, each U-shaped region forms or is provided in a bending region where the body portion preferentially bends when the left or right portion of the body portion is flexed towards or away from the user's face.

In some embodiments, the bending region tends to bend in a valley of the U-shaped region.

In some embodiments, an internal angle of the U-shaped region is less than about 130 degrees, or 120 degrees, or 110 degree, or 105 degrees.

In some embodiments, the bending regions are positioned outwardly and forwardly from the nasal prongs relative to a face side of the body portion.

In some embodiments, the patient interface is a single integrally formed component formed from a single material.

In some embodiments, the patient interface is formed from a single moulding operation.

In some embodiments, the patient interface is formed from a thermoplastic or silicone material with a Shore A hardness of approximately 5 to 60.

In some embodiments, the patient interface comprises at least one pad of a retention system for retaining the interface in position when being worn in-use by a user, the pads attached to at least one of the left and right side arms of the body portion, the pad being substantially symmetrical about a central approximately vertical axis that divides the pad into left and right sides so that the same shaped pad may be applied to both the left and right side arms of the body portion.

In some embodiments, the pad or pads comprise hook portions to connect to complementary hook or loop portions of a corresponding pad located on a user's face.

In some embodiments, a cross section of the passageway at a base of the prongs is an asymmetric cross section, one side of the cross section being flatter than an opposite side of the cross section.

In some embodiments, a passageway extending along the prong changes in shape from the asymmetric cross section at the base of the prong to a circular cross section at a tip of the prong.

In some embodiments, the cross sectional area of the prong reduces from the base to the tip of the prong.

In some embodiments, the flatter side of the prong is positioned towards a forward side of the patient interface (facing away from the user's face).

In some embodiments, the body portion comprises more material per length (greater cross sectional area) in the bridge portion than in other portions of the body portion.

In some embodiments, the bridge region comprises a solid section between the prongs so that the bridge region is more rigid than the bending regions.

In some embodiments, the bridge portion comprises wall sections that are thicker than wall sections of the bending regions so that the bridge portion is more rigid than the bending regions.

In some embodiments, the bridge portion comprises a further more rigid material to provide rigidity to the bridge region.

In some embodiments, the bridge region has a height or vertical dimension that is sufficient to provide torsional stability and prevent twisting of the bridge region in use.

In some embodiments, the passageway is positioned approximately centrally on the left and/or right portions of the body portion in a vertical direction.

In some embodiments, the passageway is positioned approximately centrally on a pad of a retention system on each of the left and right side arms for retaining the interface in position when being worn in-use by a user.

In some embodiments, a horizontal neutral bending axis of the body portion is located approximately centrally in a vertical direction on a securement system for securing the interface to the user's face.

In some embodiments, the body portion comprising varying geometries to achieve regions having more flexibility and regions having less flexibility.

In some embodiments, the thickness of the body portion is varied to provide regions having different flexibilities.

In some embodiments, the body portion has thinner thickness walls or sections surrounding the passageway in bending regions of the body portion than in other regions of the body portion.

In some embodiments, the cross sectional area of the body portion at a valley of a U shaped region of the body portion is smaller than in adjacent regions of the body portion.

In some embodiments, the body portion has a left passageway and a right passageway, and the left and right passageways are separated by a dividing section in the bridge region.

In some embodiments, the dividing section is a central region of the bridge between the two nasal prongs.

In some embodiments, the central region of the bridge region is solid.

In some embodiments, each prong has a base that is integrally formed with the bridge portion of the body portion of the patient interface, and wherein the base of each prong comprises a fillet between a wall of the prong and the bridge portion, the fillet extending around the perimeter of the prong, and wherein a radius of the fillet varies around the perimeter of the prong.

In some embodiments, the radius of the fillet is varied around the perimeter of the prong to vary the wall thickness of the prong at the base of the prong.

In some embodiments, a thickness of the prong base is varied around the perimeter of the prong.

In some embodiments, the radius of the fillet on a non-face side of the body portion is smaller than the radius of the fillet on an inner side (between the two prongs) of the prong and the radius of the fillet on an outer side of the prong.

In some embodiments, the radius of the fillet on the inner side of the prong is larger than the radius of the fillet on the outer side of the prong.

In some embodiments, the radius of the fillet on the face side of the body portion is between the radius on the inner and outer sides of the prong.

In some embodiments, each prong has a base that is integrally formed with the bridge portion of the body portion of the patient interface, and a thickness of the prong base is varied around the perimeter of the prong.

In accordance with at least one of the embodiments disclosed herein a patient interface, such as a nasal cannula, comprises:

a. a body portion to be located, in-use upon a face of a user, the body portion having left and right side arms and a bridge portion in between the left and right side arms, b. at least one, and preferably a pair of, nasal prong(s) extending from the bridge portion to be inserted into, or to direct a flow of gas into, a nare or the nares of the user's nose in an operational position, c. the body portion having at least one fluid passageway connected to the nasal prong(s) for supply of a gas to the nare(s) of the user's nose, and d. at least one pad of a retention system for retaining the interface in position on the user's face, the pad attached to at least one of the left and right side arms of the body portion, the pad being substantially symmetrical about a central axis that divides the pad into left and right sides so that the same shaped pad may be applied to both the left and right side arms of the body portion.

In accordance with at least one of the embodiments disclosed herein a patient interface, such as a nasal cannula, comprises:

a. a body portion to be located, in-use upon a face of a user, the body portion having left and right side arms and a bridge portion in between the left and right side arms, b. at least one, and preferably a pair of, nasal prong(s) extending from the bridge portion to be inserted into, or to direct a flow of gas into, a nare or the nares of the user's nose in an operational position, c. the body portion having at least one fluid passageway connected to the nasal prong(s) for supply of a gas to the nare(s) of the user's nose, d. the passageway having an asymmetric cross section at a base of the prongs, one side of the asymmetric cross section being flatter than an opposite side of the asymmetric cross section.

In some embodiments, a passageway extending along the prong changes in shape from the asymmetric cross section at the base of the prong to a circular cross section at a tip of the prong.

In some embodiments, the cross sectional area of the prong reduces from the base to the tip of the prong.

In some embodiments, the flatter side of the prong is positioned towards a forward side of the patient interface (facing away from the user's face).

In accordance with at least one of the aspects disclosed herein a patient interface, such as a nasal cannula, comprises:

a. a body portion to be located, in-use upon a face of a user, the body portion having left and right side arms and a bridge portion in between the left and right side arms, b. at least one, and preferably a pair of, nasal prong(s) extending from the bridge portion to be inserted into, or to direct a flow of gas into, a nare or the nares of the user's nose in an operational position,
c. the body portion having at least one fluid passageway connected to the nasal prong(s) for supply of a gas to the nare(s) of the user's nose,
d. wherein the patient interface is a single integrally formed component formed from a single material and the bridge portion is relatively stiff compared to other portions of the patient interface including the left and right side arms.

In some embodiments, the patient interface is formed from a thermoplastic or silicone material with a Shore A hardness of approximately 5 to 60.

In some embodiments, the body portion comprises more material per length (greater cross sectional area) in the bridge portion than in other portions of the body portion.

In some embodiments, the bridge region comprises a solid section between the prongs.

In some embodiments, the bridge region has a height or vertical dimension that is sufficient to provide torsional stability and prevent twisting of the bridge region in use.

In some embodiments, the body portion comprises varying geometries to achieve regions having more flexibility and regions having less flexibility.

In some embodiments, the thickness of the body portion is varied to provide regions having different flexibilities.

In some embodiments, the body portion has thinner thickness walls or sections surrounding the passageway in bending regions of the body portion than in other regions of the body portion.

In some embodiments, the cross sectional area of the body portion at a valley of a U shaped region of the body portion is smaller than in adjacent regions of the body portion.

In some embodiments, the body portion has a left passageway and a right passageway, and the left and right passageways are separated by a dividing section in the bridge region.

In some embodiments, the dividing section is a central region of the bridge between the two nasal prongs.

In some embodiments, the central region of the bridge region is solid.

In accordance with at least one of the aspects disclosed herein a patient interface, such as a nasal cannula, comprises:
a. a body portion to be located, in-use upon a face of a user, the body portion having left and right side arms and a bridge portion in between the left and right side arms,
b. at least one, and preferably a pair of, nasal prong(s) extending from the bridge portion to be inserted into, or to direct a flow of gas into, a nare or the nares of the user's nose in an operational position,
c. the body portion having at least one fluid passageway connected to the nasal prong(s) for supply of a gas to the nare(s) of the user's nose, wherein the passageway is positioned approximately centrally on the left and/or right side arms of the body portion in a vertical direction.

In accordance with at least one of the aspects disclosed herein a patient interface, such as a nasal cannula, comprises:
a. a body portion to be located, in-use upon a face of a user, the body portion having left and right side arms and a bridge portion in between the left and right side arms,
b. at least one, and preferably a pair of, nasal prong(s) extending from the bridge portion to be inserted into, or to direct a flow of gas into, a nare or the nares of the user's nose in an operational position,
c. the body portion having at least one fluid passageway connected to the nasal prong(s) for supply of a gas to the nare(s) of the user's nose, and
d. a pad of a retention system on each of the left and right side arms for retaining the interface in position on the user's face, wherein the passageway is positioned approximately centrally on the pad.

In accordance with at least one of the aspects disclosed herein a patient interface, such as a nasal cannula, comprises:
a. a body portion to be located, in-use upon a face of a user, the body portion having left and right side arms and a bridge portion in between the left and right side arms,
b. at least one, and preferably a pair of, nasal prong(s) extending from the bridge portion to be inserted into, or to direct a flow of gas into, a nare or the nares of the user's nose in an operational position,
c. the body portion having at least one fluid passageway connected to the nasal prong(s) for supply of a gas to the nare(s) of the user's nose, and a pad of a retention system on each of the left and right side arms for retaining the interface in position on the user's face, wherein a horizontal neutral bending axis of the body portion is located approximately centrally in a vertical direction on the pads.

In accordance with at least one of the aspects disclosed herein a patient interface, such as a nasal cannula, comprises:
a. a body portion to be located, in-use upon a face of a user, the body portion having left and right side arms and a bridge portion in between the left and right side arms,
b. at least one, and preferably a pair of, nasal prong(s) extending from the bridge portion to be inserted into, or to direct a flow of gas into, a nare or the nares of the user's nose in an operational position,
c. the body portion having at least one fluid passageway connected to the nasal prong(s) for supply of a gas to the nare(s) of the user's nose, wherein
d. each prong has a base that is integrally formed with the bridge portion of the body portion of the patient interface, and wherein the base of each prong comprises a fillet between a wall of the prong and the bridge portion, the fillet extending around the perimeter of the prong, and wherein a radius of the fillet varies around the perimeter of the prong.

In some embodiments, the radius of the fillet is varied around the perimeter of the prong to vary the wall thickness of the prong at the base of the prong.

In some embodiments, a thickness of the prong base is varied around the perimeter of the prong.

In some embodiments, the radius of the fillet on a non-face side of the body portion is smaller than the radius of the fillet on an inner side (between the two prongs) of the prong and the radius of the fillet on an outer side of the prong.

In some embodiments, the radius of the fillet on the inner side of the prong is larger than the radius of the fillet on the outer side of the prong.

In some embodiments, the radius of the fillet on the face side of the body portion is between the radius on the inner and outer sides of the prong.

In accordance with at least one of the aspects disclosed herein a patient interface, such as a nasal cannula, comprises:

a. a body portion to be located, in-use upon a face of a user, the body portion having left and right side arms and a bridge portion in between the left and right side arms,
b. at least one, and preferably a pair of, nasal prong(s) extending from the bridge portion to be inserted into, or to direct a flow of gas into, a nare or the nares of the user's nose in an operational position,
c. the body portion having at least one fluid passageway connected to the nasal prong(s) for supply of a gas to the nare(s) of the user's nose, wherein
d. each prong has a base that is integrally formed with the bridge portion of the body portion of the patient interface, and a thickness of the prong base is varied around the perimeter of the prong.

In accordance with at least one of the aspects disclosed herein a patent interface comprises a single integrally formed component formed from a single material with one or more bending or hinging regions.

In some embodiments, the patient interface comprises a bridge portion, and nasal prongs extending from the bridge portion, wherein the bridge portion is more rigid than the bending or hinging regions.

In some embodiments, the bending or hinging regions may be formed by or include at least one bending or hinging element, for example a mechanical hinge.

The term "cheek" as used in this specification and claims means any region on the user's face at or adjacent the cheekbone, and may include any region to the side of and/or below the cheekbone and/or may include any other region between by the periphery of the corresponding eye, ear and nose of the user.

The term "compensation" as used in this specification and claims, and in particular in relation to the various region(s) or site(s) Identified as such, means a region or site capable of at least one or more of the following: a changing in shape, or a flexure, or bending, or twisting, torsion, a shearing or a shear type motion, or a local displacement, or at least some other form of dynamic behaviour or response resulting from application of a force or movement applied to or resulting from a force or movement that is experienced by at least a part of the patient interface.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The Invention consists in the foregoing and also envisages constructions of which the following gives examples only.

BRIEF DESCRIPTION OF THE DRAWINGS

These and other features, aspects and advantages of the present disclosure will be described with reference to the following drawings, which are illustrative but should not be limiting of the present disclosure.

FIGS. 2A-2E show a patient interface from various angles, in particular in which a bridge portion element is to be incorporated into the interface; more particularly, FIG. 2A shows a front perspective view of an interface, FIG. 2B shows a rear perspective view of an interface, FIG. 2C illustrates a partial cross-section through a side arm of an interface, FIG. 2D shows a front perspective view of a bridge portion element, FIG. 2E shows a rear perspective view of FIG. 2D, FIG. 2F shows a wire diagram illustrating a shape of the FIG. 2A interface, in plan view, prior one or more compensation regions (or sites) becoming active, and FIG. 2G shows the wire diagram once one or more compensation regions (or sites) are activated in response to an applied force.

FIG. 3A-3C show a patient interface from various angles, in particular in which a bridge portion element is to be incorporated into the interface; more particularly, FIG. 3A shows a front perspective view of an interface, FIG. 3B shows a rear perspective view of FIG. 3B, FIG. 3C illustrates a partial cross-section through a side arm of an interface, FIG. 3D shows a wire diagram illustrating a shape of the FIG. 3A interface, in pan view, prior one or more compensation regions (or sites) becoming active, and FIG. 3E shows the wire diagram once one or more compensation regions (or sites) are activated in response to an applied force.

FIGS. 4A-4C show a patient interface from various angles, in particular in which a bridge portion element is to be incorporated into the interface; more particularly, FIG. 4A shows a front perspective view of an interface, FIG. 4B shows a rear perspective view of FIG. 4A, FIG. 4C illustrates a partial cross-section through a side arm of an interface, FIG. 4D shows a wire diagram illustrating a shape of the FIG. 4A interface, in plan view, prior one or more compensation regions (or sites) becoming active, and FIG. 4E shows the wire diagram once one or more compensation regions (or sites) are activated in response to an applied force.

FIGS. 5A-5E show a patient interface from various angles, in particular in which a bridge portion element and side arm element is to be incorporated into the interface; more particularly, FIG. 5A shows a front perspective view of an interface, FIG. 5B shows a rear perspective view of FIG. 5A, FIG. 5C illustrates a partial cross-section through a side arm and side arm element of an interface, FIG. 5D shows a front perspective view of a bridge portion element with side arm elements, FIG. 5E shows a rear perspective view FIG. 5D, FIG. 5F shows a wire diagram illustrating a shape of the FIG. 5A interface, in plan view, prior one or more compensation regions (or sites) becoming active, and FIG. 5G shows the wire diagram once one or more compensation regions (or sites) are activated in response to an applied force.

FIGS. 6A-6E show a patient interface from various angles, in particular in which a bridge portion element and side arm element is to be incorporated into the interface; more particularly, FIG. 6A shows a front perspective view of an interface, FIG. 6B shows a rear perspective view of FIG. 6A, FIG. 6C illustrates a partial cross-section through a side arm and side arm element of an interface, FIG. 6D shows a rear perspective view of a bridge portion element with side arm elements, FIG. 6E shows a front perspective view FIG. 6D, FIG. 6F shows a wire diagram illustrating a shape of the FIG. 6A interface, in plan view, prior one or more compensation regions (or sites) becoming active, and FIG. 6G shows the wire diagram once one or more compensation regions (or sites) are activated in response to an applied force.

FIGS. 7A-7E show a patient interface from various angles, in particular in which a bridge portion element and side arm element is to be incorporated into the interface; more particularly, FIG. 7A shows a front perspective view of an interface, FIG. 7B shows a rear perspective view of FIG. 7A, FIG. 7C illustrates a partial cross-section through a side arm and side arm element of an interface, FIG. 7D shows a front perspective view of a bridge portion element with side arm elements, FIG. 7E shows a rear perspective view FIG. 7D, FIG. 7F shows a wire diagram illustrating a shape of the FIG. 7A interface, in plan view, prior one or more compensation regions (or sites) becoming active, and FIG. 7G shows the wire diagram once one or more compensation regions (or sites) are activated in response to an applied force.

FIGS. 8A-8E show a patient interface from various angles, in particular in which a bridge portion element and side arm element is to be incorporated into the interface; more particularly, FIG. 8A shows a front perspective view of an interface, FIG. 8B shows a rear perspective view of FIG. 8A, FIG. 8C illustrates a partial cross-section through a side arm and side arm element of an interface, FIG. 8D shows a front perspective view of a bridge portion element with side arm elements, FIG. 8E shows a rear perspective view FIG. 8D, FIG. 8F shows a wire diagram illustrating a shape of the FIG. 8A interface, in plan view, prior one or more compensation regions (or sites) becoming active, and FIG. 8G shows the wire diagram once one or more compensation regions (or sites) are activated in response to an applied force.

FIGS. 9A-9E show a patient interface from various angles, in particular in which a bridge portion element and side arm element is to be incorporated into the interface; more particularly, FIG. 9A shows a front perspective view of an interface, FIG. 9B shows a rear perspective view of FIG. 9A, FIG. 9C illustrates a partial cross-section through a side arm and side arm element of an interface, FIG. 9D shows a front perspective view of a bridge portion element with side arm elements, FIG. 9E shows a rear perspective view FIG. 9D, FIG. 9F shows a wire diagram illustrating a shape of the FIG. 9A interface, in plan view, prior one or more compensation regions (or sites) becoming active, and FIG. 9G shows the wire diagram once one or more compensation regions (or sites) are activated in response to an applied force.

FIG. 10A shows a front perspective view of an interface, FIG. 10B shows a rear perspective view of FIG. 10A, FIG. 10C illustrates a partial cross-section through a side arm and side arm element of an interface, FIG. 10D shows a front perspective view of a bridge portion element with side arm elements, FIG. 10E shows a rear perspective view FIG. 10D.

FIG. 11A shows a front perspective view of an interface, FIG. 11B shows a rear perspective view of FIG. 11A, FIG. 11C illustrates a partial cross-section through a side arm and side arm element of an interface, FIG. 11D shows a front perspective view of a bridge portion element with side arm elements, FIG. 11E shows a rear perspective view FIG. 11D.

FIG. 12A shows a front perspective view of an interface, FIG. 12B shows a rear perspective view of FIG. 12A, FIG. 12C illustrates a partial cross-section through a side arm and side arm element of an interface, FIG. 12D shows a front perspective view of a bridge portion element with side arm elements, FIG. 12E shows a rear perspective view FIG. 12D.

FIG. 13A shows a front perspective view of an interface, FIG. 13B shows a rear perspective view of FIG. 13A, FIG. 13C illustrates a partial cross-section through a side arm and side arm element of an interface, FIG. 13D shows a front perspective view of a bridge portion element with side arm elements, FIG. 13E shows a rear perspective view FIG. 13D.

FIGS. 14A-14E show a patient interface from various angles, in particular in which a bridge portion element and side arm element is to be incorporated into the interface; more particularly, FIG. 14A shows a front perspective view of an interface, FIG. 14B shows a rear perspective view of FIG. 14A, FIG. 14C illustrates a partial cross-section through a side arm and side arm element of an interface, FIG. 14D shows a front perspective view of a bridge portion element with side arm elements, FIG. 14E shows a rear perspective view FIG. 14D, FIG. 14F shows a wire diagram illustrating a shape of the FIG. 14A interface, in plan view, prior one or more compensation regions (or sites) becoming active, and FIG. 14G shows the wire diagram once one or more compensation regions (or sites) are activated in response to an applied force.

FIGS. 15A-15E show a patient interface from various angles, in particular in which a bridge portion element and side arm element is to be incorporated into the interface; more particularly, FIG. 15A shows a front perspective view of an interface, FIG. 15B shows a rear perspective view of FIG. 15A, FIG. 15C Illustrates a partial cross-section through a side arm and side arm element of an interface, FIG. 15D shows a front perspective view of a bridge portion element with side arm elements, FIG. 15E shows a rear perspective view FIG. 15D, FIG. 15F shows a wire diagram illustrating a shape of the FIG. 15A Interface, in plan view, prior one or more compensation regions (or sites) becoming active, and FIG. 15G shows the wire diagram once one or more compensation regions (or sites) are activated in response to an applied force.

FIGS. 16A-16E show a patient interface from various angles, in particular in which a bridge portion element and side arm element is to be incorporated into the interface; more particularly, FIG. 16A shows a front perspective view of an interface, FIG. 16B shows a rear perspective view of FIG. 16A, FIG. 16C Illustrates a partial cross-section through a side arm and side arm element of an interface, FIG. 16D shows a front perspective view of a bridge portion element with side arm elements, FIG. 16E shows a rear perspective view FIG. 16D, FIG. 16F shows a wire diagram illustrating a shape of the FIG. 16A Interface, in plan view, prior one or more compensation regions (or sites) becoming active, and FIG. 16G shows the wire diagram once one or more compensation regions (or sites) are activated in response to an applied force.

FIGS. 17A-17E show a patient interface from various angles, in particular in which a bridge portion element and separate side arm elements are to be incorporated into the side arms of the interface; more particularly, FIG. 17A shows a front view of an interface, FIG. 16B shows a rear view of FIG. 17A, FIG. 17C Illustrates a front perspective view of the bridge portion element and separate side arm elements in their relative spatial arrangement when embedded in an interface, FIG. 17D is a rear perspective view of FIG. 17C, FIG. 17E is a front perspective view of the interface of FIG. 17A, FIG. 17F shows a wire diagram illustrating a shape of the FIG. 17E Interface, in plan view, prior one or more compensation regions (or sites) becoming active, and FIG. 17G shows the wire diagram once one or more compensation regions (or sites) are activated in response to an applied force.

FIG. 22A shows a close-up of a portion of a patient interface.

FIG. 22B shows a schematic Illustrating forces exerted on the patient interface shown in FIG. 22A.

FIGS. 30A to 30F show the sixth embodiment of a patient interface from various angles in an in-use configuration.

FIG. 42A Illustrates a portion of the interface of FIG. 36 and FIG. 42B Illustrates a section on line DD in FIG. 43A.

FIG. 43A Illustrates a portion of the interface of FIG. 36 and FIG. 44B Illustrates a section on line EE in FIG. 20A.

DETAILED DESCRIPTION OF PREFERRED EMBODIMENTS

Figure 1:
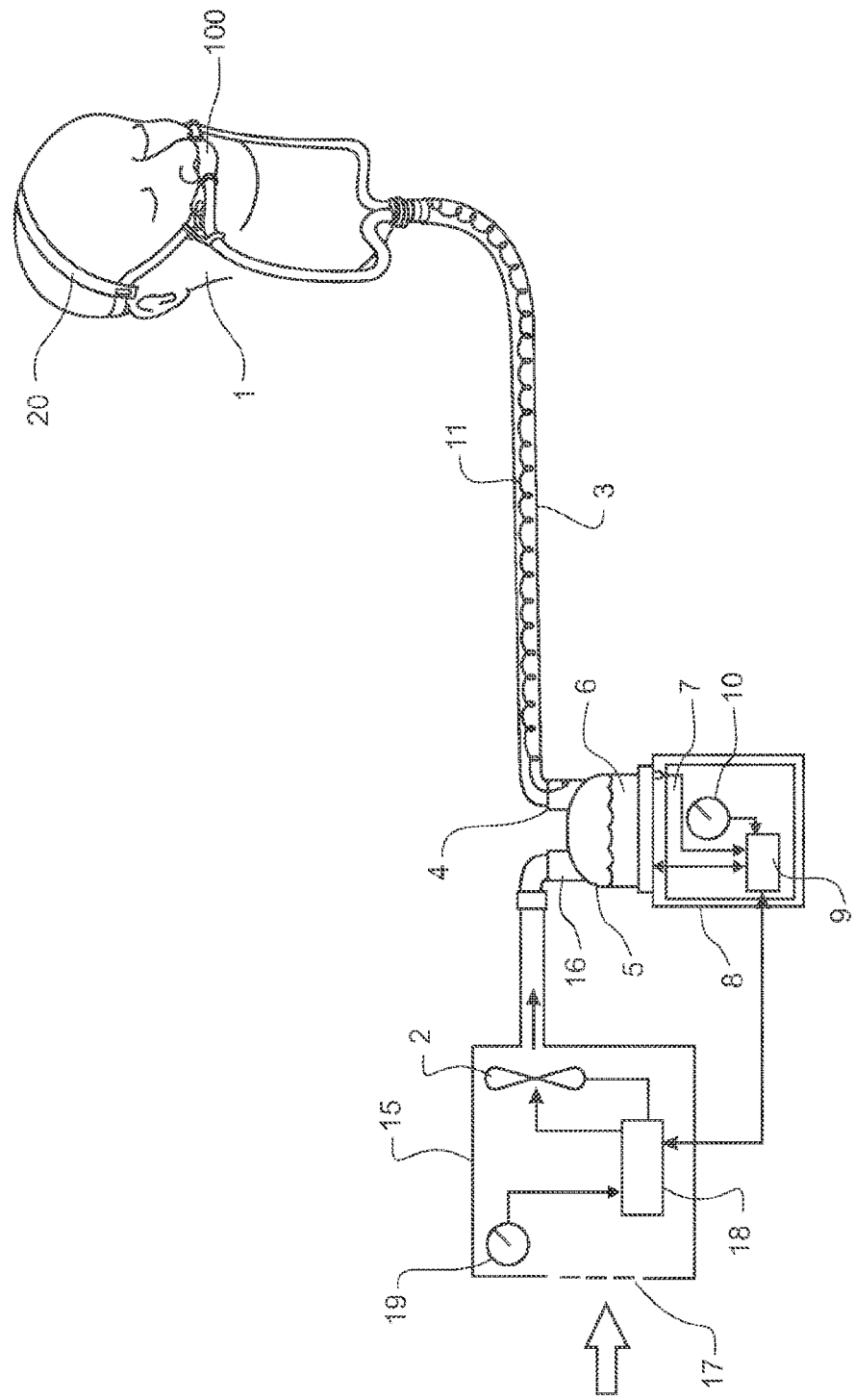
FIG. 1 illustrates a generalised setup of a humidification system for delivering a flow of humidified gas to a patient interface being worn by a user.

The present disclosure relates to a patient interface which is located, in-use, upon a user's face, and which compensates movement.

By compensating movement, a patient interface may be provided with Improved or greater stability upon a user.

Improvements in stability may result in greater comfort of wear by a user and/or Improved or more consistent delivery of therapy for the user when the interface is being worn and is in-use. For example, minimising or at least going some way to ameliorating the transfer or translation of forces or movements to the gas outlet of a patient interface (i.e. the part of the interface most closely associated with delivery of gases to a user), may provide particular benefits in that delivery of therapy is not Interrupted, or is at least minimised, and comfort of the user is maintained.

As such, a patient interface which is operational to be an effective self-compensating device in response to forces or movements applied to it would be desirable.

In those patient interfaces such as nasal cannula, nasal prongs are typically associated with the gas outlets of the interface. Prong flicking is a problem associated with movement of the patient interface, the nasal prongs move from their Intended position and may Irritate the nares of the user or may even be disturbed sufficiently so as to no longer be positioned appropriately within the nares. Such disturbance to the gas outlets or nasal prongs is to be avoided where possible.

The patient interface of the present Invention advantageously provides Improvements in the delivery of respiratory care with a ventilator or a gases supply, or in combination with a gas humidification system or other gases supply systems for supplying gases to a patient, or for delivery of any other gases to a patient.

Various preferred forms of patient interface will be described with reference to an in-hospital respiratory care system as may be used by adults and/or in paediatrics and/or neonates. It will be appreciated that the described patient interface embodiments be used in delivering various respiratory therapies such as high flow therapy, PAP therapies (e.g. CPAP or BIPAP), and ventilation therapies, but not exclusively; and such patient interfaces may be of the sealing or non-sealing types depending on the desired therapy.

As relatively high gas delivery flow rates may be used with the embodiments or configurations described herein, the gases being supplied or delivered to the user or patient can may be delivered to different parts of the user's or a patient's airway. It will be appreciated that the relatively high gas delivery flow rates may be used for either adults, children, or Infants (eg: neonates or paediatric patients) and the flow rate will be chosen or adjusted accordingly. The embodiments of the patient interface described herein Include flow ranges that are suitable for use with an adult and flow ranges that are suitable for neonates or paediatric patients.

For example, according to those various embodiments and configurations described herein, a flow rate of gases supplied or provided to an interface or via a system, such as through a flowpath, may comprise, but is not limited to, flows of at least about 2, 3, 4, 5, 10, 20, 30, 40, 50, 60, 70, 80, 90, or 100 L/min, or more, and useful ranges may be selected between any of these values (for example, about 40 to about 80, about 50 to about 80, about 60 to about 80, about 70 to about 100 L/min, about 70 to 80 L/min).

Such relatively high flow rates of gases may assist in providing the supplied gases into a user's airway, or to different parts of a user's airway, for example such flow rates may allow for a delivery of such gases to the upper or lower airway regions. Upper airway region typically Includes the nasal cavity, pharynx and larynx, while the lower airway region typically Includes the trachea, primary bronchi and lungs.

'High flow therapy' as used in this disclosure may refer to delivery of gases to a patient at a flow rate of greater than or equal to about 5 or 10 litres per minute (5 or 10 LPM) for adults. In some configurations, 'high flow therapy' may refer to the delivery of gases to an adult patient at a flow rate of between about 5 or 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. For example, according to those various embodiments and configurations described herein, a flow rate of gases supplied or provided to an interface or via a system, such as through a flowpath, may comprise, but is not limited to, flows of at least about 5, 10, 20, 30, 40, 50, 60, 70, 80, 90, or 100 L/min, or more, and useful ranges may be selected between any of these values (for example, about 40 to about 80, about 50 to about 80, about 60 to about 80, about 70 to about 1000 L/min, about 70 to 80 L/min).

For neonates and premature babies 'high flow therapy' may refer to the delivery of gases at a flow rate between 0 LPM to 40 LPM, i.e. 0.1 LPM upwards, or between about 5 LPM to 35 LPM, or about 10 LPM to about 30 LPM, or about 15 LPM to about 25 LPM. For example, according to those various embodiments and configurations described herein, a flow rate of gases supplied or provided to an interface or via a system, such as through a flowpath, may comprise, but is not limited to, flows of at least about 0.1, 5, 10, 15, 20, 25, 30, 35, or 40 LPM, or more, and useful ranges may be selected between any of these values (for example, about 5 to about 15, about 20 to about 40, about 30 to about 40). Typically, a delivery of gases at a flow rate between 8 LPM and 10 LPM is suitable for neonates.

For pediatric patients, 'high flow therapy' may refer to the delivery of gases to at a flow rate of between about 2 or 5 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. For example, according to those various embodiments and configurations described herein, a flow rate of gases supplied or provided to an interface or via a system, such as through a flowpath, may comprise, but is not limited to, flows of at least about 2, 3, 4, 5, 10, 20, 30, 40, 50, 60, 70, 80, 90, or 100 L/min, or more, and useful ranges may be selected between any of these values (for example, about 40 to about 80, about 50 to about 80, about 60 to about 80, about 70 to about 1000 L/min, about 70 to 80 L/min). Generally, the flow rate is supplied at 2L/kg of body weight for pediatric patients.

Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

High flow therapy has been found effective in meeting or exceeding the patient's normal peak inspiratory demand, to Increase oxygenation of the patient and/or reduce the work of breathing. Additionally, high flow therapy may generate a flushing effect in the nasopharynx such that the anatomical dead space of the upper airways is flushed by the high Incoming gas flows. This creates a reservoir of fresh gas available of each and every breath, while minimising re-breathing of carbon dioxide, nitrogen, etc. It will also be appreciated that various aspects of the present invention may be applied to any form of patient interface including, but not limited Indirect nasal masks (which covers the nose), direct nasal masks Including nozzles or pillows that enter or engage the nares of the wearer, oral masks (which cover the mouth), or full face masks (which cover the nose and mouth), and mouthpieces but will be described with reference to a nasal cannula.

Similarly, it will also be appreciated that various aspects of the present invention may be applied using any form of a patient interface in conjunction with any suitable form of headgear or retention system or securement system for securing a patient interface upon a user, suitable for the retention of the patient interface to be retained upon a user for delivery of the desired therapy, for example such as that securement system as described in PCT/NZ2011/000218 (published as WO 2012/053910, the contents of which are herein Incorporated by reference).

In one particularly preferred embodiment, the interface is a nasal cannula of the non-sealing nasal prong type of delivery system. Such a nasal cannula may be utilised for delivery of high flow, low pressure therapy to a user.

Therapy delivery at high flow, low pressure, may for example, but not exclusively, be provided at the following: from just over 9 L/min to 120 L/min, of about 20 L/min to about 50 L/min (e.g. for adult users), of about 5 L/min to about 30 L/min (e.g. for paediatric users), of about just over 0 L/min to about 8 L/min (e.g. for neonatal users).

A patient interface according to the present Invention may be used in respiratory care systems, for example humidified CPAP or in-hospital respiratory care systems.

FIG. 1 illustrates a typical humidifying respiratory system. A patient 1 is receiving humidified and pressurised gases through a patient interface 100, shown in this example as a nasal cannula assembly, connected to a humidified gases transportation pathway or inspiratory conduit 3 that in turn is connected to a humidifier 8 (including humidification chamber 5) that is supplied with gases from a blower 15 or other appropriate gases supply means. Headgear 20 is provided to support and retain the patient interface against the patient's face. The inspiratory conduit 3 is connected to the outlet 4 of a humidification chamber 5 which contains a volume of water 6. Humidification chamber 5 is preferably formed from a plastics material and may have a highly heat conductive base (for example an aluminium base) which is in direct contact with a heater plate 7 of humidifier 8. The humidifier 8 is provided with control means or electronic controller 9 which may comprise a microprocessor based controller executing computer software commands stored in associated memory. Gases flowing through the inspiratory conduit 3 are passed to the patient by way of the patient interface 100.

Controller 9 receives input from sources such as user input means or dial 10 through which a user of the device may, for example, set a predetermined required value (preset value) of humidity or temperature of the gases supplied to patient 1. In response to the user set humidity or temperature value input via dial 10 and other possible inputs such as Internal sensors that sense gases flow or temperature, or by parameters calculated in the controller, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. It should be noted that it is possible to obtain the relationship between the humidity of the gases in humidification chamber 5 and the temperature of the heater plate 7. Accordingly, it is possible to utilise the heater plate temperature in an algorithm or a look-up table to determine the humidity of the gases.

The blower 15 may be provided with a variable speed pump or fan 2 which draws air or other gases through the blower inlet 17. The speed of variable speed pump or fan 2 may be controlled by a further control means or electronic controller 18 (or alternatively the function of this controller 18 could be carried out by the other controller 9) in response to inputs from controller 9 and a user set predetermined required value (preset value) of pressure or fan speed via dial 19.

A heating element 11 may be provided within the conduit or tubing 3 to help prevent condensation of the humidified gases within the conduit. Such condensation is due to the temperature of the walls of the conduit being close to the ambient temperature, (being the temperature of the surrounding atmosphere) which is usually lower than the temperature of the humidified gases within the conduit. The heater element effectively replaces the energy lost from the gases through conduction and convection during transit through the conduit. Thus the conduit heater element ensures the gases delivered are at an optimal temperature and humidity.

FIG. 1 illustrates the use of the patient interface 200 in a respiratory therapy system 100. The respiratory therapy system 100 comprises a flow generator 104. The flow generator 104 receives gases from a gases inlet 102 and propels them to a humidifier 106. The humidifier 106 heats and humidifies the gases. Heated and humidified gases are passed through a gases outlet 108. Gases move from the gas outlet 108 to a gas conduit 110. The gas conduit 110 comprises a heater 112 that reduces or prevents the condensation of moisture along the walls of the gas conduit 110. The heater 112 can comprise a resistive heating wire. The respiratory therapy system 100 comprises a controller 114 that controls the operation of the flow generator 104. The controller 114 also controls the operation of the humidifier 106. The respiratory therapy system 100 comprises an input/output module 116. The Input/output module (I/O) 116 comprises means for a user to Interact with and set parameters for the flow generator 104 and/or humidifier 106, as well as receive Information regarding the operation of respiratory therapy system 100 and its components. The I/O module 116 may comprise, for example, buttons, knobs, dials, switches, levers, touch screens, speakers, displays and/or other input or output elements. In some configurations, the humidifier 106 may not be present. In some configurations, the gas conduit 110 may not have a heater 112.

Preferred embodiments of the invention will now be described for the patient Interface 200 with reference to FIGS. 2 to 17.

Referring to FIGS. 2-17, various alternative configurations and preferred forms of a patient interface are shown.

In a first embodiment, there is provided a patient interface 200 that comprises at least one side arm 201 (and preferably a pair of the side arms, each side arm labelled as item 201) that extends laterally from a substantially central bridge portion 202 that is to be located, in-use, in or about a user's septum region.

The, or each, side arm 201 is connected to a substantially resilient, or relatively more rigid, bridge portion element 203. The bridge portion element 203 defines a substantially predetermined spatial relationship for an outlet or outlets 204 of a gas delivery system with the, or each, of the side arms 201. In this manner, the spatial relationship of the outlets 204 (and for example nasal prongs 208 that can be provided in fluid connection with such outlets 204), can be held in a constant referenced relationship with each other.

Providing for nasal prongs 208, or for other forms of gas delivery systems fluidly connected to the gas outlets 204 as may be suitable depending on the patient interface, in a constant referenced spatial relationship is useful as the nasal prongs are maintained in substantially a predetermined positioning for a user. This may allow for minimisation of prong flicking or other prong Irritation of a user's nares.

In a second embodiment, there is provided a patient interface 200 that comprises at least one side arm 201 (and preferably a pair of the side arms, each side arm labelled as item 201) that extends laterally from a substantially central bridge portion 202 to be located, in-use, in or about a user's septum region.

The, or each, side arm 201 comprises one or more predefined or predisposed points or localised compensation regions (or sites) 205 positioned along the side arm 201. The various one or more compensation regions (or sites) can accommodate or facilitate a compensation of the patient can act or work to accommodate or facilitate a compensation of the patient interface in or at one or more of the compensation regions (or sites) when the Interface experiences or has a force applied to it.

The, or each, side arm 201 is connected to a substantially resilient, or relatively more rigid, bridge portion element 203. The bridge portion element 203 defines a substantially predetermined spatial relationship for an outlet or outlets 204 of a gas delivery system with the, or each, of the side arms 201.

In a third embodiment, there is provided a patient interface 200 that comprises at least one side arm 201 (and preferably a pair of the side arms, each side arm labelled as item 201), that extends laterally from a substantially central bridge portion 202 to be located, in-use, in or about a user's septum region.

The, or each, side arm 201 comprises at least one substantially resilient, or relatively more rigid, side arm element 206. The or each side arm element 206 defines at least in part a form or curvature of the, or each, side arm 201 and, each side arm 201 and/or side arm element can comprise one or more predefined or predisposed points or localised compensation regions (or sites) 205. The various one or more compensation regions (or sites) can positioned along the or each side arm and/or the or each side arm element 206 to accommodate a compensation of the patient interface in or at one or more of the compensation regions (or sites) 205.

The, or each, side arm element 206 is connected, or is inter-connected via a connecting material, to a substantially resilient, or relatively more rigid, bridge portion element 203. The bridge portion element 203 defines a substantially predetermined spatial relationship for an outlet or outlets 204 of a gas delivery system with the, or each, of the side arms 201.

A connecting material may be a material that forms a, or part of, a side arm 201, and may for example comprise of a thermoplastic elastomer.

With reference to the accompanying description. Those regions or sites labelled in the accompanying figures as 205 or 205s Indicate compensation regions (or sites) of either a side arm 201 or a side arm element 206.

The following additional description is provided with reference to the above embodiments and with reference to the accompany figures. It will be appreciated various Iterations and alternative embodiments are provided by the description herein, and the figures are provided for Illustrative purposes.

In various forms of this Invention, it is particularly advantageous to provide for a bridge portion 202 or bridge portion element 203, or the bridge portion via the bridge portion element, that is or can be substantially Isolated from forces as may be applied to or experienced by the patient interface 200.

A force applied to, or experienced by, the patient interface 200 may be experienced by a side arm or side arms 201 of the interface, or a side arm element 206, or any other part of the interface 200.

For example, such a force may be the result of an impingement of a tube or conduit which is a part of a breathing circuit or the gases supply system for the patient interface 200 (i.e. so-called "tube drag" or a user or anyone else, whether Intentional or not, pulling or tugging on a tube or conduit, which in turn applies a force to the interface which is otherwise retained in a desired operational position on a user).

Forces may for example include movement or flexure or bending or twist or torsion or compression or extension (such as tension forces) of the patient interface 200 (or parts of the interface). These may be as a result of (whether directly or Indirectly) a user changing the shape of their face upon which the patient interface is located. Changes in shape mean the patient interface 200 moves or receives these forces (i.e. some form of dynamic behaviour is experienced by the patient interface).

Accordingly, each side arm 201 or those side arms 201 which may additionally Incorporate a side arm element 206, are provisioned with the one or more predefined or predisposed points or localised compensation regions (or sites) 205 at various positions or locations along the side arm element 206.

The various compensation regions (or sites) can accommodate or facilitate a compensation of the applied force, so as to go at least some way to Isolating or absorbing or damping the force, or at least minimising the transfer or translation of any such forces from disturbing the gas outlet(s) from a desired therapy delivery location. For example, where nasal prongs 208 may be fluidly connected to those outlets 204, it is desirable to minimise or avoid movement of the prongs 208 in user's nares.

The side arm (or arms) 201, or the or each side arm element 206, can respond (or be activated in response) to applied forces to the patient interface. In particular, the one or more of the compensation regions (or sites) 205 can respond (or be activated) so as to accommodate such forces, or at least some of the forces. The compensation by the regions (or sites) 205 may be by way of a flexure or bending (or the other responses as noted above) of the side arm 201 or side arm element 206 (or both of these).

Accordingly, the or each side arm 201 and/or the or each side arm element 206 which may be provided as a part of the side arms 201 can facilitate a self-compensatory system for ameliorating forces or movements experienced by the patient interface from being Imparted to the bridge portion 202 or bridge portion element 203. For example, this in turn can impact on spatial stability of the gas outlets 204 and optionally any nasal prongs 208, in the nares of a user's nose.

Similarly, the side arms 201 or the side arm element 206 which may be provided as a part of the side arms 201, can facilitate a self-compensatory system for ameliorating forces or movements experienced by the patient interface from being Imparted to other parts or portions of the patient interface 200 itself. In this way, forces or movements experienced by one part or region of the patient interface may be at least somewhat Isolated from being transferred or translated the remainder of the patient interface 200. Those forces or movements which are transferred or translated to other parts of the patient interface 200 may preferably be at reduced force or lower movement levels/amounts, or may be transferred or translated such that other parts of the patient interface 200 may in turn Isolate or absorb forces or movements.

In view of the above, it will be appreciated the side arm or side arms 201, and optionally in combination with side arm elements 206, are capable of acting as patient Interface stabilisers or a patient interface stabilising system, or at least as a part of such a stabiliser or stabilising system.

Bridge and Side Arm are Single Piece or are Assembled Together from Multiple Pieces The bridge portion 202 and side arms 201 may be provided as a single piece or unitary component. The patient interface is advantageously a unitary component that is easier to manufacture because the tooling and assembly process is relatively simple. However, in some embodiments, the bridge portion 202 and side arms 201 or may be assembled together from separate or multiple parts.

Similarly, the bridge portion element 203 and the side arm element or elements 206 may be provided as a single piece or unitary component, or may be assembled together from separate or multiple parts. For example, the bridge portion element 203 and the side arm element or elements 206 can be integrally formed as a single component.

As shown in the various figures of this specification, the bridge portion 202 is typically disposed Intermediate of a pair of side arms 201. Accordingly, the bridge portion element 203 is typically disposed Intermediate of the side arm elements 206 of a pair of side arms 201.

As is for example shown in FIG. 17A-E, there may be provided a patient interface 200 having bridge portion element 203 and at least one of the side arm element or elements 206, each of which are separate components. Each of these separate components can be substantially inter-connected, or provided in an inter-connected relationship with each other by a connecting material, such as a material of a side arm 201.

In view of the above, it will be appreciated the bridge portion element 203 may in certain embodiments be provided as a component that is discontinuous from or with the one or more side arm elements 206.

In yet other embodiments, a side arm 201 may comprise one or more separate side arm elements 206 (see for example FIGS. 17A-E), each of those one or more separate side arm elements 206 can be spaced apart through, or along a length of, the side arm 201 in which it or they are located. Various other arrangements can be contemplated depending on the complexity or sophistication of the side arm 201 and side arm elements 206 for providing a plurality of compensation regions (or sites) 205. For example, a plurality of side arm elements 206 may be spaced apart as an array through or along the length of one or each side arm 201 in which they are located.

Where a separate bridge portion element 203 and separate side arm element or elements 206 are provided, these may be made to be in connection, or are inter-connected, with each other, via one or a pair of associated side arm(s) 201. It will be appreciated that the bridge portion element 203 may optionally be associated with a side arm element 206 as a single component, yet additional ones of side arm elements 206 provided as separate components can be located in or along the side arm element. In this manner, a number of alternative compensation regions (or sites) 205 may be provided.

For example, although not shown, additional side arm elements may be located along the length of the side arms in the interface 200 shown in FIGS. 17A-E. IN such embodiments, additional compensation regions (or sites) 205 would be provided along the length of the side arm 201, depending on the location and structuring of such additional side arm elements 206.

Each side arm element 206, whether separate or as part of a continuous component comprising other side arm elements 206, can provide for a relatively resilient portion, with a material of the side arm Interposed between each, or adjacent to each, separate side arm element. In other words, the material of the side arm 201 interposed between side arm elements may Itself provide for a compensation region (or site) 205 which facilitates a compensation in response to a force.

As shown in the various figures of this specification, the bridge portion 202 is typically disposed Intermediate of a pair of side arms 201. Accordingly, the bridge portion element 203 is typically disposed Intermediate of the side arm elements 206 of a pair of side arms 201.

Bridge Defines Prong/Gas Outlet Spacing/Spatial Relationship

The bridge portion element 203 is advantageously of a dimension (sufficient) to span the width of a user's septum region, or is configured to establish or define a distance or the width between gas outlets 204, or is defined by a maximum distance substantially spanning from one nasolabial fold to another nasolabial fold of a user.

The bridge portion element 203 may Include one or a pair of cut-outs or shaped portions 207 to locate, position or house one outlet or a pair of the outlet outlets for a gas delivery system supplying gas to a user's airway.

The bridge portion element 203 with the cut-outs or shaped portions 207 advantageously enables for the gas outlets 204 to be maintained in a constant referenced relationship with each other, more preferably such that where nasal prongs 208 are provided in fluid connection with the outlets 204, the nasal prongs 208 are maintained in a constant referenced relationship so as to minimise nasal prong movement in the nares of a user, or issues of prong flicking.

The bridge portion element 203 can includes one or a pair of cut-outs or shaped portions 207 to locate, position or house one nasal prong or a pair of nasal prongs, such as those labelled as Item 208, either connected to the outlet or outlets 204, or as the outlet or outlets themselves, for a gas delivery system supplying gas to a user's nare or nares.

It will be appreciated different types and styles of gas delivery system outlets for patient engagement can be provided. In the figures, nasal prongs 208 are Illustrated, typically these being of the non-sealing style or nasal prong. However, it will be appreciated that different forms of outlets can be provided, as may be suitable depending on the therapy to be delivered and the style or type of patient interface. For example, nasal prongs of the sealing style (e.g. those which may utilise "nasal pillows" or other nasal sealing systems for nasal prongs) may be used, or a nasal mask system or full face masks as may be often used for delivery positive airway pressure therapies, or patient interfaces more commonly utilised for high flow (but not of the sealing type) therapy delivery may be utilised.

It will be appreciated the patient interface may be constructed of any suitable materials, although medical grade materials are the preference. For example, the bridge portion element and side arm elements can be, or comprise of, a polymeric material.

Various polymeric materials, whether alone or in combination with others may be utilised. Particularly preferred are medical grade polymers.

Polymers may be a combination of any one or more of: thermoplastic elastomer(s), polypropylene based elastomer(s), liquid silicone rubber(s), or breathable thermoplastic polyurethane(s), or breathable polyamides, more preferably polymers may be those such as, but not limited to, polyolefins, thermoplastic elastomers, or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A hardness of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

Bending Directions

Each one or more of the predefined or predisposed points or localised regions (or sites) 205 preferably facilitates a flexure or bending or hinging and/or elastic deformation in response to a force or movement input.

The one or more compensation regions (or sites) 205 can provide for regions or sites of bending or hinging region though or about:
- at least one plane passing through the interface
- a plurality of parallel planes passing through the interface
- at least two different (non-parallel) planes passing through the interface
- at least two different (orthogonal) planes passing through the interface.

For example, the embodiments of FIGS. 5, 6, 7, 8, 9 are generally Illustrative of a side arm element 206 having compensation regions (or sites) 205 where there is at least one or a series of hinging or bending or flexure regions or sites (i.e. the compensation regions (or sites), where the hinging or bending or flexure is (preferably primarily) through one plane passing through the interface 200, where those planes are parallel to each other.

It will be appreciated that the compensation regions (or sites) 205 can configured so that different planes of bending or hinging or flexure are each provided, for example off-set planes, whether orthogonal or not, parallel or not, allow compensation in a variety of planes to effectively operate in combination to Isolate or absorb or dampen force experienced by the interface from being transferred or translated to the bridge portion or bridge portion element.

FIG. 10 for example Illustrates one embodiment where the compensation regions (or sites) allow for hinging or bending or flexing through multiple planes, as for example is shown by the wire diagrams FIGS. 10F-I.

The compensation regions (or sites) may be moulded or shaped cut-out portions or tapered (thinned or thickened) portions of the side arms 201 or side arm elements 206 to provide for a variety of planes through which hinging or bending or flexing may be preferentially facilitated.

The compensation regions (or sites) may be preferentially located or positioned more towards a rear side of a side arm 201 or a side arm element 206, or may be located or positioned more towards a front side of a side arm or side arm element (or may be provided more centrally).

In certain embodiments, one or more of the compensation regions (or sites) 205 can flex or bend (or are hinged or locally displaceable or may elastically deform or move or respond) to a force or movement input more preferentially in a first direction or first set of directions and less preferentially in another direction or another set of directions. For example, each one or more of the various compensation regions (or sites) 205 can be adapted or configured to substantially resist or be more resistive to a flexure or bending (or hinging or elastic deformation) in the less preferential direction or set of directions compared to a more preferential direction of flexure or bending (or any of the other hinging or elastic deformation responses).

In one particularly preferred mode, the first direction or first set or directions is/are in a substantially transverse plane (e.g. XY plane of a user's body). More particularly, the first direction or first set of directions may be in a substantially transverse plane in a ventral direction or a dorsal direction, or may be both in the ventral direction and the dorsal direction.

In other preferred modes, additional preferential directions or set of directions (e.g. extra first direction or set of directions) may be one or more of: a substantially transverse plane, a substantially sagittal plane, a substantially coronal plane.

In yet another preferred mode, the first direction or the first set of directions is in a direction or directions which substantially facilitate the side arm 201 or side arm element 206 moving or bending relative to the bridge portion 202 or bridge portion element 203.

For example, a compensation region (or site) 205 may enable a bending or flexure etc in an anterior direction or a posterior direction of a user's body. In this way, each of the various regions (or sites) 205 are adapted or configured to more readily or with less resistance, be capable of a bending or flexure etc in such a direction, yet more resistive to a flexure or bending etc in another direction.

It will therefore be appreciated that one or more or a series of such compensation regions (or sites) 205 can be provided along a side arm 201 or side arm element 206 to provide for a customised arrangement of preferential bending or flexure etc regions or sites 205 capable of responding to forces or movements experienced by the patient interface 200. In this way, at least some degree of absorption of the force or movement or Isolation or amelioration from translation or transferal of such forces or movements to other parts of the Interface may be achieved. In particular, preferably the transfer or translation of forces or movements to the gas outlets 204 and for example nasal prongs 208 is desired to be avoided or minimised.

According to this embodiment, the side arm 201 or side arm element 206 (or both) may be formed of a substantially resilient material or may be configured to provide for a substantial resilience to flexure or bending (or hinging or elastic deformation) in the side arm 201 or side arm element 206 compensation regions (or sites) 205 selected from one or more of the following:
- provided between a single compensation region (or site) 205 positioned laterally outward from a bridge portion 202 or a bridge portion element 203 and an outer end 209 of the side arm 201 or side arm element 206,
- provided between an outer-more compensation region (or site) 205 of a side arm 201 or side arm element 206 and an outer end 209 of the side arm 201 or side arm element 206, provided between each of a series of compensation regions (or sites) 205 of a side arm 201 or side arm element 206, provided between two compensation regions (or sites) 205 positioned laterally outward from the bridge portion 202 or bridge portion element 203, and between an outer-more compensation region (or site) 205 of a side arm 201 or side arm element 206 and an outer end 209 of the side arm element 206.

Figure 2D:
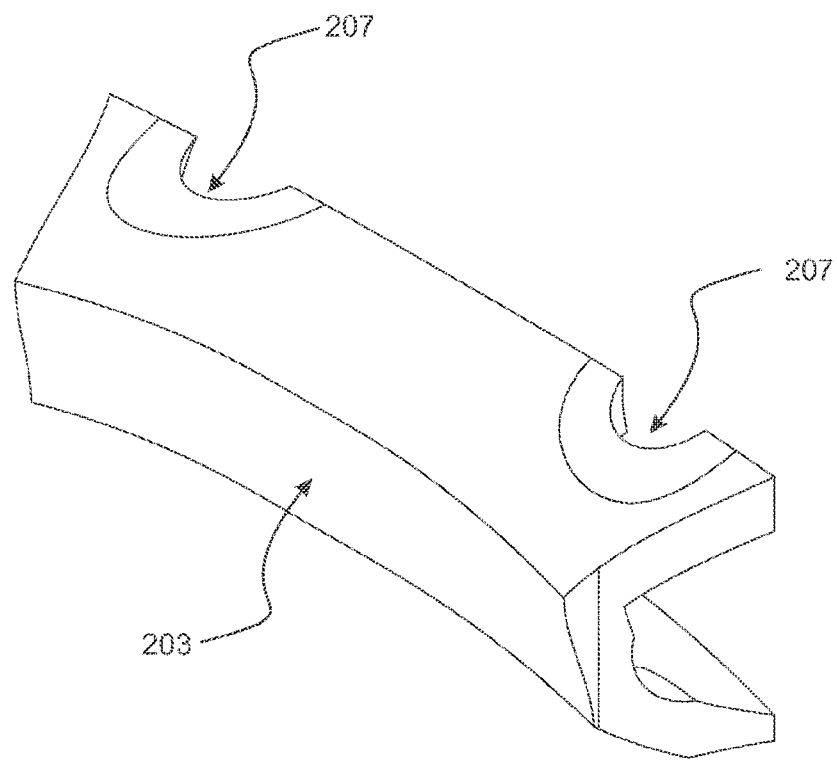
Figure 2E:
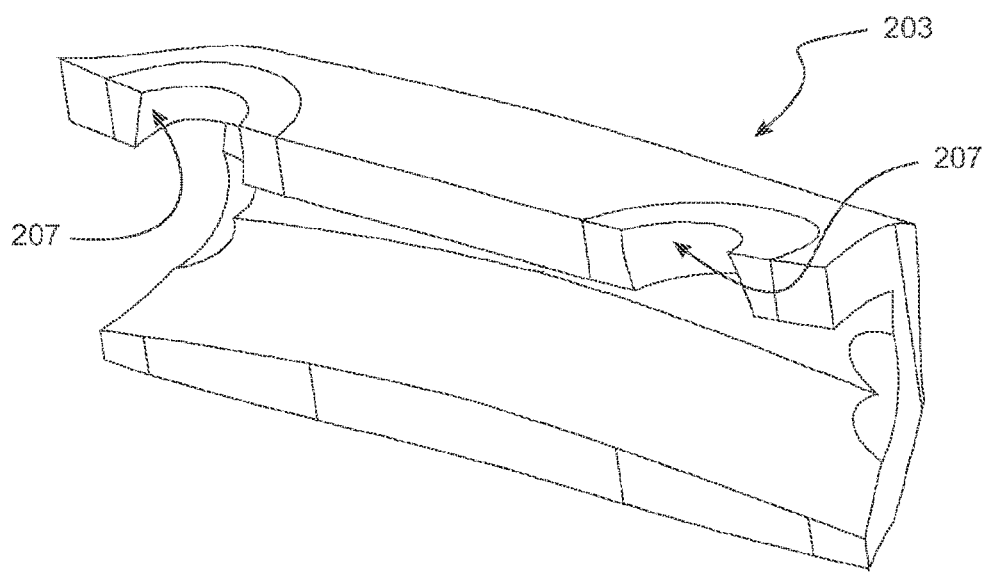

In one embodiment, FIGS. 2A-G Illustrate a patient interface 200 comprising a bridge portion element 203 connected to a pair of side arms 201 via the connecting material of each side arm. Compensation regions (or sites) 205 are Indicated at the junction or connection between the bridge portion element 203 and the side arm 201 material. Additional compensation regions (or sites) 205s are Indicated on the side arms 201, the side arms 201 being formed or shaped so as to provide for such compensation regions (or sites) 205s. In particular, FIG. 2F Illustrates a shape of the patient interface prior to the interface and the compensation regions (or sites) 205, 205s responding to a force that is applied or experienced by the interface, whilst FIG. 2G Illustrates a shape of the interface 200 when the compensation regions (or sites) are behaving to compensate for the applied or experienced force.

In further embodiments, FIGS. 3A-C and 4A-C each Illustrate a patient interface 200 similar to that of FIGS. 2A-E. A gas supply conduit is shown housed or located by items 213 for delivery of gas to the outlets 204 and nasal prongs 208. Compensation regions (or sites) are shown as 205, 205s. The compensation regions (or sites) 205, 205s allow for the patient interface to respond to applied forces to in turn minimise or Isolate the transfer or translation to the bridge portion and in turn the gas outlets 204 and nasal prongs 208. Note that FIGS. 3D and 4D Illustrate a shape of the patient interface prior to the interface acting to compensate for a force, whilst FIGS. 3E and 4E Illustrate a shape of the interface when the compensation regions (or sites) 205, 205s are working in response to the force.

Figure 5C:
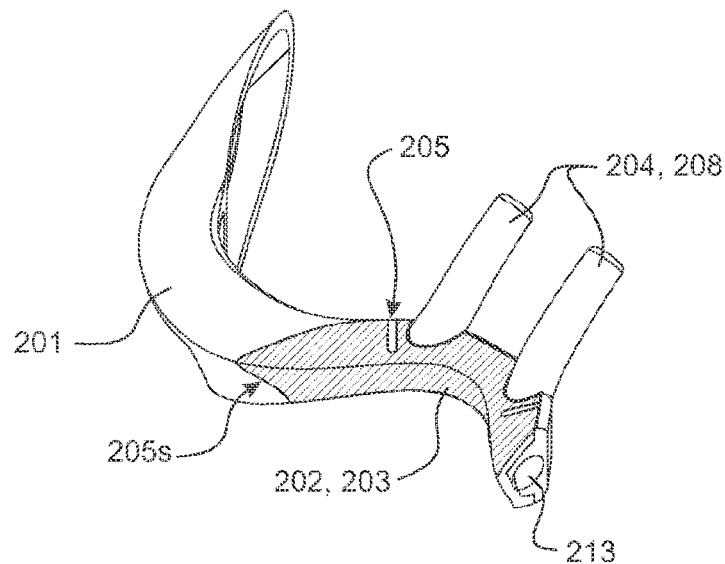
Figure 5D:
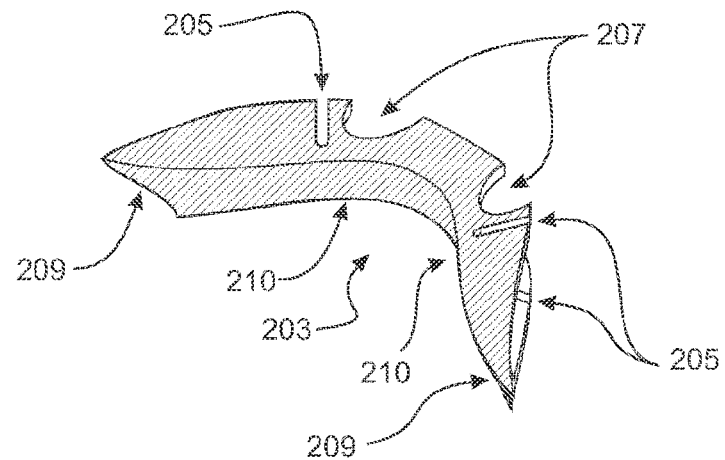
Figure 5E:
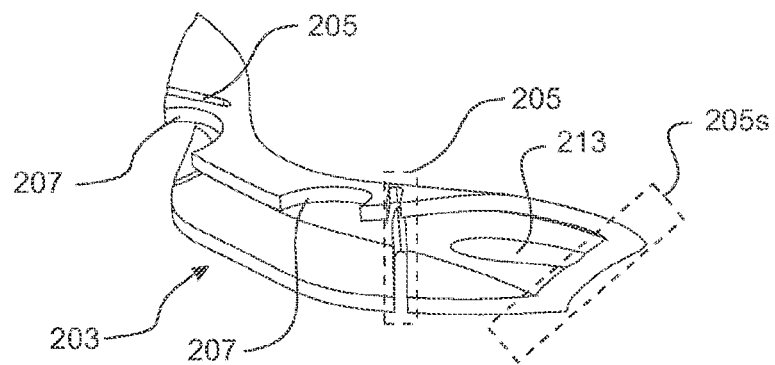

In one embodiment, one or each side arm 201 or one or each side arm element 206 may comprise of a single compensation region (or site) 205, 205s that is configured for such flex or bend (or any of the other responses, such as hinging or local displacements or elastic deformation or movement). For example, see FIG. 5A-5E, illustrating one such embodiment where a compensation region (or site) 205 is located near the bridge portion, and is a portion of the side arm element 206 with some material removed (e.g. can be a slot or notch or slit or cut-out or can be shaped or moulded in this way) The compensation region (or site) 205 is provided more to the rear side of the side arm element, and allows for a hinging or preferential bending or flexure of the side arm element in this region. It will be appreciated that at the outer end 209 of the or each side arm element 206 there may be an optionally additional compensation region (or site) 205, 205s where a side arm 201 is attached or connected (i.e. an inter-connection) to the side arm element. At such a region (or site) 205, 205s, a difference in material characteristics may result in an effective additional region (or site) 205, 205s for flex or bending etc. However, this may be an optional feature. FIGS. 5F, 5G Illustrate various nodes for preferred compensation regions (or sites) 205, 205s as may be provided by the side arms or side arm elements. FIG. 5F is a shape of the Interface 200 prior to application (or response by the compensation regions (or sites)), whilst FIG. 5G is a shape of the interface once the compensation regions (or sites) are in action.

In another embodiment, for example that of FIG. 6A-E, a side arm element 206 is provided with at least two points or localised compensation regions (or sites) 205, 205s, and there may also be the optional compensation region (or site) 205 at the outer end of the side arm element 206 at the junction with the side arm 201 material, for example different material characteristics of the side arm and side arm element can interact or Intersect to provide for such an additional compensation region (or site). Still further, yet another compensation region (or site) can be provided by the side arm 201 itself (e.g. as a bowing of the side arm material in response to a force, such as a change in shape of a user's face/cheek upon which the side arm may be releasably connected through a retention system or securement system). As seen, the side arm element 206 has a first compensation region (or site) 205 located at an inner-more end of the side arm element (near or adjacent to the bridge portion element), such a first region (or site) 205 being a slot or notch or slit or cut-out or moulded cavity or void out of the front side or face of the side arm element 206. A second compensation region (or site) 205 is then provided more laterally outward from the first region or site, and is shown as a dip or recess (or otherwise thinned portion or reduced material) formed in a top and bottom surfaces of the side arm element.

The wire diagrams of FIGS. 6F-G demonstrate at least one embodiment of how the interface of FIG. 6A may respond to an applied force, when the regions (or sites) 205 bend or hinge or flex.

In each of the various embodiments shown, it will be appreciated that at the outer end 209 of the or each side arm element 206 there may be a region 205, or optionally 205s, where a side arm 201 is attached or connected to the side arm element 206. At such a region (or site) 205, 205s, a difference in material characteristics, or other shaping or forming of the side arm 201 or side arm element 206, or their junction, may result in an effective additional region (or site) 205 or 205s for flex or bending etc.

Wire diagrams for the nodes Illustrating location and operation of compensation regions (or sites) 205, 205s for each of these embodiments is provided by FIGS. 6F-G, 7F-G, 8F-G, 9F-G, 10F-G (as a top view of the nodal points shown on FIG. 10D), 10H-I (as a front view of the nodal points shown in FIG. 10D), 11F-G, 11H-I (as an example where an additional compensation region (or site) is provide outwardly or at the junction of the side arm 201 with the side arm element 206), 12F-G, 13F-G, 14F-G, 15F-G, 16F-G. Again, the shape of the interface 200 prior to a force being applied (or the compensation regions (or sites) being operational is those of the first referenced figure above, with the second figure referenced being once the compensation regions (or sites) 205, 205s have been activated or are working/responding to an applied force.

Taking into account the various embodiments discussed above, it will be appreciated that in various modes, configurations or adaptations, one or more of the following may be provided:

at least one point or localised compensation region (or site) 205 may be located at an inner-more end 210 of a side arm 201 or a side arm element 206 in a connection with the bridge portion 202 or bridge portion element 203 (for example, the or each side arm element 206 may be configured to flex or bend (or are hinged or locally displace or may elastically deform or move) relative to the bridge portion element 203).

at least one of the points or localised regions (or sites) 205 may be located at a junction or connection between a side arm 201 or a side arm element 206 and the bridge portion 202 or bridge portion element 203 at least one of the points or localised regions (or sites) 205 may be located in or at a zone of the bridge portion 202 or bridge portion element 203 defined substantially by a peripheral or laterally outer edge of a user's septum region.

Side Arm Elements or Side Arms Allow for Provisioning of a Space/Gap for a Gas Supply to an Outlet or Outlets In yet further embodiments, the side arm 201 or side arm element 206, either each Independently, or by their combination, can be shaped or configured or adapted to provide for a passageway 213. Such a passageway 213 is formed by one or more of, a lumen or a void space or cavity or other recess through a side arm 201 and/or a side arm element 206.

Such a passageway 213 allows for receiving of a gas supply (from a source) and for channeling delivering of that gas to a user via the outlet or outlets 204; or, alternatively allows for the receipt of a gas supply conduit (not shown, but which may be received or fitted into such an item 213) for then delivering the gas to a user via the outlet or outlets 204.

Such a passageway 213 in or through the side arm 201 or side arm element 206, or both, allows for the formation of a conduit or lumen through which gas may be directed or supplied for delivery to an outlet or outlets 204.

The passageway 213, or a conduit or lumen (or channel) so formed by any one or more of a lumen or a void space or cavity or other recess through a side arm 201 and/or a side arm element 206, can be defined at least in part by the side arm 201 and at least in part the side arm element 206 (i.e. the side arm element 206 may itself forms one part of a wall of such an item 213, and the side arm 201 may itself forms another part or the remainder of the item 213).

Each side arm 201 can include a port for accessing the passageway 213. Such a port can be located on a front face of each side arm, at an outer more end of the side arm. The port is preferably located below a horizontal mid-line of patient interface, and more preferably is oriented so as to accept a gas supply conduit or other gas connection from a direction below or beneath a side arm.

The portion of the passageway 213 that is formed at least in part by the side arm element(s) can be at least 10%, or at least 20%, or at least 30%, or at least 40%, or at least 50%, or at least 60%, or at least 70%, or at least 80%, or at least 90%, or may be in the range of about 1-99%, or about 5-95%, or about 10-90%, or about 15-85%, or about 20-80% or about 30-70%, or about 40-60%, or about 30-50%, of a wall circumference or a wall perimeter (for example of a unit length section) of the passageway so formed.

As the wall of the passageway may be formed by a combination of the side arm 201 and the side arm element 206, the side arm 201 may provide for the remainder of the wall circumference or a wall perimeter that is otherwise formed by the side arm element.

Minor Projections

Where a side arm element 206 is utilised, one or more minor projections 211 can be provided about or along such an element 206. These various minor projections 211 are engageable or provided to be of a shape or configuration to be associated with a material of the side arm 201. For example, see FIGS. 15A-15E Illustrating such minor projections 211.

Minor projections 211 provide for extensions of the side arm element 206 in a variety of directions or planes, and may in some embodiments, provide for a structural detail of a side arm element 206 upon which a side arm 201 may be engaged, for example such as in an overmoulded arrangement, or the material for the side arm 201 can be provided to otherwise to be engaged with the minor projections 211. In this way, such minor projections 211 can be effectively Implanted into a side arm 201. Such Implantation may provide for yet still further regions (or sites) 205, or other stiffening or strengthening of a side arm 201 or a side arm element 206, or their combination. For example, Interaction of a minor projection 211 with the material of a side arm 201 can provides for a particular resistance to flexure or bending (or hinging or elastic deformation) of a side arm element 206 of the side arm 201, or their combination.

As is for example shown in FIGS. 15A-15E, the material of the side arm 201 can surround the minor projections 211. The material of the side arm 201 can be at least partially compressible (or may be at least partially Incompressible), or of desired characteristics such that the minor projections 211 can translate a flexure or bending (or hinging or elastic deformation) of a side arm element 206 as a compression of the material of the side arm 201 (or as an extension or stretch of the side arm material in response to a force, such as a tension).

In this way, the side arm material when compressed by minor projections, or other parts of the side arm element (such as the walls of notches or slits or slots or other cut-outs in which the side arm material may be located), operates to resist hinging or flexure of bending as a result of Its material characteristic. Similarly, the side arm material may resist an extension or stretch, for example as a result of the notches or slits or slots or other cuts-outs changing shape or Increasing their angles in response to an applied force.

Various Iterations of patient interface 200 are shown in the accompanying figures—however, these Illustrations should not be seen as limiting of particular arrangements. Where a patient interface 200 utilises a side arm 201 in combination with a side arm element 206, the material of the side arm 201 may for example in some forms encapsulate or substantially envelope a side arm element 206 (e.g. may be a complete or whole encapsulation or enveloping); yet in other alternative forms may only partially encapsulate or envelope the side arm element 206.

The material(s) of the side arm 201 can be used to fill any voids or gaps that may otherwise be present between the side arm 201 and the side arm element 206. In this way, the side arm material(s) can provide material which is Interposed in voids or gaps or around other shapes (such as the regions (or sites) 205) of the side arm element 206. As noted above, the material(s) of the side arm 201 may be wholly or partially encapsulating or enveloping of the side arm element 206.

The material(s) of the side arm 201 can be selected according to particularly preferred characteristics. The Interaction of the regions (or sites) 205 or the minor projections 211 (or both of these) with the material(s) of the side arm 201 may work in conjunction with one or more of the predefined or predisposed points or localised regions (or sites) 205 to allow the flex or bend (or hinging or elastic deformation or movement or response) to a force or movement input more preferentially in a first direction or first set of directions and less preferentially in another direction or another set of directions, yet provide some resistance to such a flex or bend.

Side Arms Extend about Each Side of the Face

In particular embodiments, and for example when a pair of side arms 201 is provided for a patient interface, each of the side arms 201 is adapted to extend laterally from the bridge portion 202, one of the side arms 201 of a pair of side arms can extend substantially about a left side of a user's face and the other side arm can extend substantially about a right side of a user's face.

The or each side arm 201 can extend substantially laterally away from or outwardly from a user's sagittal plane. The or each side arm element 206 can extend a substantial length of or along or through each such side arm 201 that comprises such a side arm element.

Accordingly, a pair of side arms 201 may be provided in which a patient interface 200 is able to be positioned upon a user's face with each of the side arms 201 providing a part of a retention system or securement system which can be coupled or associated with a headgear. In this way, the patient interface 200 may be retained or secured upon a user's face in a desired operational position.

Each of the side arms 201 or side arm elements 206 may in turn respond to forces or movements experienced by the patient interface to Isolate or absorb or dampen at least somewhat ameliorate the likelihood of a transfer or translation of such a force or movement to other parts of the patient interface.

In preferred embodiments, there is a minimisation of the forces or movements from being transferred or translated to the bridge portion 202 or bridge portion element 203 (or both). This may allow for a more stable location or positioning of the gas outlets 204, and any such nasal prongs 208 associated with the bridge portion 202 or bridge portion element 203. In turn, this may help to reduce movements of such gas outlets or nasal prongs from moving near a user's nose or their nares, to assist in avoiding prong flicking. Prong flicking is an undesirable outcome of movement of the gas outlets 204 or nasal prongs 208. Prong flicking may Irritate a user and may Interrupt delivery of therapy.

As Illustrated in particular figures, the or each side arm element 206 may be configured as a plurality of element limbs 212 (i.e. a side arm element 206 may be bifurcated or otherwise split or branched into a series of element limbs 212). One or more of these side arm element limbs 212 may themselves comprise one or more of the minor projections 211 described previously.

With reference to FIGS. 2A-2E, there is provided an embodiment in which a bridge portion 202 includes a bridge portion element 203, such a bridge portion element 203 defining a pair of notches cut-outs or shaped portions 207. The portions 207 provide a predefined outlet 204 pathway or a port to which a nasal prong 208 may be fluidly connected so as to direct a flow of gas to the nares of a user's nose. As seen in FIG. 2C, there is a passageway 213 in or through the side arm 201. Similarly, the bridge portion element 203 is shaped or formed so as to allow the supply of gas through the lumen or void space or cavity or recess 213 to be directed or supplied for delivery to an outlet or outlets 204.

In the embodiment of FIGS. 2A-E, the side arms 201 include their own regions (or sites) 205s, which may for example be a general bowing of the side arm by the side arm material in response to a force.

With reference to FIGS. 3A-C and 4A-C, there is provided an embodiment in which a bridge portion 202 includes a bridge portion element 203, such a bridge portion element 203 defining a pair of cut-outs or shaped portions defining a spatial arrangement for outlets 204 and out of which a pair of nasal prongs 208 extend. In addition, upon each side arm 201 is a gas supply conduit locator 214 as part of a passageway 213 for locating or housing a gas supply conduit. The gas supply conduit may be fixed in placed with the locator or in the passageway 213 (for example may be glued in place). The bridge portion element 203 also includes such an item 213 for receiving delivery of a gas supply and for then channeling such gas to the outlets 204 and nasal prongs 208.

In the embodiment of FIGS. 3A-C, the gas supply conduit provides for some resistance or at least some restraint as to extension of the side arms laterally outward side arms 201.

In the embodiment of FIGS. 4A-C, the gas supply conduit provides for an even shorter length between a fixed position, fixed to one or each of locators 214, and in doing so provides an even greater resistance to extension of the side arms laterally outward from the bridge portion.

With reference to FIGS. 5A-E, there is provided an embodiment in which the bridge portion 202 includes a bridge portion element 203 with a pair of left and right side arm elements 206. The bridge portion element 203 defines a pair of cut-outs or shaped portions 207 defining a spatial arrangement for outlets 204 and out of which a pair of nasal prongs extend. The side arm elements 206 include at least one region (or site) 205 about which a hinging capability is provided. The hinging capability allows for the side arm elements 206 to bend or flex or hinge so as to absorb or at least to some degree ameliorate the transfer or translation of a force or movement applied to these side arm elements 206 from reaching the bridge portion 202 and bridge portion element 203 which define the spatial arrangement of the gas outlets 204 and prongs 208. As shown, the regions (or sites) 205 can be notches or slits or slots or cut-outs from the side arm element 206. In addition, the junction or connection of materials between the side arm 201 and side arm element 206 can provide for an additional region (or site) 205 about which some flex or bending etc may occur. The level to which flex or bending etc may occur may at least in part depend upon the materials of the side arm 201 and side arm element 206 used and their relative characteristics. As is shown in FIG. 5C, the side arm 201 is shaped or formed so as to include a passageway 213 for locating or housing a gas supply conduit, or at least forming a part of such a lumen or passage. The bridge portion element 203 is also shaped so as to facilitate such a passageway 213 when in combination with the side arm 201, for example see FIG. 5E.

With reference to FIGS. 6A-E, there is provided an embodiment in which the bridge portion 202 includes a bridge portion element 203 with a pair of left and right side arm elements 203. The bridge portion element 203 defines a pair of cut-outs or shaped portions 207 defining a spatial arrangement for outlets 204 and out of which a pair of nasal prongs extend. The side arm elements 206 include at least two regions (or sites) 205. A first of the regions (or sites) 205 is located an inner more end 210 of the side arm element 206, close to the junction between the bridge portion element 203 and the side arm element 206. A second of the regions or sites (205) is located toward an outer more end 209 of the side arm element 206. The first region (or site) allows for a preferential first direction or first set of directions to be provided where the side arm element can bend or flex or move outwardly from a user's face (i.e. In a transverse ventral direction), whilst the second region (or site) allows for a preferential first direction or first set of directions to be provided where the side arm element can bend or flex or move Inwardly toward a user's face (i.e. In a transverse dorsal direction).

Figure 6C:
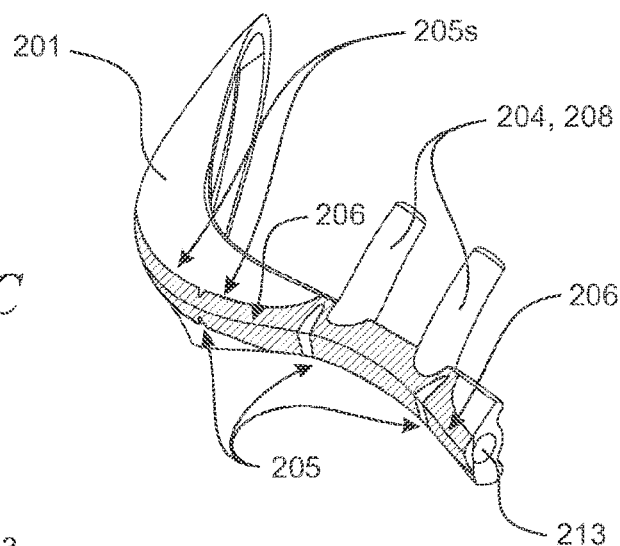
Figure 6D:
Figure 6E:
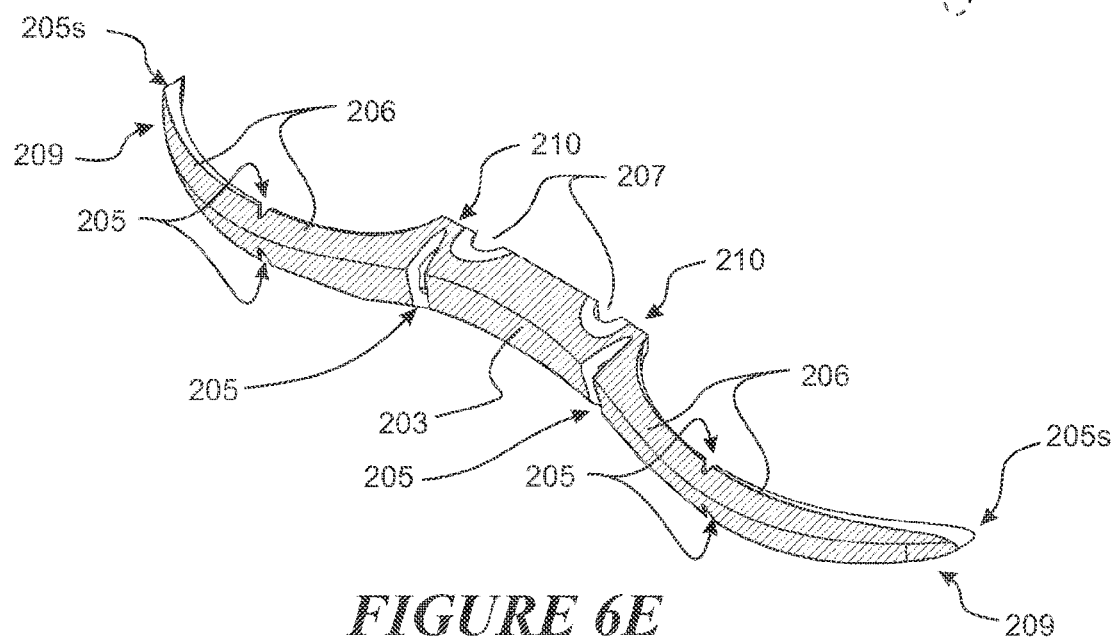

In addition, the junction or connection of materials between the side arm 201 and side arm element 206 can provide for an optional additional region (or site) 205. The level to which flex or bending etc may occur may at least in part depend upon the materials of the side arm 201 and side arm element 206 used and their relative characteristics. As is shown in FIG. 6C, the side arm 201 is shaped or formed so as to include a lumen or a void space or cavity or other recess 213 for locating or housing a gas supply conduit, or at least forming a part of such a lumen or passage. The bridge portion element 203 is also shaped so as to facilitate such an item 213 when in combination with the side arm 201, for example see FIG. 6D.

In the embodiment of FIGS. 6A-E, the side arms 201 include their own regions (or sites) 205s.

As with the embodiment described in relation to FIGS. 6A-E, each of the embodiments of FIGS. 7-16 illustrate further alternative arrangements utilising a plurality of regions or sites (205), and a variety of more preferential first directions, for configuration of a patient interface 200 provisioned with a self-compensating ability to minimise forces or movements applied or experienced by the patient interface from being transferred or translated to the bridge portion 202 or bridge portion element 203, and in turn the gas outlets 204 and for example nasal prongs as may be fluidly connected thereto.

Figure 7C:
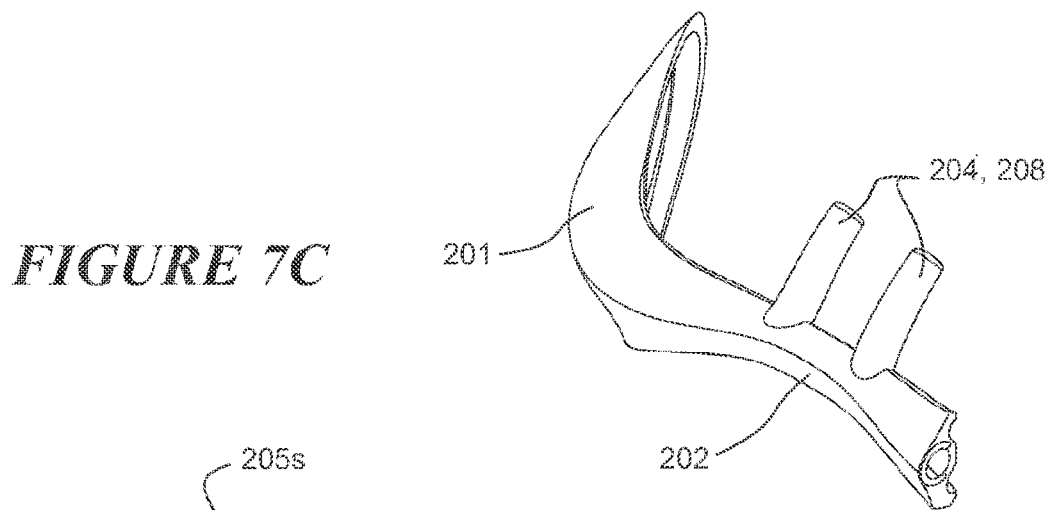
Figure 7D:
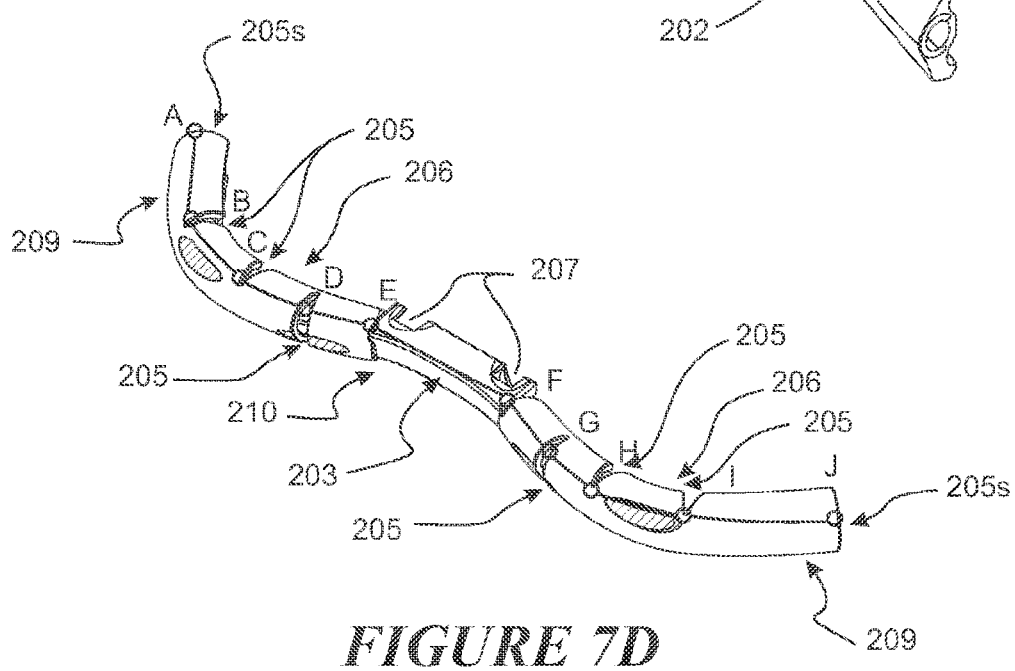
Figure 7E:
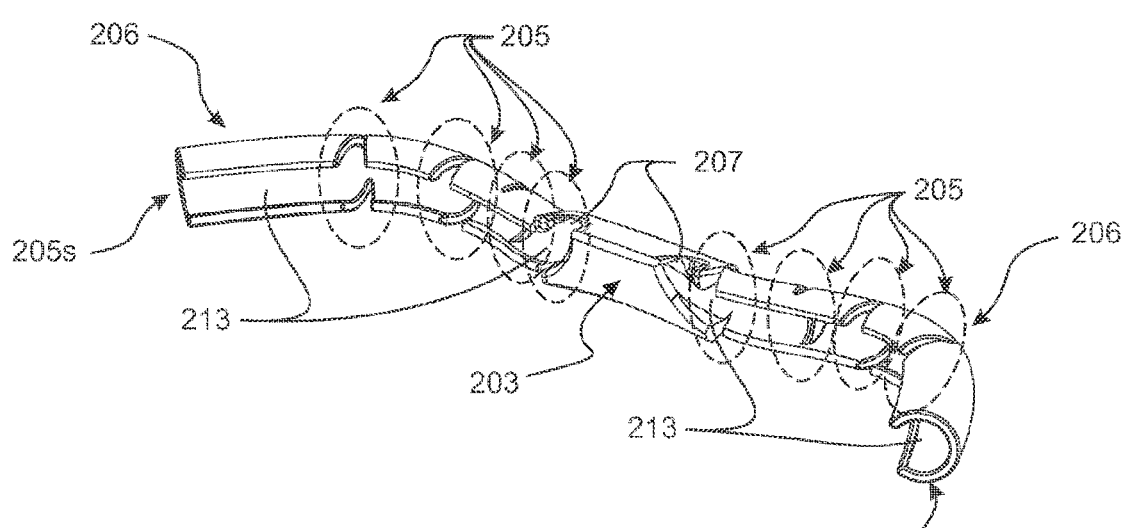

The embodiment of FIGS. 7A-E, illustrates at least three regions (or sites) 205, as well as the optional additional region (or site) 205 as may be facilitated at the junction at the outer end of a side arm element 206 with a side arm 201. A first of the regions (or sites) 205 is located at an inner more end 210 of the side arm element 206, whilst a second and third regions (or sites) 205 are located more outwardly along the length of the side arm element 206. It should be noted that the second and third (i.e. the more outwardly located) regions (or sites) 205 are configured for a more preferential bending or flexure in a different direction to the first region (or site) more Inwardly. This can allow for a variety of bending or flexure directions to be provisioned along the side arm element 206. As is shown in FIG. 7C, the side arm 201 is shaped or formed so as to include a lumen or a void space or cavity or other recess 213 for locating or housing a gas supply conduit, or at least forming a part of such a lumen or passage. The bridge portion element 203 is also shaped so as to facilitate such an item 213 when in combination with the side arm 201, for example see FIG. 7E.

In at least the embodiment of FIGS. 7A-E, the side arms 201 can include their own regions (or sites) 205s as Indicated. Such side arm regions (or sites) 205s may be enabled by thinned thickened sections or side arm material or other shapes of the side arm to enable hinging or bending or flexure in preferential directions or planes.

Figure 8C:
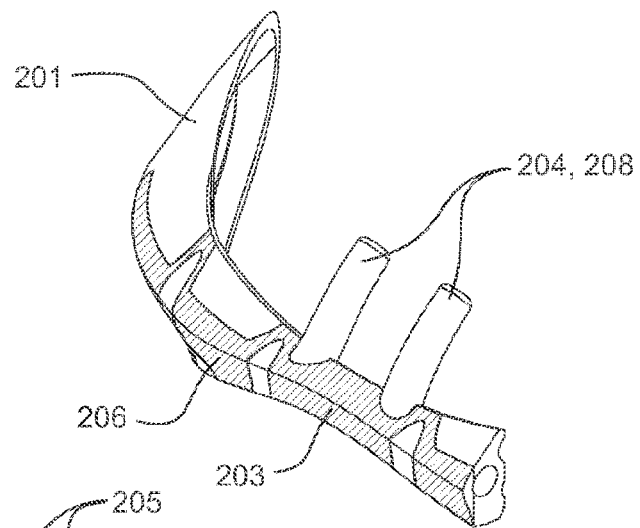
Figure 8D:
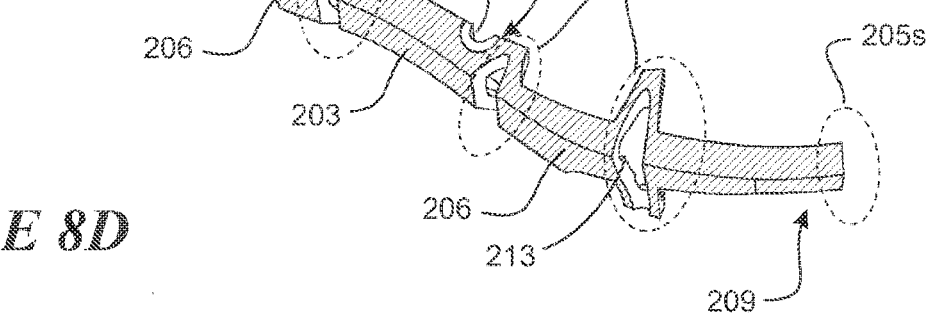
Figure 8E:
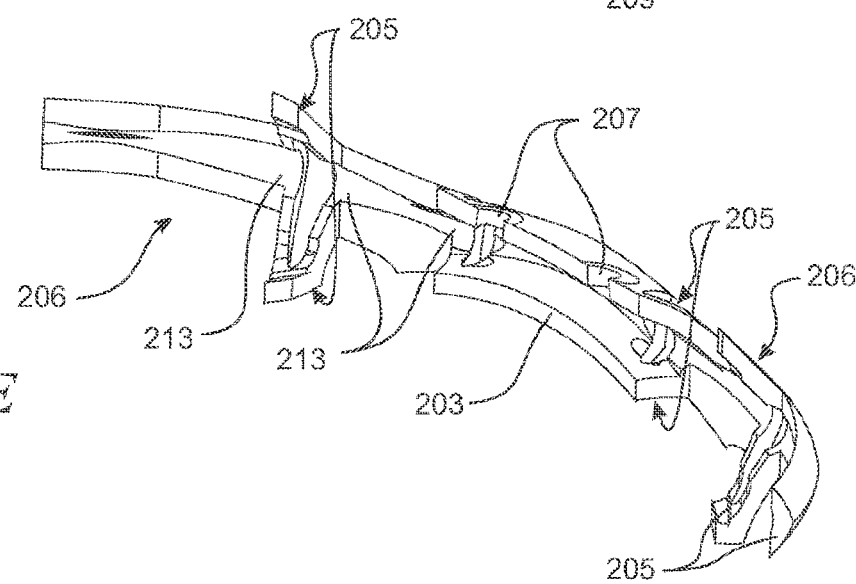

The embodiment of FIGS. 8A-E, illustrates at least two regions (or sites) 205, as well as the optional additional region (or site) 205 as may be facilitated at the junction at the outer end of a side arm element 206 with a side arm 201. A first region (or site) 205 is located more Inwardly (i.e. closer to the bridge portion element 203) and a second region (or site) 205. Different geometries of each region (or site) 205 allow for different types or levels of bending or flexure by each region (or site) 205. As is shown in FIG. 8C, the side arm 201 is shaped or formed so as to include a lumen or a void space or cavity or other recess 213 for locating or housing a gas supply conduit, or at least forming a part of such a lumen or passage. The bridge portion element 203 is also shaped so as to facilitate such an item 213 when in combination with the side arm 201, for example see FIG. 8E.

Figure 9C:
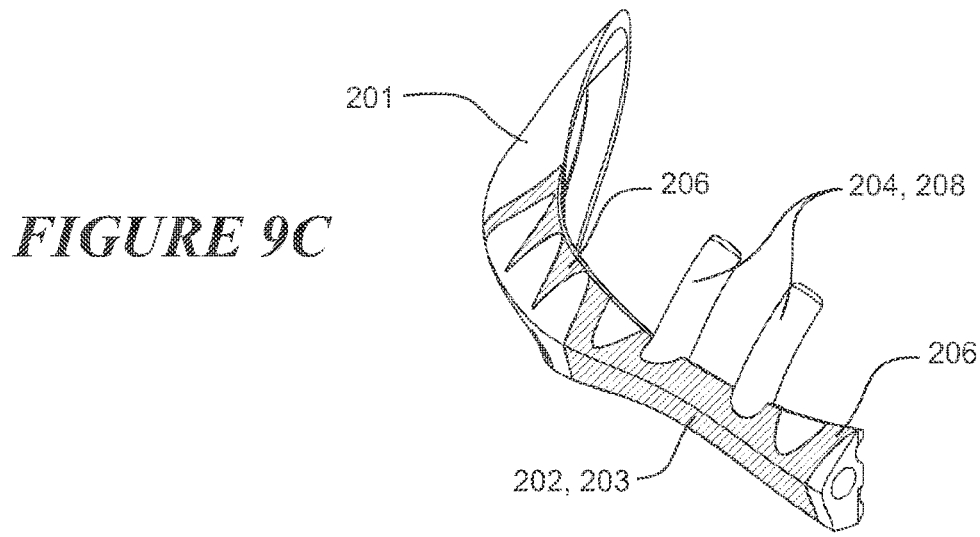
Figure 9D:
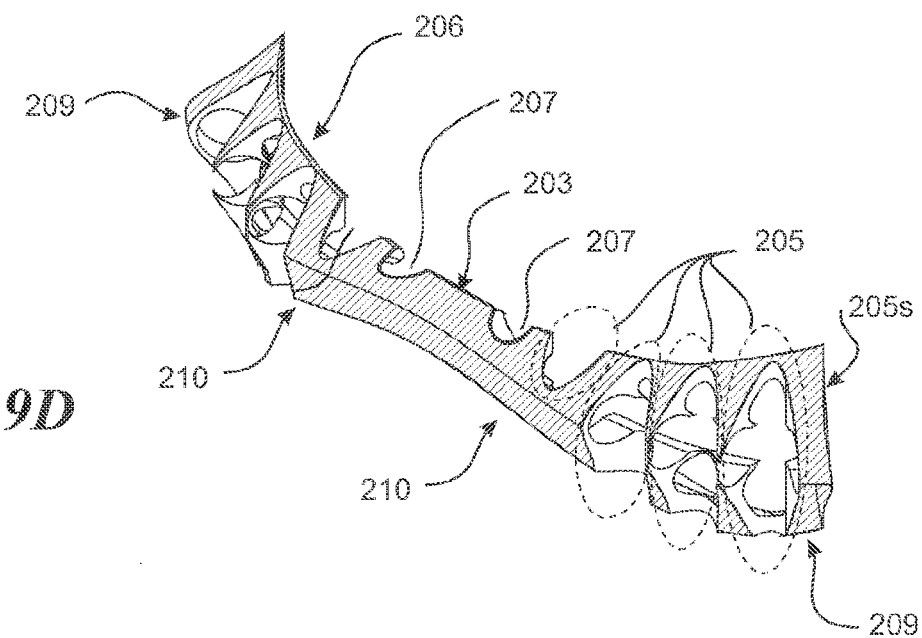
Figure 9E:
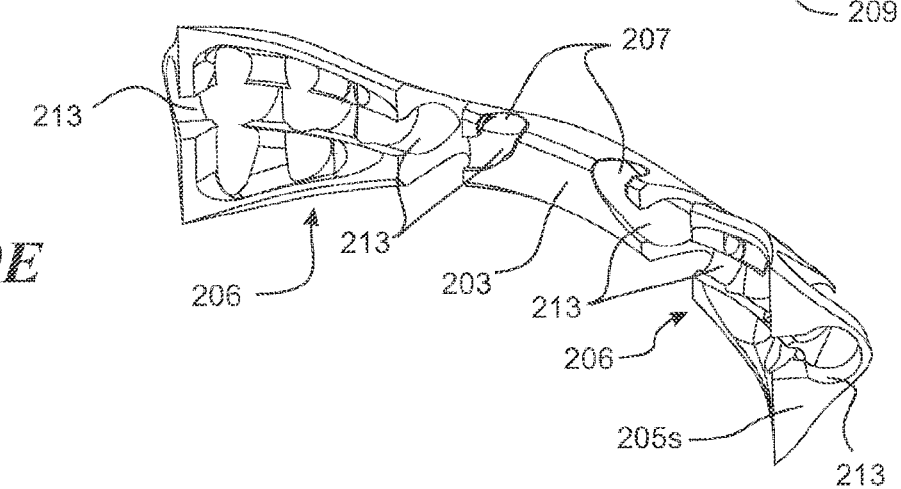

The embodiment of FIGS. 9A-E, illustrates at least two regions (or sites) 205, as well as the optional additional region (or site) 205 as may be facilitated at the junction at the outer end of a side arm element 206 with a side arm 201. In this embodiment, a series of regions (or sites) 205 may be sequentially arranged or arrayed along the length or body of the side arm element 206. A first of the regions (or sites) 205 is located more Inwardly and closest to the bridge portion element 203. This first region (or site) 205 may allow for a first preferential direction or set of directions which is different to the preferential direction or set of directions provided for by the subsequently arranged regions (or sites) 205 located more outwardly this first region (or site) 205. As is shown in FIG. 9C, the side arm 201 is shaped or formed so as to include a lumen or a void space or cavity or other recess 213 for locating or housing a gas supply conduit, or at least forming a part of such a lumen or passage. The bridge portion element 203 is also shaped so as to facilitate such an item 213 when in combination with the side arm 201, for example see FIG. 9E.

Figure 10F:
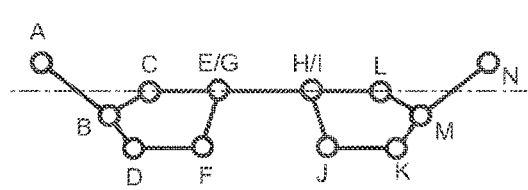
FIG. 10F shows a wire diagram illustrating a shape of the FIG. 10A interface, in plan view, prior one or more compensation regions (or sites) becoming active.
Figure 10G:
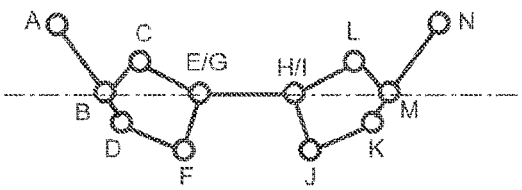
FIG. 10G shows the wire diagram once one or more compensation regions (or sites) are activated in response to an applied force.
Figure 10H:
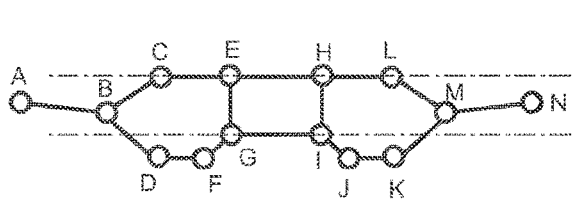
FIG. 10H shows a wire diagram illustrating a shape of the FIG. 10A interface, as a front view, prior one or more compensation regions (or sites) becoming active.
Figure 10I:
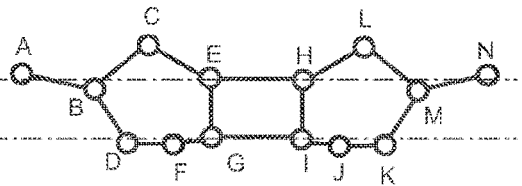
FIG. 10I shows the wire diagram once one or more compensation regions (or sites) are activated.
Figure 10A:
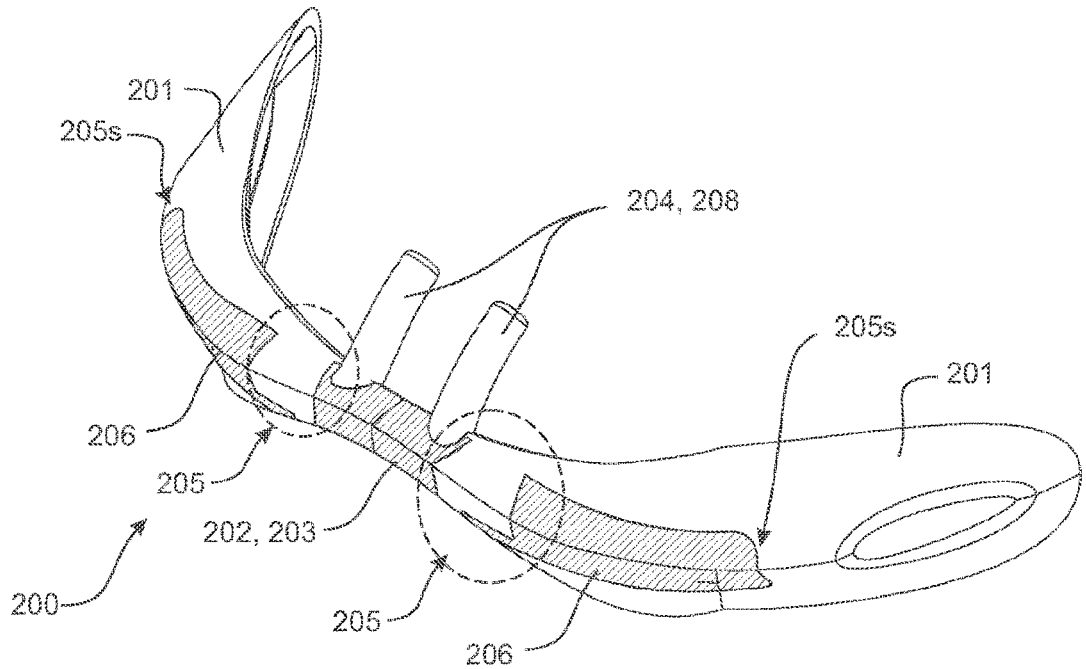
FIGS. 10A-10E show a patient interface from various angles, in particular in which a bridge portion element and side arm element is to be incorporated into the interface; more particularly.
Figure 10B:
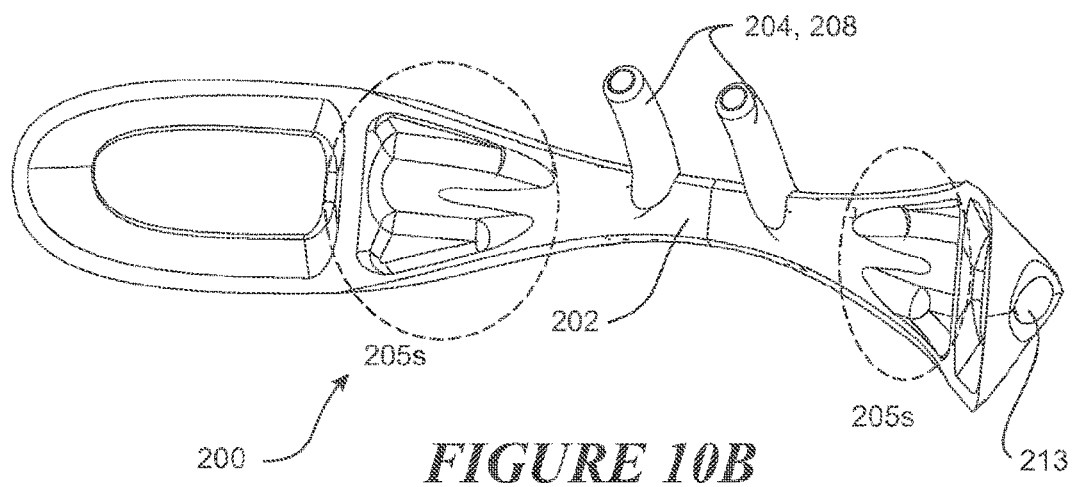
Figure 10C:
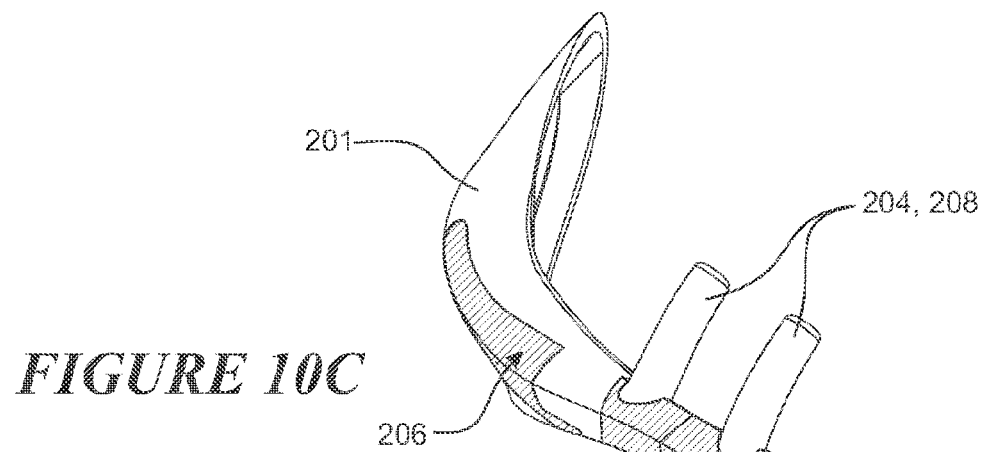
Figure 10D:
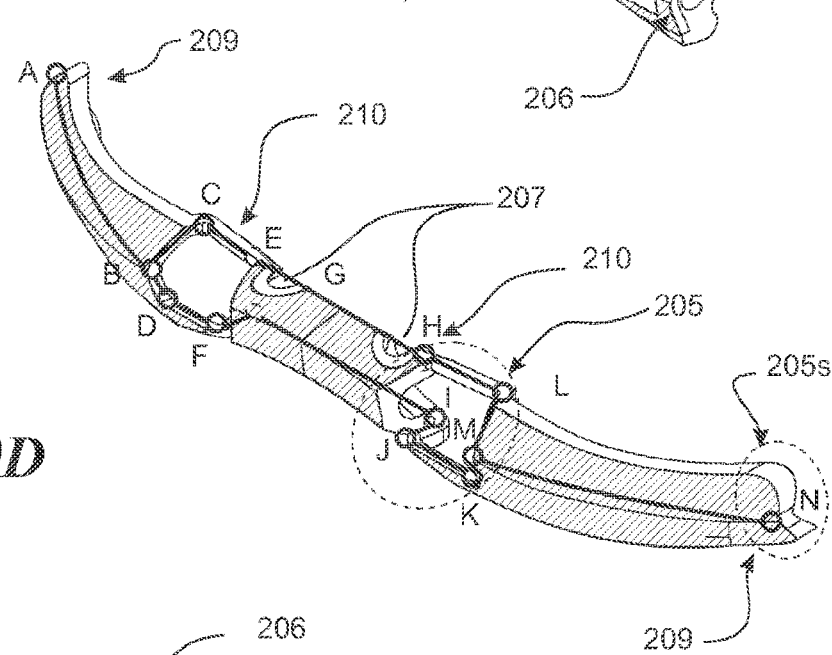
Figure 10E:
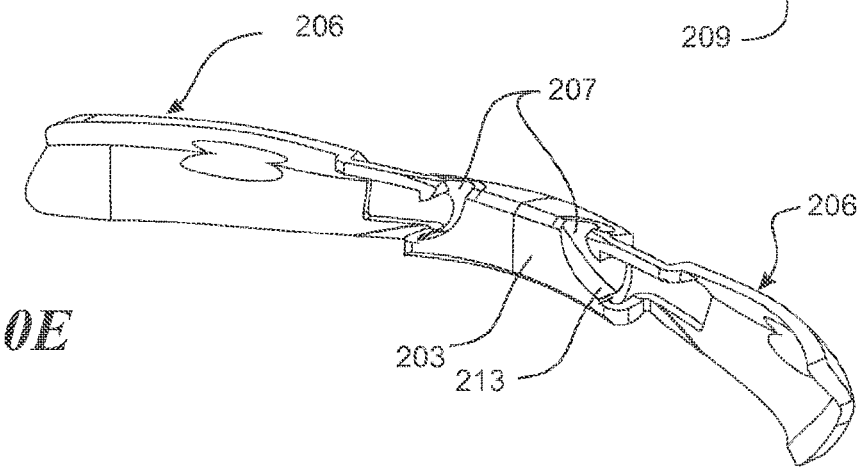
Figure 11F:
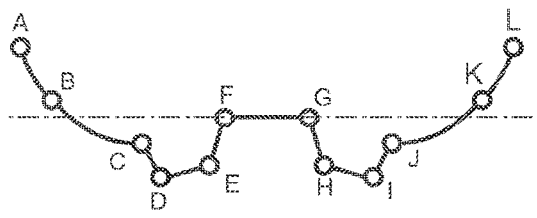
FIG. 11F shows a first wire diagram illustrating a shape of the FIG. 11A interface, in plan view, prior one or more compensation regions (or sites) becoming active.
Figure 11G:
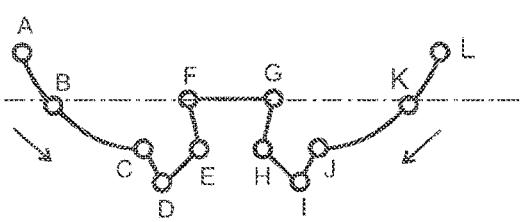
FIG. 11G shows the wire diagram once one or more compensation regions (or sites) are activated in response to an applied force.
Figure 11H:
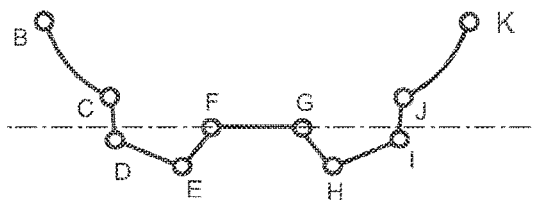
FIG. 11H shows a second wire diagram illustrating a shape of the FIG. 11A interface, in plan view, prior one or more compensation regions (or sites) becoming active.
Figure 11I:
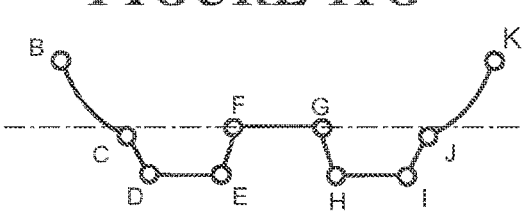
FIG. 11I shows the wire diagram once one or more compensation regions (or sites) are activated.
Figure 11A:
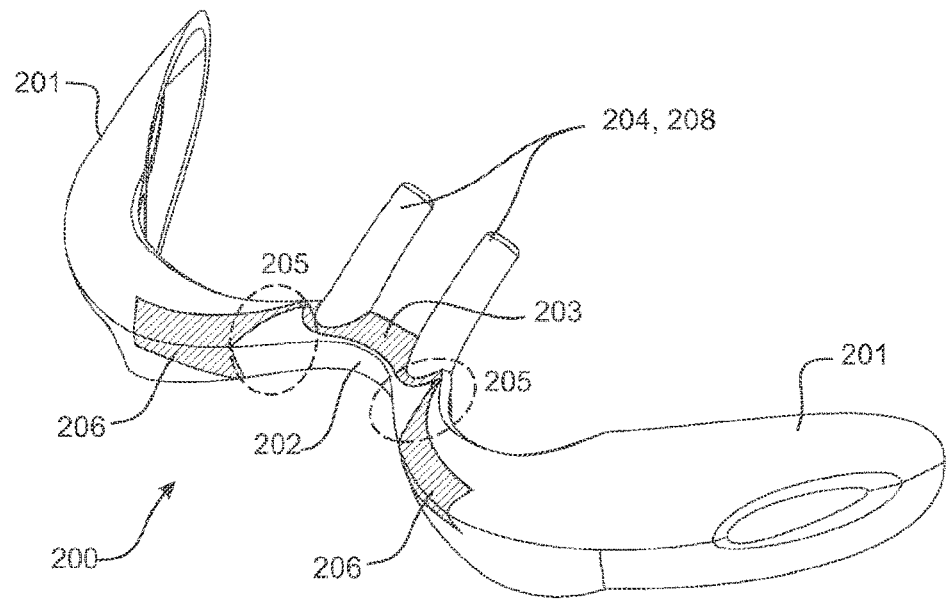
FIGS. 11A-11E show a patient interface from various angles, in particular in which a bridge portion element and side arm element is to be incorporated into the interface; more particularly.
Figure 11B:
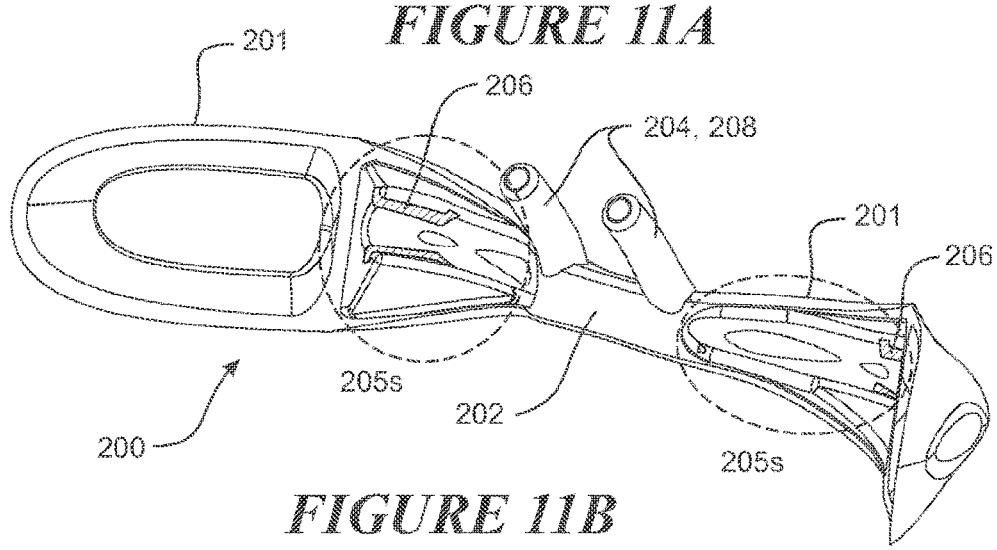
Figure 11C:
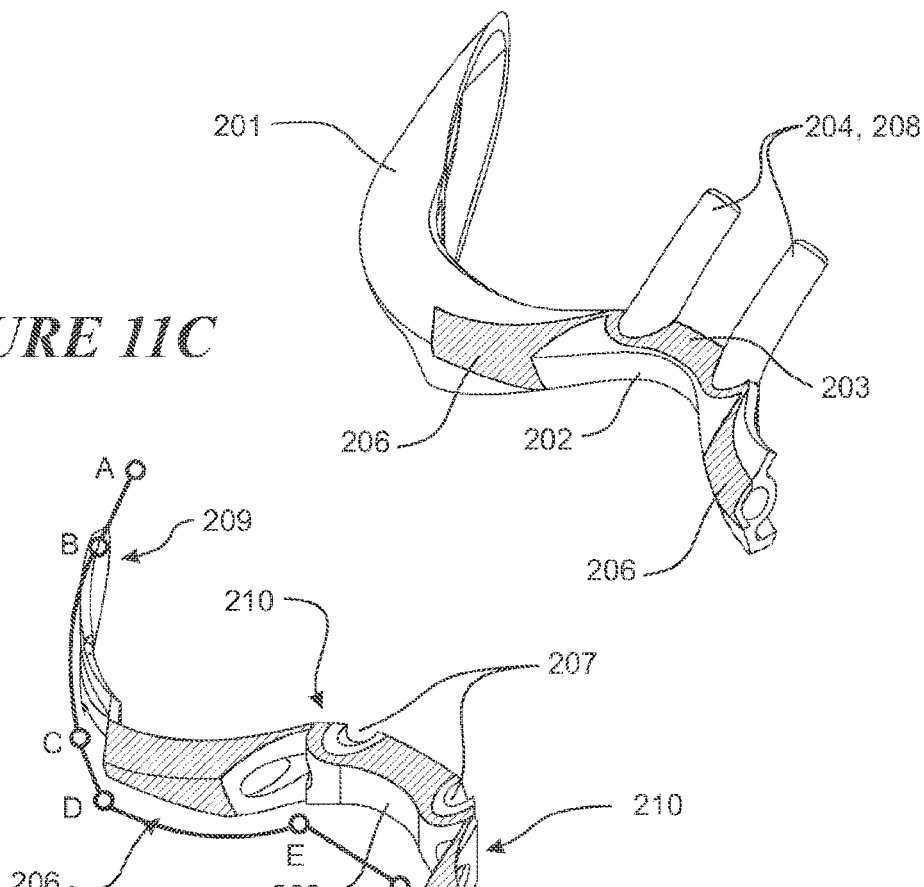
Figure 11D:
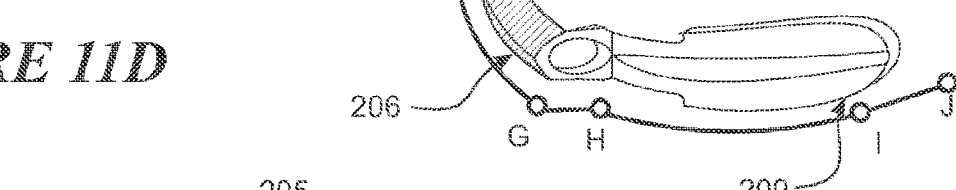
Figure 11E:
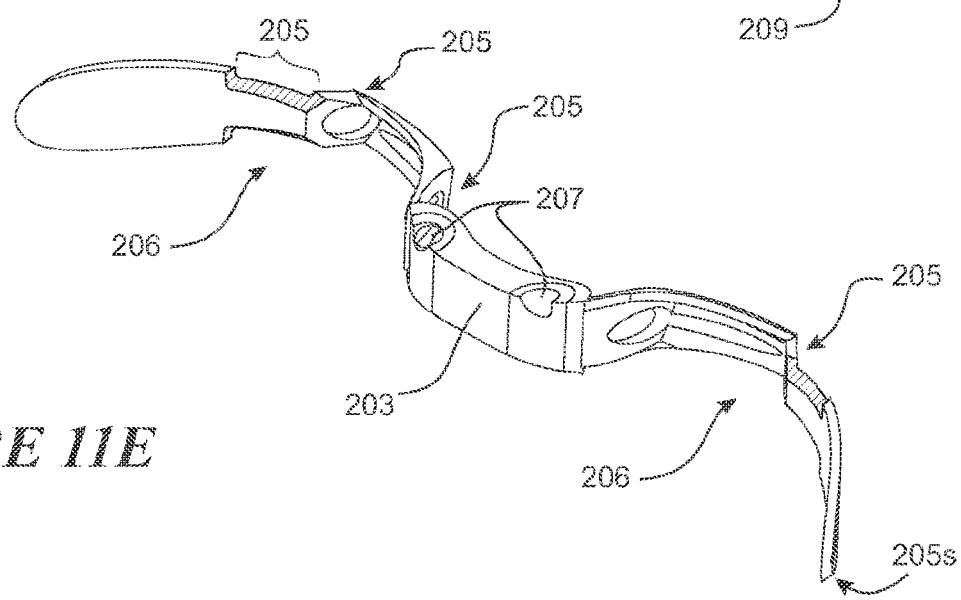
Figures 12F, 12G:
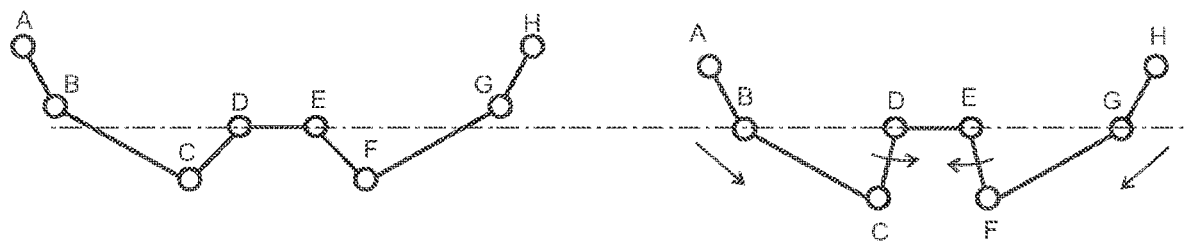
FIG. 12F shows a wire diagram illustrating a shape of the FIG. 9A interface, in plan view, prior one or more compensation regions (or sites) becoming active.
FIG. 12G shows the wire diagram once one or more compensation regions (or sites) are activated in response to an applied force.
Figure 12A:
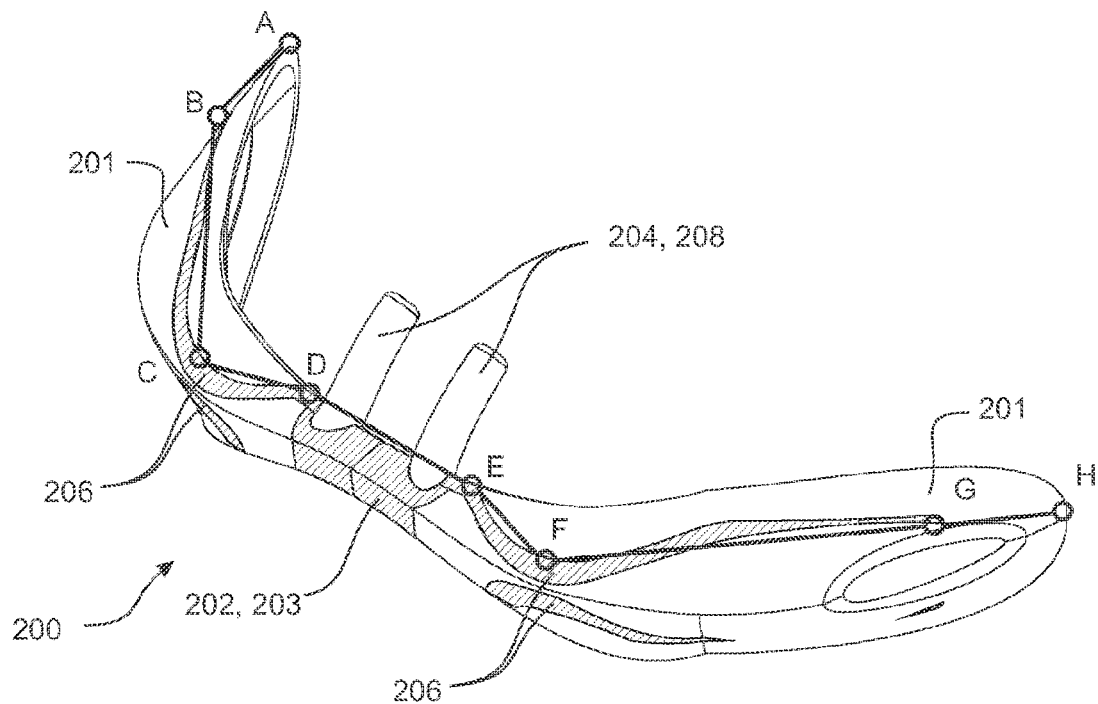
FIGS. 12A-12E show a patient interface from various angles, in particular in which a bridge portion element and side arm element is to be incorporated into the interface; more particularly.
Figure 12B:
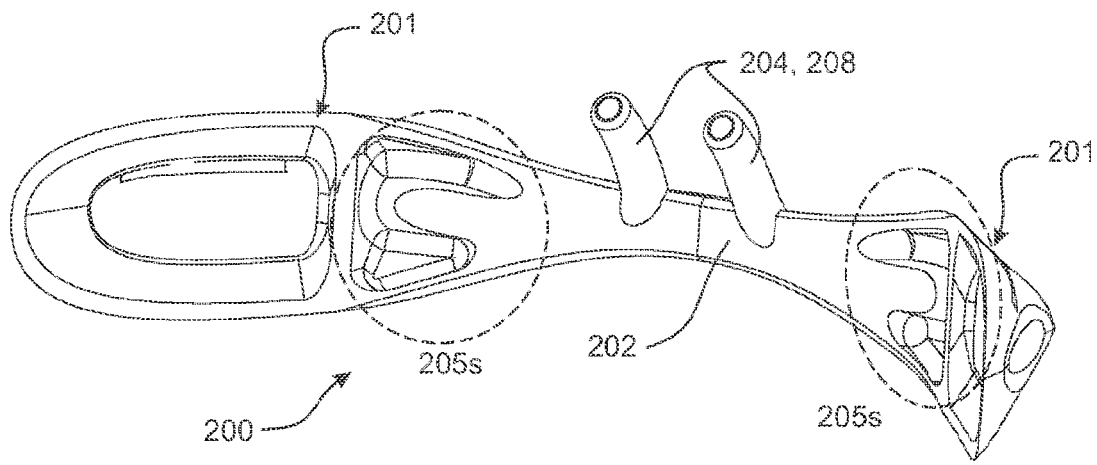
Figure 12C:
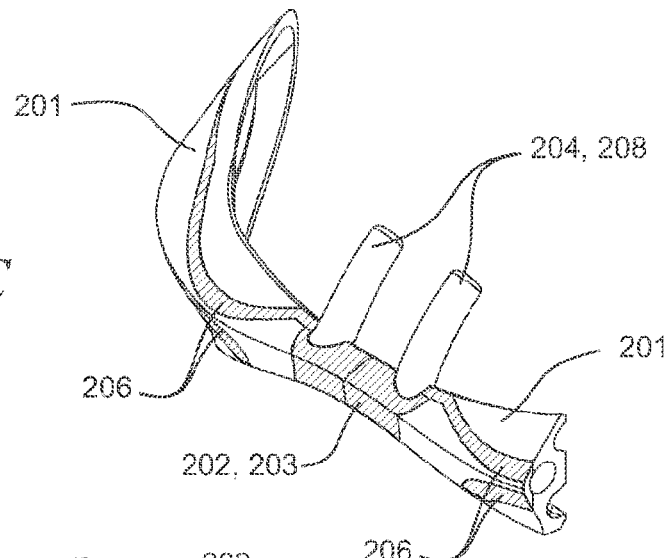
Figure 12D:
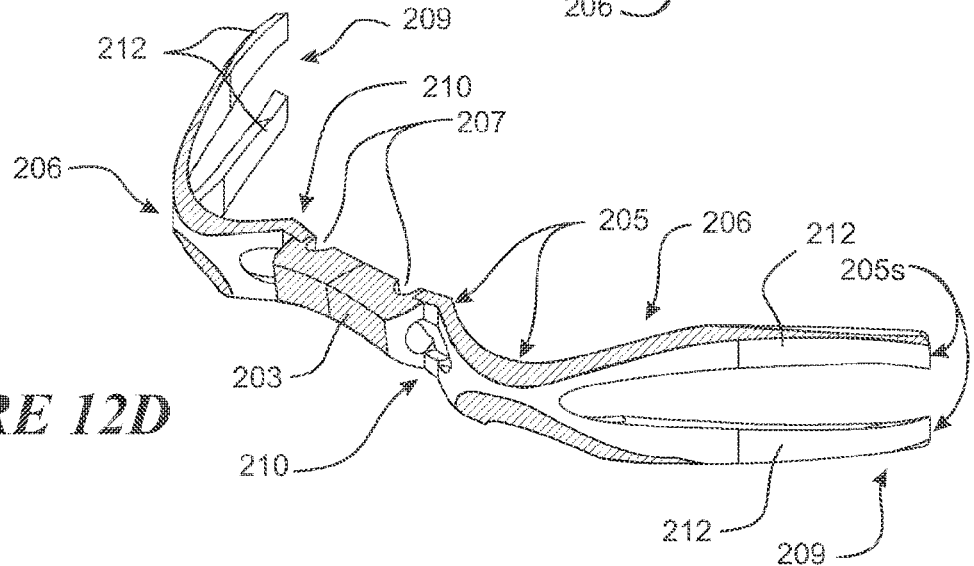
Figure 12E:
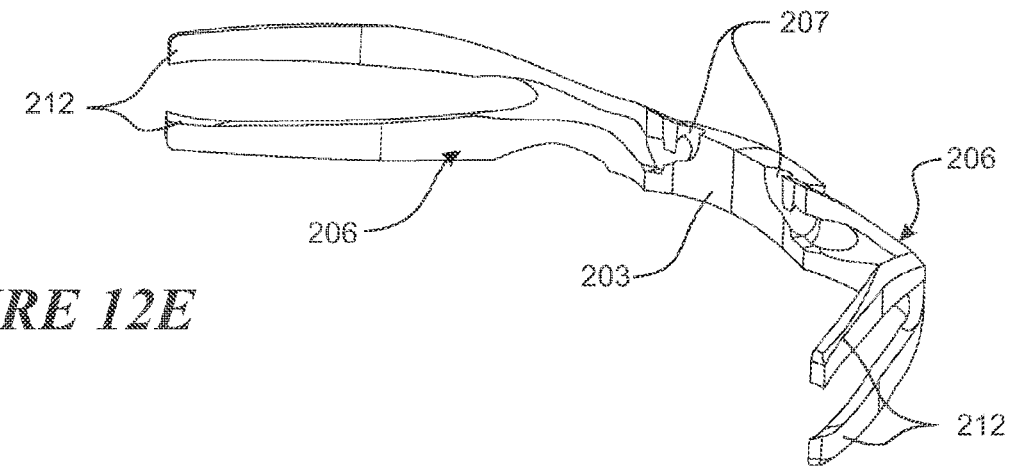
Figure 13F:
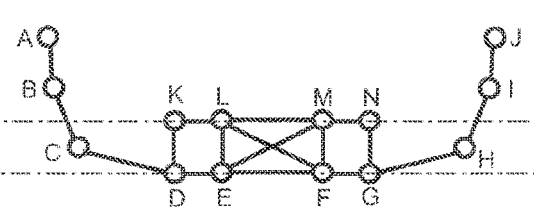
FIG. 13F shows a wire diagram illustrating a shape of the FIG. 13A interface, in plan view, prior one or more compensation regions (or sites) becoming active.
Figure 13G:
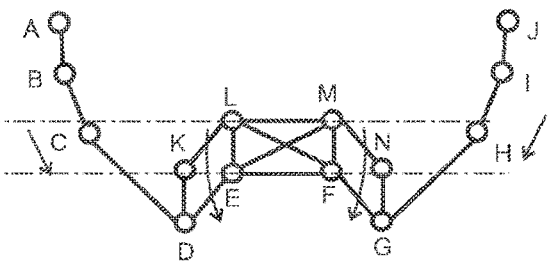
FIG. 13G shows the wire diagram once one or more compensation regions (or sites) are activated in response to an applied force.
Figure 13A:
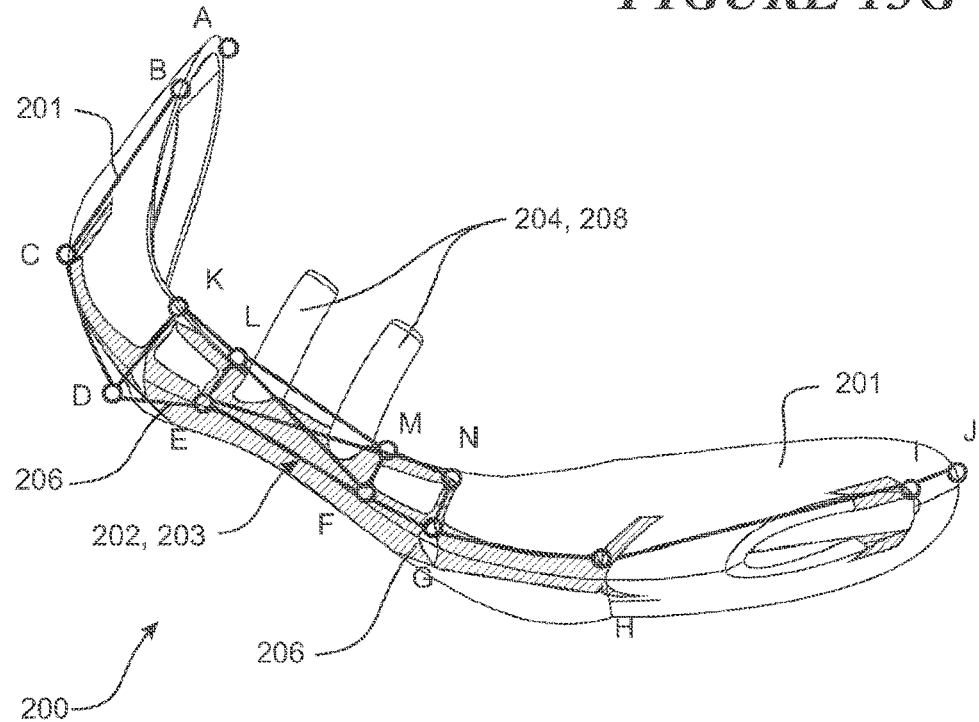
FIGS. 13A-13E show a patient interface from various angles, in particular in which a bridge portion element and side arm element is to be incorporated into the interface; more particularly.
Figure 13B:
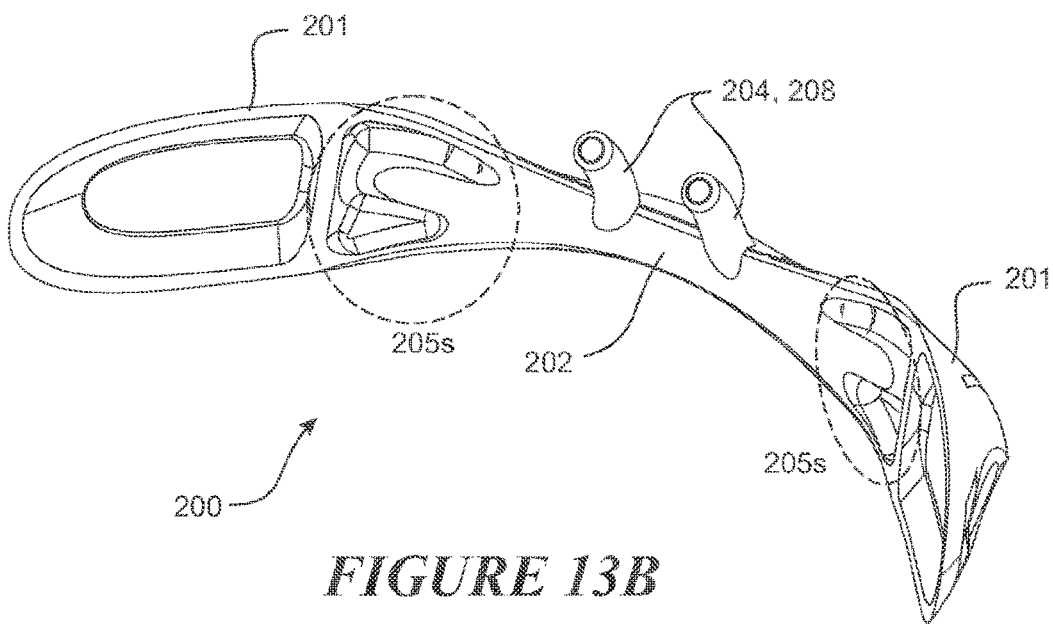
Figure 13C:
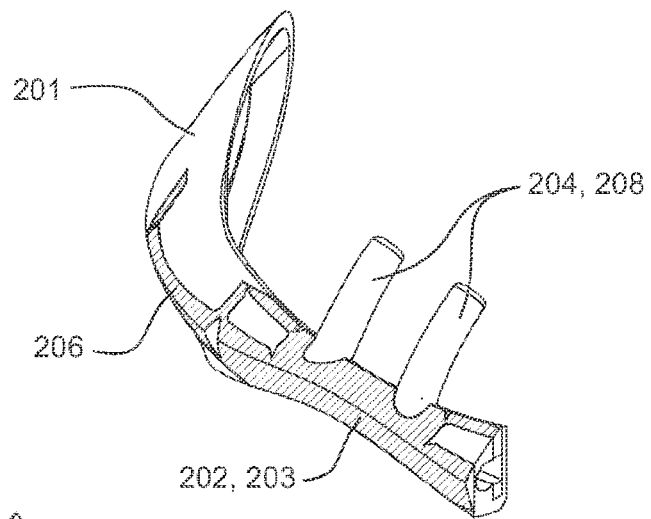
Figure 13D:
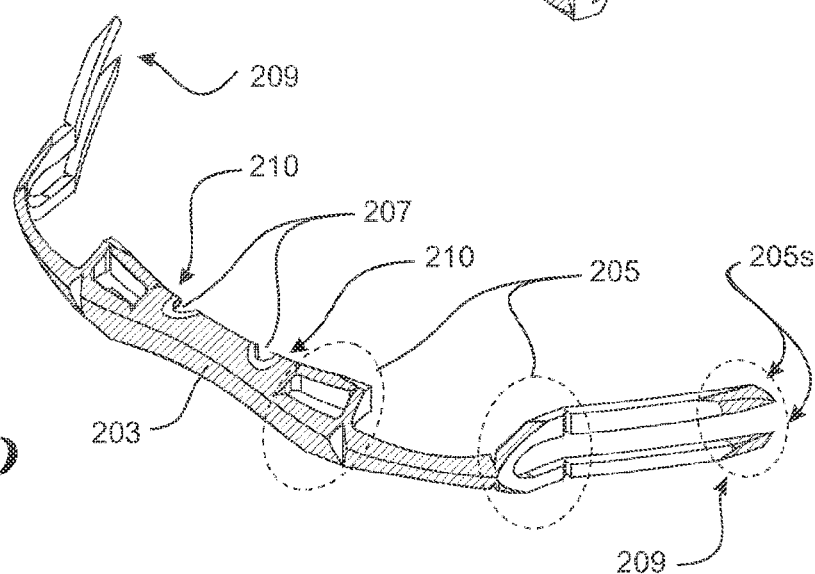
Figure 13E:
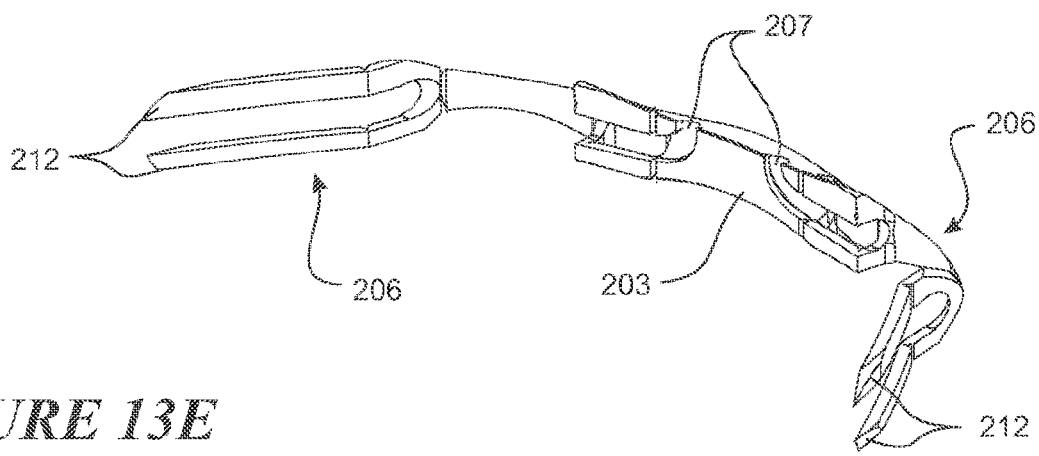
Figure 14A:
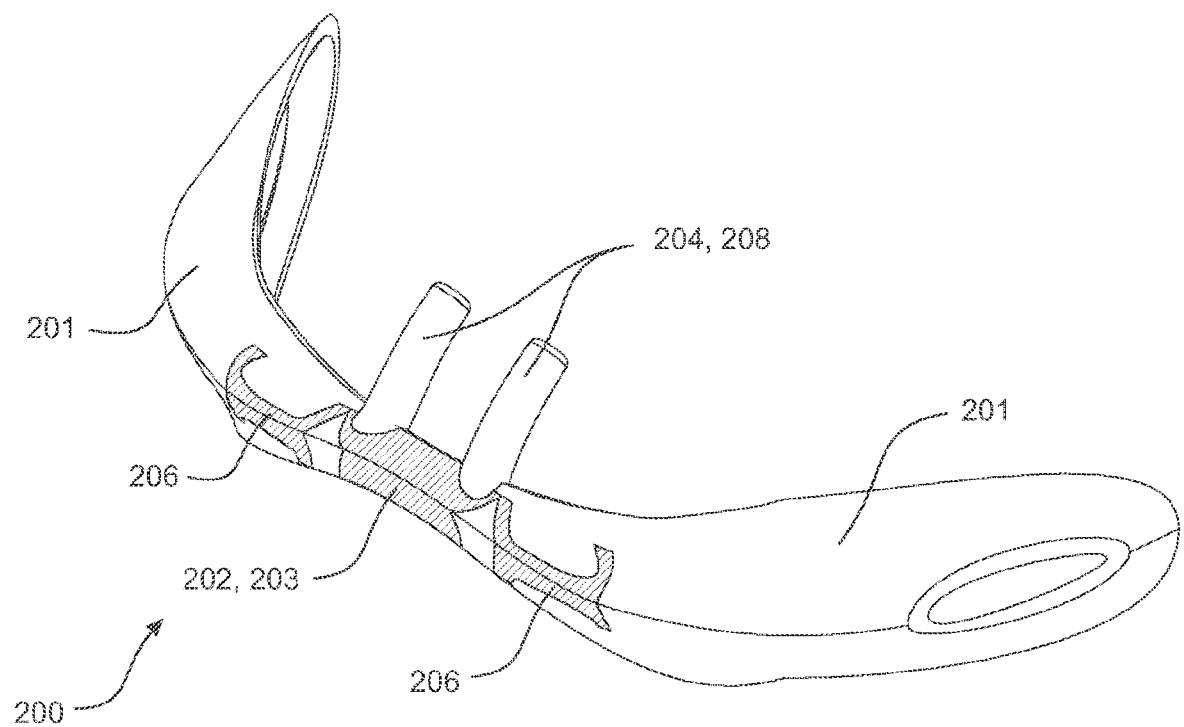
Figure 14B:
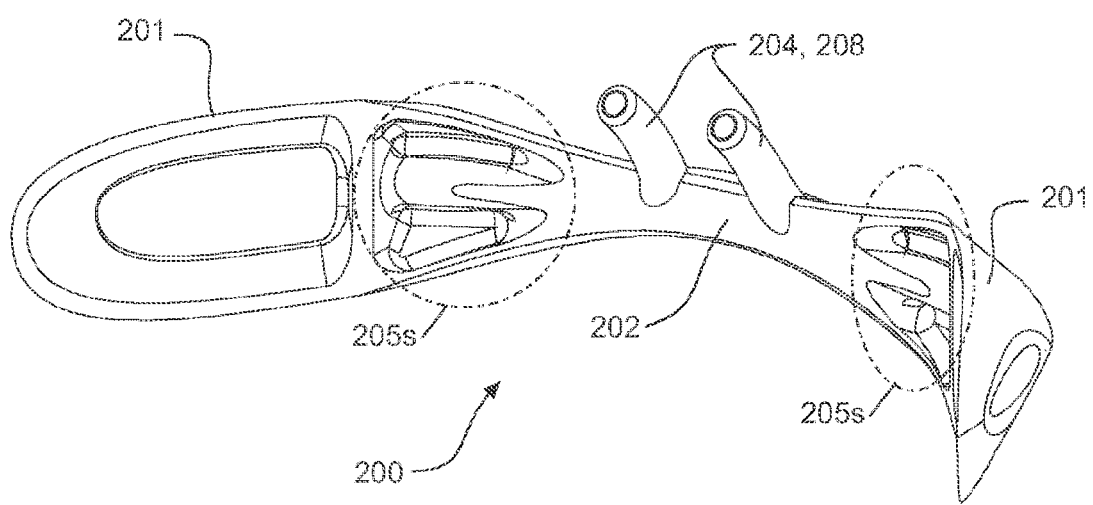
Figure 15A:
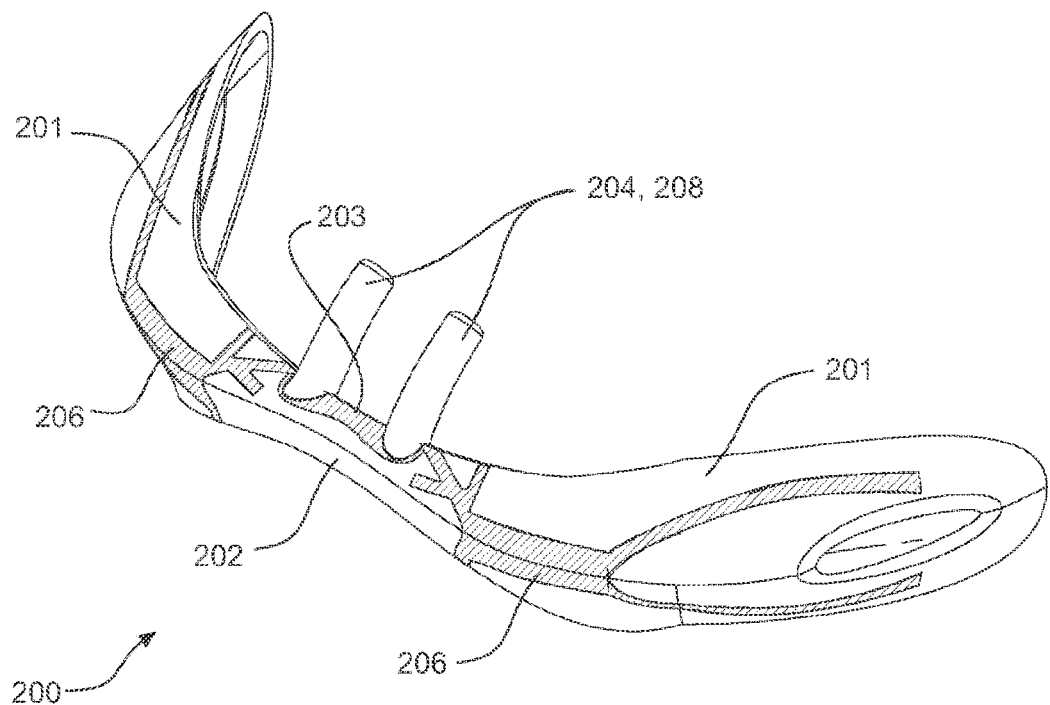
Figure 15B:
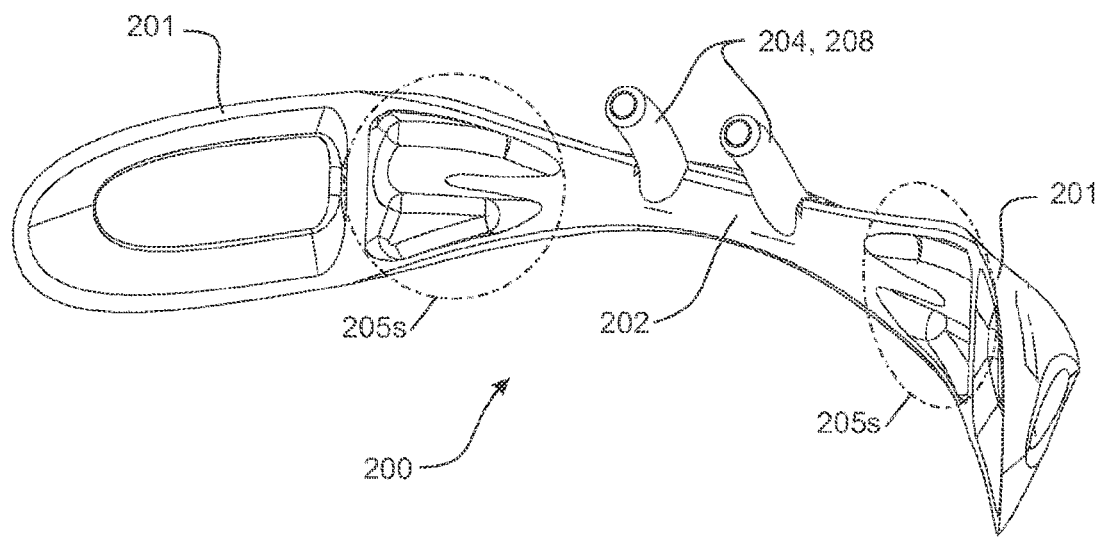
Figure 16A:
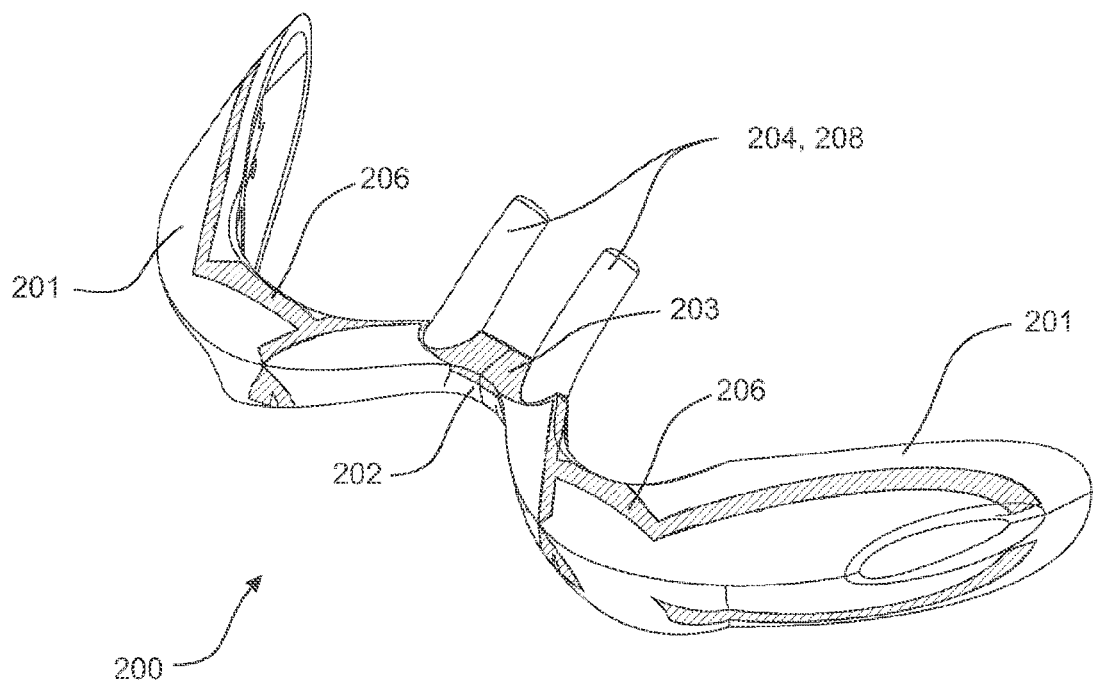
Figure 16B:
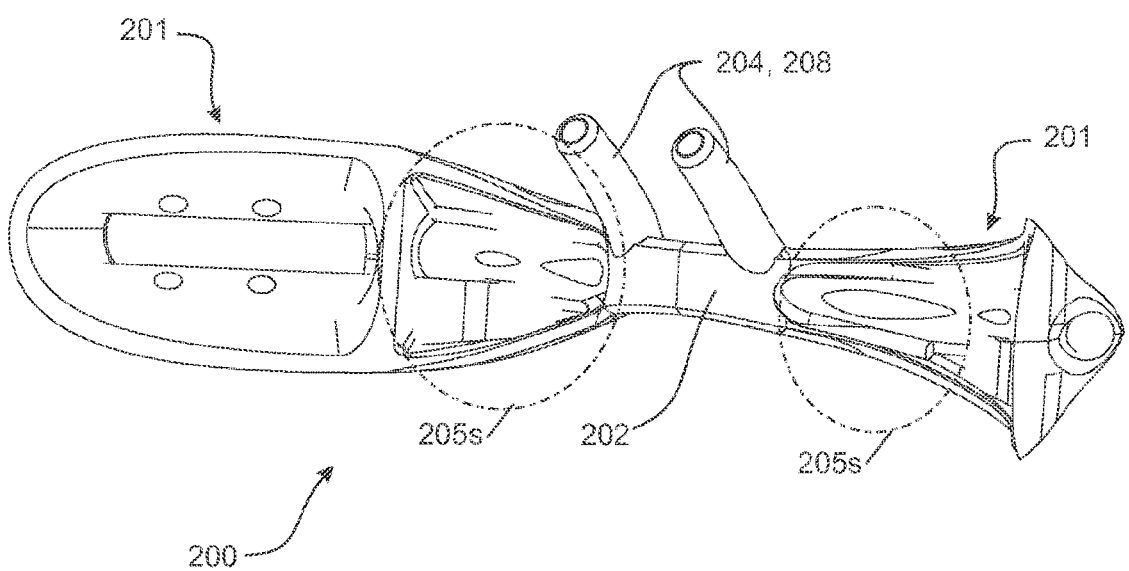

The embodiment of FIGS. 10A-E, illustrates at least two regions (or sites) 205, as well as the optional additional region (or site) 205 as may be facilitated at the junction at the outer end of a side arm element 206 with a side arm 201. In this embodiment, a first region (or site) 205 may allow for a first preferential direction or set of directions which is different to the preferential direction or set of directions provided for by the subsequently arranged regions (or sites) 205 located more outwardly this first region (or site) 205. For example, the region (or site) 205 located at the more inward position 210 of the side arm element 206 provides for a complex or multiple flex or bending facility, for example in multiple (different) planes. As is shown in FIG. 10C, the side arm 201 is shaped or formed so as to include a lumen or a void space or cavity or other recess 213 for locating or housing a gas supply conduit, or at least forming a part of such a lumen or passage. The bridge portion element 203 is also shaped so as to facilitate such an item 213 when in combination with the side arm 201, for example see FIG. 10E.

Each of FIGS. 11-16 illustrate yet further arrangements of side arm elements 206 utilised in conjunction with a bridge portion 202, a bridge portion element 203 and side arms 201. In each of these embodiments, the side arm 201 is shaped or formed so as to include a lumen or a void space or cavity or other recess 213 for locating or housing a gas supply conduit, or at least forming a part of such a lumen or passage. The bridge portion element 203 is also shaped so as to facilitate such an item 213 when in combination with the side arm 201. Still further, each of these figures Illustrates variety and plurality of arranged regions (or sites) 205 which provide for a set or array, whether the same or different or other combinations, of bending or flexure or hinging etc that is more preferential in a first direction or first set of directions than another direction or another set of directions. Accordingly, a patient interface 200 can be provided with any one or more of the configurations provided herein, or alternative combinations thereof.

As shown in the various figures, a material(s) used for the side arm 201 can form a part of the dynamic capabilities of a side arm element 206, or the side arm 201 itself. For example, the side arm 201 material can surround or encapsulate or envelope (whether partially or wholly) the side arm element 206. The side arm 201 material can then be Interposed between or about the minor projections 211 or the side arm element limbs 212. In this way, the side arm 201 material can provide for a resilience or resistance to flexure or bending or hinging, or may act to provide such a resistance, yet absorb the forces or movements experienced by the patient interface.

In use, the side arm or arms 201 is/are to be positioned upon a user's face, for example upon or about the facial cheeks. A headgear of a suitable type (such as that of a headstrap and a back-strap or other variants) is connectable to the side arms 201 to provide for a retention system to hold or retain the patient interface 200 upon a user. In particularly preferred embodiments of this Invention, the patient interface 200 is a nasal cannula Including a pair of side arms 201 and a pair of nasal prongs 208 in fluid connection with gas outlets 204.

Figure 18:
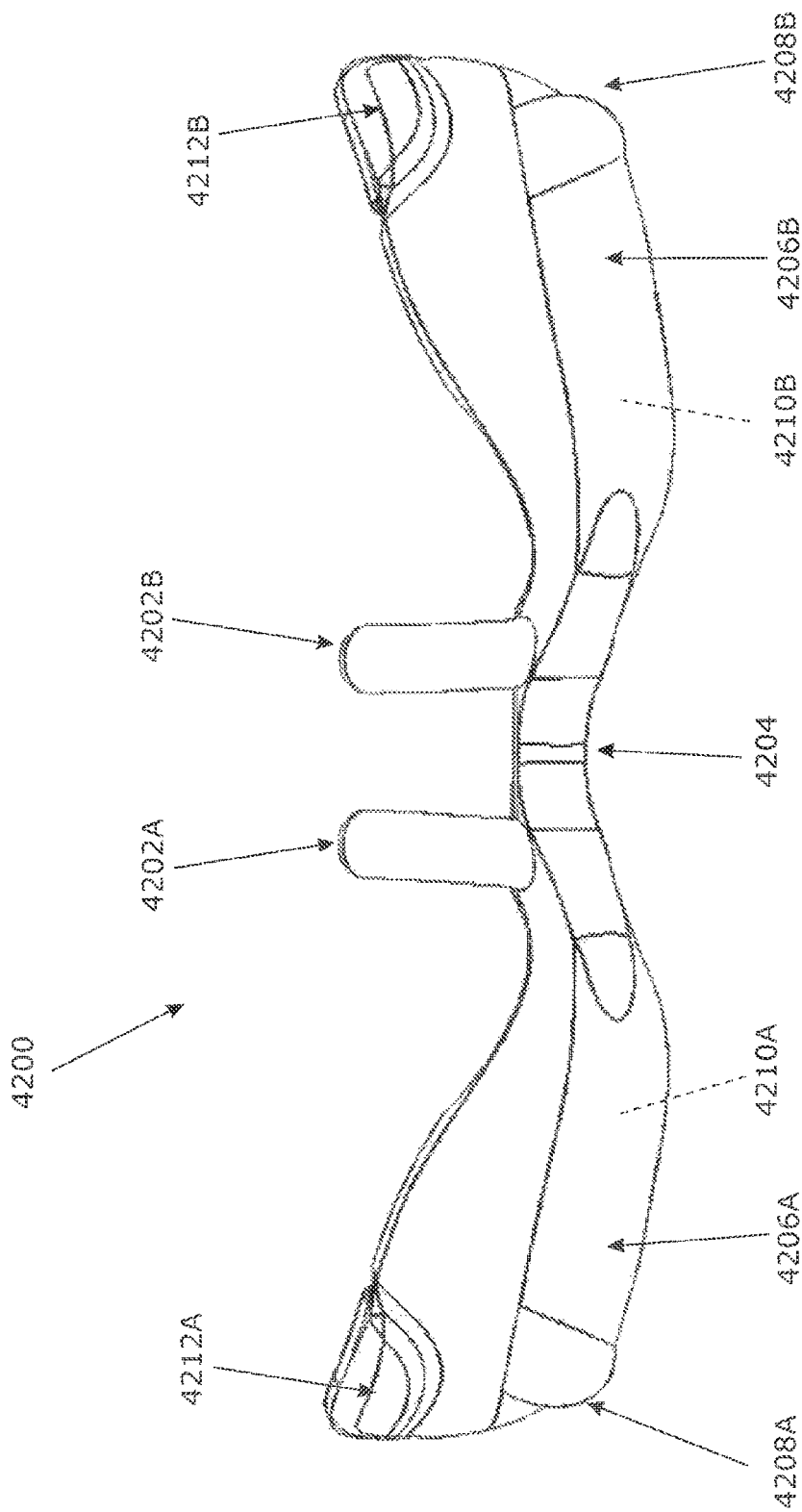
FIG. 18 shows a front view of a patient interface.

With reference to the non-limiting exemplary embodiment Illustrated in FIG. 18, a patient interface 4200 is shown. In the illustrated configurations the patient interface 4200 comprises a nasal cannula. In some alternative configurations the patient interface 4200 may comprise a sealing or non-sealing Interface. For example, the patient interface 4200 may comprise a nasal mask, an oral mask, an oro-nasal mask, a full face mask, a nasal cannula, an unsealed oro-nasal Interface, a nasal pillows mask, an endotracheal tube, a combination of the above or some other gas conveying system or apparatus. Certain features, aspects and advantages of the illustrated nasal cannula may be envisaged in other patient interfaces.

With further reference to FIGS. 18-23, the patient interface 4200 comprise first and second nasal delivery elements 4202A, 4202B adapted to rest in the nares of a patient. The Illustrated nasal delivery elements 4202A, 4202B are substantially tubular and direct gases passing through the patient interface 4200 to the patient. The nasal delivery elements 4202A, 4202B are shaped and angled such that they generally extend Inwardly towards the septum of the patient in use. The nasal delivery elements 4202A, 4202B end in tips that, in use, point towards the back of the patient's head. It should be understood that in some configurations, the nasal delivery elements 4202A, 4202B could have different shapes. For example, although the average cross-section of the nasal delivery elements 4202A, 4202B in the illustrated configurations is substantially circular, in some configurations the cross-section of the nasal delivery elements 4202A, 4202B could be substantially ellipsoidal, substantially square, or substantially rectangular. In some configurations, the cross-section of the nasal delivery elements 4202A, 4202B could vary along the length of the nasal delivery elements 4202A, 4202B. In some configurations, the first and second nasal delivery elements 4202A, 4202B may have different characteristics. For example, the first nasal delivery element 4202A may be smaller or shorter than the second nasal delivery element 4202B. Some examples of nasal delivery elements having different characteristics are shown in commonly-owned WO2015/020540, the disclosure of which is hereby Incorporated by reference in its entirety. In some configurations, only one nasal delivery element may be used. In some configurations, more than two (for example, three or four) nasal delivery elements may be used.

The first and second nasal delivery elements 4202A, 4202B extend from first and second side arms (also referred to as first and second arms) 4206A, 4206B of the patient Interface 4200. The first and second side arms 4206A, 4206B comprise Internal gas delivery lumen 4210A, 4210B that receive gases from gases inlets 4208A, 4208B of the first and second side arms 4206A, 4206B and channel the gases to the first and second nasal delivery elements 4202A, 4202B. The gases inlets 4208A, 4208B Interface with a pair of gases delivery conduits 4218A, 4218B (see FIG. 1). In the illustrated configuration, the gases delivery conduits 4218A, 4218B are integrally formed or Inseparably connected to the gases inlets 4208A, 4208B. The gases delivery conduits 4218A, 4218B in turn are integrally formed or Inseparably connected to a gas conduit connector 222. The gas conduit connector 222 is configured to releasably Interface with a complementary connector 118 in pneumatic communication with the gas conduit 110 (described elsewhere in this disclosure with reference to FIG. 1). Other configurations are contemplated. For example, in some configurations, the patient interface 4200 may be configured such that the first and second nasal delivery elements 4202A, 4202B receive gases from a single Internal gas delivery lumen positioned in either the first or second side arms 4206A, 4206B, and the single Internal gas delivery lumen in turn receives gases from a single gases delivery conduit. In some configurations, no such gases delivery conduits 4218A, 4218B are necessary, and one or more gases inlets 4208A, 4208B may Interface directly with the gas conduit 110 (or Indirectly via the complementary connector 118 and/or gas conduit connector 222). In some such configurations, the first or second side arms 4206A, 4206B may be integrally formed or be in the form of a single continuous piece together with the gas conduit 110. In some configurations one or more of the gases delivery conduits 4218A, 4218B are removably coupled to one or more of the gases inlets 4208A, 4208B. In some configurations one or more of the gases delivery conduits 4218A, 4218B are removably coupled to gas conduit connector 222.

The first and second side arms 4206A, 4206B of the patient interface 4200 are adapted to rest on the face of the patient. In the illustrated configuration, the first and second side arms 4206A, 4206B are adapted to rest on opposing cheeks of the patient. To fix the first and second side arms 4206A, 4206B in place on the face of the patient, patient facing sides of the first and second side arms 4206A, 4206B are provided with attachment structures 4216A, 4216B adapted to maintain the patient interface 4200 in a desired alignment with the face (e.g. In this configuration, such that the nasal delivery elements 4202A, 4202B are comfortably and non-sealingly positioned in the nares). The attachment structures 4216A, 4216B are configured such that they can interface with fixation structures attached to the face. In some configurations, the attachment structures 4216A, 4216B and the fixation structures can be structured such that they are complementary to one another. For example, the attachment structures 4216A, 4216B may comprise 'loop' portions (constructed from, for example, textiles or plastics) that are adhered or otherwise secured to patient facing sides of the first and second side arms 4206A, 4206B and the fixation structures may comprise 'hook' pads that are adhered or otherwise secured to the face (e.g. for a 'hook-and-loop' style connection). Some examples of hook-and-loop style connections are disclosed in commonly-owned WO2012/053910, the disclosure of which is hereby Incorporated by reference in its entirety. Other configurations are contemplated. For example, in some configurations, the attachment structures 4216A, 4216B may Interface directly with the face (e.g. through the use of adhesive pads or other structures). In some configurations, only a single attachment structure may be used, or more than two (for example, three or four) attachment structures may be used. In some configurations, the attachment structures 4216A, 4216B may comprise features other than 'loop' portions. For example, the attachment structures 4216A, 4216B may comprise 'hook' portions that Interface with complementary 'loop' portions on the fixation structures. As another example, the attachment structures 4216A, 4216B may comprise snap-fit features or other mechanical Interlock features that Interface with features on the fixation structures. In some configurations, the patient interface 4200 may not comprise attachment structures. In some configurations, the patient interface 4200 may comprise headgear adapted to retain the patient interface 4200 in a desired orientation or alignment on the face. The headgear may comprise, for example, one or more straps configured to extend around the head of the patient, buckles to adjust the tightness of the straps by modifying the effective length of the straps, caps, coifs, hats, helmets, and/or one or more other features.

A bridge 4204 connects the first and second side arms 4206A, 4206B. The bridge 4204 is an extension of the first and/or second side arms 4206A, 4206B that comprises no internal gas lumen, and serves to help keep the nasal delivery elements 4202A, 4202B in a desired orientation with respect to one another. Other configurations are contemplated. For example, in some configurations, the bridge 4204 could be constructed from a second material or a different material to the rest of the interface e.g. the first and second arms. In some such configurations, only one of the side arms 4206A, 4206B comprises an internal gas lumen and/or gases inlet. In some configurations the bridge 4204 extends between a first connection point on the first side arm 4206A and a second connection point on the second side arm 4206B. In some such configurations, the first and/or second connection points may comprise one or more moveable joints. In some such configurations, the one or more joints may comprise one or more hinging regions. As part of the hinging regions there may be hinged joints. In some such configurations, the one or more joints may comprise one or more pivoting joints. The one or more joints may allow for movement of the bridge 4204 relative to the first and/or second side arms 4206A, 4206B.

Figure 19:
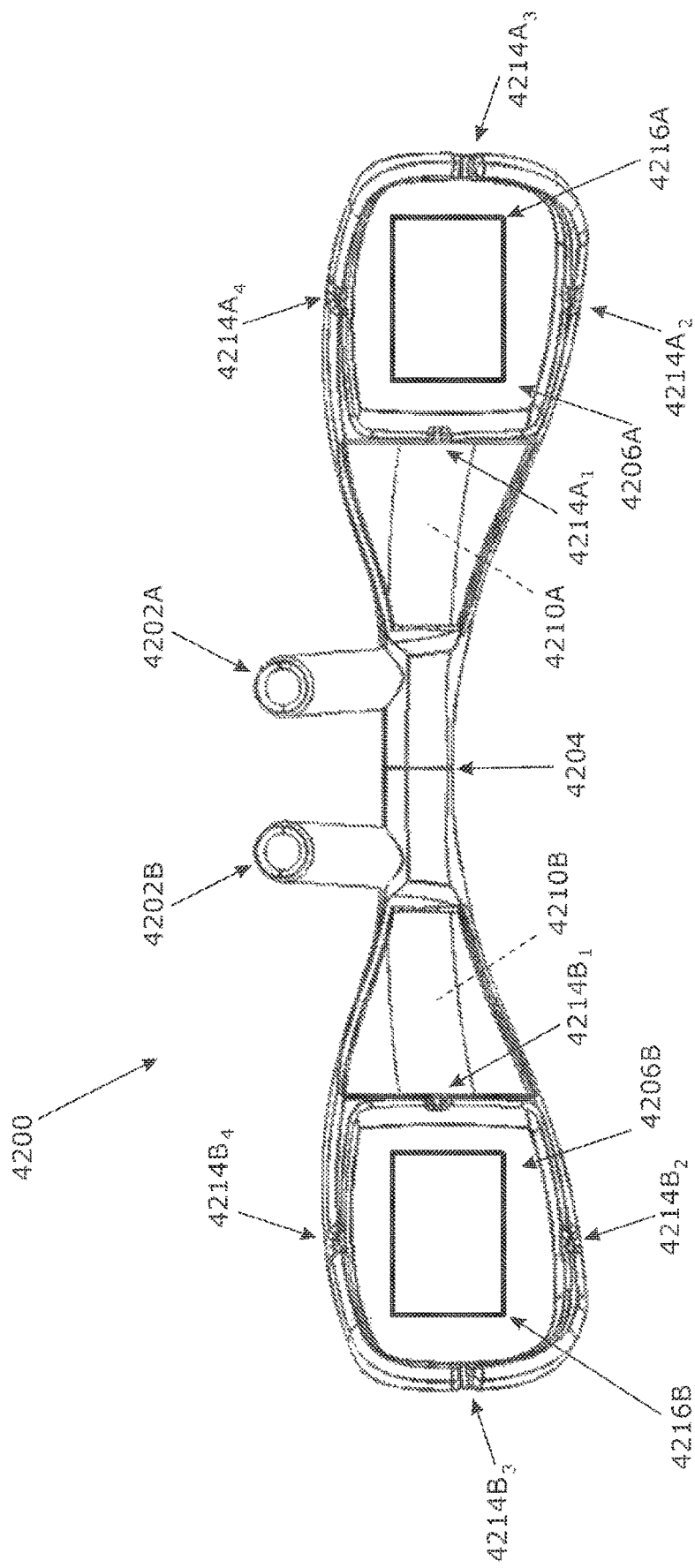
FIG. 19 shows a rear view of the patient interface shown in FIG. 2.
Figure 20:
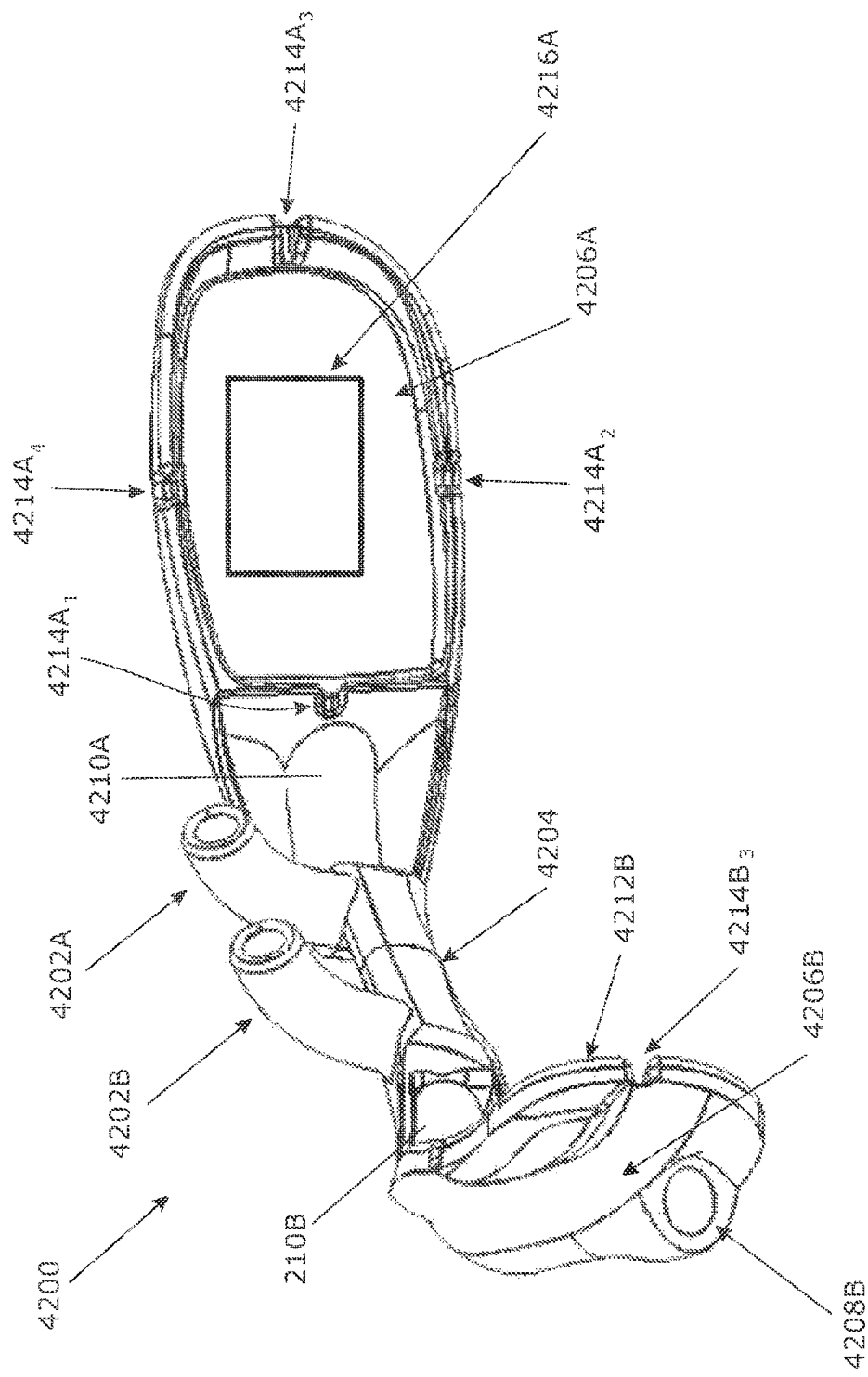
FIG. 20 shows a side perspective view of the patient interface shown in FIG. 2.
Figure 23:
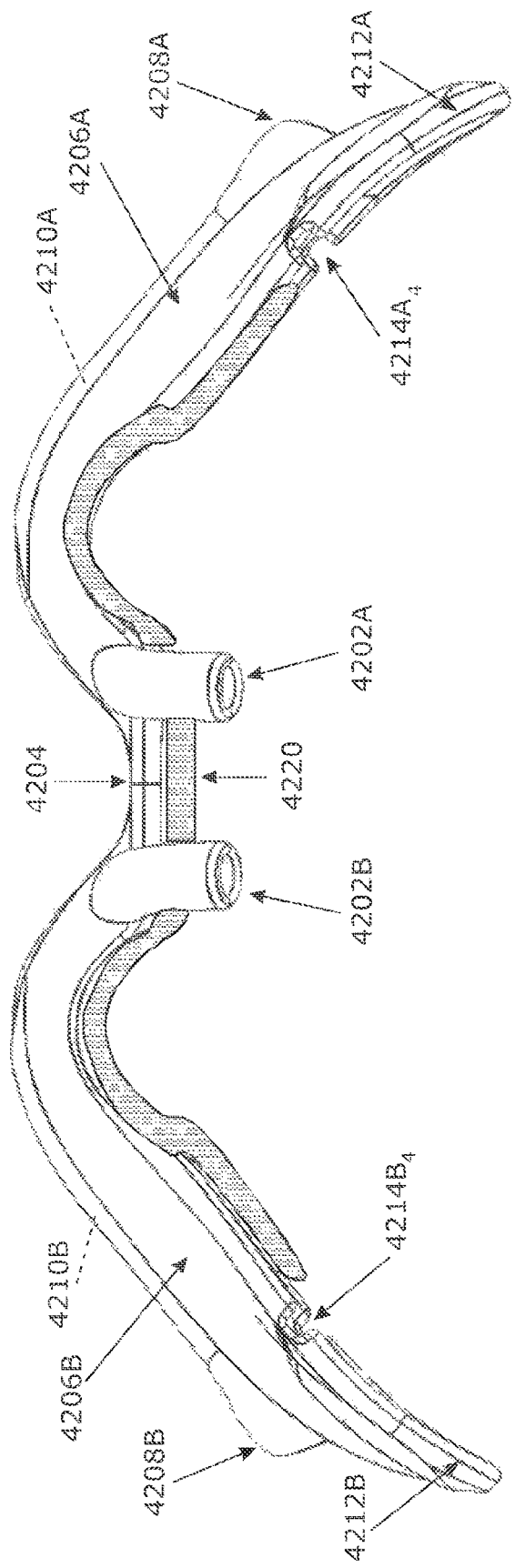
FIG. 23 shows an elevated rear view of a patient interface.

As seen in FIG. 19, the first and second side arms 4206A, 4206B decrease in width as they extend towards the nasal delivery elements 4202A, 4202B and/or bridge 4204. The attachment structures 4216A, 4216B are positioned on relatively wide portions of the first and second side arms 4206A, 4206B proximal to the outer edges of the first and second side arms 4206A, 4206B to Improve stability of the patient interface 4200 on the face when the attachment structures 4216A, 4216B are used together with the fixation structures. Additionally, as seen in FIG. 23, the patient interface 4200 is generally shaped or configured such that it substantially matches contours of the face. The patient interface 4200 is also configured such that when forces $F_1$ are exerted on the first and second side arms 4206A, 4206B urging the outer edges of the side arms 4206A, 4206B Inwardly towards the bridge 4204 (which may be exerted, for example, due to compression of the face against pillows or due to facial expression of emotional states), inner portions of the side arms 4206A, 4206B and/or the bridge 4204 act as hinging regions to cause forces $F_2$ to be exerted on the nasal delivery elements 4202A, 4202B, causing the nasal delivery elements 4202A, 4202B to move towards the patient. This motion of the nasal delivery elements 4202A, 4202B towards the patient can help to retain the nasal delivery elements 4202A, 4202B in the nares of the patient.

With further reference to FIG. 18, outer edges of the first and second side arms 4206A, 4206B comprise detachment structures 4212A, 4212B. The detachment structures 4212A, 4212B are positioned on outer portions of the side arms 4206A, 4206B spaced apart from the gases inlets 4208A, 4208B. In the illustrated configuration, the detachment structures 4212A, 4212B are tabs that comprise inner regions of reduced thickness relative to adjacent portions of the side arms 4206A, 4206B. Outside of the inner regions of the tabs and towards the outer edge of the side arms 4206A, 4206B, the tabs additionally comprise outer regions of normal thickness or Increased thickness relative to the same adjacent portions of the side arms 4206A, 4206B. The tabs are configured such that the outer regions may be grasped by the patient or another person (for example, a healthcare professional such as but not limited to a nurse or physician) and pulled. When pulled, the outer regions may rotate around the inner regions and sufficient force may be exerted on the patient interface 4200 such that the attachment structures 4216A, 4216B are detached from the fixation structures present on the face. The detachment structures 4212A, 4212B thus may be used to more easily detach the patient interface 4200 from the face. Other configurations are contemplated. For example, in some configurations, only a single detachment structure may be positioned on a single body of the patient interface 4200. In some configurations, the patient interface 4200 may comprise more than two (for example, three or four) detachment structures. In some configurations, the detachment structures 4212A, 4212B may be positioned on other portions of the side arms 4206A, 4206B or on other portions of the patient Interface 4200. In some configurations, the detachment structures 4212A, 4212B may comprise structures other than tabs. For example, the detachment structures 4212A, 4212B may comprise flat extensions of the first and/or second side arms 4206A, 4206B that can be pulled or otherwise manipulated to separate the patient interface 4200 from the face.

Figure 21A:
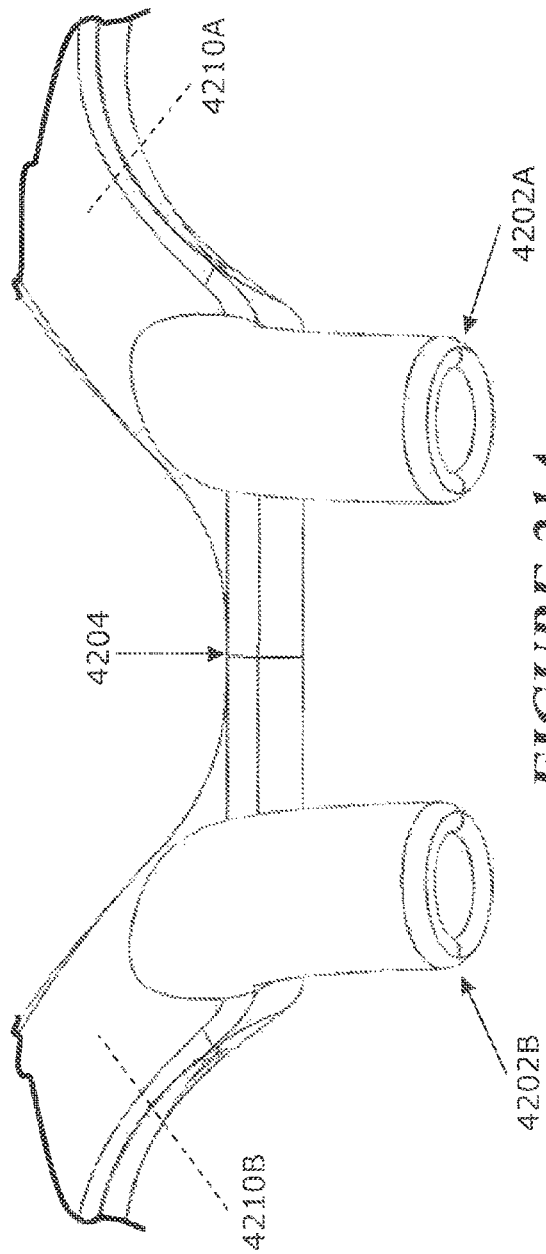
FIG. 21A shows a close-up of the elevated rear view shown in FIG. 21.
Figure 21B:
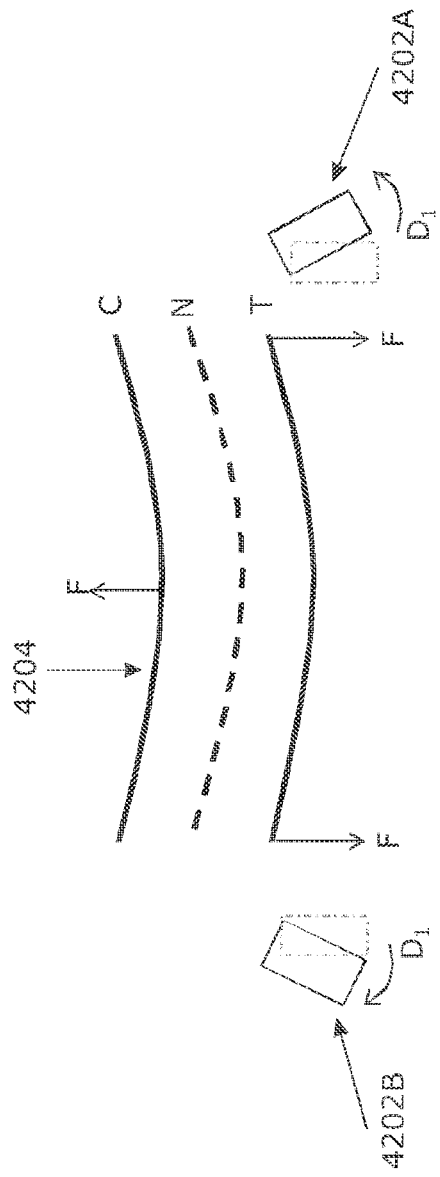
FIG. 21B shows a schematic Illustrating forces exerted on the patient interface shown in FIG. 21A.

With reference to FIGS. 21A and 21B, a close up view of the patient interface 4200 is shown. FIG. 24B in particular shows a schematic diagram of the bridge 4204 and nasal delivery elements 4202A, 4202B and Illustrates the bridge 4204 as a beam, showing the neutral axis N, compression side C, and tension side (e.g. patient facing side) T of the bridge 4204. As described elsewhere in this disclosure with reference to FIG. 23, as forces are exerted on the first and second side arms 4206A, 4206B to urge the side arms Inwardly towards the bridge 4204, the shape of the patient interface 4200 causes the nasal delivery elements 4202A, 4202B to move towards the patient such that the nasal delivery elements 4202A, 4202B are retained in the nares of the patient. However, some of the forces F that act to urge the nasal delivery elements 4202A, 4202B can also act to urge the nasal delivery elements 4202A, 4202B apart, causing them to be displaced from one another. In some cases, the nasal delivery elements 4202A, 4202B are caused to splay apart, rotating displacement angles D1 in substantially opposing directions from one another. As shown in FIG. 21B, the forces F cause the patient facing side of the bridge 4204 to be under tension, effectively lengthening and curving the patient facing side of the bridge 4204 and causing the nasal delivery elements 4202A, 4202B to splay (see the dashed outlines in FIG. 21B representing the unsplayed positions of the nasal delivery elements 4202A, 4202B). The opposing side of the bridge 4204 similarly becomes compressed and generally does not retain its curvature or shape due to the forces F. When the nasal delivery elements 4202A, 4202B splay apart from one another, in some cases the nasal delivery elements 4202A, 4202B distort against the inner sides of the nares and can 'pop' or be displaced to lie outside of the nares, which can be inconvenient for the patient or another person servicing the patient.

FIGS. 22A and 22B demonstrate a modified patient interface 4200. The modified patient interface 4200 comprises a supporting structure 4220 positioned on a patient facing side of the bridge 4204. In the illustrated configuration, the supporting structure 4220 is configured to stiffen the bridge 4204 to resist the tendency for the nasal delivery elements 4202A, 4202B to splay when forces F are applied to the bridge 4204 (e.g. the supporting structure 4220 functions as a stiffening structure 4204). Effectively, as shown in schematic diagram of FIG. 22B, the presence of the supporting structure 4220 on the patient facing side of the bridge 4204 causes the neutral axis N to shift from being approximately in the center or middle of the bridge 4204 to being closer to the tension side T of the bridge 4204. The tensile strength of the bridge 4204 may be improved. For the same force F, then, the nasal delivery elements 4202A, 4202B will only be displaced by smaller displacement angles D2 and may be less likely to be distort against the inner sides of the nares or be displaced to lie outside of the nares.

In some configurations, the supporting structure 4220 is at least in part constructed from a textile material. For example, the supporting structure 4220 can be constructed from a woven, non-woven or knitted textile material. In the illustrated configuration, the supporting structure 4220 is constructed from a polymer (e.g. polypropylene) sheet. Constructing the supporting structure 4220 from a textile material gives the supporting structure 4220 sufficient strength to move the neutral axis and resist splaying of the nasal delivery elements 4202A, 4202B. Additionally, the use of textile materials on the patient facing side of the bridge 4204 may maintain or Improve the comfort of the patient interface 4200 on the face and help to reduce or prevent pressure sores arising as a consequence of extended use of the patient interface 4200 on the face. However, in other configurations, other forms of supporting structures, including but not limited to sheets, films, plates, panels, slabs and other masses of various shapes and sizes, and other materials, including but not limited to polymers, plastics, metals, ceramics, cloths, waxes, and other materials of various qualities may be used for the supporting structure 4220. Although in the Illustrated configuration the supporting structure 4220 is approximately of constant thickness over the entire length and width of the supporting structure 4220, in some configurations the supporting structure 4220 may have uneven thickness along the length and/or width of the supporting structure 4220 (for example, in some cases the supporting structure 4220 may have a 'bumpy' or 'wavy' patient facing surface).

In some configurations, the supporting structure 4220 is adhered to the patient facing side of the bridge 4204. In some configurations, the supporting structure 4220 and/or bridge 4204 are configured to rest against the philtrum of the user. In some configurations, the supporting structure 4220 may be attached to the patient facing side of the bridge 4204 according to other joining structures or means. For example, in some configurations, the supporting structure 4220 may be overmoulded onto the patient facing side of the bridge 4204, adhered to the patient facing side of the bridge 4204 (for example, via the use of one or more adhesives or glues), melt-bonded to the patient facing side of the bridge 4204, welded via the use of ultrasonic or high frequency welding, sown, stapled, screwed and/or bolted. In some configurations, the supporting structure 4220 may be chemically bonded to the bridge 4204. In some such configurations, the supporting structure 4220 may be constructed from the same material (for example, the same plastic, e.g. polypropylene) as the bridge 4204 (and possibly the same material as other portions of the patient interface 4200). For example, if the supporting structure 4220 and the bridge 4204 are both constructed from polypropylene (in this example the supporting structure 4220 being a polypropylene textile and the bridge 4204 being another polypropylene mass), the chemical bonding may be easier to facilitate and may allow for a more seamless and aesthetically acceptable join between the supporting structure 4220 and the bridge 4204.

Figure 24:
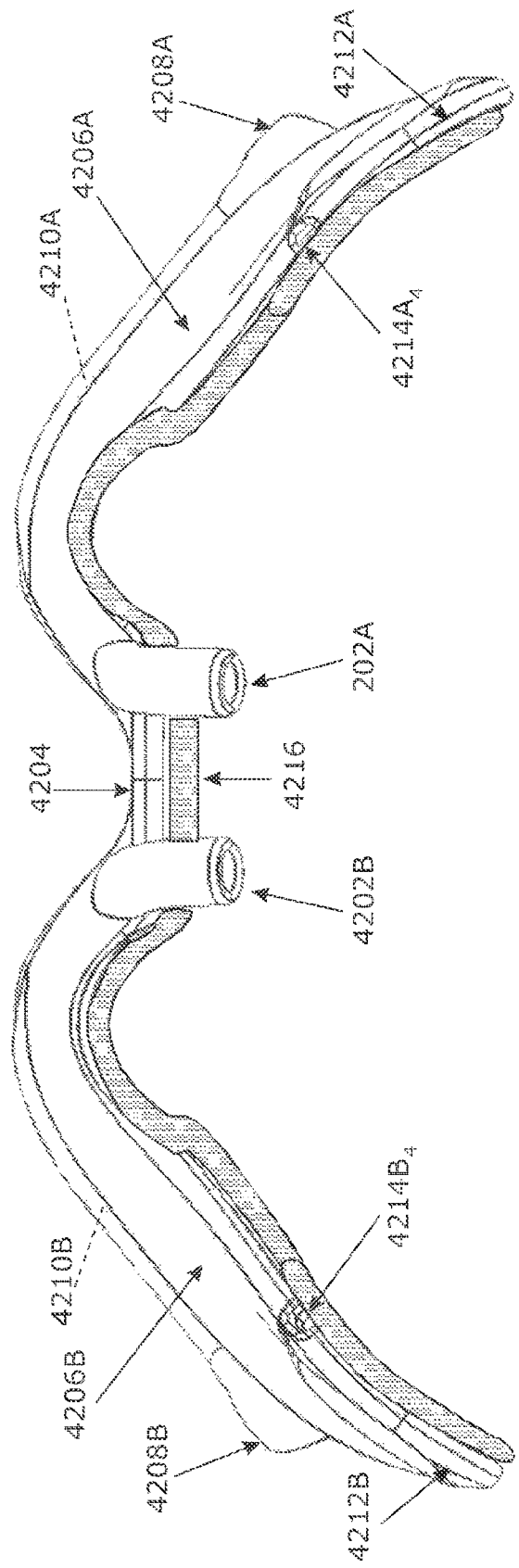
FIG. 24 shows an elevated rear view of a patient interface.

It should be understood that the supporting structure 4220 need not necessarily be located only on the patient facing side of the bridge 4204. In some configurations, and as seen in FIG. 24, the supporting structure 4220 may extend across at least a portion of the first and/or second side arms 4206A, 4206B. The supporting structure 4220 may be present in the form of a strip having substantially the same width as the bridge 4204 over the length of the supporting structure 4220. In other configurations, the supporting structure 4220 may decrease in width over the length of the supporting structure 4220. In still other configurations, the supporting structure 4220 may Increase in width over the length of the supporting structure 4220. In some such configurations, the width of the supporting structure 4220 increases such that it comes near to or matches the width of the first and/or second side arms 4206A, 4206B (which in the illustrated configuration Increase in width as they extend outwardly from the bridge 4204 and/or nasal delivery elements 4202A, 4202B). In some configurations, and as seen in FIG. 23, the supporting structure 4220 may extend over the entire length of the patient interface 4200, including over the bridge 4204 and over the first and second side arms 4206A, 4206B. In some configurations, the supporting structure 4220 may be discontinuous over the length of the supporting structure 4220 (for example, the supporting structure 4220 may be in the form of three non-contiguous segments).

In some configurations, if the supporting structure 4220 extends into the sections of the patient facing portion of the side arms 4206A, 4206B that normally hold one or more of the attachment structures 4216A, 4216B, the supporting structure 4220 could be configured to be used as one or more of the attachment structures 4216A, 4216B. In some such configurations, one or more of the attachment structures 4216A, 4216B need not be present, and the supporting structure 4220 can be configured to fulfill the function of one or more of the attachment structures 216, 4216B. For example, the supporting structure 4220 may comprise 'loop' sections that may Interface with complementary 'hook' sections on fixation structures secured to the face. As another example, the supporting structure 4220 may be directly adhered to the face.

It should be understood that the supporting structure 4220 need not necessarily be located on patient facing sides of the patient interface 4200 (including but not limited to the first side arm 4206A, second side arm 4206B, and/or bridge 4204). In some configurations, the supporting structure 4220 may be positioned on other sides of the patient Interface 4200 (including but not limited to sides of the bridge 4204, first side arm 4206A and/or second side arm 4206B that face away from the face and/or oppose one or more patient facing sides) given that the material and/or structure and/or configuration of the supporting structure 4220 shifts the neutral axis in an appropriate way such that the prongs resist splaying upon the application of forces urging the first and/or second side arms Inwardly towards the bridge 4204 and/or first and/or second nasal delivery elements 4202A, 4202B. In some configurations, the supporting structure 4220 rests on a non-user facing side of the bridge 4204. In some configurations, the supporting structure 4220 rests on a non-user facing side of the first and/or second side arms 4206A, 4206B. In the illustrated configuration, the supporting structure 4220 is configured to resist tension forces. The supporting structure 4220 provides resistance to bending of the bridge 4204 by shifting the neutral axis. In some configurations, the supporting structure 4220 can resist compression to shift the neutral axis. In further alternative configurations, the supporting structure 4220 is configured to resist shear forces.

The patient interface of the present disclosure advantageously provides Improvements in the delivery of respiratory care with a ventilator or a gases supply, or in combination with a gas humidification system or other gases supply systems for supplying gases to a patient, or for delivery of any other gases to a patient.

With reference to the embodiments shown in FIGS. 25A to 26C, a patient Interface 2201/2301, such as a nasal cannula, has a pair of respective left 2201/2301 and right 2303/2303 side arms (also referred to as body portions), to be located, in-use upon a face of a user, and at least one, and preferably a pair of, nasal prong(s) 2205/2305, 2207/2307 to be inserted into, or to direct a flow of gas into, a nare or the nares of the user's nose. The patient interface 2201/2301 also has a bridge 2209/2309 attached to and extending from a connection point with the left side arm or body portion to a connection point with the right side arm or body portion. The bridge 2209/2309 comprises substantially Inelastic components.

One or each of the respective connection points has a primary moveable joint 2211/2311, 2213/2313, such as a hinged or pivoting joint, allowing for a primary movement of the bridge relative to a respective side arm or body portion. The primary moveable joint enables relative rotation between the end of the bridge 2209/2309 and the respective side arm or body portion about at least one axis. The primary movement joint is one or a combination of: an articulating joint, a pin-and-barrel type joint, a ball and socket type joint. The Interface also has a facial pad 2215/2315, 2217/2317 associated with each side arm. Each facial pad is contoured to engage a region of the user's face.

Figure 25A:
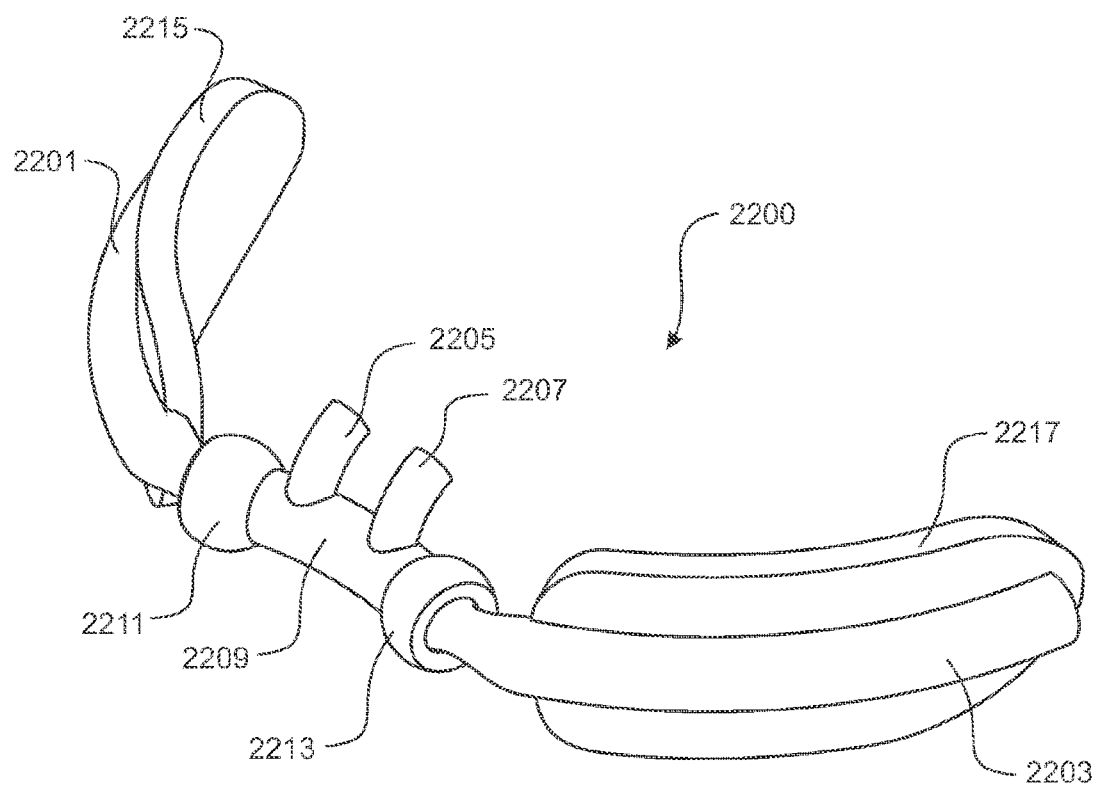
FIGS. 25A to 25C show an embodiment of a patient interface from various angles.
Figure 25B:
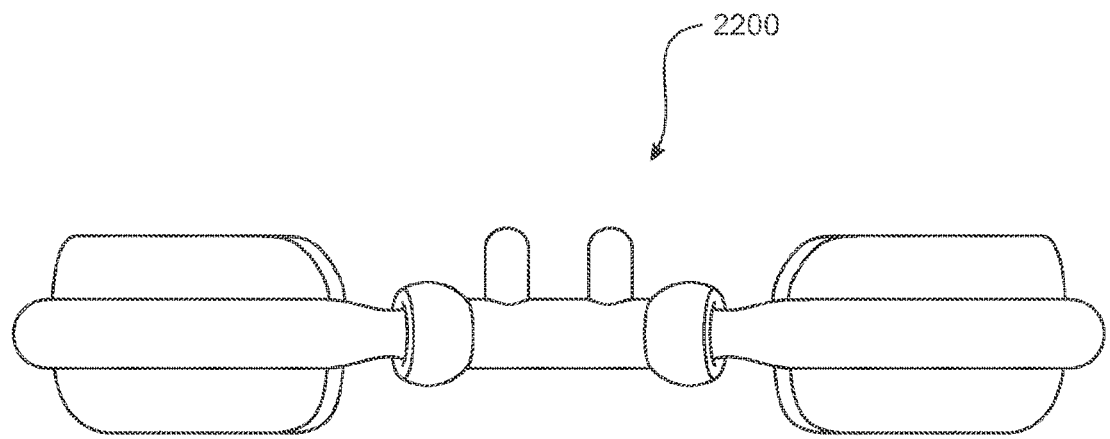
Figure 25C:
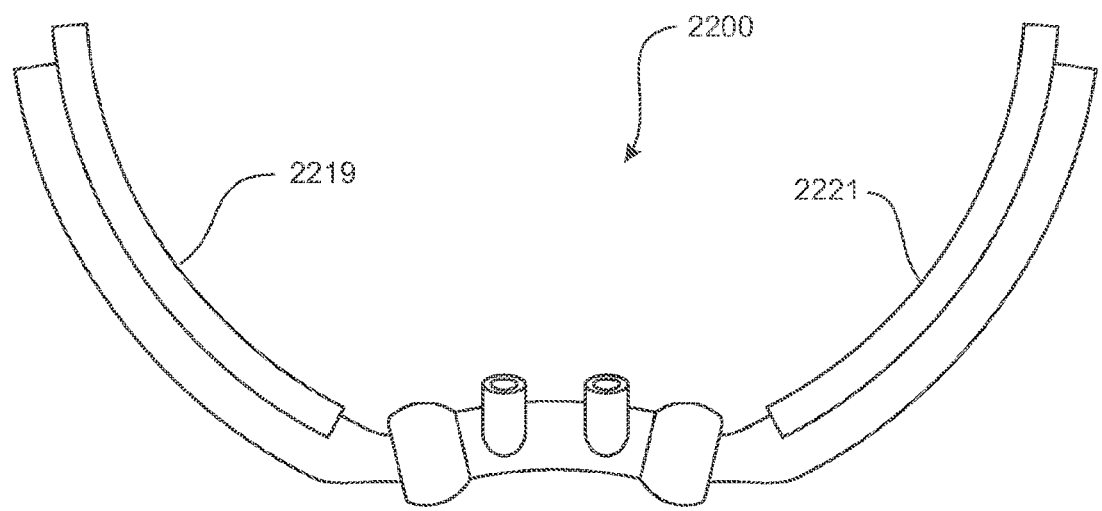

With reference to the embodiment shown in FIGS. 25A to 25C, the bridge 2209 includes the at least one, and preferably the pair, of nasal prong(s) 2205, 2207. Each primary moveable joint is provided between an end of the bridge 2209 and an inner end of the respective side arm. The primary moveable joint enables relative rotation between the end of the bridge and the respective side arm about three substantially orthogonal axes. The primary moveable joint comprises a ball and socket type joint 2211, 2213. A pair of primary moveable joint is provided between each end of the bridge 2209 and an inner end of the respective left 2201 and right 2203 side arms. A displacement of the position of one or both of the left 2201 and/or right body 2203 portions, when the patient interface is in-situ upon a user's face, is transmitted to one or each primary moveable joint in a manner so as to minimise displacement of the bridge and the prong or prongs in relation to the user's nare(s).

Figure 26A:
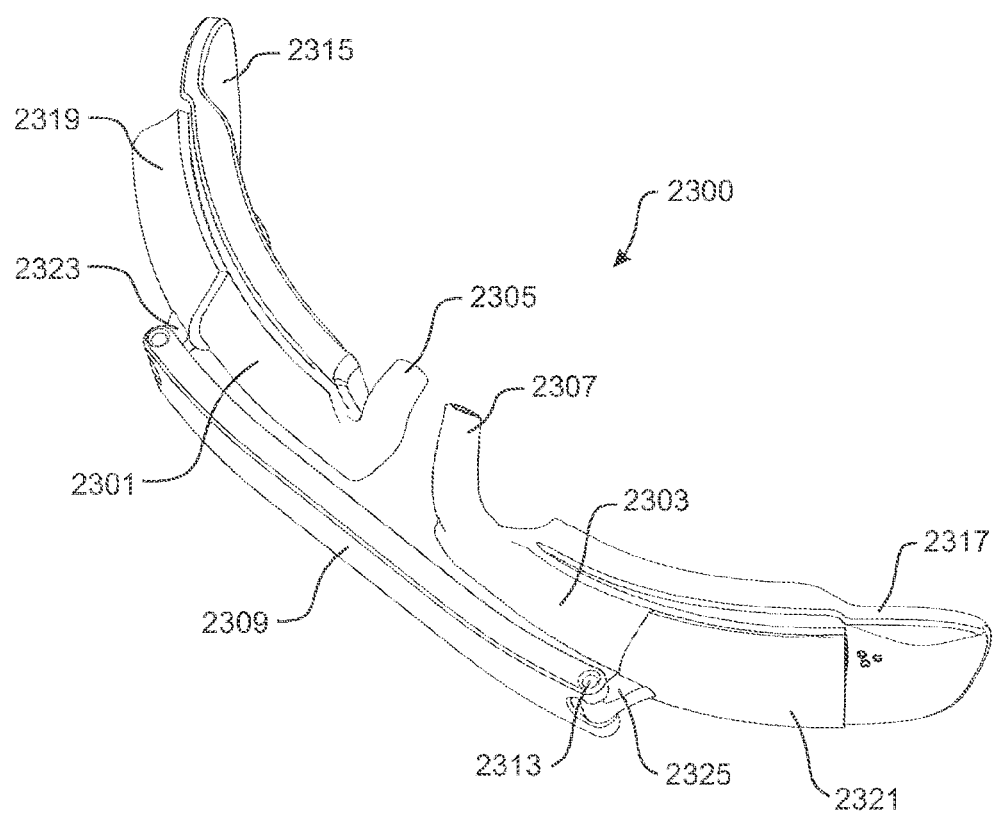
FIGS. 26A to 26C show another embodiment of a patient interface from various angles.
Figure 26B:
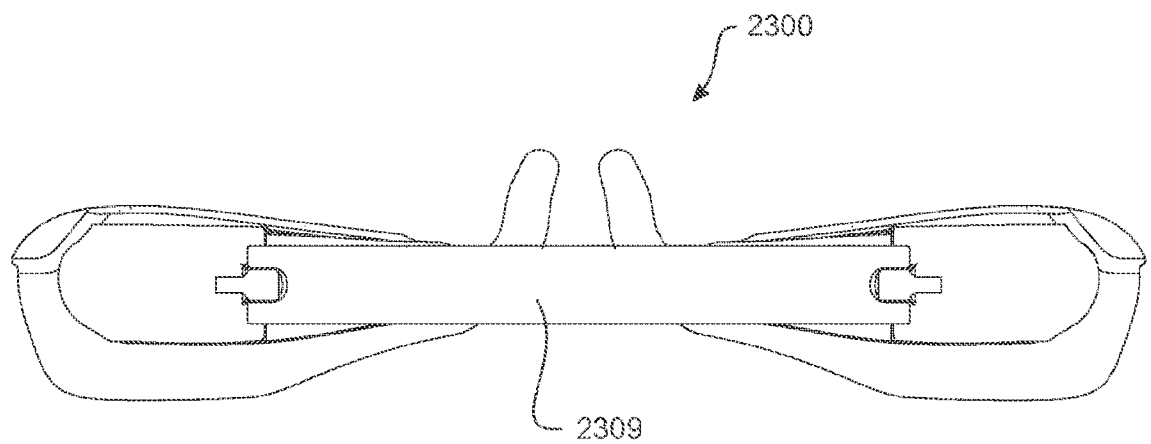
Figure 26C:
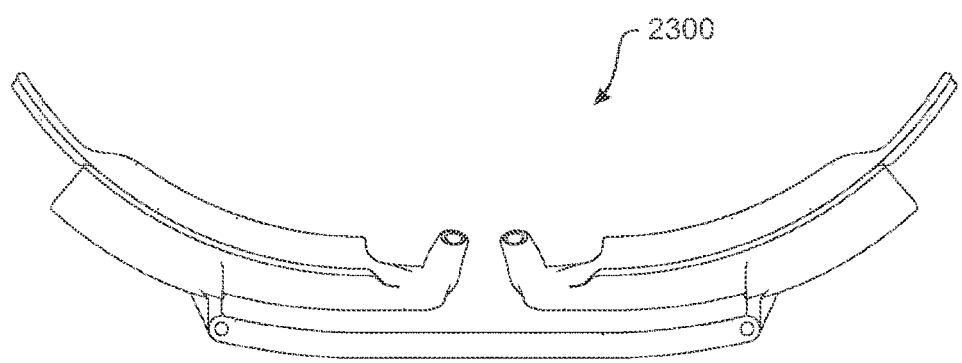

With reference to FIGS. 26A to 26C, the at least one, and preferably the pair of, nasal prong(s) 2305, 2307 extend from one, or each, of the inner-more ends of the respective left 2301 and/or right 2303 side arms, or from a region of one or both of the respective side arms substantially adjacent to the inner-more ends and wherein the bridge 2309 is a bar extending over or adjacent said nasal prong(s).

In this embodiment, the patient interface further comprises a mounting 2319, 2321 attached to a respective side arm to facilitate the connection point for the bar 2309, the mounting comprising a secondary moveable joint, such as a hinged or pivoting joint 2311, 2313, allowing for a secondary movement of the mount relative to the respective side arm to which it is attached, with the bar attached to the mounting via the primary moveable joint.

The mounting 2319, 2321 is slidably attached to the respective side arm to enable adjustment of the relative position along the side arm to thereby adjust the distance between the prongs. A displacement of the position of one or both of the left 2301 and/or right 2303 side arms, when the patient interface is in-situ upon a user's face, is transmitted to the bar via the connection point(s) or the mounting(s) and the respective primary and/or secondary moveable joints in a manner so as to minimise movement of the prong or prongs in relation to the user's nare(s).

The primary and secondary moveable joints are aligned for allowing movement of attached components in substantially the same orientation. In an alternative embodiment, the primary and secondary moveable joints may be non-aligned for allowing movement in dissimilar orientations. In another alternative embodiment, the bar may have one or more additional moveable joints.

The side arms, including the nasal prongs, are relatively flexible or conformable relative to the bar and/or mounting (s), which are relatively Inflexible or non-conformable. The connection point or the mounting(s) Include a finger extending outwardly therefrom upon which the primary moveable joint is located for connection to the bar. The bar is an over-centre component of the patient interface, with the connection points or mounting(s) positioned symmetrically upon each of the respective side arm (s). The secondary moveable joint is one or a combination of: an articulating joint, a pin-and-barrel type joint, and a ball and socket type joint.

With reference to the embodiments shown in FIGS. 27A to 28B, a patient Interface, such as a nasal cannula, has a body portion 2601 to be located, in-use upon a face of a user. The patient interface has at least one, and preferably a pair of, nasal prong(s) 2605/2705, 2607/2707 extending from the body portion to be inserted into, or to direct a flow of gas into, a nare or the nares of the user's nose in an operational position. The body 2601 has at least one hollow region 2619/2719, 2721 having a fluid passage connected to the nasal prong(s) for supply of a gas to the nare(s) of the user's nose. During supply of fluid through the fluid passage, the hollow region 2619/2719, 2721 substantially resists transmittal of a displacement force from one or more regions of the body portion to the nasal prong(s) 2605/2705, 2607/2707 and maintains the operational position of the prongs.

Figure 27A:
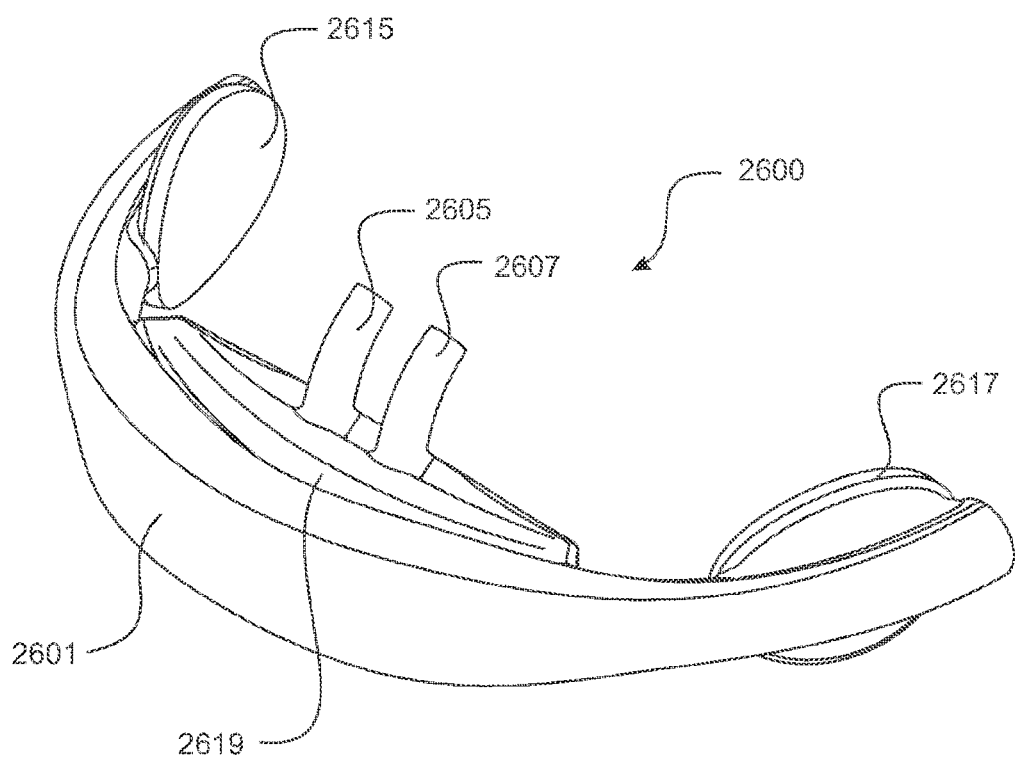
FIGS. 27A to 27C show another embodiment of a patient interface from various angles.
Figure 27B:
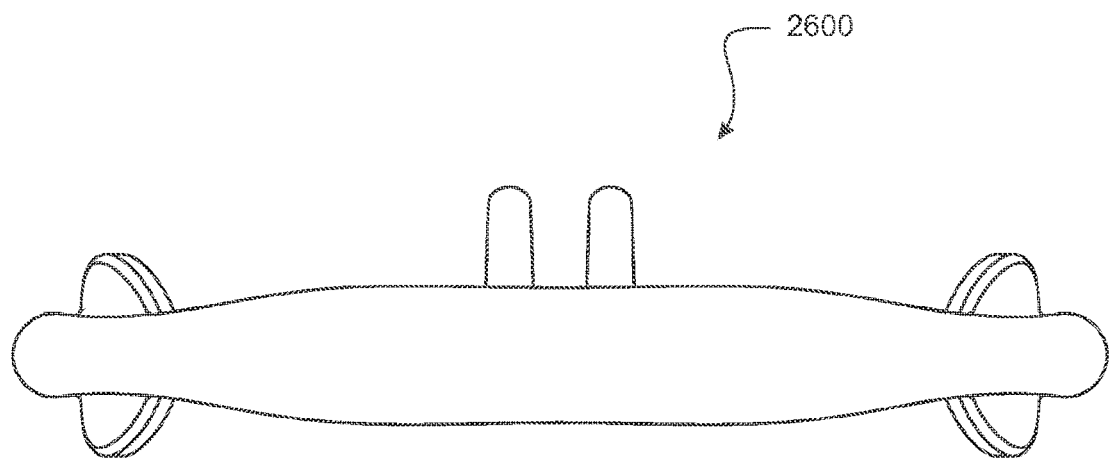
Figure 27C:
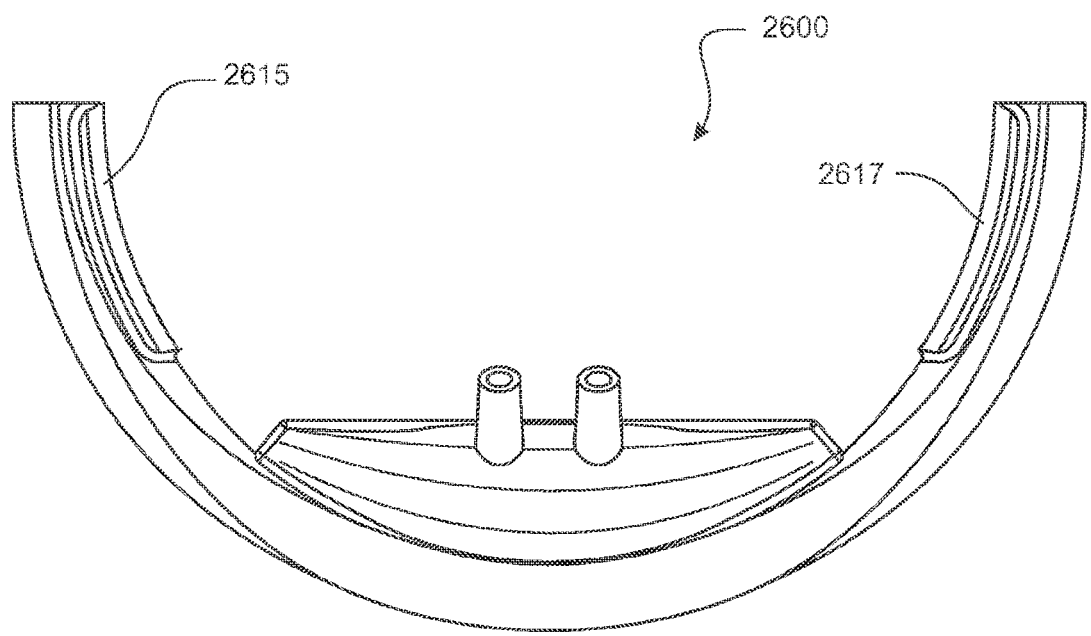

With reference to the embodiment shown in FIGS. 27A to 27C, the body portion 2601 comprises a substantially rigid frame 2601a and at least one relatively soft hollow region 2619 extending from the rigid frame. The at least one hollow region 2619 is inflatable to expand in a direction of extension of the nasal prong(s). The hollow region 2619 is coupled to the nasal prong(s) and Inflatable during supply of a gas to the nare(s) of the user's nose. The hollow region 2619 locates against a user's philtrum or upper lip region in at least the Inflated state to substantially maintain the nasal prong(s) in the operational position.

In the inflated state, the hollow region 2619 is substantially deeper than a depth of a frame of the body portion adjacent the hollow region. Either end of the body portion 2601 comprises a user facial contacting surface 2615, 2617 contoured to engage the user's facial cheek region in use. The body portion 2601 or at least either end of the body portion is shaped or curved to substantially complement a user's facial structure in use.

Figure 28A:
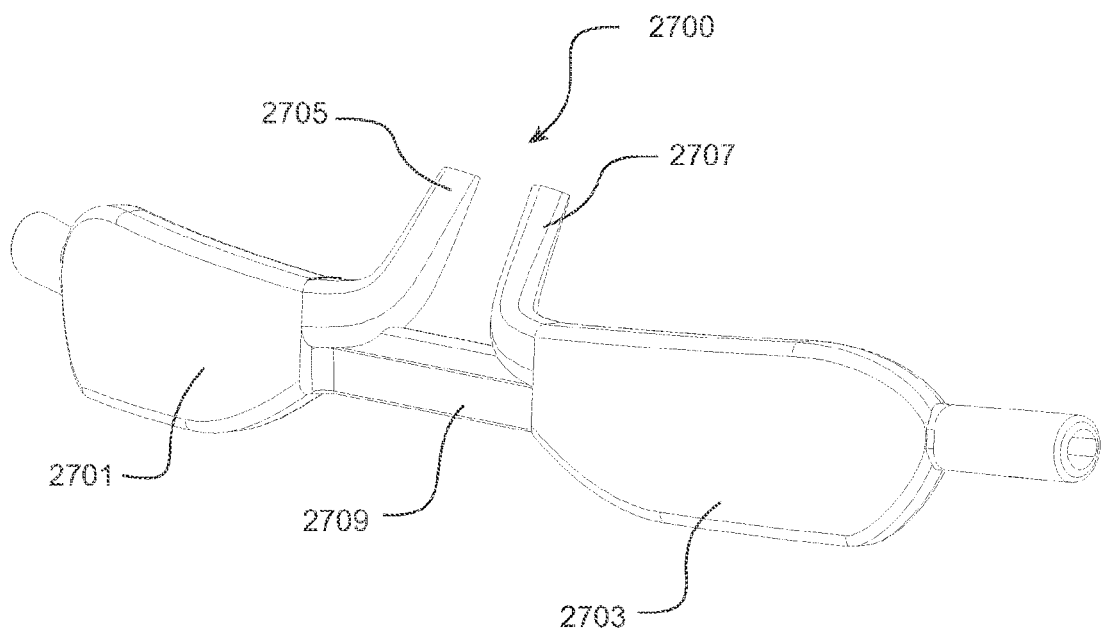
FIGS. 28A to 28B show another embodiment of a patient interface from various angles.
Figure 28B:
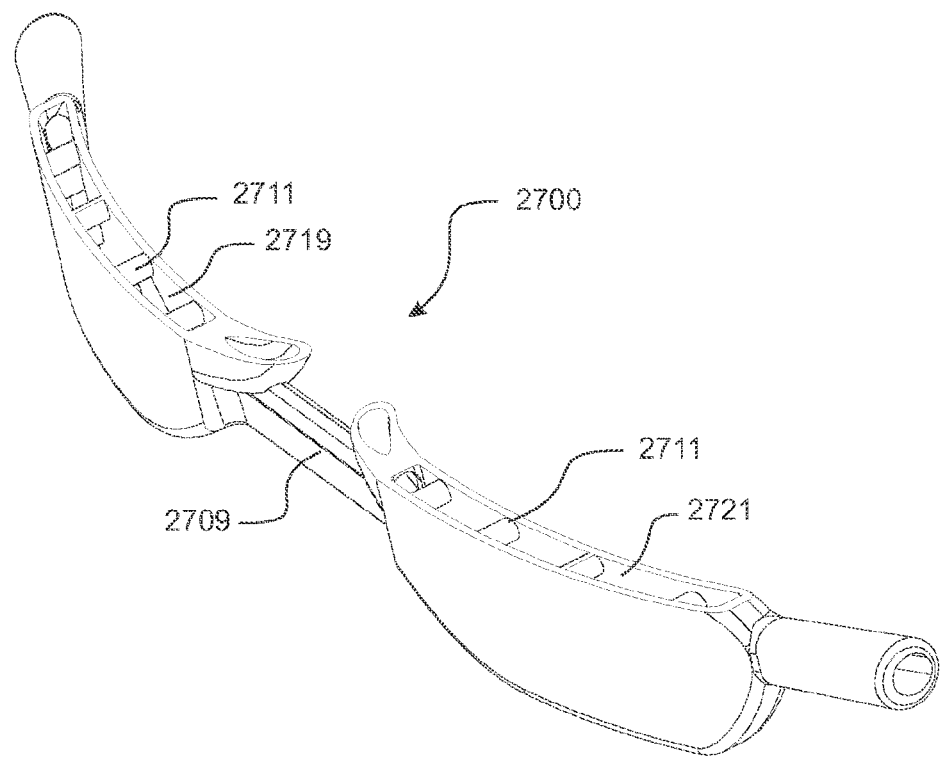

With reference to the embodiment shown in FIGS. 28A to 28B, the body portion comprises a pair of respective left 2701 and right 2703 side arm. The left side arm 2701 and right 2703 side arm are substantially flexible. The nasal prong(s) 2705, 2707 extend from one, or each, of the inner-more ends of the respective left and/or right side arms, or from a region of one or both of the respective side arms substantially adjacent to the inner-more ends. A bridge portion 2709 connects the inner-more ends of the respective left and side arm. The bridge portion 2707 is substantially rigid relative to the left and right side arm.

At least one, and preferably both, left 2701 and/or right body 2703 segments comprise a hollow region 2719, 2721, each having a fluid passage for delivering a supply of a gas to the respective nasal prong.

The patient interface 2700 comprises one or more Internal support columns extending between opposing Internal surfaces of the hollow region to maintain an open fluid passage. The one or more Internal support columns comprise a plurality of support columns spatially distributed within the hollow region.

Figure 29A:
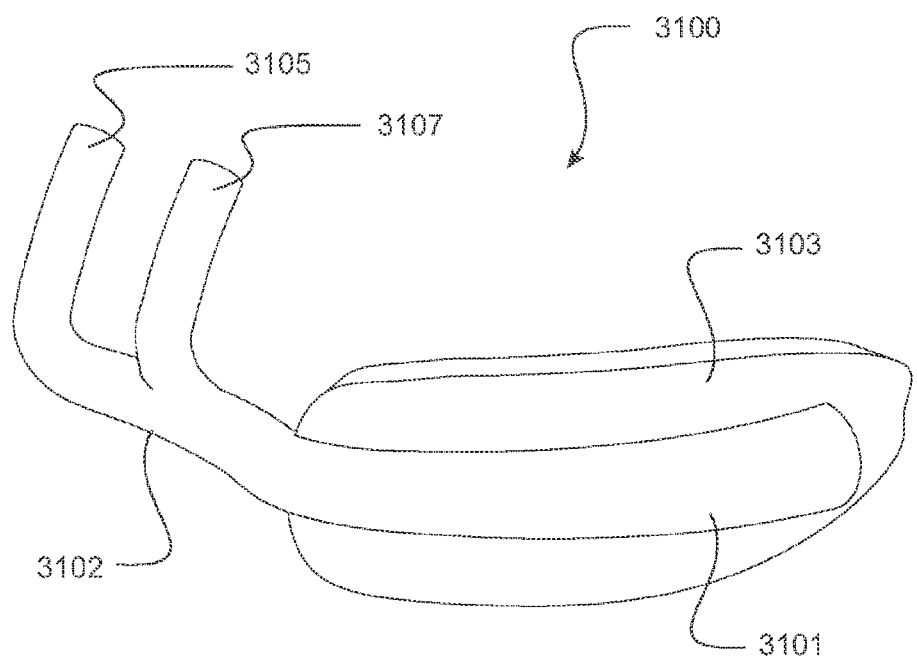
FIGS. 29A to 29C show another embodiment of a patient interface from various angles.
Figure 29B:
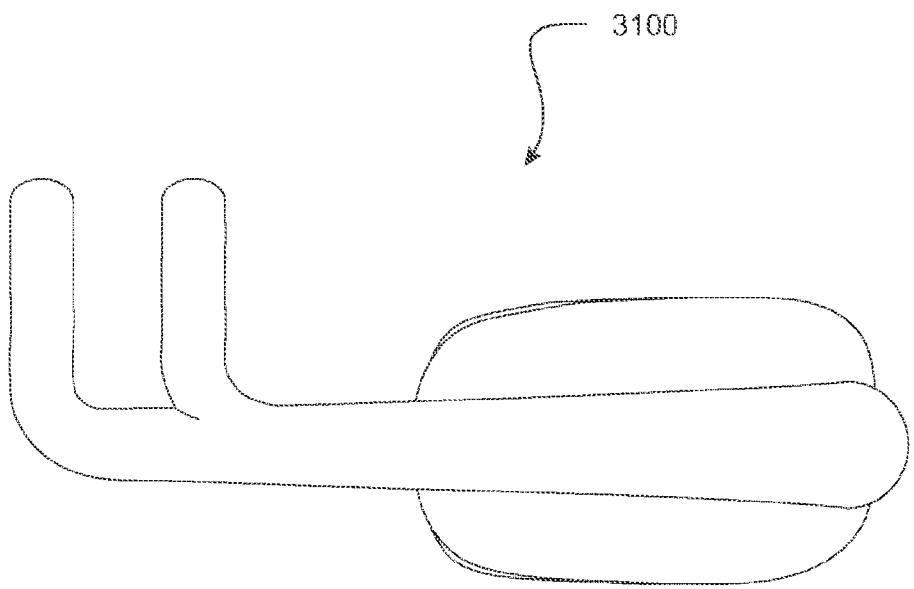
Figure 29C:
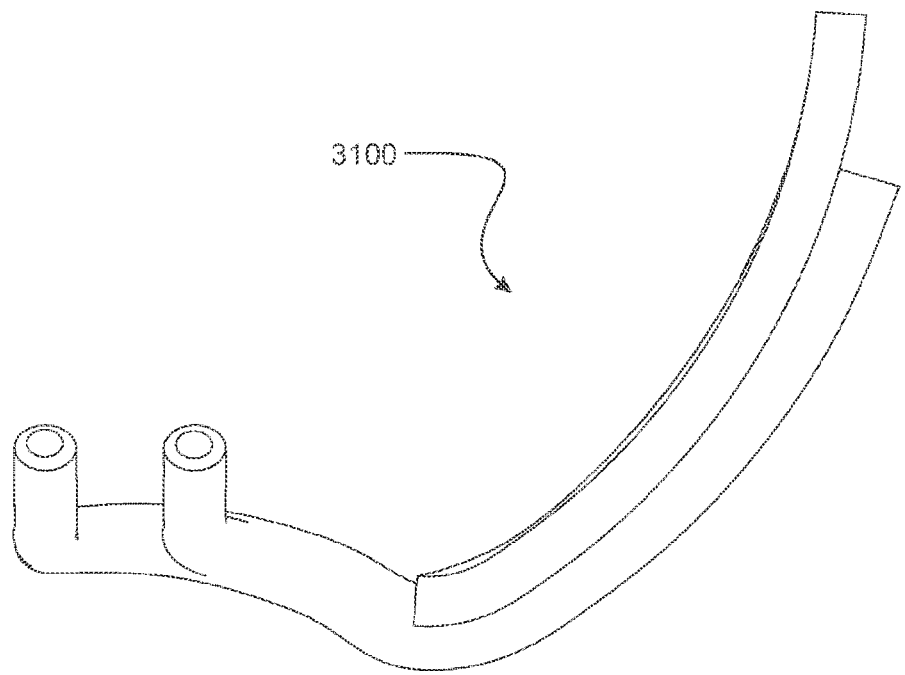

With reference to the embodiment shown in FIGS. 29A to 29C, a patient interface 3100, such as a nasal cannula, has a body portion 3103, to be located, in-use, upon a face of a user, a bridge portion 3102 extending away from the body portion, and at least one, and preferably a pair of, nasal prong(s) 3105, 3107 extending from the bridge portion to be Inserted into, or to direct a flow of gas into, a nare or the nares of the user's nose in an operational position. The body portion actively adjusts using potential from the system or stored in the cannula. The body portion is located, in-use, upon one facial cheek of a user and the other facial cheek of the user is free from the interface.

Figure 34A:
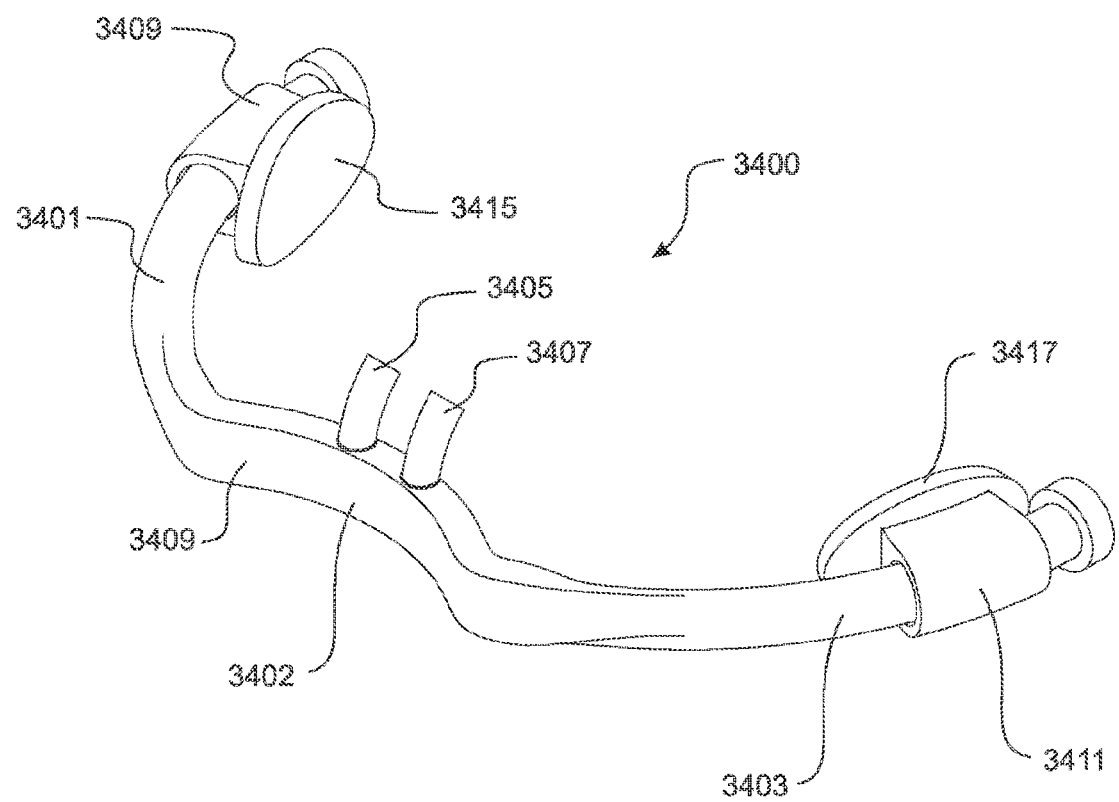
FIGS. 34A to 34C show another embodiment of an interface from various angles.
Figure 34B:
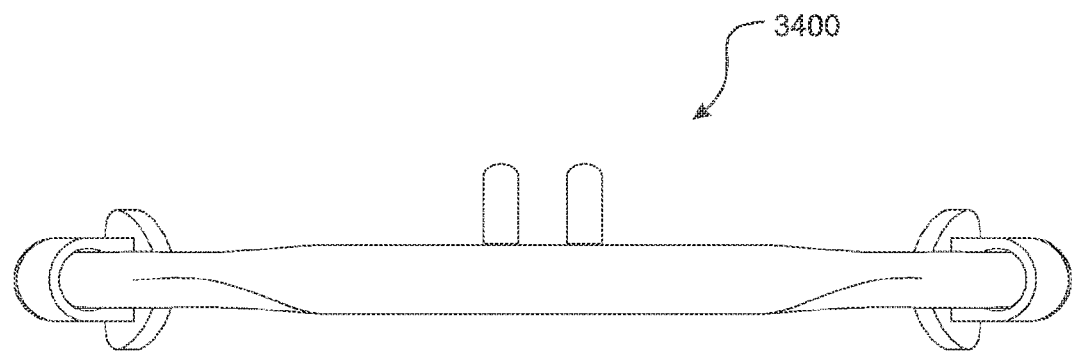
Figure 34C:
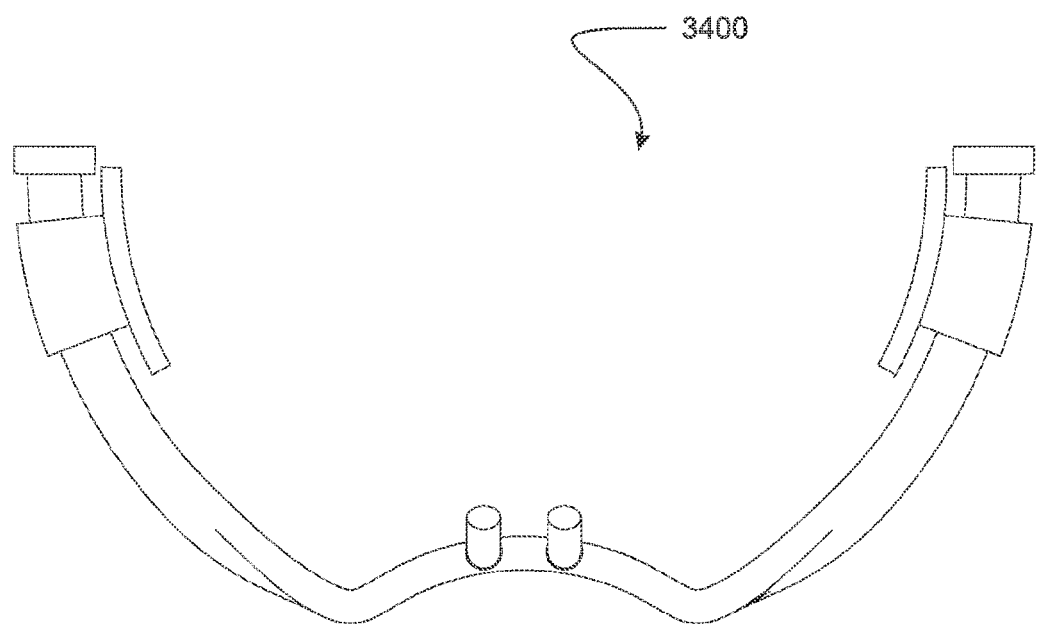
Figure 35:
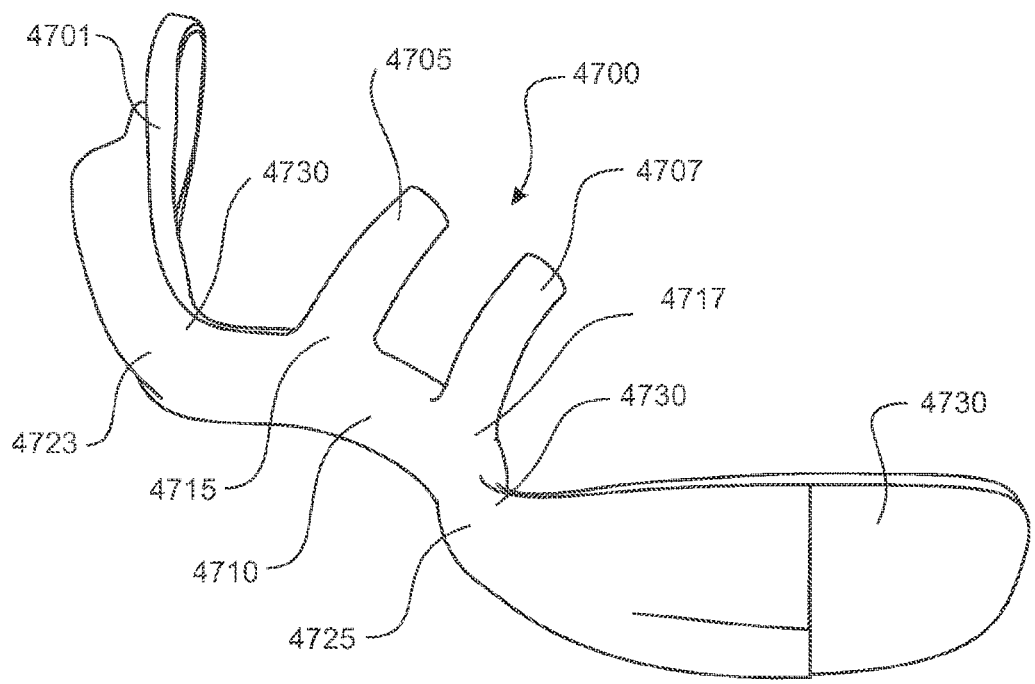
FIG. 35 shows another embodiment of a patient interface.

With reference to the embodiment shown in FIGS. 34A-34C, a patient interface 3400, such as a nasal cannula, has an elongate body 3402 to be to be located, in-use, upon a face of a user. The body 3402 has at least one, and preferably a pair of, nasal prong(s) 3405, 3407 to be inserted into, or to direct a flow of gas into, a nare or the nares of the user's nose, and at least one, and preferably a pair of, facial contacting surface(s) 3415, 3417 movably coupled to the body 3402 to respond to force(s) or movement(s), or both, experienced by facial contacting surface(s) and at least partially alleviate the transfer of such force(s) and/or movement(s) to the body and to the nasal prong(s).

Each facial contacting surface 3415, 3417 is contoured to engage a facial cheek of the user. Each facial contacting 3415, 3417 surface is movably coupled to an end portion of the body, preferably slidably coupled to the body. Each facial contacting surface 3415, 3417 has a hollow guide 3409, 3411 associated therewith for slidably receiving a portion of the body 3402 there through.

The patient interface 3400 further comprises a resilient member (not visible) associated with each facial contacting surface 3415, 3417. The resilient member is coupled between the facial contacting surface 3415, 3417 and the body and biases the facial contacting surface(s) 3415, 3417 towards a centre of the body 3402. In the preferred embodiment shown, the resilient member comprises a compression spring.

The body 3402 comprises a bridge portion 3409 from which the nasal prong(s) 3405, 3407 extend(s). The bridge portion 3409 is Inwardly curved to extend towards the user's septum in situ. The body (preferably the whole of the body) 3402 is substantially rigid and substantially hollow and fluidly coupled to the nasal prong(s) to enable the flow of gases there through. At least one end, and preferably both ends, of the body are configured to fluidly couple a gases flow path of a breathing circuit.

Figure 32:
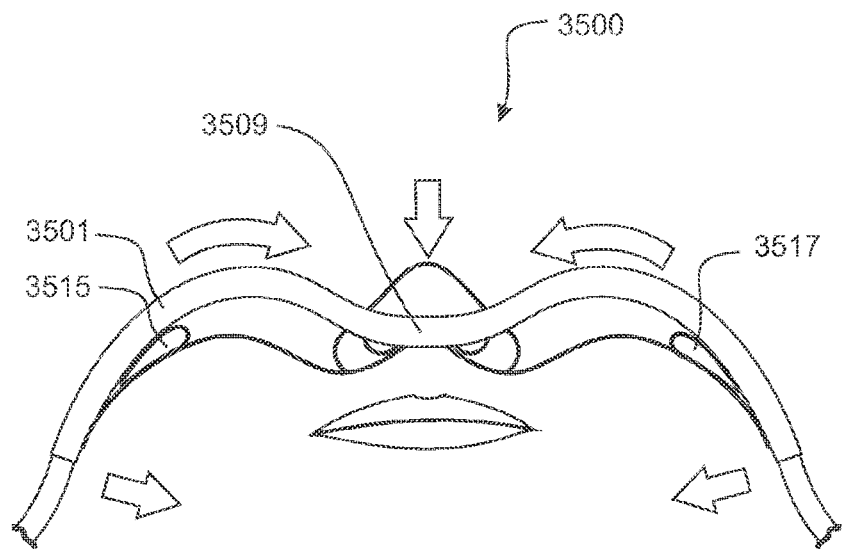
FIG. 32 shows another embodiment of a patient interface.
Figure 33:
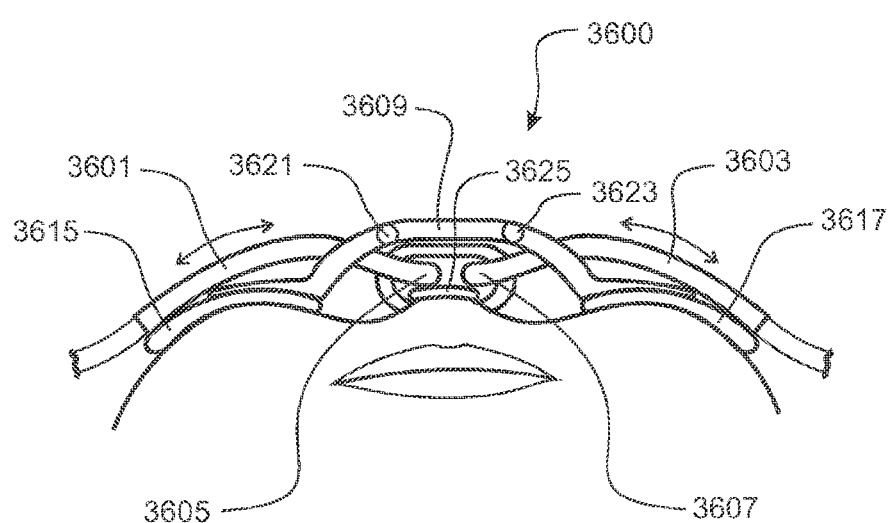
FIG. 33 shows another embodiment of a patient interface.

With reference to the embodiment shown in FIGS. 32 and 33, a patient interface 3500/3600, such as a nasal cannula, has a body 3501/3601 to be located, in-use upon a face of a user. The body 3501/3601 includes at least one, and preferably a pair of, nasal prong(s) 3605, 3607 to be inserted into, or to direct a flow of gas into, a nare or the nares of the user's nose in an operational position. The patient interface 3500/3600 also has at least one 3501, and preferably a pair of 3601, 3603, active element(s) each configured to activate in response to input energy to move at least one other region of the body to retain the nasal prong(s) in the operational position.

The input energy is non-mechanical energy. At least one active element 3501/3601, 3603 is configured to convert the input energy into mechanical energy to move the at least one other region of the body. Each active element 3501/3601, 3603 comprises at least one, and preferably a pair of, expansion element(s) configured to expand in response to the input energy to move at least one other region adjacent the nasal prong(s) to retain the nasal prong or prongs in the operational position.

The expansion element(s) Is/are located on a user engaging side of the body. The expansion element(s) is/are configured to locate adjacent a facial cheek of the user in situ.

The patient interface also has one or more hinges, pivots or articulated joints, or any combination thereof operable in response to activation of one or more of the active element(s). The patient interface has one or more hinges at a bridge portion of the body from which the nasal prong(s) extend.

With reference to the embodiment shown in FIG. 32, the expansion element(s) form(s) the body 3501 and Is/are configured to expand in response to the input energy to move a bridge portion 3509 of the body 3501 from which the nasal prong(s) extend towards and/or against the philtrum of the user in situ.

The at least one active element 3501 is an electromechanical element configured to receive electrical activation energy to move at least one other region of the body. The electromechanical element is coupled to an electrical circuit and is activated in response to an electrical activation signal generated by a change in voltage, resistance or current or any combination in the electrical circuit.

A movement, or force, or both, experienced by one or more regions of the body generates the electrical activation signal. Movement of the one or more regions of the body causes electrical contacts of the circuit to engage and generate the electrical activation signal. Movement of the one or more regions of the body causes a change in electrical resistance in the circuit to generate the electrical activation signal.

The electromechanical element is or comprises a conductive polymer, or bimetallic strips, or any combination thereof. Alternatively, the electromechanical element may be or comprise a pair of electromagnets.

The patient interface further comprises at least one, and preferably a pair of facial contacting pads 3515, 3517 configured to engage a user's face in use, wherein an end or either end of the bridge portion is coupled to the facial contacting pad or the facial contacting pads respectively.

With reference to the embodiment shown in FIG. 33, the input energy is exhibited through a change in humidity at one or more regions of the body and the at least one active element 3601, 3603 is configured to activate in response to a threshold humidity, or a change in humidity, or both, to move the at least one other region of the body to retain the nasal prong(s) in the operational position.

The body 3501 is flexible in at least one or more regions to deform in response to expansion of the expansion element(s) and cause the bridge portion 3609 to move towards the philtrum in situ. The bridge portion 3609 comprises one or more hinges 3621, 3623. The bridge portion 3609 is preferably a rigid component to prevent or at least substantially Inhibit the expansion element(s) from moving upwards and encourages the expansion element(s) to move downwards onto the user's philtrum The active elements 3601, 3603 are configured to absorb water and expand in response to a threshold humidity, or a change in humidity, or both, to thereby move the at least one other region of the body. The active element 3601, 3603, or at least part of the active element 3601, 3603, is located adjacent a base of an associated nasal prong and is configured to engage the philtrum in situ, and wherein expansion of the active element or the part of the active element causes the nasal prong to pivot towards the back of the user's respective nare to retain the nasal prong in the operational position. The at least one active element 3601, 3603 is or comprises a polymeric material configured to expand with Increasing humidity. The at least one active element forms at least a portion of the body.

The body comprises a left side arm and a separate right side arm, each of left and right side arms having an active element and a nasal prong associated therewith. The patient Interface further comprises a bridge portion 3609 bridging over the active elements of the left and right side arms respectively to retain the elements against the user's philtrum in situ.

The patient interface further comprises at least one, and preferably a pair of facial contacting pads 3615, 3617 configured to engage a user's face in use, wherein an end or either end of the bridge portion is coupled to the facial contacting pad or the facial contacting pads respectively. The patient interface further comprises another facial contacting pad 3625 that is configured to engage a user's face in use, in particular, their philtrum.

With reference to the embodiment shown in FIGS. 30A to 30F, a patient interface 3700, such as a nasal cannula, has a body portion having left 3701 and right side arms 3703 to be located, in-use upon a face of a user. The patient interface 3700 has at least one, and preferably a pair of, nasal prong(s) 3705, 3707 extending from the left and right side arms to be inserted into, or to direct a flow of gas into, a nare or the nares of the user's nose in an operational position. In the operational position, the left and right side arms are positioned upon a user's facial cheeks in a substantially curved manner, which is described in more detail below.

Figure 30A:
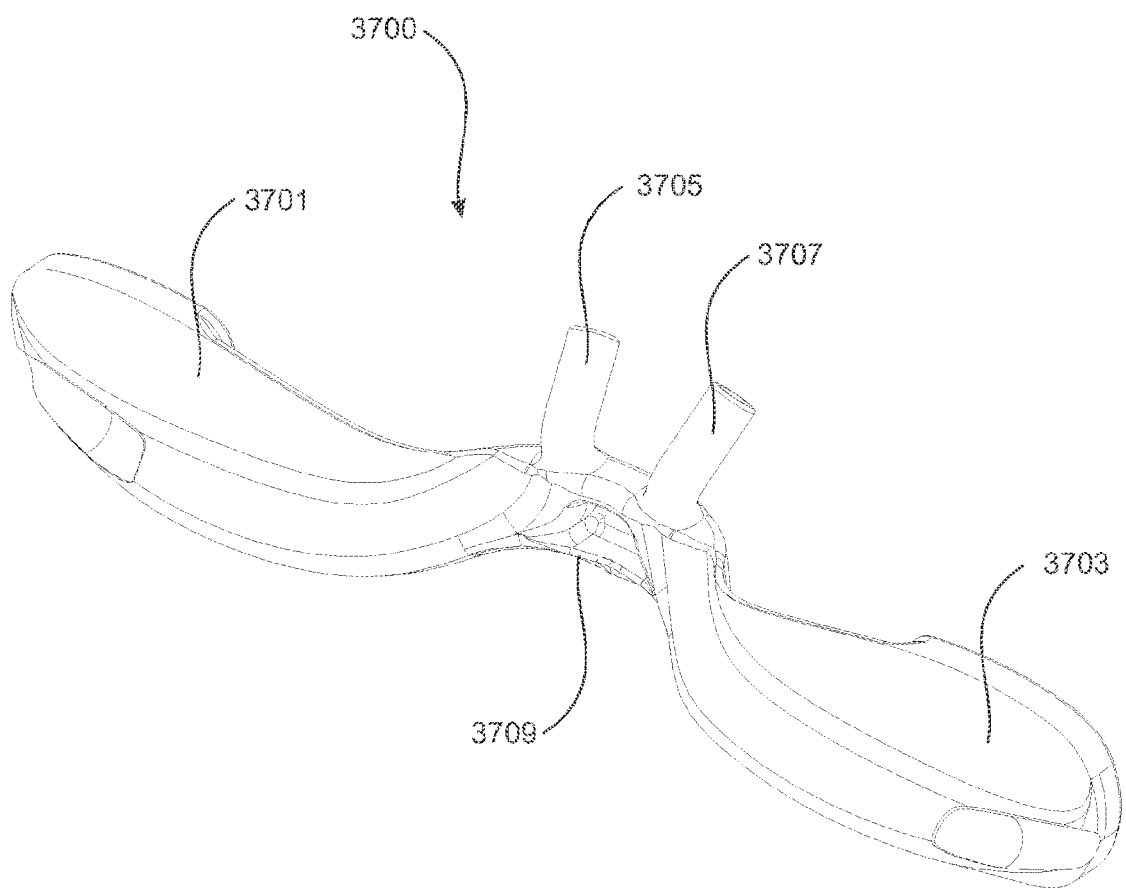
FIGS. 30A to 30C show another embodiment of a patient interface from various angles in a non-use configuration.
Figure 30B:
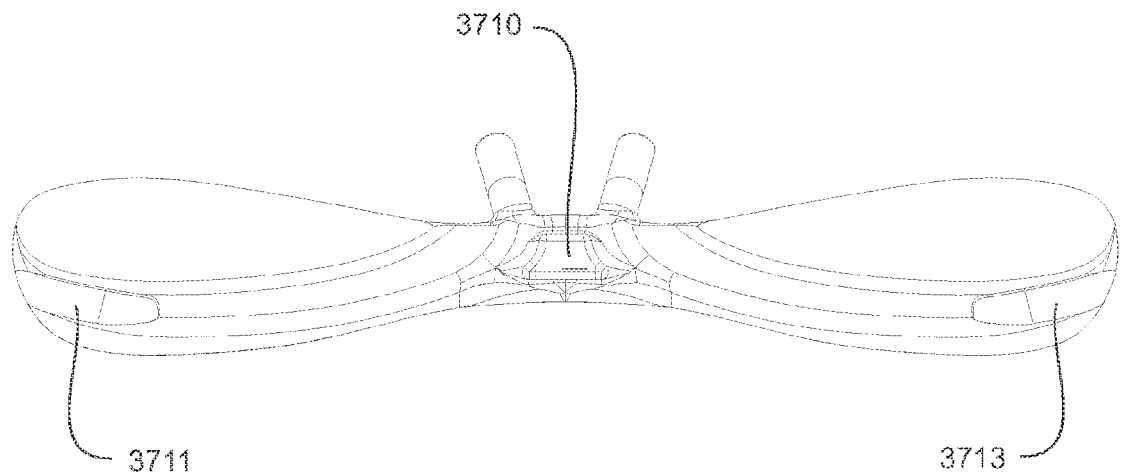
Figure 30C:
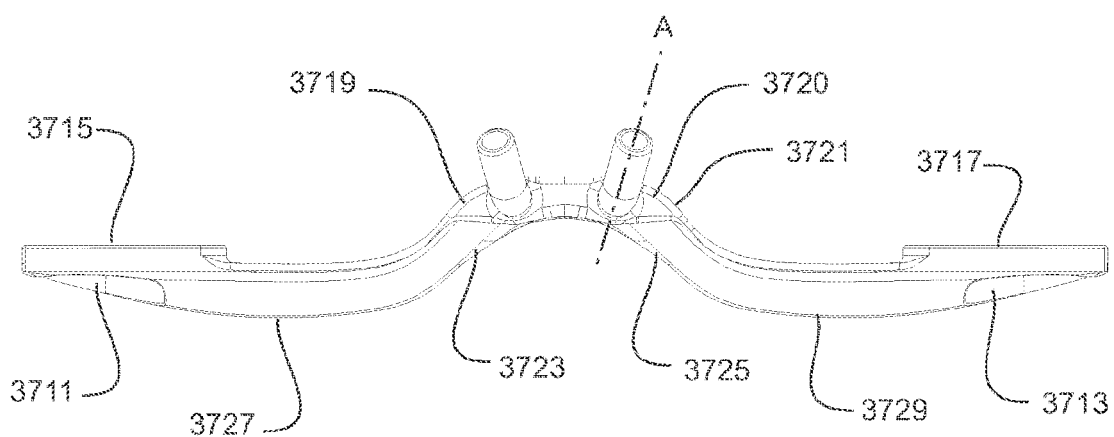
Figure 30D:
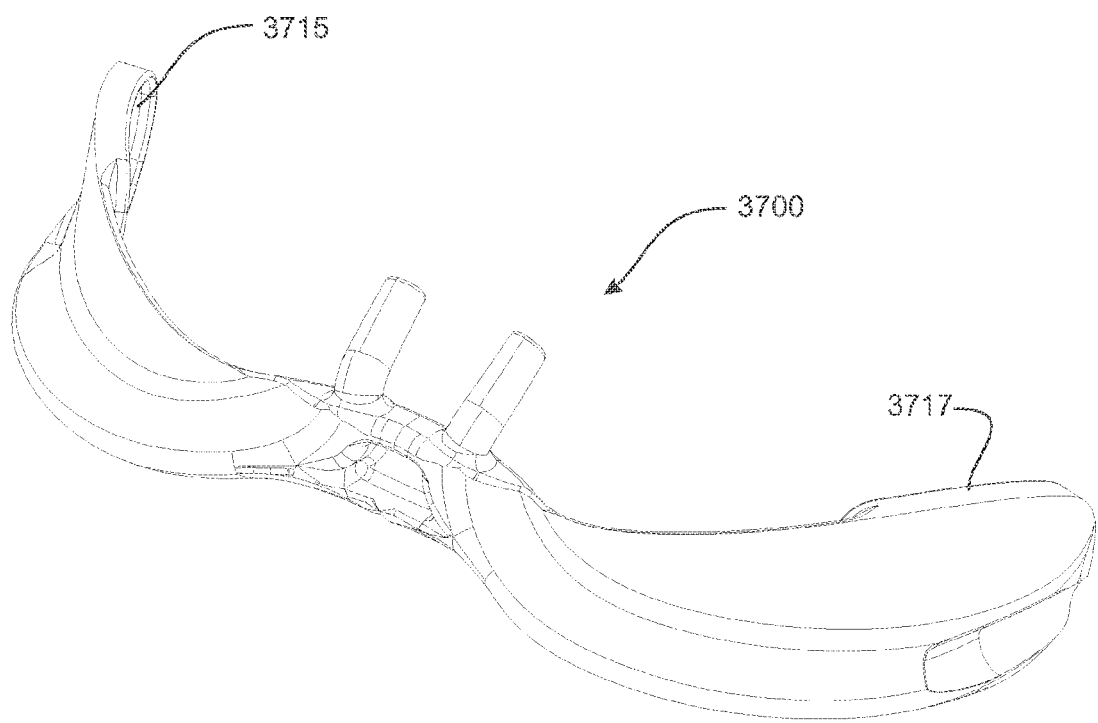
Figure 30E:
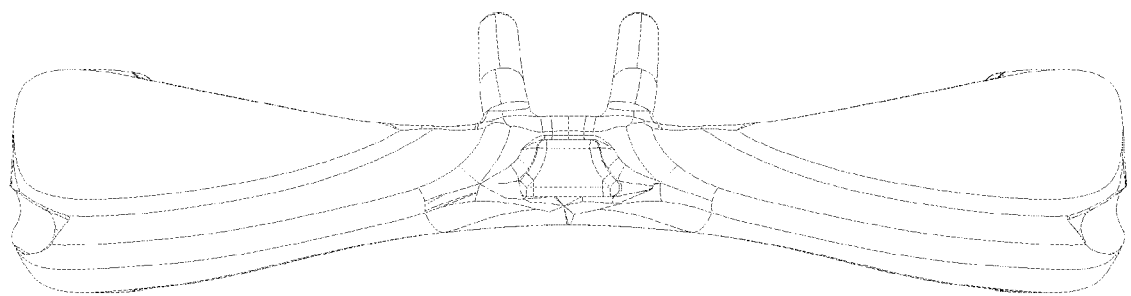

The patient interface 3700 has a non-use configuration, shown in FIGS. 30A to 30C, in which the body portion is substantially planar or at least either end of the body portion is substantially planar and substantially co-planar with the other end of the body portion. As shown in FIG. 30C, in this configuration, the facial contacting surfaces 3715, 3717 at each end are substantially planar surfaces that are substantially co-planar with each other. The at least one, and preferably pair of, nasal prong(s) extend(s) in a direction outwardly away from a central plane of the body portion.

In alternative embodiments, either or both ends 3701, 3703 of the body portion are substantially co-planar; that is they may be offset relative to each other. Additionally or alternatively, either or both ends 3701, 3703 of the body portion, the facial contacting surfaces 3715, 3717 may have a slight curve or other shape while in the non-use configuration. Either or both ends 3701, 3703 of the body portion are preloaded/pre-stressed so they are urged back towards the co-planar arrangement.

The patient interface 3700 has a bridge portion 3710 with a cavity that is concave when viewed in a direction opposite to that of a user. The cavity may be filled or at least partially filled with a soft and/or flexible material. Alternatively, the cavity may be filled or at least partially filled with a relatively stiffer material. A benefit of filling the cavity with a suitable material is that the cavity will not attract and/or retain dirt. As described above, either or both ends 3701, 3703 of the body portion are preloaded. This preload causes the bridge portion to move towards and contact the philtrum of the user as the face contact portions are stretched, bent, and placed onto the face of the user.

The cavity, whether vacant, partially filled, or filled, reduces the elastic/spring force experienced by the user on their philtrum compared to a bridge without a cavity. One or more other sections of the patient interface may have cavities that may or may not be filled, or at least partially filled, with a soft and/or flexible material or a relatively stiffer material. In the preferred embodiment, the bridge has been shown and described to be relatively flexible and/or resilient. In an alternative embodiment, the bridge may comprise a relatively stiff bridge portion so as to define at least a starting orientation and/or or spatial location of the nasal prongs. The relatively stiff portion may be a filled or partially filled cavity as described above, or may be a co-moulded or overmoulded part of the patient interface.

When viewed from above, the left and right side arms Initially extend outwardly from the bridge in a flared manner before transitioning into the substantially planar sections. The transitions 3719, 3721 between the bridge and left and right side arms are smooth, arcuate transitions. The transitions 3719, 3721 have relatively large radiuses so pressure from the bridge and the transitions 3719, 3721 on the user's face is spread evenly over their philtrum. The transitions 3719, 3721 are spaced outwardly from the prongs. In particular, the centre of the curve 3720 of each transition is positioned outwardly relatively to a midline or longitudinal axis A of the adjacent prong to reduce movement of the prongs in use. The thickness of the patient interface between the surfaces 3721 and 3725 are relatively thin to reduce the elastic/spring force experienced by the user on their philtrum.

The exterior surfaces 3727, 3729 of the left and right side arms opposite the facial contacting surfaces 3715, 3717 are slightly arcuate and convex when viewed in a direction opposite to that of the user; however, the general shape of the left and right side arms is substantially planar when in the non-use configuration. The exterior surfaces 3727, 3729 have a relatively low profile and relatively less material so that the patient interface has flexibility. The facial contacting surfaces 3715, 3717 are spaced away a relatively small distance from the adjacent part of the left and right side arms. The profile of the portions of the patient Interface that flex may be designed to minimise kinking in either the in-use or the non-use configurations. For example, the portions of the patient interface that flex may have ridges, corrugations, or cut outs to minimise or eliminate kinking of the patient interface.

The left and right side arms are to be positioned, in-use, upon a user's face. Preferably, the left and right side arms of the body portion are to be positioned, in-use, upon a user's facial cheeks. The patient interface has an in-use configuration, shown In FIGS. 30D to 30F, in which the body portion, or at least the left and right side arms, is/are shaped or curved to substantially complement a user's facial structure in use and the nasal prong(s) extend(s) in a direction substantially parallel to a central plane of the body portion, or at least extend at less of an angle than in the non-use configuration. In particular, the facial contacting surfaces 3715, 3717 are arcuate, concave surfaces when viewed from the user's position. The left and right side arms are substantially arcuate, when viewed from the position shown in FIG. 30F. In this configuration, the transition between the bridge and the left and right side arms are also smooth, arcuate transitions.

The body portion is a single, integrally formed component. As shown in FIGS. 30A to 30F, the body portion and the at least one, and preferably a pair of, nasal prong(s) are a single, integrally formed component; that is, the patient interface 3700 is a single, integrally formed component.

The prongs in the non-use configuration may be angled outwards from each other at an angle that is greater than 0° and less than 180°. For example, the angle between the prongs may be greater than 0° and up to about 60°, between about 5° and about 55°, between about 10° and about 50°, between about 15° and about 45°, between about 20° and about 40°, about 5°, about 10°, about 30°, about 32°, about 45°, about 60°, about 80°, about 90°, about 100°, about 120°, about 140°, about 160°, or about 170°. When the Interface is stretched and/or applied to the user's face, the interface 3700 straightens the prongs into a substantially parallel configuration.

The Interface is a nasal cannula comprising a pair of nasal prongs as the outlets of the cannula, and in which a headgear or retention system is attachable to the cannula for retaining the nasal cannula in position when being worn in-use by a user. The retention system (or securement system) may comprise a releasable connection system for releasably connecting or securing the patient interface to a user's face (for example the releasable connection system may comprise hook and loop or hook and hook type connectors for such a system) Such a releasable connection or securement system may comprise at least one pad (comprising materials such as hydrocolloid) attached to a user's face upon which the patient Interface may be releasably engageable thereto.

It will also be appreciated that various aspects of the present disclosure may be applied using any form of a patient interface in conjunction with any suitable form of headgear or retention system or securement system for securing a patient interface upon a user, suitable for the retention of the patient interface to be retained upon a user for delivery of the desired therapy, for example such as that securement system as described in PCT/NZ2011/000218 (published as WO 2012/053910, the contents of which are herein incorporated by reference. Accordingly, one or a pair of side arms may be provided in which a patient interface is able to be positioned upon a user's face with each or both of the side arms providing a part of a retention system or securement system which can be coupled or associated with a headgear. In this way, the patient interface may be retained or secured upon a user's face in a desired operational position.

The body portion, or at least either end of the body portion, comprise(s) a resilient and/or flexible material.

The patient interface 3700 is, or comprises, a polymeric material. The polymeric material is one or a combination of any one or more of: thermoplastic elastomer(s), polypropylene based elastomer(s), liquid silicone rubber(s), or breathable thermoplastic polyurethane(s), or breathable polyamides, more preferably polymers may be those such as, but not limited to, polyolefins, thermoplastic elastomers, or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A hardness of less than about 30, or about 30 to about 90, or about 30 to about 80, or about 30 to about 70, or about 30 to about 60, or about 30 to about 50 or about 30 to about 40, or about 30, or about 40, or about 50, or about 60, or about 70, or about 80, or about 90. In embodiments in which the cavity is filled with a material, that material preferably has a Shore A hardness of about 0 to about 30, or about 10 to about 20, or about 10, or about 15, or about 20, or about 30.

The area of the patient interface Intended to be in contact with a user's philtrum may have a comfort enhancing surface finish. For example, a shallow pattern, a sandblasted surface finish, a bead blasted surface finish, a roughened or patterned surface finish, dots, channels, or grooves or other surface relief features.

The body portion can be shaped or configured or adapted to provide for a passageway 3711, 3713. Such a passageway 3711, 3713 is formed by one or more of, a lumen or a void space or cavity or other recess through the body portion.

Such a passageway 3711, 3713 allows for receiving of a gas supply (from a source) and for channeling delivering of that gas to a user via the prongs 3705, 3707; or, alternatively allows for the receipt of a gas supply conduit (not shown, but which may be received or fitted into such an item 3711, 3713) for then delivering the gas to a user via the prongs(s). Such a passageway 3711, 3713 in or through the side arm 201 or side arm element 206, or both, allows for the formation of a conduit or lumen through which gas may be directed or supplied for delivery to the prongs 3705, 3707.

Figure 30F:
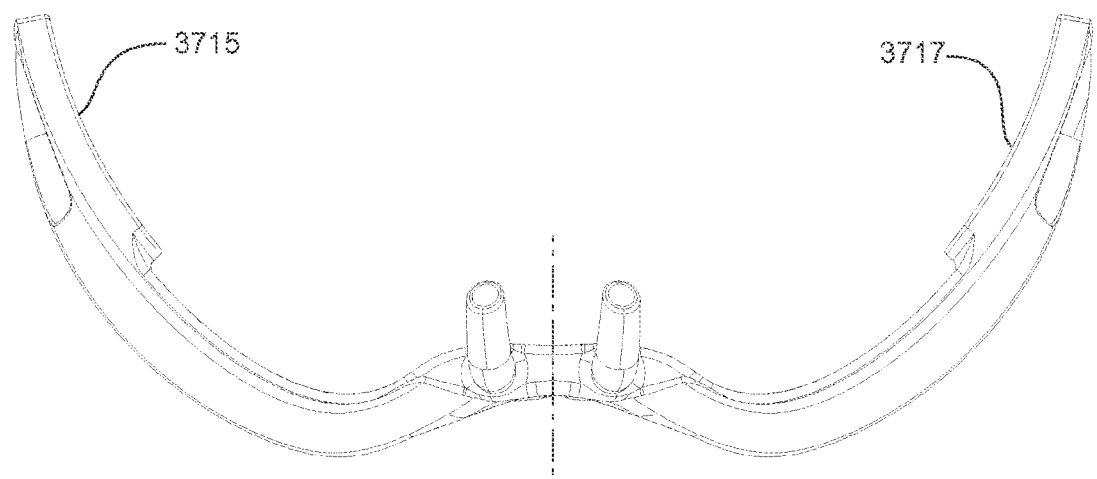
Figure 31:
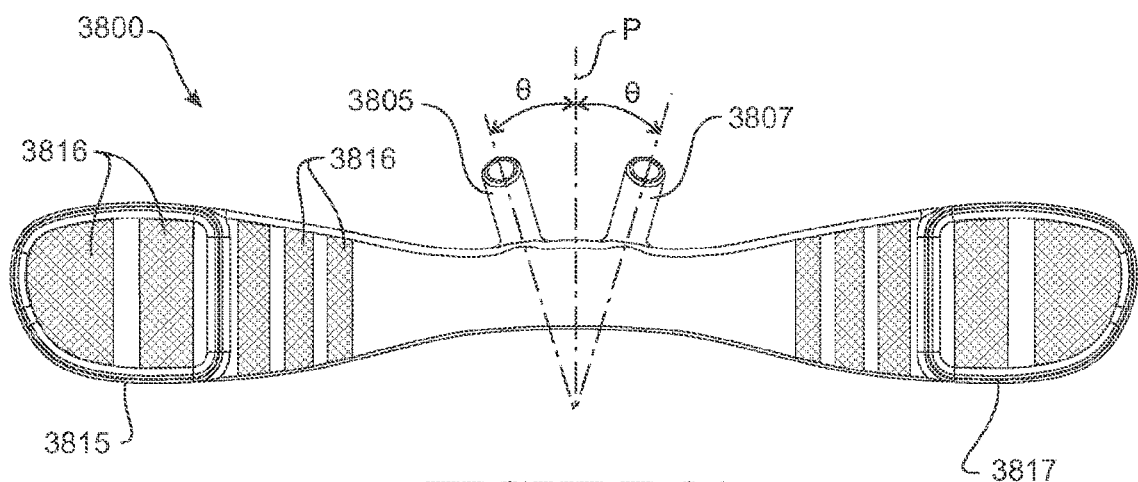
FIG. 31 is a modification of the embodiment shown in FIGS. 30A to 30C and 31A to 31C Including one part of a releasable connection system, such as for a securement system, in one example being loop material, for releasably connecting the patient interface to a user's face.

FIG. 31 shows an alternative embodiment 3800 that is modification of the embodiment shown in FIGS. 30A to 30F Including loop material 3816 for releasably connecting the patient interface to a user's face. The loop material 3816 is preferably part of a hook and loop connector for a releasable connection system for releasably connecting the patient interface to a user's face. In the embodiment shown, the loop material 3816 is in sections with spaces between the sections so that when the patient interface is placed on a user's face, the loop material does not bunch or gather. Alternatively, the loop material 3816 may be a single piece of material that extends from the end of the or each side arm towards the centre of the patient interface. In this embodiment, the loop material is flexible such that it does not bunch or gather when the patient interface is in use. In another alternative embodiment, the loop material may be in contiguous or adjacent sections with full or partial cuts between the sections so that when the patient interface is in use, the sections are allowed to move relative to each other and do not bunch or gather.

With reference to the embodiments shown in FIGS. 30A to 30F and 31, and in particular, FIGS. 30F and 31, each of the prongs 3705/3805, 3707/3807 extend at angles Θ relative to the central plane P of the patient interface. The angle is defined by angle between the central axis extending through each of the prongs and the central plane. As described above, the prongs in the non-use configuration may be angled outwards from each other, which is shown in FIG. 31. In the in-use configuration, the properties of the material from which the patient interface is formed, together with the shape of the patient interface, allow the prongs to be at least extend at less of an angle than in the non-use configuration.

With reference to the embodiment shown in FIGS. 35 to 45, a patient interface 4700, such as a nasal cannula, has a body portion having left 4701 and right side arms 4703 to be located, in-use upon a face of a user. The patient interface 4700 has at least one, and preferably a pair of, nasal prong(s) 4705, 4707 to be inserted into, or to direct a flow of gas into, a nare or the nares of the user's nose. In use the left and right side arms are positioned upon a user's facial cheeks.

The patient interface 4700 has a bridge portion 4710. The nasal prong(s) 4705, 4707 extend from the bridge portion. In some embodiments the bridge portion may be relatively stiff so as to define at least a starting orientation and/or or spatial location of the nasal prongs. By "relatively stiff" It is meant that the bridge portion is stiffer than other portions of the body portion, such that other portions of the body portion bend or otherwise deform before the bridge portion bends or deforms in use. The bridge portion is stiffer either because it is thicker in width and/or height. Alternatively the bridge may be stiffer by comprising a bridge portion element.

When viewed from above, the bridge portion transitions into the left and right side arms by extending outwardly in a flared or curved manner away from a user's face side of the bridge portion. The left and right side arms 4701, 4703 curve away from the bridge portion rearwardly from a front extent of the body portion of the interface. A curvature of the user's face side 4720 of the bridge portion and/or transition regions 4719, 4721 between the bridge and left and right side arms is smooth. The face side of the bridge portion and/or transition regions 4719, 4721 have relatively large radiuses so pressure from the bridge and the transition regions 4719, 4721 on the user's face is spread evenly over their philtrum or upper lip region between the user's upper lip and nose. The transition regions 4719, 4721 are spaced outwardly from the prongs.

Figure 36:
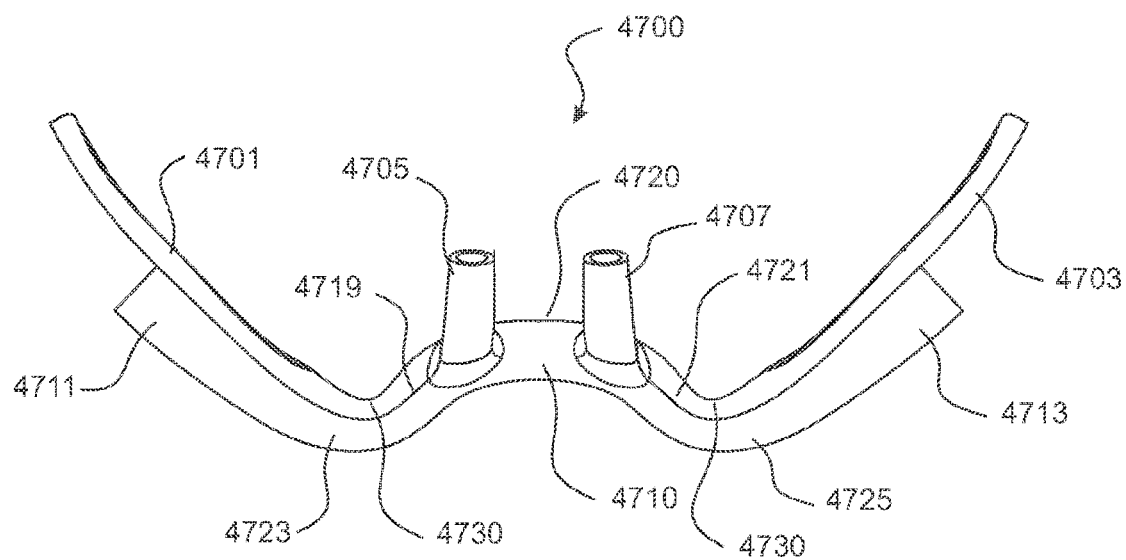
FIG. 36 is a plan view of the interface of FIG. 39.
Figure 37:
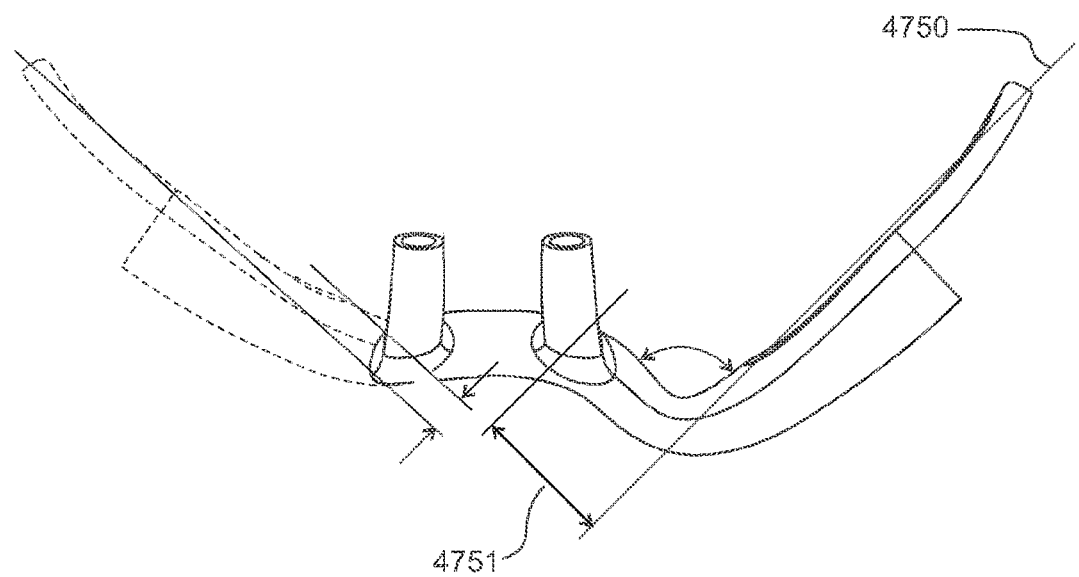
FIG. 37 shows half of the interface of FIG. 39 and a half of another Interface for comparison.

In some embodiments, as described above, the body portion extends forwardly from each side of the bridge portion 4710 to a position forward of the bridge portion, and then extends rearwardly so that ends of the body portion are positioned rearward of the bridge portion. This arrangement provides an approximate 'U' shape between each nasal prong 4705, 4707 and the left or right side arms 4701, 4703 of the body portion when viewed from above, as shown in FIG. 36. The U-shaped regions 4723, 4725 each provide a hinging or bending region where the body portion tends to bend when the left or right side of the body portion is flexed Inwards to meet the user's face. In some embodiments the U-shaped region tends to bend at the base or bottom of the valley 4730 of the U-shaped region. However the bending region in some embodiments may bend in a region that extends for a distance along the body portion. The bending region may not only bend at a discrete point on the body portion but may bend over an area or region of the body portion.

The bend or hinge region 4723, 4725 isolates flexing of the left and right side portions of the interface from the bridge portion and therefore from the nasal prongs. This results in facial movement that may be transmitted into the left and right sides of the interface being at least partially Isolated from the prongs so that the position of the prongs in the nares of a user is not disturbed in use by movement of the user's face.

The U shape of the body portion at the bending regions positions the bending regions outwardly and forwardly from the nasal prongs relative to a face side of the body portion. This arrangement further aids in flexibility of the bending portions, as it spaces a general plane 4750 of the left and right sides of the body portion further away from the nasal prongs compared to an interface without U shaped regions, for example as Indicated by the dashed lines on the left hand side in FIG. 37. Movement of the user's face is generally on the general plane 4750 of the left and right side portions and spacing this plane further from the nasal prongs Indicated by arrow 4751 in FIG. 37 further Isolates the facial movement from the prongs, to assist in reducing the effect of facial movement on the position of the prongs in the user's nares. The flexibility of the bending region may determine how large the distance between the general plane of each of the left and right sides of the body portion and the respective nasal prong should be.

In some embodiments the bending or hinging regions may be formed by or Include at least one bending or hinging element, for example a mechanical hinge. For example a mechanical hinge may be moulded into the hinging or being regions of the body portion.

The body portion of the interface of FIGS. 35 to 45 is a single, integrally formed component. As shown, the left and right side arms, the bending portions, the bridge portion and the at least one, and preferably the pair of, nasal prong(s) are a single, integrally formed component; that is, the patient interface 4700 is a single, integrally formed component. In some embodiments the patient interface is formed from a single moulding operation.

The patient interface 4700 is formed of a polymeric material. The polymeric material is one or a combination of any one or more of: thermoplastic elastomer(s), polypropylene based elastomer(s), liquid silicone rubber(s), or breathable thermoplastic polyurethane(s), or breathable polyamides, more preferably polymers may be those such as, but not limited to, polyolefins, thermoplastic elastomers, or breathable thermoplastic elastomers, for example thermoplastic elastomer families, such as styrene block copolymers, copolyester elastomers, or thermoplastic polyolefin elastomers or thermoplastic polyurethane elastomers. In a preferred embodiment the patient interface has a body portion made from a thermoplastic or silicone material with a Shore A hardness of approximately 5 to 60. In some embodiments the body portion has a Shore A hardness of about 10 to 50, or about 10 to 40, or about 20 to 40, or about 10 to 30. In some embodiments the body portion is made from Thermolast® K.

The Interface of FIGS. 35 to 45 may comprise a retention system for retaining the interface in position when being worn in-use by a user, as described in earlier embodiments. As described earlier, the retention system (or securement system) may comprise a releasable connection system for releasably connecting or securing the patient Interface to a user's face such as hook and loop or hook and hook type connectors. Such a releasable connection or securement system may comprise at least one pad (comprising materials such as hydrocolloid) attached to a user's face upon which the patient interface may be releasably engageable thereto. For example a pad may be attached to each of the left and right hand sides of the body portion of the interface, the pad comprising one half of a hook and loop or hook and hook connection. And a corresponding pad comprising a second half of the hook and loop or hook and hook connection may be attached to the face of the user.

In some embodiments, the pad to be attached to the body portion is substantially symmetrical about a central upright (e.g. vertical or approximately vertical) axis that divides the pad into left and right sides, for example as shown in FIG. 32A, so that the same shaped pad may be applied to both the left and right hand sides 4701, 4703 of the body portion. In some embodiments the pad may be symmetrical about a horizontal axis. In some embodiments the pad may be symmetrical about both a vertical axis and horizontal axis.

Symmetrical retention pads simplify the manufacturing process as the same loop pad can be applied to either side of the interface Increasing production speed and reducing operator error. This also means the only one type of pad needs to be stored for both the left and right sides of the interface. The pads may not be symmetrical along a horizontal. A pad may be attached to a recessed area in each of the left and right side arms of the body portion of the interface. The recessed area 4760 is Illustrated in FIG. 38B. The recess in which the pad is positioned may also be symmetrical so that the left and right hand sides of the recess are of the same or similar shape, to match the shape of the pad.

In the various embodiments or configurations described herein, the use of a two-part connection system allows for attachment, removal and re-attachment of an interface to a user's face. This can allow for a suitable re-positioning of the interface for example for Improved comfort or delivery of therapy (or both).

Further, in the various embodiments of configurations as described herein, one part of the releasable connection system is provided on the patient interface. That part of the releasable connection system provided on the patient interface Is Itself provided in connection with the interface in various ways, one of which can be by an overmoulding or an overmoulded connection of the interface to or about the part. By overmoulding of a portion of the interface to the part of the releasable connection system, a more durable or robust attachment or engagement of the part to the interface may be achieved. The material used to form or be moulded into the interface can be simultaneously allowed to flow about or onto a part of the releasable connection system, such as a pad or patch comprising loops (or alternatively hooks). This can allow for a more Integrated part comprising such loops or hooks into the patient interface. Optionally, for example, the overmoulding or overmoulding connection can extend at least about a perimeter of the part (so as to provide for a connection/attachment of the part to the interface), and the material of such an overmoulding may optionally extend partially or wholly across a face of the part from which a component of the releasable connection system may extend. For example, where the part provides for a hook or a loop, or another type of a two-part releasable connection system, the overmoulding may extend about the perimeter of such a part or may extend across partially or wholly the face from which the hook or the loop, or the another type of a two-part releasable connection system may extend therefrom.

The part which may be overmoulded to the interface may be a loop part or a hook part of a two-part connection system.

Figure 38A:
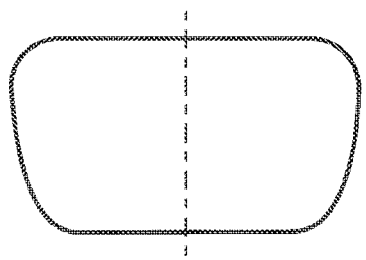
FIG. 38A Illustrates a symmetrical pad of a patient interface securement system.
Figure 38B:
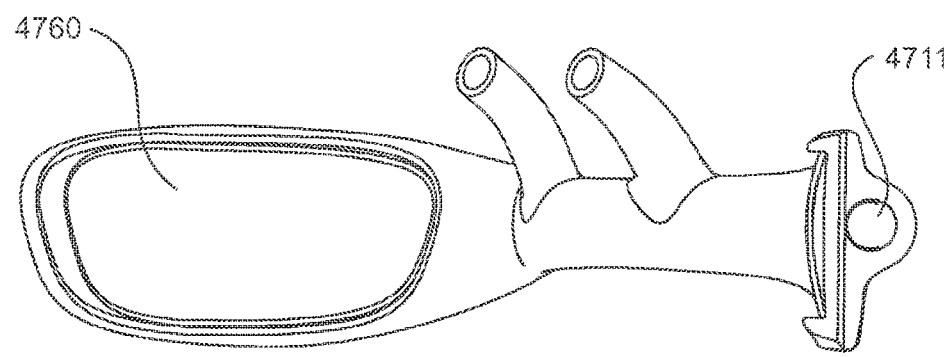
FIG. 38B shows the interface of FIG. 39 from another angle.
Figure 39A:
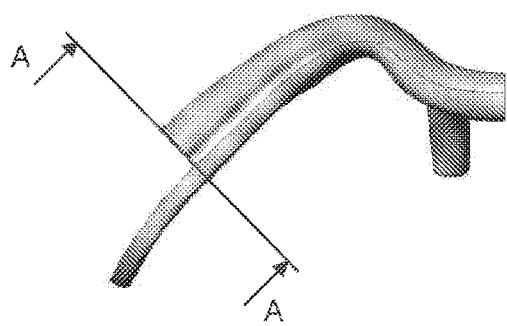
FIG. 39A Illustrates a portion of the interface of FIG. 36 and FIG. 39B Illustrates a section on line AA in FIG. 39A.
Figure 39B:
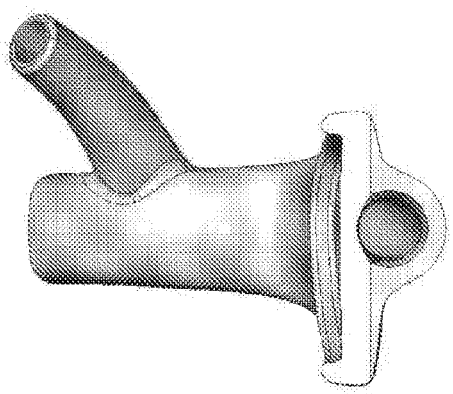

FIGS. 38A, B Illustrate where a hook or a loop pad section or part can be positioned into the recessed section 4760. It is contemplated that a loop part may be particularly provided in such a section 4760, while a hook part may be provided on the other part of a two-part connection system (for example a pad or patch which may be provided on a user's face).

The overmoulding of such a part is advantageous because it can allow the loop or hook pad part to be positioned and held more accurately than a gluing operation which is done, often by people. The overmoulding can provide for a stronger bond between the loop or hook pad part section and the patient interface. The moulded arrangement of loop or hook pad part and patient interface may be more robust, and there is less likelihood of the loop or hook pad part section peeling off or tearing or ripping off the section of the interface to which it is attached. More particularly, because it is the patient interface that is itself overmoulded upon the part, the part comprising the hook or loop or other part of a two-part connection system, allows for a more Integrated arrangement of an interface and a part of a releasable connection system, and therefore a more robust and enduring or durable connection of the Interface with the part.

In an alternative configuration, there may also be provided an arrangement in which the part to be attached to the patient interface may be done so in a manner once the Interface has been first moulded or formed (or manufactured). For example, using a moulded or formed (or manufactured) Interface, a subsequent or additional over-moulding step or stage may be conducted to provided for an over-moulding which connected or attaches each of the part and the interface together through an overmoulding connection. As discussed below, the moulding material may be allowed to flow to extend about the perimeter of such a part or may extend across partially or wholly the face of the part.

The overmoulding material of the loop or hook pad part section may be controlled to ensure that the polymer or plastic in the overmoulding flows to cover some of the loop or hook pad part but not all of the loop or hook pad part. The overmoulded section still maintains exposure of enough loops or hooks of the part to allow for a connection to the opposing part of the two-part connection system, for example a hook part of a pad or patch provided on the user's face.

In some alternative embodiments, the overmoulding material may be controlled to extend or flow through some of the loop or hook part so as to integrally bond the part to the interface to which it is to be attached.

The overmoulding may be performed as part of the interface (e.g. nasal cannula) moulding process Itself, or may be conducted as a subsequent step. Alternatively, the overmoulding may be performed once the interface body (e.g. nasal cannula body) is formed.

In other embodiments or configurations, the loop or hook part is overmoulded as part of the interface manufacturing process, and therefore uses the same material as the rest of the interface body (e.g. nasal cannula body) to ensure a secure bond (i.e. material compatibility is not compromised between the interface and the overmoulding material).

It will be appreciated the pad as shown in FIG. 38A may be the 'part' as described above which may be attached to the patient interface via an overmoulding process or by an overmoulded material for connecting or attaching the pad or 'part' to an interface. FIG. 38B shows a recessed region 4760 which may preferably receive the 'part' or pad. It will be appreciated that 'part' as discussed here which is one part of a two-part releasable connection system may be provided at other parts of an interface, for example as shown in other figures, the two-part connection system may utilise pads or parts provided at other regions of the Interface. Overmoulding of such parts or pads to the interface is provided as another way in which these may be attached or connected to the interface, for example providing for a more secure or robust connection or attachment. Such an overmoulding can avoid the use of adhesives or glues which may otherwise be required for such an attachment or connection of the pad or part to the interface.

In a particularly preferred embodiment, the nasal cannula is formed or moulded, and in doing so is simultaneously overmoulded onto the part, such as a pad comprising of loops (which form one part of a two-part releasable connection system). Such a part having loops can be held in place and the plastic or polymer used to form the cannula is allowed to flow over/around the loop comprising part to then become formed with the cannula Itself as an integrated loop pad.

As such, it will be appreciated in one embodiment a patient interface may be formed, such as by a moulding process, and during that process, a part comprising of one of a two-part connection system (e.g. loops or hooks) may be integrated Into the interface so formed (i.e. the part is formed as an integral part of the interface during formation of the Interface Itself). In an alternative embodiment, a patient interface may be formed, such as by a moulding process, and after that process, a part comprising of a two-part connection system (e.g. loops or hooks) may be integrated to form a part of the interface by an overmoulding connection (i.e. the interface and part are attached or connected to each other by an overmoulding material).

As described above, the body portion comprises a bending region 4723, 4725 in between the left and right side arms 4701, 4703 of the body portion and the bridge portion 4710. Preferably the pad area 4760 of the body portion for receiving a pad of a retention system is located outwardly of the bending region 4723, 4725. In other words the retention system does not bridge or cover over the bending region, so that the securement system is separated or Isolated from the bridge portion by the bending region.

The body portion can be shaped or configured or adapted to provide for a passageway 4711, 4713. Such a passageway 4711, 4713 may be formed by one or more of, a lumen or a void space or cavity or other recess through the body portion.

Such a passageway 4711, 4713 allows for receiving of a gas supply (from a source) and for channeling delivering of that gas to a user via the prongs 4705, 4707; or, alternatively allows for the receipt of a gas supply conduit (not shown, but which may be received or fitted into such an item 4711, 4713 for then delivering the gas to a user via the prongs(s)). Such a passageway 4711, 4713 in or through the side arm 4701, 4703 allows for the formation of a conduit or lumen through which gas may be directed or supplied for delivery to the prongs 4705, 4707.

In some embodiments a cross section of the passageway 4711, 4713 changes along its length to provide or impart different structural features or characteristics to the body portion of the interface such that the body portion has regions of differing flexibility. Unless the context suggests otherwise, the term "cross section" is Intended to mean a lateral cross section of the passageway, being across the passageway and not along a length of the passage way. The passageway may go through cross sectional transition points along the length of the passageway.

The changing cross section along the length of the flow path is Illustrated in FIGS. 38A to 41B. As shown in FIG. 39B, a cross-section of the passageway at or near where a breathing tube or conduit couples with the passageway is substantially circular to fit a circular tube or conduit.

Figure 40A:
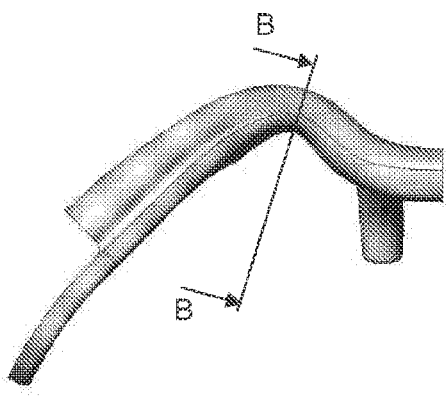
FIG. 40A Illustrates a portion of the interface of FIG. 36 and FIG. 40B Illustrates a section on line BB in FIG. 40A.
Figure 40B:
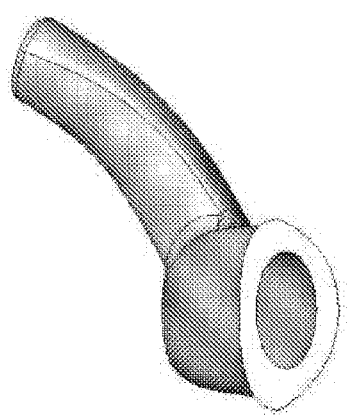

Moving along the passageway from the breathing tube or conduit towards the nasal prongs, the cross section of the passageway changes from being circular to being oval or elongated having a longer axis arranged in a vertical or upright direction (approximately parallel to a user's face in use) compared to a direction into the user's face, as shown in FIG. 40B.

The elongated cross section provides a low profile Interface meaning the interface stands off the face of the user by a smaller distance, as the passageway is flatter for a given cross sectional area of the passageway. Also, the elongated cross section provides greater flexibility for bending in a lateral direction, e.g. a direction into the face of the user, which is along the shorter axis of the elongated cross section. In other words, the flatter or elongated cross section is easier to bend about an axis that is approximately parallel to a user's face, compared to a circular cross section of the same or of a similar area. For example, as shown in FIG. 38B, the cross section of the bending regions 4723, 4725 described above are preferably elongated with a longer axis arranged approximately parallel to the user's face and a shorter axis arranged approximately perpendicular to the user's face. The elongate cross section and the U shape of the body portion combine to create a bending region that preferentially bends laterally towards and away from the user's face compared to other regions of the body portion. The bending regions reduce the likelihood that prongs pop out of the user's nares (e.g. forwardly) due to facial movements. The described bending regions are created without the use of any type of mechanical hinge structure, but rather due to the elongated or oval shape of the air passageway allowing the body portion to buckle or bend more easily at the flatter regions.

With reference to the embodiment of FIG. 35 to 45, it will be appreciated that the patient interface may Include one or more of the side arm or bridge elements described above. Those elements will be or comprise a material that is relatively more rigid than the remainder of the patient interface and will have the suitable features and functions, as described above in relation to the earlier embodiments. The side arm elements and/or bridge portion element will add stability and structure to the patient interface while still maintaining the flexibility provided by the other features of the patient interface.

The bending regions allow for more flexibility of movement at the user's cheeks. The bending regions are wider than what they might be if the passageway was circular. The longer axis of the elongate cross section helps to ensure that the body portion flexes predominantly in a direction substantially horizontal or lateral direction (i.e. the left or right portion bending Inwards toward the bridge of the body portion) and without twisting or buckling in other directions (i.e. bending across the user's face).

Figure 41A:
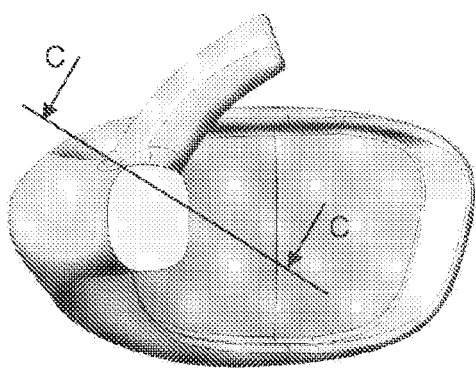
FIG. 41A Illustrates a portion of the interface of FIG. 36 and FIG. 41B Illustrates a section on line CC in FIG. 41A.
Figure 41B:
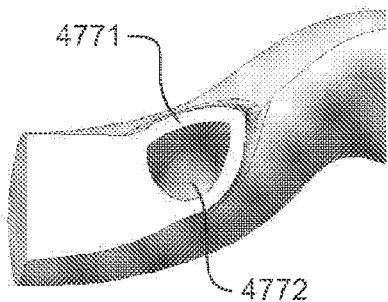

The cross section of the passageway transitions into an asymmetric shape at the base of the nasal prong, wherein one side of the cross section is flatter than an opposite side of the cross section, as shown in FIG. 41B. The asymmetric shape may be loosely described as having a 'D' shape. Benefits of the 'D' shape are discussed below.

In some embodiments, one or both prongs comprise a 'D' shaped or asymmetric shaped passageway along a portion of the length of the passageway or may comprise a 'D' shaped/asymmetric shaped passageway along the full length of the prong. In the illustrated embodiment of FIGS. 39A to 43B, continuing along the prong, the cross section of the passageway moves from being D shaped towards being circular so that the passageway at an exit or tip of the prong is approximately circular, as shown in FIG. 43B. FIG. 42B shows the cross-section approximately mid way along the prong. The cross sectional area may reduce slightly from the base of the prong towards the tip of the prong.

The different cross sectional area of the passageway from the tube or conduit end to the base of the prong is preferably substantially constant to maintain a similar resistance to flow along the passageway. Thus flow resistance due to changing shape from circular to a flattened shape is substantially avoided. As stated above the passageway may constrict slightly along the prongs towards the prong tips.

With reference to FIG. 41B, in some embodiments the nasal prong comprises an asymmetrical cross section at least a base region or end of the prong. The asymmetric shape comprises one side 4771 that is flatter than an opposite side 4772 of the cross section. The asymmetric shape may be loosely described as having a 'D' shape.

The flatter side of the prong is positioned towards a forward side or non face contacting side of the patient interface (facing away from the user's face). The asymmetric shape is particular beneficial from a manufacturing point of view. The shape allows for Improved part lines and allows for part lines to be moved away from a sensitive part of the nose. Part lines are formed where mould tool move apart to allow the moulded component to be formed. The part line can often be a rough/sharp line. Therefore it is desirable to move the part lines away from the face, and having the flat sided prong makes it easier to manufacture, since the tool design becomes easier. In the flat sided or asymmetric shape, the flat side of the tool remains stationary and the curved side of the tool moves toward and away from the flat portion. For a typically more rounded prong a more complicated arrangement is required with two moving tools that move toward each other and away from each other. Further, the shape provides for shape edges on the part lines to be avoided or reduced, which aids in comfort to the user during use.

No sharp edges are formed on the prong at the part line. This makes it more comfortable for the patient as no sharp edges are in contact with the patient. The more rounded side of the prongs is positioned on the user's face side of the prong and maintains comfort at the base of the nares. The rearward rounded shape also maintains structural stability at the base of the prong; the flatter side of the 'D' shape is more likely to buckle in response to an applied force compared to the rounded side. Further, the asymmetric shape does not significantly alter the air flow resistance of the passageway along the prong. In some embodiments the radius of a fillet between the prong and the bridge portion may be Increased to provide additional rigidity at the base of the prong. Further discussion of this arrangement is provided below.

In some embodiments the bridge portion 4710 between the two bending portions 4723, 4725 from which the prongs extend can be stiffened to prevent outward movement of the prongs relative to each. Stiffening may be achieved by Including more material in the bridge region (e.g. thicker wall sections) without the use of a strengthening member embedded in the body portion.

In some embodiments the height or vertical dimension of the bridge region 4710 is larger compared with other patient interfaces. The height of the bridge region is best shown in the front view of FIG. 44. The Increased vertical dimension helps to Improve torsional stability and prevent twisting of the body portion and prongs out of the nares when flexed, and also may help to spread load or contact area on the user's philtrum. The height of the bridge region should be less than the philtrum to maintain patient comfort. The height of the bridge region required may depend on how flexible the bending regions of the body portion are to Isolate movement of the left and right side arms from the bridge and prevent or reduce the occurrence of the prongs popping from the user's nares.

Figure 44:
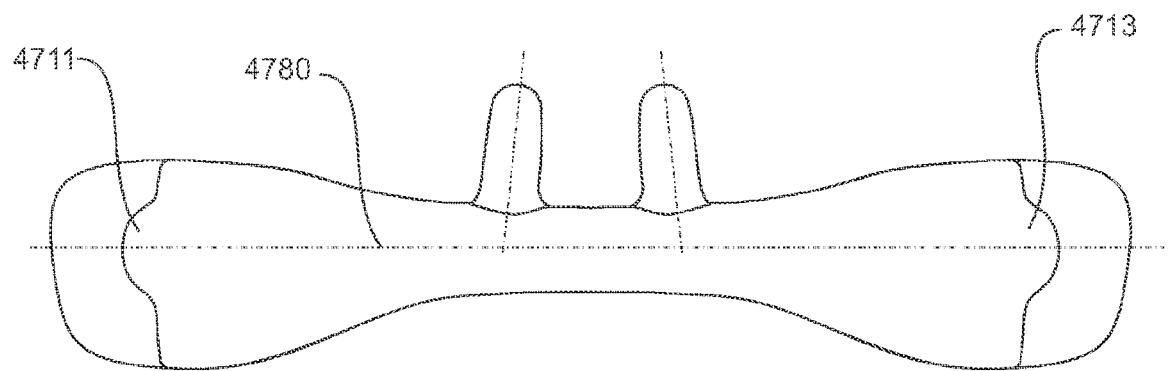
FIG. 44 is a front view of the interface of FIG. 36.

As described above, the radius of the curvature of the bridge region and the areas of the body portion between the bending regions 4723, 4725 and the bridge region 4710 is relatively large. This arrangement helps to ensure no sharp edges are in contact with the patient. In some embodiments the prong are angled inward slightly as shown in FIG. 44.

In some embodiments the passageway 4711, 4713 is positioned approximately in the middle of the cheek pad in a vertical direction. This arrangement may provide for a more predictable behaviour in the way the body portion deforms, and may encourage the prongs to move in a substantially horizontal direction rather than a substantially vertical direction when a force is applied to a breathing tube or conduit, which helps to prevent the prongs from popping or flipping out of the user's nares.

By arranging the passageway approximately centrally in a vertical direction on the body portion, the horizontal neutral bending axis 4780 of the body portion is also located approximately centrally in a vertical direction. This may place the neutral axis approximately centrally on the securement system for securing the interface to the user's face, which helps to reduce forces acting to pull or tear the interface from the user's face, compared to if the neutral axis was closer to an upper or lower edge of the body portion.

Also, having the tube or conduit extending centrally from the interface with the passageway located centrally on the body portion helps to maintain the correct position of the prongs in the user's nare. For example, an upward force on a tube positioned nearer to the base of the body portion may cause the middle of the body portion to move outwards and the prongs to rotate outwards from the user's nose, which is less preferred.

As described above the interface 4700 comprises features to ensure the body portion has requisite flexibility in required areas for an improved fit with the user's face. For example, as described the body portion may comprise a passageway with a varying shaped cross section and/or shaped regions to provide regions that are prone to bending, to for example Isolate movement of the users face (e.g. cheeks) from the nasal prongs. Flexibility of the body portion may be enhanced by varying material, geometry or thickness of sections, Including hinging points, and varying the shape of tubular portions such as the passageway along the body portion and along the prongs as described above.

As described above, in preferred embodiments the patient interface 4700 is a single, integrally formed component made from a thermoplastic or silicone material. A single unitary component is easier to manufacture than an interface comprising many parts and/or different materials, for example some materials over-moulded with other materials. Varying geometries of the body portion are chosen to achieve regions having more flexibility and regions having less flexibility in a single unitary component formed from a single material.

As described above, in a preferred embodiment the bending regions 4723 and 4725 are more flexible than the bridge portion and the left and right side arms of the body portion. At least part of the passageway extends through the bending regions and is shaped to aid flexibility. The passageway extends into the bridge region 4710 and along the prongs, however, the bridge region preferably comprises a solid section having more material than adjacent bending regions 4723, 4725, so that the bridge region is more rigid. The prongs should not be so flexible that they collapse or are too easily compressed within the nose. Thus, the aim of the varying geometry of the body portion is to cause any buckling and bending or flexing to occur at the bending regions rather than in the bridge region.

The thickness of the body portion material may be varied to aid in maintaining the various flexible and less flexible regions. The body portion may have thinner walls or sections surrounding the passageway in the bending regions than in other regions of the body portion. In some embodiments, the cross sectional area of the body portion material at the valley 4730 of the U shaped regions 4723, 4725 is smaller than in adjacent regions of the body portion. In a preferred embodiment, the body portion provides a left passageway and a right passageway, wherein the left and right passageways 4711, 4713 are separated by a dividing section in the bridge region. The dividing section is a central region of the bridge between the two nasal prongs. The central region of the bridge region may be solid to provide relative rigidity to the bridge region. In some embodiments, the bridge portion comprises wall sections that are thicker than wall sections of the bending regions so that the bridge portion is more rigid than the bending regions. The thicker walls of the bridge portion provide more material to the bridge portion than in the hinging or bending regions to impart more rigidity to the bridge portion. In some embodiments the bridge portion comprises a further more rigid material to provide rigidity to the bridge region. For example a more rigid or stiff material may be moulded into the bridge portion, for example by a 2-shot overmould or multiple moulding processes.

In some embodiments the left and right side arms or regions of the body portion are soft, to easily flex on the user's face. The left and right regions are preferably more flexible than the bridge region. In some embodiments the left and right regions are more flexible than the nasal prongs. In some embodiments the bending regions are more flexible in at least one plane than the prongs, the bridge region, and the left and right side arms.

Each prong has a base 4715, 4717 that is integrally formed with the bridge portion 4710 of the body portion of the patient interface. In some embodiments the base of each prong comprises a fillet between a wall of the prong and the bridge portion. The fillet extends around the perimeter of the prong. The fillet curves the outer surface of the prong into the outer surface of the bridge portion.

In some embodiments the radius of the fillet at the base of each prong varies around the perimeter of the prong to Improve stability of the prong and reduce buckling or bending of the prong at the base of the prong. The larger the radius of the fillet the smoother the transition from the outer surface of the bridge portion to the outer surface of the prong, which may reduce the likelihood the prong bends or creases at the base.

In some embodiments the radius of the fillet at the base of each prong is varied around the perimeter of the prong to vary the wall thickness of the prong at the base 4715, 4717 of the prong 4705, 4707. The larger the radius of the fillet the thicker the material at the base of the prong may be and therefore the stiffer the base becomes. Varying the fillet radius around the prong base to vary the thickness of the base may be used to vary the stiffness of the prong base around the perimeter of the prong.

The thickness of the prong base may be varied in other ways, for example the geometry of the passageway may be varied to vary the wall thickness of the prong at the base of the prong with a constant fillet radius on the outside of the body portion between the prong and the bridge portion. However, this arrangement for varying the thickness of the prong wall may be less preferred as increasing the wall thickness in this way may reduce the cross sectional area of the passageway resulting in an increase in flow resistance.

Figure 45:
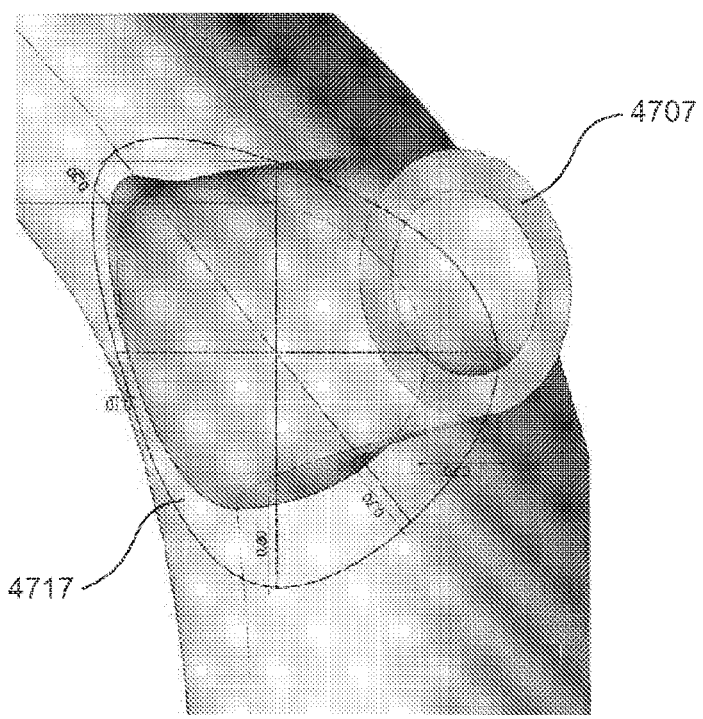
FIG. 45 illustrates a portion of the interface of FIG. 36 showing a base of a nasal prong.

The fillet radius may be varied according to size constraints of the particular patient interface. For example, with reference to FIG. 45, in some embodiments it may be desirable to have a fillet with a smaller radius between the prong and the bridge portion on a non-face side of the body portion, and a fillet with a larger radius on an inner side (between the two prongs) of the prong and on an outer side of the prong. The radius of the fillet on the inner side of the prong may be larger than the radius of the fillet on the outer side of the prong. The fillet on the face side of the body portion may have a radius that is between the radius on the inner and outer sides of the prong. Example dimensions are shown in FIG. 45, but other arrangements may also be useful.

In an alternative embodiment, the patient interface comprises the features of the embodiment described in relation to FIGS. 35 to 45 together with side arm elements and or bridge portion elements.

In particular, such an embodiment comprises a body portion to be located, in-use upon a face of a user, the body portion having left and right side arms and a bridge portion between the left and right side arms. The patient interface has at least one nasal prong extending from the bridge portion to be inserted into, or to direct a flow of gas into, a nare or the nares of the user's nose in an operational position. The body portion having at least one fluid passageway connected to the nasal prong(s) for supply of a gas to the nare(s) of the user's nose. A cross section of the passageway varies along the length of the body portion to provide regions of varying flexibility along the body portion. In this embodiment, each of the left and right side arms may comprise one or more predefined or predisposed points or localised compensation regions (or sites) positioned along the or each side arm to accommodate a compensation of the patient interface in or at one or more of compensation regions (or sites), configured to accommodate a force by way of flexure or bending or hinging or other displacement. One or more of the compensation regions (or sites) may be a region or site of bending or hinging region though or about at least two different (non-parallel) planes passing through the interface. In this embodiment, the side arms may comprise one or more side arm elements that are provided to or within the side arms of the interface, the side arm elements being formed from a rigid material to provide rigidity to the side arms/portions. The side arm element may further comprise one or more cut outs or notches to allow the side arms to flex/hinge in response to forces applied to or experienced by the side arms. Additionally or alternatively to one or more side arm elements, the bridge portion may comprise a bridge portion element and the bridge portion, the bridge portion element, or both the bridge portion and bridge portion element is/are substantially Isolated from forces applied or to, or experienced by, the patient interface.

Figure 46:
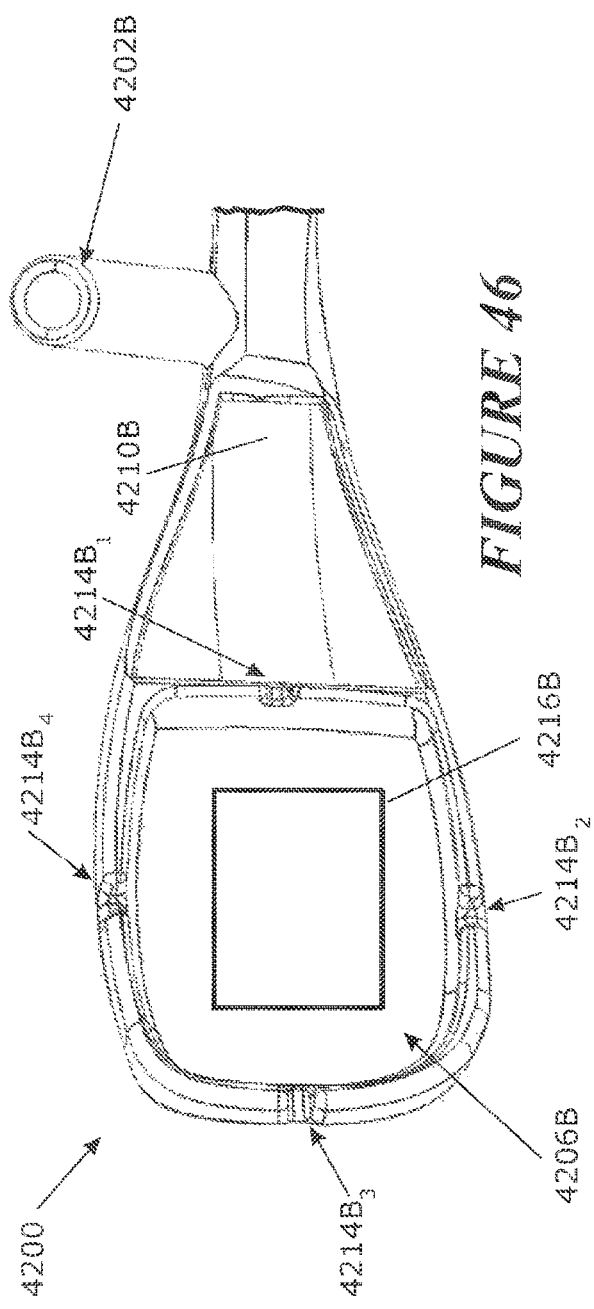
FIGS. 46 and 47 show rear views of a portion of the patient interface shown in FIG. 2.
Figure 47:
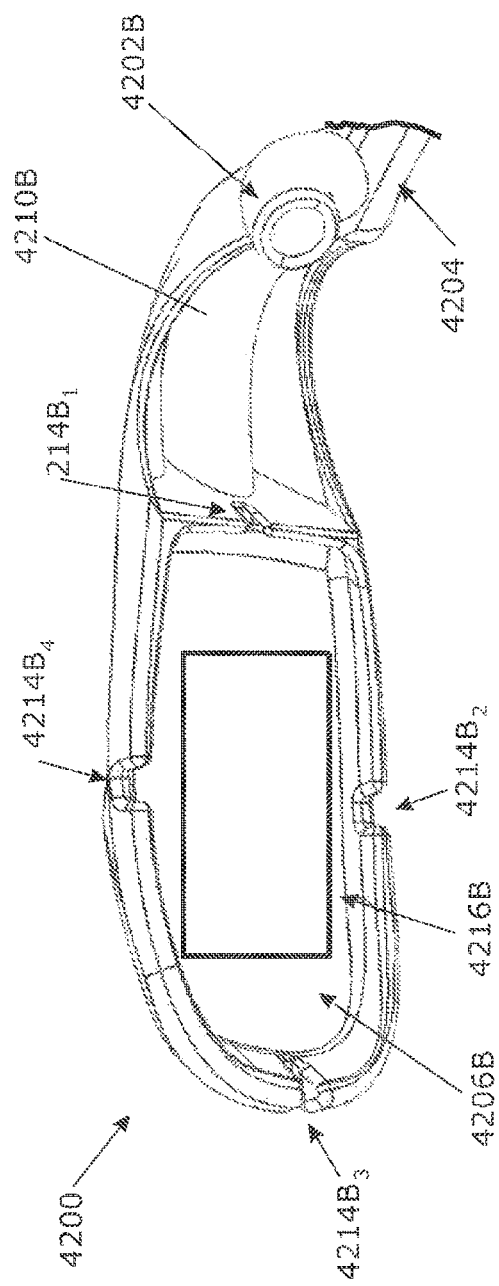
Figure 48:
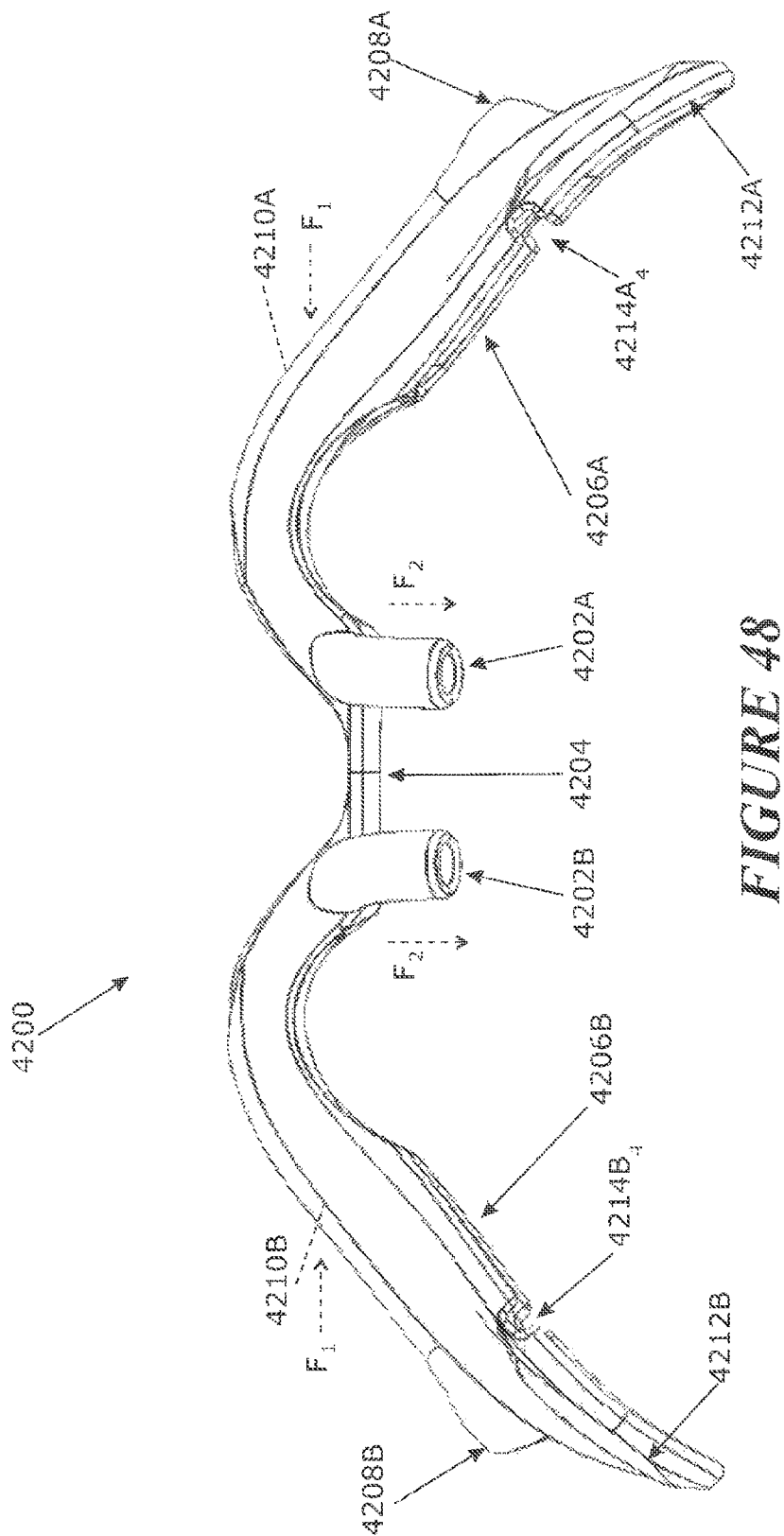
FIG. 48 shows an elevated rear view of a portion of the patient interface shown in FIG. 18.

Additionally or alternatively to the embodiments described above, further attention is given to the first and second side arms 4206A, 4206B. With reference to FIGS. 46 and 47, the second side arm 4206B is shown. It should be understood that in the illustrated configurations the patient interface 4200 is substantially symmetrical. In other configurations, the patient interface 4200 may be asymmetrical. As seen in FIGS. 46 and 47, the second side arm 4206B comprises regions of reduced thickness $4214B_1$, $4214B_2$, $4214B_3$, $4214B_4$ positioned on outer edges of the second side arm 4206B (except for one region $4214B_1$ positioned on an outer edge of an inwardly facing portion of a flange defining a section of a patient facing portion of the body 4206B adapted to hold the second attachment structure 4216B). The regions of reduced thickness $4214B_1$, $4214B_2$, $4214B_3$, $4214B_4$ may, for example, be notches or cut-outs along the second side arm 4206B. The regions of reduced thickness $4214B_1$, $4214B_2$, $4214B_3$, $4214B_4$ are configured to Increase the flexibility of portions of the second side arm 4206B configured to rest over the cheek of the patient. Improving the flexibility of the patient interface 4200 in this area using the regions of reduced thickness $4214B_1$, $4214B_2$, $4214B_3$, $4214B_4$ can improve the conformability of the patient interface 4200 to the contours of the face, particularly when forces F1 are exerted on the side arms 4206A, 4206B (see FIG. 48). Other configurations are contemplated. For example, in some configurations regions of reduced thickness may be positioned elsewhere on the second side arm 4206B or bridge 4204 to Improve the conformability of the patient interface 4200. As disclosed, it should be understood that similar regions of reduced thickness are positioned on the first side arm 4206A. However, in some configurations, only one body might comprise regions of reduced thickness. Although in the illustrated configuration four regions of reduced thickness $4214B_1$, $4214B_2$, $4214B_3$, $4214B_4$ are used on the second side arm 4206B, it should be understood that fewer or greater than four regions (for example, one, two, three, five or six regions) may be used. In some configurations, the second side arm 4206B may comprise no regions of reduced thickness. In some configurations (not Illustrated) the first and/or second side arms 4206A, 4206B may comprise one or more hinging points associated with each respective body to allow each body to pivot or move relative to the bridge 4204 or the other respective body. In some configurations at least a portion of one of the side arms can pivot relative to the bridge 4204 and/or the other respective body.

The particular embodiments of Interface described herein can be suitable for Infants, neonates or children and providing flow therapy to these patients. It is particularly useful for use with Infants, neonates or children because their faces move a lot. However, it will be appreciated that the particular embodiments of the interface described herein can be used to treat adults using high flow therapy too.

Unless the context clearly requires otherwise, throughout the description and the claims, the words "comprise", "comprising", and the like, are to be construed in an inclusive sense as opposed to an exclusive or exhaustive sense, that is to say, in the sense of "Including, but not limited to."

Although the present disclosure has been described in terms of certain embodiments, other embodiments apparent to those of ordinary skill in the art also are within the scope of this disclosure. Thus, various changes and modifications may be made without departing from the spirit and scope of the disclosure. For Instance, various components may be repositioned as desired. Moreover, not all of the features, aspects and advantages are necessarily required to practice the present disclosure. Accordingly, the scope of the present disclosure is Intended to be defined only by the claims that follow.

Various embodiments have been described by way of example. In some embodiments, any one or more of the features of one or more of the embodiments described may be combined with one or more features of other embodiment(s).

Language of degree used herein, such as the terms "approximately," "about," "generally," and "substantially," as used herein represent a value, amount or characteristic close to the stated value, amount or characteristic that still performs a desired function or achieves a desired result. For example, the terms "generally parallel" and "substantially parallel" refer to a value, amount or characteristic that can depart from exactly parallel by less than or equal to 15 degrees, 10 degrees, 5 degrees, 3 degrees, 1 degree, 0.1 degree, or otherwise.

In this specification and claims, terms such as top, bottom, above, below, vertically and horizontally are intended to be with reference to a user with the patient interface positioned on the user's face with the user in a vertical standing position, unless the context suggests otherwise. The terms inner or inward and outer or outward and similar such terms are intended to be with reference to a central vertical plane of the patient interface (i.e. a sagittal plane of the user) with the patient interface positioned on a user's face, unless the context suggests otherwise. The terms forwards, backwards, rearwards are intended to be with reference to a user with the patient interface positioned on the user's face, unless the context suggests otherwise.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The foregoing description of the invention Includes preferred forms thereof. Modifications may be made thereto without departing from the scope of the invention.

Additional Features

Item A1. A patient interface comprising:
a. a first body adapted to rest on a first portion of a face of a user;
b. a second body (hereinafter the first body and second body mean a pair of side arms) adapted to rest on a second portion of the face of the user;
c. a bridge linking the first and second bodies; and
d. a supporting structure positioned over at least a part of the bridge.

Item A2. The patient interface of item A1, wherein the supporting structure is positioned over at least a part of a user facing portion of the bridge.

Item A3. The patient interface of any one of items A1-2, wherein the supporting structure is at least in part formed from a textile material.

Item A4 The patient interface of item A3, wherein the textile material is a woven, non-woven or knitted textile material.

Item A5 The patient interface of any one of items A1-2, wherein the supporting structure is at least in part formed from a moulded polymer.

Item A6 The patient interface of item A5, wherein the supporting structure is formed from a moulded polymer sheet.

Item A7 The patient interface of any one of items A1-6, wherein the supporting structure and bridge are formed at least in part from the same polymer.

Item A8 The patient interface of any one of items A1-7, wherein the first body is adapted to rest on a cheek of the user.

Item A9 The patient interface of any one of items A1-8, wherein the first and second bodies are adapted to rest on opposing cheeks of the user.

Item A10 The patient interface of any one of items A1-9, wherein the first and/or second bodies comprise one or more nasal delivery elements adapted to rest in one or more nares of the user.

Item A11 The patient interface of item A10, wherein the one or more nasal delivery elements are configured to allow for ambient gases outside of the patient interface to pass through the nares.

Item A12 The patient interface of any one of items A10-11, wherein the one or more nasal delivery elements are shaped or angled such that they extend Inwards towards a septum of the user.

Item A13 The patient interface of any one of items A10-12, wherein the one or more nasal delivery elements are shaped or angled such that tips of the one or more nasal delivery elements point, in use, towards a back of the user's head.

Item A14 The patient interface of any one of items A10-13, wherein the first and/or second bodies comprise one or more gas delivery lumen in pneumatic communication with the one or more nasal delivery elements.

Item A15 The patient interface of item A14 further comprising one or more gas delivery conduits in pneumatic communication with the one or more gas delivery lumen.

Item A16 The patient interface of any one of items A1-15, wherein the supporting structure extends along the first and/or second bodies.

Item A17 The patient interface of item A16, wherein the supporting structure extends along user facing portions of the first and/or second bodies.

Item A18 The patient interface of item A17, wherein at least a portion of the supporting structure present on the user facing portions of the first and/or second bodies is adapted to Interface with one or more fixation structures secured to the face to fasten the patient interface to the face.

Item A19 The patient interface of any one of items A1-18, wherein the patient interface is shaped so as to match contours of the face of the user.

Item A20 The patient interface of any one of items A1-19, wherein the first and/or second bodies comprise one or more regions of reduced thickness relative to adjacent regions of the first and/or second bodies.

Item A21 The patient interface of item A20, wherein the one or more regions of reduced thickness are positioned on portions of the first and/or second bodies that rest on one or more cheeks of the user.

Item A22 The patient interface of any one of items A20-21, wherein the one or more regions of reduced thickness are positioned on outer edges of the first and/or second bodies.

Item A23 The patient interface of any one of items A1-22, further comprising one or more attachment structures secured to user facing portions of the first and/or second bodies, the one or more attachment structures adapted to Interface with one or more fixation structures secured to the face to fasten the patient interface to the face.

Item A24 A nasal cannula comprising:
a. first and second bodies adapted to rest on opposing cheeks of a user;
b. at least one nasal delivery element extending from the first and/or second bodies adapted to non-sealingly rest in one or more nares of the user;
c. a bridge linking the first and second bodies; and
d. a stiffening structure positioned over at least a part of the bridge.

Item A25 The nasal cannula of item A24, wherein the stiffening structure is positioned over at least a part of a user facing portion of the bridge.

Item A26 The nasal cannula of any one of items A24-25, wherein the stiffening structure is at least in part formed from a moulded polymer.

Item A27 The nasal cannula of item A26, wherein the stiffening structure is formed from a moulded polymer sheet.

Item A28 The nasal cannula of any one of items A24-25, wherein the stiffening structure is at least in part formed from a textile material.

Item A29 The nasal cannula of item A28, wherein the textile material is a woven, non-woven or knitted textile material.

Item A30 The nasal cannula of any one of items A24-29, wherein the stiffening structure and bridge are formed at least in part from the same polymer.

Item A31 The nasal cannula of any one of items A24-30, wherein the at least one nasal delivery element is shaped or angled such that it extends Inwardly towards a septum of the user.

Item A32 The nasal cannula of any one of items A24-31, wherein the at least one nasal delivery element is shaped or angled such that a tip of the at least one nasal delivery element points, in use, towards a back of the user's head.

Item A33 The nasal cannula of any one of items A24-32, wherein the first and/or second bodies comprise one or more gas delivery lumen in pneumatic communication with the at least one nasal delivery element.

Item A34 The nasal cannula of item A33, further comprising one or more gas delivery conduits in pneumatic communication with the one or more gas delivery lumen.

Item A35 The nasal cannula of any one of items A24-34, wherein the stiffening structure extends along the first and/or second bodies.

Item A36 The nasal cannula of item A35, wherein the stiffening structure extends along user facing portions of the first and/or second bodies.

Item A37 The nasal cannula of item A36, wherein at least a portion of the stiffening structure present on the user facing portions of the first and/or second bodies is adapted to Interface with one or more fixation structures secured to the face to fasten the nasal cannula to the face.

Item A38 The nasal cannula of any one of items A24-37, wherein the nasal cannula is shaped so as to match contours of the face of the user.

Item A39 The nasal cannula of any one of items A24-38, wherein the first and/or second bodies comprise one or more regions of reduced thickness relative to adjacent regions of the first and/or second bodies.

Item A40 The nasal cannula of item A39, wherein the one or more regions of reduced thickness are positioned on outer edges of the first and/or second bodies.

Item A41 The nasal cannula of any one of items A24-40, further comprising one or more attachment structures secured to user facing portions of the first and/or second bodies, the one or more attachment structures adapted to Interface with one or more fixation structures secured to the face to fasten the nasal cannula to the face.

Item A42 A nasal cannula comprising:
a. a first body adapted to rest on a first portion of a face of a user;
b. a second body adapted to rest on a second portion of the face of the user; and
c. at least one nasal delivery element extending from the first and/or second bodies adapted to non-sealingly rest in one or more nares of the user;
d. wherein the first and/or second bodies comprise one or more regions of reduced thickness relative to adjacent regions of the first and/or second bodies.

Item A43 The nasal cannula of item A42, wherein the first and second bodies are adapted to rest on opposing cheeks of the user.

Item A44 The nasal cannula of any one of items A42-43, wherein the one or more regions of reduced thickness are positioned on portions of the first and/or second bodies that rest on one or more cheeks of the user.

Item A45 The nasal cannula of any one of items A42-44, wherein the one or more regions of reduced thickness are positioned on outer edges of the first and/or second bodies.

Item A46 The nasal cannula of any one of items A42-45, further comprising a bridge linking the first and second bodies.

Item B1. A patient interface comprising:
a. one side arm or preferably a pair of said side arms extending laterally from a substantially central bridge portion to be located, in-use, in or about a user's septum region,
b. wherein the or each said side arm is connected to a substantially resilient, or relatively more rigid, bridge portion element, the bridge portion element defining a substantially predetermined spatial relationship for an outlet or outlets of a gas delivery system with the or each said side arm.

Item B2. A patient interface comprising:
a. one side arm or preferably a pair of said side arms extending laterally from a substantially central bridge portion to be located, in-use, in or about a user's septum region,
b. the or each said side arm comprising one or more predefined or predisposed points or localised compensation regions (or sites) positioned along the side arm to accommodate or facilitate a compensation of the patient interface in or at one or more of the compensation regions (or sites), and
c. wherein the or each said side arm is connected to a substantially resilient, or relatively more rigid, bridge portion element, the bridge portion element defining a substantially predetermined spatial relationship for an outlet or outlets of a gas delivery system with the or each said side arm.

Item B3. A patient interface comprising:
a. one side arm or preferably a pair of said side arms extending laterally from a substantially central bridge portion to be located, in-use, in or about a user's septum region,
b. the or each said side arm comprising at least one substantially resilient, or relatively more rigid, side arm element, the side arm element defining at least in part a form or curvature of the or each side arm and having one or more predefined or predisposed points or localised compensation regions (or sites) positioned along the or each side arm and/or the or each side arm element to accommodate a compensation of the patient interface in or at one or more of compensation regions (or sites), and
c. wherein the or each said side arm element is connected, or is inter-connected via a connecting material, to a substantially resilient, or relatively more rigid, bridge portion element, the bridge portion element defining a substantially predetermined spatial relationship for an outlet or outlets of a gas delivery system with the or each said side arm.

Item B4. The Interface of any one of items B1-3, wherein the bridge portion or bridge portion element (or both) is/are substantially Isolated from forces as may be applied or to, or may be experienced by, the patient interface.

Item B5. The Interface of any one of items B1-4, wherein a force applied to the patient interface may be experienced by a side arm or side arms of the interface, the compensation regions (or sites) of the side arm or the side arm element, or both, accommodate the force by way of a flexure or bending or hinging or other displacement of the side arm or the side arm element, or both.

Item B6. The Interface of any one of items B1-5, wherein the side arm or arms are patient interface stabilisers.

Item B7. The Interface of any one of items B1-6, wherein the bridge portion element and the side arm element or elements are separate parts assembled to form a unitary component.

Item B8. The Interface of any one of items B1-7, wherein the bridge portion element and the side arm element or elements is a single component, or at least the bridge portion and at least one side arm element is a single component.

Item B9. The Interface of any one of items B1-8, wherein the bridge portion element and the side arm element or elements are integrally formed as a single component, or at least the bridge portion element and at least one side arm element is integrally formed as a single component.

Item B10. The Interface of any one of items B1-9, wherein the bridge portion element and the side arm element or elements is formed as an integral component.

Item B11. The Interface of any one of items B1-6, wherein the bridge portion element and at least one of the side arm element or elements are separate components, each of which may be substantially Interconnected, or provided in an interconnected relationship with each other by a material of the patient interface, such as of a side arm or side arms.

Item B12. The Interface of any one of items B1-6, wherein the bridge portion element is a component discontinuous with one or more side arm elements.

Item B13. The Interface of any one of items B1-6, wherein a side arm comprises one or more separate side arm elements, each of said one or more separate side arm elements being spaced apart through, or along a length of, a said side arm.

Item B14. The Interface of Items BB 13, wherein each of the one or more separate side arm elements are spaced apart as an array through or along the length of one or each said side arm.

Item B15. The Interface of any one of items B1 to 6, wherein the bridge portion element and the side arm element or elements are separate parts provided in connection, or are inter-connected, with each other, via one or a pair of associated side arm(s) and optionally the bridge portion, an associated side arm comprising of one or more associated side arm elements.

Item B16. The Interface of any one of items B13-15, wherein each separate side arm element provides for a relatively resilient portion, a material of the side arm Interposed between each, or adjacent to each, separate side arm element, the material of the side arm providing for a compensation region (or site).

Item B17. The Interface of any one of items B1-6, wherein the patient interface comprises a bridge portion element, and at least one separate side arm element located in each one of a pair of side arms.

Item B18. The Interface of any one of items B1-17, wherein the bridge portion is disposed intermediate of a pair of side arms.

Item B19. The Interface of any one of items B1-18, wherein the bridge portion element is disposed intermediate of the side arm elements of a pair of side arms.

Item B20. The Interface of any one of items B1-19, wherein the bridge portion element is of a dimension (sufficient) to span the width of a user's septum region, or is a distance or the width between gas outlets, or is defined by a maximum distance substantially spanning from one nasolabial fold to another nasolabial fold of a user.

Item B21. The Interface of any one of items B1-20, wherein the bridge portion element Includes one or a pair of cut-outs or shaped portions to locate, position or house at least one, or a pair of, outlet(s) for a gas delivery system supplying gas to a user's airway.

Item B22. The Interface of any one of items B1-21, wherein the bridge portion element Includes one or a pair of cut-outs or shaped portions to locate, position or house one nasal prong or a pair of nasal prongs as the outlet or outlets for a gas delivery system supplying gas to a user's nare or nares.

Item B23. The Interface of any one of items B1-22, wherein one or more of the compensation regions (or sites) facilitates a flexure or bending or hinging or localised displacement and/or elastic deformation.

Item B24. The Interface of any one of items B1-23, wherein one or more of the compensation regions (or sites) is a region or site of bending or hinging region though or about at least one plane passing through the interface.

Item B25. The Interface of any one of items B1-23, wherein one or more of the compensation regions (or sites) is a region or site of bending or hinging region though or about a plurality of parallel planes passing through the interface.

Item B26. The Interface of any one of items B1-23, wherein one or more of the compensation regions (or sites) is a region or site of bending or hinging region though or about at least two different (non-parallel) planes passing through the interface.

Item B27. The Interface of any one of items B1-23, wherein one or more of the compensation regions (or sites) is a region or site of bending or hinging region though or about at least two different (orthogonal) planes passing through the interface.

Item B28. The Interface of any one of items B1-27, wherein the one or more compensation regions (or sites) flex or bend (or are hinged or may locally displace or elastically deform or move) more preferentially in a, or one or more first direction(s), or first set of directions and less preferentially in another direction or another set of directions.

Item B29. The Interface of Items BB 28, wherein the one or more compensation regions (or sites) are configured or adapted to substantially resist flexure or bending (or hinging or local displacement or elastic deformation) in a less preferential direction or set of directions.

Item B30. The Interface of Items BB 28 or 29, wherein the first direction or first set or directions is/are in a substantially transverse plane.

Item B31. The Interface of any one of items B28-30, wherein the first direction or first set of directions is/are in a substantially transverse plane in a ventral direction or a dorsal direction, or may be both in the ventral direction and the dorsal direction.

Item B32. The Interface of any one of items B28-31, wherein the first direction or first set of directions is/are in one or more of: a substantially transverse plane, a substantially sagittal plane and/or in a substantially coronal plane.

Item B33. The Interface of any one of items B28-32, wherein the first direction or the first set of directions is in a direction or directions which substantially facilitate the side arm element moving or bending relative to the bridge portion element.

Item B34. The Interface of any one of items B1-33, wherein the side arm element is formed of a substantially resilient material or is configured or adapted to provide substantial resilience to flexure or bending (or to hinging or local displacement or elastic deformation) in the side arm element regions selected from one or more of the following:
  a. provided between a single compensation region (or site) positioned laterally outward from the bridge portion element and an outer end of the side arm element,
  b. provided between an outer-more compensation region (or site) of the side arm element and an outer end of the side arm element,
  c. provided between each of a series of compensation regions (or sites) of the side arm element,
  d. provided between two compensation regions (or sites) positioned laterally outward from the bridge portion element, and between an outer-more compensation region (or site) of the side arm element and an outer end of the side arm element.

Item B35. The Interface of any one of items B1-34, wherein each side arm element comprises a single compensation region (or site).

Item B36. The Interface of any one of items B1-34, wherein each side arm element comprises two compensation regions (or sites).

Item B37. The Interface of any one of items B1-34, wherein each side arm element comprises three compensation regions (or sites).

Item B38. The Interface of any one of items B1-34, wherein each side arm element comprises a plurality of compensation regions (or sites).

Item B39. The Interface of any one of items B1-34, wherein at least one compensation region (or site) is located at an inner-more end of a side arm element in a connection with the bridge portion element.

Item B40. The Interface of any one of items B1-39, wherein at least one of the compensation regions (or sites) is located at a junction or connection between a side arm element and the bridge portion element.

Item B41. The Interface of any one of items B1-40, wherein at least one of the compensation regions (or sites) is located in or at a zone of the bridge portion element defined substantially by a peripheral, or laterally outer, edge of a user's septum region.

Item B42. The Interface of any one of items B1-41, wherein the or each side arm element is/are configured to flex or bend (or are hinged or locally displaces or may elastically deform or move) relative to the bridge portion element.

Item B43. The Interface of any one of items B1-42, wherein a side arm element further comprises one or more minor projections.

Item B44. The Interface of Items BB 43, wherein the one or more minor projections are engageable, or provided to be of a shape or configuration to be associated, with a material of the side arm.

Item B45. The Interface of Items BB 43 or 44, wherein Interaction or engagement of the minor projection with the material of the side arm provides for a resistance to flexure or bending (or hinging or elastic deformation) of a side arm element.

Item B46. The Interface of any one of items B43-45, wherein the material of the side arm is at least partially compressible (or may be substantially Incompressible or partially compressible), such that the minor projection(s) can translate a force or movement experienced by a side arm element as a compression of the material of the side arm (or can translate a force or movement experienced by a side arm element as an extension of the material when the material is placed under tension by the minor projection(s)).

Item B47. The Interface of any one of items B43-46, wherein the material of the side arm encapsulates or envelops the at least one side arm element.

Item B48. The Interface of Items BB 47, wherein a side arm partially encapsulates or partially envelops at least one side arm element.

Item B49. The Interface of Items BB 47, wherein the side arm wholly encapsulates or envelops at least one side arm element.

Item B50. The Interface of any one of items B1-49, wherein a material of the side arm fills one or more voids between the side arm element and the side arm.

Item B51. The Interface of any one of items B1-50, wherein a material of the side arm surrounds the side arm element, locating a side arm element in, or at, or adjacent to, the one or more predefined or predisposed points or localised compensation regions (or sites).

Item B52. The Interface of any one of items B1-51, wherein when a pair of side arms is provided, each of the side arms extend laterally from the bridge portion, one side arm of the pair of side arms provided to extend substantially about a left side of a user's face and the other side arm of the pair of side arms provided to extend substantially about a right side of a user's face.

Item B53. The Interface of any one of items B1-48, wherein the or each side arm extends substantially about a user's face, optionally along at least a part of a user's cheek.

Item B54. The Interface of any one of items B1-53, wherein the or each side arm extends substantially laterally away from or outwardly from a user's sagittal plane.

Item B55. The Interface of any one of items B1-54, wherein the or each side arm element extends at least a portion of a length or a substantial length of or along or through each such side arm comprising said side arm element.

Item B56. The Interface of any one of items B1-55, wherein the or each side arm element comprises of a plurality of side arm element limbs.

Item B57. The Interface of Items BB 56, wherein a side arm element limb comprises or Includes one or more minor projections.

Item B58. The Interface of any one of items B1-57, wherein the or each side arm or side arm element, or both, forms or is formed to provide at least a part of a passageway for receiving of a gas supply to be delivered to a user via the outlet or outlets or for receiving of a conduit for delivering a gas to a user via the outlet or outlets.

Item B59. The Interface of Items BB 58, wherein the side arm forms the passageway.

Item B60. The Interface of Items BB 59, wherein the side arm element(s) form the passageway.

Item B61. The Interface of any one of items B58-60, wherein the portion of the passageway formed at least in part by the side arm element(s) is at least 50% of a wall circumference or wall perimeter (for example of a unit length section) of the passageway so formed.

Item B62. The Interface of Items BB 61, wherein the portion of the passageway formed at least in part by the side arm is a remainder of the wall circumference or wall perimeter (for example of a unit length section) that is otherwise formed by the side arm element(s).

Item B63. The Interface of any one of items B58-62, wherein the passageway is a void space or cavity or recess in or through the side arm(s) or side arm element(s), or both, through which gas may be directed or supplied for delivery to the outlet or outlets.

Item B64. The Interface of any one of items B58-63, wherein the passageway, is defined at least in part by the side arm and at least in part the side arm element.

Item B65. The Interface of any one of items B1-64, wherein a side arm comprises a port for accessing a passageway that extends to the gas outlet(s) for delivery of a gas to the gas outlet(s).

Item B66. The Interface of Items BB 65, wherein each side arm of a pair of side arms comprises a port for accessing a passageway that extends through each side arm to an associated gas outlet.

Item B67. The Interface of Items BB 65 or 66, wherein each side arm provides for a separate passageway for separate delivery of gas to an associated gas outlet.

Item B68. The Interface of any one of items B1-67, wherein the side arm or arms is/are to be positioned, in-use, upon a user's face.

Item B69. The Interface of any one of items B1-68, wherein the side arm or arms is/are to be positioned, in-use, upon a user's facial cheeks.

Item B70. The Interface of any one of items B1-69, wherein the interface is a nasal cannula comprising a pair of nasal prongs as the outlets, and wherein a headgear or retention system is attachable to a pair of side arms for retaining the nasal cannula in position when being worn in-use by a user.

Item B71. The Interface of Items BB 70, wherein the retention system comprises a releasable connection system for releasably connecting the patient interface, such as at least a rear of each side arm, to a user's face (for example the releasable connection system may comprises of hook and loop or hook and hook type connectors for such a releasable system)

Item B72. The Interface of Items BB 71, wherein the releasable connection system comprises at least one pad attached to a user's face upon which the patient interface may be releasably engageable thereto.

Item B73. The Interface of any one of items B1-72, wherein the bridge portion element is, or comprises, a polymeric material.

Item B74. The Interface of any one of items B1-73, wherein the or each side arm element is, or comprises, a polymeric material.

Item B75. The Interface of Items BB 73 or 74, wherein the polymeric material is one or a combination of any one or more of: thermoplastic elastomer(s), polypropylene based elastomer(s), liquid silicone rubber(s), or breathable thermoplastic polyurethane(s), or breathable polyamides, more preferably polymers may be those such as, but not limited to, polyolefins, thermoplastic elastomers, or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

Item C1. A patient interface, such as a nasal cannula, comprising:
  a. a body portion to be located, in-use upon a face of a user, the body portion having left and right side arms and a bridge portion in between the left and right side arms,
  b. at least one, and preferably a pair of, nasal prong(s) extending from the bridge portion to be inserted into, or to direct a flow of gas into, a nare or the nares of the user's nose in an operational position, c. the body portion having at least one fluid passageway connected to the nasal prong(s) for supply of a gas to the nare(s) of the user's nose, d. wherein, a cross section of the passageway varies along the length of the body portion to provide regions of varying flexibility along the body portion.

Item C2. A patient interface of item C1, wherein the cross section of the passageway varies in shape along at least a portion of the length of the body portion.

Item C3. A patient interface of item C2, wherein the cross section varies from a substantially circular cross section at or near an outer end for connection with (either releasably or permanently) a breathing tube or conduit, to an elongated cross section, the elongated cross section having a longer axis arranged substantially vertically (parallel to a user's face).

Item C4. A patient interface of item C3, wherein the elongated cross section is provided in or forms a bending region or hinging portion of the body portion, the elongated cross section providing greater flexibility for bending of the body portion towards or away from the user's face in a direction of a shorter axis of the elongated cross section.

Item C5. A patient interface of item C3 or C4, wherein the elongated cross section is adjacent to the bridge portion of the body portion between a said prong and an inlet to the passageway at which a breathing tube or conduit is attached.

Item C6. A patient interface of item C4, wherein the body portion preferentially bends towards and away from the user's face in the bending regions of the body portion.

Item C7. A patient interface of any one of items C2 to C6, wherein a cross sectional area of the passageway is substantially constant along the portion of the length of the body portion.

Item C8. A patient interface of any one of the preceding C items, wherein the bridge portion is relatively stiff compared to other portions of the patient interface.

Item C9. A patient interface of any one of the preceding C items, wherein the bridge portion transitions into the left and right side arms by extending outwardly in a flared or curved manner away from a user's face side of the bridge portion, the left and right side arms curving away from the bridge portion rearwardly from a front extent of the body portion.

Item C10. A patient interface of any one of the preceding C items, wherein curvature(s) of the user's face side of the bridge portion and/or transition regions between the bridge portion and the left and right side arms has a relatively large radius (or radiuses) so that pressure from the bridge and/or the transition regions on the user's face is spread over the user's philtrum or upper lip region.

Item C11. A patient interface of any one of the preceding C items, wherein the body portion extends forwardly from each side of the bridge portion to a position forward of the bridge portion, and then extends rearwardly so that distal ends of the left and right side arms are positioned rearward of the bridge portion at least in an in-use position.

Item C12. A patient interface of item C11, wherein the body portion comprises a U-shaped region between each nasal prong and the left and right side arms when the body portion is viewed from above, an inside of the U-shaped region facing the user's face in use.

Item C13. A patient interface of item C12, wherein each U-shaped region forms or is provided in a bending region where the body portion preferentially bends when the left or right side arms is flexed towards or away from the user's face.

Item C14. A patient interface of item C13, wherein the bending region tends to bend in a valley of the U-shaped region.

Item C15. A patient interface of item C12, wherein an internal angle of the U-shaped region is less than about 130 degrees, or 120 degrees, or 110 degree, or 105 degrees.

Item C16. A patient interface of item C13, wherein the bending regions are positioned outwardly and forwardly from the nasal prongs relative to a face side of the body portion.

Item C17. A patient interface of any one of the preceding C items, wherein the patient interface is a single integrally formed component formed from a single material.

Item C18. A patient interface of item C17, wherein the patient interface is formed from a single moulding operation.

Item C19. A patient interface of item C17, wherein the patient interface is formed from a thermoplastic or silicone material with a Shore A hardness of approximately 5 to 60.

Item C20. A patient interface of any one of the preceding C items, comprising at least one pad of a retention system for retaining the interface in position when being worn in-use by a user, the pads attached to at least one of the left and right side arms, the pad being substantially symmetrical about a central approximately vertical axis that divides the pad into left and right sides so that the same shaped pad may be applied to both the left and right side arms, optionally each pad of the one pad is attached to the respective left or right side arms by overmoulding with an overmoulding material, whether attached by the interface being moulded integrally with the pad or the pad or subsequently attached to the interface by an overmoulding of the interface and pad.

Item C21. A patient interface of item C20, wherein the pad or pads comprise hook portions to connect to complementary hook or loop portions of a corresponding pad located on a user's face.

Item C22. A patient interface of any one of the preceding C items, wherein a cross section of the passageway at a base of the prongs is an asymmetric cross section, one side of the cross section being flatter than an opposite side of the cross section.

Item C23. A patient interface of item C22, wherein a passageway extending along the prong changes in shape from the asymmetric cross section at the base of the prong to a circular cross section at a tip of the prong.

Item C24. A patient interface of item C22 or C23, wherein the cross sectional area of the prong reduces from the base to the tip of the prong.

Item C25. A patient interface of any one of items C22 to C24, wherein the flatter side of the prong is positioned towards a forward side of the patient interface (facing away from the user's face).

Item C26. A patient interface of any one of the preceding C items, wherein the side arms comprises more material per length (greater cross sectional area) in the bridge portion than in other portions of the body portion.

Item C27. A patient interface of any one of the preceding C items, wherein the bridge region comprises a solid section between the prongs so that the bridge region is more rigid than the bending regions.

Item C28. A patient interface of any one of the preceding C items, wherein the bridge portion comprises wall sections that are thicker than wall sections of the bending regions so that the bridge portion is more rigid than the bending regions.

Item C29. A patient interface of any one of the preceding C items, wherein the bridge portions comprises a further more rigid material to provide rigidity to the bridge region.

Item C30. A patient interface of any one of the preceding C items, wherein the bridge region has a height or vertical dimension that is sufficient to provide torsional stability and prevent twisting of the bridge region in use.

Item C31. A patient interface of any one of the preceding C items wherein the passageway is positioned approximately centrally on the left and/or right side arms in a vertical direction.

Item C32. A patient interface of any one of the preceding C items wherein the passageway is positioned approximately centrally on a pad of a retention system on each of the left and right side arms for retaining the interface in position when being worn in-use by a user.

Item C33. A patient interface of any one of the preceding C items wherein a horizontal neutral bending axis of the body portion is located approximately centrally in a vertical direction on a securement system for securing the interface to the user's face.

Item C34. A patient interface of any one of the preceding C items wherein the body portion comprising varying geometries to achieve regions having more flexibility and regions having less flexibility.

Item C35. A patient interface of item C34, wherein the thickness of the body portion is varied to provide regions having different flexibilities.

Item C36. A patient interface of item C35, wherein the body portion has thinner thickness walls or sections surrounding the passageway in bending regions of the body portion than in other regions of the body portion.

Item C37. A patient interface of item C34, wherein the cross sectional area of the body portion at a valley of a U shaped region of the body portion is smaller than in adjacent regions of the body portion.

Item C38. A patient interface of any one of the preceding C items wherein the body portion has a left passageway and a right passageway, and the left and right passageways are separated by a dividing section in the bridge region.

Item C39. A patient interface of item C38, wherein the dividing section is a central region of the bridge between the two nasal prongs.

Item C40. A patient interface of item C39, wherein the central region of the bridge region is solid.

Item C41. A patient interface of any one of the preceding C items, wherein each prong has a base that is integrally formed with the bridge portion of the body portion of the patient interface, and wherein the base of each prong comprises a fillet between a wall of the prong and the bridge portion, the fillet extending around the perimeter of the prong, and wherein a radius of the fillet varies around the perimeter of the prong.

Item C42. A patient interface of item C41, wherein the radius of the fillet is varied around the perimeter of the prong to vary the wall thickness of the prong at the base of the prong.

Item C43. A patient interface of item C41 or C42, wherein a thickness of the prong base is varied around the perimeter of the prong.

Item C44. A patient interface of any one of items C41 to C43, wherein the radius of the fillet on a non-face side of the body portion is smaller than the radius of the fillet on an inner side (between the two prongs) of the prong and the radius of the fillet on an outer side of the prong.

Item C45. A patient interface of item C44, wherein the radius of the fillet on the inner side of the prong is larger than the radius of the fillet on the outer side of the prong.

Item C46. A patient interface of item C45, wherein the radius of the fillet on the face side of the body portion is between the radius on the inner and outer sides of the prong.

Item C47. A patient interface of any one of the preceding C items, wherein each prong has a base that is integrally formed with the bridge portion of the body portion of the patient interface, and a thickness of the prong base is varied around the perimeter of the prong.

Item C48. A patient interface, such as a nasal cannula, comprising:
  a. a body portion to be located, in-use upon a face of a user, the body portion having left and right side arms and a bridge portion in between the left and right side arms,
  b. at least one, and preferably a pair of, nasal prong(s) extending from the bridge portion to be inserted into, or to direct a flow of gas into, a nare or the nares of the user's nose in an operational position,
  c. the body portion having at least one fluid passageway connected to the nasal prong(s) for supply of a gas to the nare(s) of the user's nose, and
  d. at least one pad of a retention system for retaining the interface in position on the user's face, the pad attached to at least one of the side arms, the pad being substantially symmetrical about a central axis that divides the pad into left and right sides so that the same shaped pad may be applied to both the left and right side arms.

Item C49. A patient interface, such as a nasal cannula, comprising:
  a. a body portion to be located, in-use upon a face of a user, the body portion having left and right side arms and a bridge portion in between the side arms,
  b. at least one, and preferably a pair of, nasal prong(s) extending from the bridge portion to be inserted into, or to direct a flow of gas into, a nare or the nares of the user's nose in an operational position,
  c. the body portion having at least one fluid passageway connected to the nasal prong(s) for supply of a gas to the nare(s) of the user's nose,
  d. the passageway having an asymmetric cross section at a base of the prongs, one side of the asymmetric cross section being flatter than an opposite side of the asymmetric cross section.

Item C50. A patient interface of item C49, wherein a passageway extending along the prong changes in shape from the asymmetric cross section at the base of the prong to a circular cross section at a tip of the prong.

Item C51. A patient interface of item C49 or C50, wherein the cross sectional area of the prong reduces from the base to the tip of the prong.

Item C52. A patient interface of any one of items C49 to C51, wherein the flatter side of the prong is positioned towards a forward side of the patient interface (facing away from the user's face).

Item C53. A patient interface, such as a nasal cannula, comprising:
  a. a body portion to be located, in-use upon a face of a user, the body portion having left and right side arms and a bridge portion in between the left and right side arms,
  b. at least one, and preferably a pair of, nasal prong(s) extending from the bridge portion to be inserted into, or to direct a flow of gas into, a nare or the nares of the user's nose in an operational position, c. the body portion having at least one fluid passageway connected to the nasal prong(s) for supply of a gas to the nare(s) of the user's nose, d. wherein the patient interface is a single integrally formed component formed from a single material and the bridge portion is relatively stiff compared to other portions of the patient interface including the left and right side arms.

Item C54. A patient interface of item C53, wherein the patient interface is formed from a thermoplastic or silicone material with a Shore A hardness of approximately 5 to 60.

Item C55. A patient interface of any one of the preceding C items, wherein the body portion comprises more material per length (greater cross sectional area) in the bridge portion than in other portions of the body portion.

Item C56. A patient interface of any one of items C53 to C55, wherein the bridge region comprises a solid section between the prongs.

Item C57. A patient interface of any one of items C53 to C56, wherein the bridge region has a height or vertical dimension that is sufficient to provide torsional stability and prevent twisting of the bridge region in use.

Item C58. A patient interface of any one of items C53 to C57, wherein the body portion comprises varying geometries to achieve regions having more flexibility and regions having less flexibility.

Item C59. A patient interface of item C58, wherein the thickness of the body portion is varied to provide regions having different flexibilities.

Item C60. A patient interface of item C59, wherein the body portion has thinner thickness walls or sections surrounding the passageway in bending regions of the body portion than in other regions of the body portion.

Item C61. A patient interface of item C58, wherein the cross sectional area of the body portion at a valley of a U shaped region of the body portion is smaller than in adjacent regions of the body portion.

Item C62. A patient interface of any one of items C53 to C61, wherein the body portion has a left passageway and a right passageway, and the left and right passageways are separated by a dividing section in the bridge region.

Item C63. A patient interface of item C62, wherein the dividing section is a central region of the bridge between the two nasal prongs.

Item C64. A patient interface of item C63, wherein the central region of the bridge region is solid.

Item C65. A patient interface, such as a nasal cannula, comprising:

a. a body portion to be located, in-use upon a face of a user, the body portion having left and right side arms and a bridge portion in between the left and right side arms, b. at least one, and preferably a pair of, nasal prong(s) extending from the bridge portion to be inserted into, or to direct a flow of gas into, a nare or the nares of the user's nose in an operational position, c. the body portion having at least one fluid passageway connected to the nasal prong(s) for supply of a gas to the nare(s) of the user's nose, d. wherein the passageway is positioned approximately centrally on the left and/or right portions of the body portion in a vertical direction.

Item C66. A patient interface, such as a nasal cannula, comprising:

a. a body portion to be located, in-use upon a face of a user, the body portion having left and right side arms and a bridge portion in between the left and right side arms, b. at least one, and preferably a pair of, nasal prong(s) extending from the bridge portion to be inserted into, or to direct a flow of gas into, a nare or the nares of the user's nose in an operational position, c. the body portion having at least one fluid passageway connected to the nasal prong(s) for supply of a gas to the nare(s) of the user's nose, and d. a pad of a retention system on each of the left and right side arms for retaining the interface in position on the user's face, wherein the passageway is positioned approximately centrally on the pad.

Item C67. A patient interface, such as a nasal cannula, comprising:

a. a body portion to be located, in-use upon a face of a user, the body portion having left and right side arms and a bridge portion in between the left and right side arms, b. at least one, and preferably a pair of, nasal prong(s) extending from the bridge portion to be inserted into, or to direct a flow of gas into, a nare or the nares of the user's nose in an operational position, c. the body portion having at least one fluid passageway connected to the nasal prong(s) for supply of a gas to the nare(s) of the user's nose, and d. a pad of a retention system on each of the left and right side arms for retaining the interface in position on the user's face, wherein a horizontal neutral bending axis of the body portion is located approximately centrally in a vertical direction on the pads.

Item C68. A patient interface, such as a nasal cannula, comprising:

a. a body portion to be located, in-use upon a face of a user, the body portion having left and right side arms and a bridge portion in between the left and right side arms, b. at least one, and preferably a pair of, nasal prong(s) extending from the bridge portion to be inserted into, or to direct a flow of gas into, a nare or the nares of the user's nose in an operational position, c. the body portion having at least one fluid passageway connected to the nasal prong(s) for supply of a gas to the nare(s) of the user's nose, wherein d. each prong has a base that is integrally formed with the bridge portion of the body portion of the patient interface, and wherein the base of each prong comprises a fillet between a wall of the prong and the bridge portion, the fillet extending around the perimeter of the prong, and wherein a radius of the fillet varies around the perimeter of the prong.

Item C69. A patient interface of item C68, wherein the radius of the fillet is varied around the perimeter of the prong to vary the wall thickness of the prong at the base of the prong.

Item C70. A patient interface of item C68 or 69, wherein a thickness of the prong base is varied around the perimeter of the prong.

Item C71. A patient interface as claimed in any one claims 68 to 70 wherein the radius of the fillet on a non-face side of the body portion is smaller than the radius of the fillet on an inner side (between the two prongs) of the prong and the radius of the fillet on an outer side of the prong.

Item C72. A patient interface of item C71, wherein the radius of the fillet on the inner side of the prong is larger than the radius of the fillet on the outer side of the prong.

Item C73. A patient interface of item C72, wherein the radius of the fillet on the face side of the body portion is between the radius on the inner and outer sides of the prong.

Item C74. A patient interface, such as a nasal cannula, comprising:
a. a body portion to be located, in-use upon a face of a user, the body portion having left and right side arms and a bridge portion in between the left and right side arms,
b. at least one, and preferably a pair of, nasal prong(s) extending from the bridge portion to be inserted into, or to direct a flow of gas into, a nare or the nares of the user's nose in an operational position,
c. the body portion having at least one fluid passageway connected to the nasal prong(s) for supply of a gas to the nare(s) of the user's nose, wherein
d. each prong has a base that is integrally formed with the bridge portion of the body portion of the patient interface, and a thickness of the prong base is varied around the perimeter of the prong.

Item C75. A patient interface comprising a single integrally formed component formed from a single material with one or more bending or hinging regions.

Item C76. A patient interface of item C75, comprising a bridge portion, and nasal prongs extending from the bridge portion, wherein the bridge portion is more rigid than the bending or hinging regions.

Item C77. A patient interface of item C75 or C76, wherein the bending or hinging regions may be formed by or Include at least one bending or hinging element, for example a mechanical hinge.

The invention claimed is:

1. A patient interface comprising:
a body portion to be located, in-use upon a face of a user, the body portion having a left side arm and a right side arm, and a bridge portion between the left side arm and the right side arm;
at least one nasal prong extending from the bridge portion, the at least one nasal prong configured to direct a flow of gas into a nare of a user's nose in an operational position;
a retention system comprising at least one pad configured to retain the patient interface to a user's cheeks in use;
wherein the body portion has at least one fluid passageway connected to the at least one nasal prong for supplying a gas to the nare of the user's nose;
wherein, a cross-section of the at least one fluid passageway varies in shape along at least a portion of a length of the body portion to provide one or more bending regions between the bridge portion and the left side arm and the right side arm;
wherein the cross-section of the one or more bending regions is configured to provide greater flexibility for bending of the body portion at the one or more bending regions;
wherein the one or more bending regions are curved away from and spaced a distance from the face of the user; and
wherein the one or more bending regions are positioned between the bridge portion and the at least one pad.

2. The patient interface of claim 1, wherein the cross-section of the at least one fluid passageway varies from a circular cross-section at or near an outer end for connection with a breathing tube or conduit, to an elongated cross-section, the elongated cross-section having a longer axis arranged vertically.

3. The patient interface of claim 2, wherein the elongated cross-section forms the one or more bending regions, the elongated cross-section providing greater flexibility for bending of the body portion towards or away from a user's face in a direction of a shorter axis of the elongated cross-section.

4. The patient interface of claim 1, wherein the cross-section of the at least one fluid passageway transitions into an asymmetric or D-shape at a base of the at least one nasal prong, wherein one side of the cross-section is flatter than an opposite side of the cross-section.

5. The patient interface of claim 4, wherein the cross-section of the at least one fluid passageway transitions from asymmetric or D-shaped at the base of the at least one nasal prong to circular at a tip of the at least one nasal prong.

6. The patient interface of claim 1, wherein the body portion has a U-shaped region in the one or more bending regions.

7. The patient interface of claim 6, wherein the one or more bending regions tend to bend in a valley of the U-shaped region.

8. The patient interface of claim 7, wherein an internal angle of the U-shaped region is less than 130 degrees.

9. The patient interface of claim 1, wherein the bridge portion is more rigid than the one or more bending regions such that, in response to movement of the left side arm or the right side arm, the one or more bending regions flex to at least partially isolate the bridge portion from the movement of the left side arm or the right side arm.

10. The patient interface of claim 1, wherein the bridge portion comprises a solid section between a pair of nasal prongs so that the bridge portion is more rigid than the one or more bending regions.

11. The patient interface of claim 1, wherein the bridge portion has a height or vertical dimension that is sufficient to provide torsional stability and prevent twisting of the bridge portion in use.

12. The patient interface of claim 1, the at least one pad attached to at least one of the left side arm and the right side arm.

13. The patient interface of claim 1, retention system comprising a two-part releasable attachment arrangement.

14. The patient interface of claim 13, wherein the two-part releasable attachment arrangement comprises a dermal patch and a user interface patch,
wherein the dermal patch comprises a patient side configured to be attached to a user's skin and a user interface patch side configured to engage with the user interface patch,
wherein the user interface patch comprises a dermal patch side configured to engage with the user interface patch side of the dermal patch and an interface side configured to attach to the patient interface.

15. The patient interface of claim 1, wherein the bridge portion transitions into the left and right side arms by curving outwardly away from a face-contacting side of the bridge portion, the left and right side arms curving rearwardly from a front portion of the body portion, a curvature of the face-contacting side of the bridge portion or a transition region between the bridge portion and the left side arm and the right side arm having a relatively large radius so that pressure from the bridge portion or the transition region on a user's face is spread over a user's philtrum or a user's upper lip region.

16. The patient interface of claim 1, wherein the one or more bending regions have greater flexibility than the left side arm and the right side arm.

17. The patient interface of claim 1, wherein the left side arm and the right side arm have greater flexibility than the bridge portion.

18. The patient interface of claim 1, wherein the patient interface is a single integrally formed component formed from a single material in a single moulding operation, and wherein the patient interface is formed from a thermoplastic or silicone material with a Shore A hardness of between 5 to 60.

* * * * *

UNITED STATES PATENT AND TRADEMARK OFFICE
CERTIFICATE OF CORRECTION

| | |
|---|---|
| PATENT NO. | : 12,048,814 B2 |
| APPLICATION NO. | : 17/304233 |
| DATED | : July 30, 2024 |
| INVENTOR(S) | : Chelsea Erin Johnson et al. |

It is certified that error appears in the above-identified patent and that said Letters Patent is hereby corrected as shown below:

In the Specification

In Column 9, Line 23, delete "Interaction" and insert --interaction--.

In Column 15, Line 35, delete "Include" and insert --include--.

In Column 18, Line 50, delete "Interface," and insert --interface,--.

In Column 27, Line 37 (Approx.), delete "Identified" and insert --identified--.

In Column 27, Line 59, delete "Invention" and insert --invention--.

In Column 31, Line 15, delete "Illustrates" and insert --illustrates--.

In Column 31, Line 20, delete "Interface," and insert --interface,--.

In Column 31, Line 31, delete "Illustrates" and insert --illustrates--.

In Column 31, Line 36, delete "Interface," and insert --interface,--.

In Column 31, Line 46, delete "Illustrates" and insert --illustrates--.

In Column 31, Line 52, delete "Interface," and insert --interface,--.

In Column 31, Line 64, delete "Illustrating" and insert --illustrating--.

In Column 32, Line 1, delete "Illustrating" and insert --illustrating--.

In Column 32, Line 20, delete "Including" and insert --including--.

Signed and Sealed this
Thirty-first Day of December, 2024

Derrick Brent
*Acting Director of the United States Patent and Trademark Office*

CERTIFICATE OF CORRECTION (continued)
U.S. Pat. No. 12,048,814 B2

In Column 32, Line 31, delete "Interface" and insert --interface--.

In Column 32, Line 32, delete "Illustrates" and insert --illustrates--.

In Column 32, Line 36, delete "Illustrates" and insert --illustrates--.

In Column 32, Line 37, delete "Illustrates" and insert --illustrates--.

In Column 32, Line 38, delete "Illustrates" and insert --illustrates--.

In Column 32, Line 39, delete "Illustrates" and insert --illustrates--.

In Column 32, Line 40, delete "Illustrates" and insert --illustrates--.

In Column 32, Line 41, delete "Illustrates" and insert --illustrates--.

In Column 32, Line 42, delete "Illustrates" and insert --illustrates--.

In Column 32, Line 43, delete "Illustrates" and insert --illustrates--.

In Column 32, Line 44, delete "Illustrates" and insert --illustrates--.

In Column 32, Line 45, delete "Illustrates" and insert --illustrates--.

In Column 32, Line 61, delete "Improved" and insert --improved--.

In Column 32, Line 63, delete "Improved" and insert --improved--.

In Column 33, Line 3, delete "Interrupted," and insert --interrupted,--.

In Column 33, Line 12, delete "Intended" and insert --intended--.

In Column 33, Line 12, delete "Irritate" and insert --irritate--.

In Column 33, Line 17, delete "Invention" and insert --invention--.

In Column 33, Line 18, delete "Improvements" and insert --improvements--.

In Column 33, Line 39, delete "Infants" and insert --infants--.

In Column 33, Line 42, delete "Include" and insert --include--.

In Column 33, Line 58, delete "Includes" and insert --includes--.

In Column 33, Line 60, delete "Includes" and insert --includes--.

CERTIFICATE OF CORRECTION (continued)
U.S. Pat. No. 12,048,814 B2

In Column 34, Line 61, delete "Increase" and insert --increase--.

In Column 34, Line 65, delete "Incoming" and insert --incoming--.

In Column 35, Line 3, delete "Indirect" and insert --indirect--.

In Column 35, Line 4, delete "Including" and insert --including--.

In Column 35, Line 18, delete "Incorporated" and insert --incorporated--.

In Column 35, Line 29, delete "Invention" and insert --invention--.

In Column 35, Line 59, delete "Internal" and insert --internal--.

In Column 36, Line 43, delete "Input/output" and insert --input/output--.

In Column 36, Line 44, delete "Interact" and insert --interact--.

In Column 36, Line 46, delete "Information" and insert --information--.

In Column 36, Line 55, delete "Interface" and insert --interface--.

In Column 37, Line 13, delete "Irritation" and insert --irritation--.

In Column 37, Line 27, delete "Interface" and insert --interface--.

In Column 37, Line 64, delete "Indicate" and insert --indicate--.

In Column 38, Lines 1-2, delete "Iterations" and insert --iterations--.

In Column 38, Lines 3-4, delete "Illustrative" and insert --illustrative--.

In Column 38, Line 5, delete "Invention," and insert --invention,--.

In Column 38, Line 8, delete "Isolated" and insert --isolated--.

In Column 38, Line 19, delete "Intentional" and insert --intentional--.

In Column 38, Line 27, delete "Indirectly)" and insert --indirectly)--.

In Column 38, Line 33, delete "Incorporate" and insert --incorporate--.

In Column 38, Line 40, delete "Isolating" and insert --isolating--.

In Column 38, Line 60, delete "Imparted" and insert --imparted--.

CERTIFICATE OF CORRECTION (continued)
U.S. Pat. No. 12,048,814 B2

In Column 39, Line 2, delete "Imparted" and insert --imparted--.

In Column 39, Line 5, delete "Isolated" and insert --isolated--.

In Column 39, Line 11, delete "Isolate" and insert --isolate--.

In Column 39, Line 15, delete "Interface" and insert --interface--.

In Column 39, Line 34, delete "Intermediate" and insert --intermediate--.

In Column 39, Line 36, delete "Intermediate" and insert --intermediate--.

In Column 40, Line 16, delete "Interposed" and insert --interposed--.

In Column 40, Line 19, delete "Itself" and insert --itself--.

In Column 40, Line 23, delete "Intermediate" and insert --intermediate--.

In Column 40, Line 25, delete "Intermediate" and insert --intermediate--.

In Column 40, Line 35, delete "Include" and insert --include--.

In Column 40, Line 51, delete "Item" and insert --item--.

In Column 40, Line 56, delete "Illustrated," and insert --illustrated,--.

In Column 41, Line 39, delete "Illustrative" and insert --illustrative--.

In Column 41, Line 51, delete "Isolate" and insert --isolate--.

In Column 41, Line 54, delete "Illustrates" and insert --illustrates--.

In Column 42, Line 47, delete "Isolation" and insert --isolation--.

In Column 42, Line 49, delete "Interface" and insert --interface--.

In Column 43, Line 10, delete "Illustrate" and insert --illustrate--.

In Column 43, Line 14, delete "Indicated" and insert --indicated--.

In Column 43, Lines 16-17 (Approx.), delete "Indicated" and insert --indicated--.

In Column 43, Line 19, delete "Illustrates" and insert --illustrates--.

In Column 43, Line 23, delete "Illustrates" and insert --illustrates--.

CERTIFICATE OF CORRECTION (continued)
U.S. Pat. No. 12,048,814 B2

In Column 43, Line 27, delete "Illustrate" and insert --illustrate--.

In Column 43, Line 33, delete "Isolate" and insert --isolate--.

In Column 43, Line 35, delete "Illustrate" and insert --illustrate--.

In Column 43, Line 37, delete "Illustrate" and insert --illustrate--.

In Column 43, Line 61, delete "Illustrate" and insert --illustrate--.

In Column 43, Line 64, delete "Interface" and insert --interface--.

In Column 44, Line 8, delete "Intersect" and insert --intersect--.

In Column 44, Line 39, delete "Illustrating" and insert --illustrating--.

In Column 45, Line 11, delete "Independently," and insert --independently,--.

In Column 45, Line 61, delete "Illustrating" and insert --illustrating--.

In Column 46, Line 4, delete "Implanted" and insert --implanted--.

In Column 46, Line 4, delete "Implantation" and insert --implantation--.

In Column 46, Line 7, delete "Interaction" and insert --interaction--.

In Column 46, Line 16 (Approx.), delete "Incompressible)," and insert --incompressible),--.

In Column 46, Line 27, delete "Its" and insert --its--.

In Column 46, Lines 31-32, delete "Increasing" and insert --increasing--.

In Column 46, Line 33 (Approx.), delete "Iterations" and insert --iterations--.

In Column 46, Line 34 (Approx.), delete "Illustrations" and insert --illustrations--.

In Column 46, Line 46, delete "Interposed" and insert --interposed--.

In Column 46, Lines 52-53, delete "Interaction" and insert --interaction--.

In Column 47, Line 18, delete "Isolate" and insert --isolate--.

In Column 47, Line 33, delete "Irritate" and insert --irritate--.

In Column 47, Line 33, delete "Interrupt" and insert --interrupt--.

CERTIFICATE OF CORRECTION (continued)
U.S. Pat. No. 12,048,814 B2

In Column 47, Line 34, delete "Illustrated" and insert --illustrated--.

In Column 48, Line 56, delete "In" and insert --in--.

In Column 48, Line 60, delete "Inwardly" and insert --inwardly--.

In Column 48, Line 60, delete "In" and insert --in--.

In Column 49, Line 32, delete "Inwardly." and insert --inwardly.--.

In Column 49, Lines 42-43, delete "Indicated." and insert --indicated.--.

In Column 49, Line 51, delete "Inwardly" and insert --inwardly--.

In Column 50, Line 3, delete "Inwardly" and insert --inwardly--.

In Column 50, Line 45, delete "Illustrates" and insert --illustrates--.

In Column 50, Lines 59-60, delete "Interposed" and insert --interposed--.

In Column 51, Line 5, delete "Invention," and insert --invention,--.

In Column 51, Line 6, delete "Including" and insert --including--.

In Column 51, Line 10, delete "Illustrated" and insert --illustrated--.

In Column 51, Line 14, delete "Interface." and insert --interface.--.

In Column 51, Line 17, delete "Interface," and insert --interface,--.

In Column 51, Line 25, delete "Illustrated" and insert --illustrated--.

In Column 51, Line 29, delete "Inwardly" and insert --inwardly--.

In Column 51, Line 49, delete "Incorporated" and insert --incorporated--.

In Column 51, Line 57, delete "Interface" and insert --interface--.

In Column 51, Line 58, delete "Internal" and insert --internal--.

In Column 51, Line 62, delete "Interface" and insert --interface--.

In Column 51, Line 65, delete "Inseparably" and insert --inseparably--

In Column 51, Line 67, delete "Inseparably" and insert --inseparably--.

In Column 52, Line 2, delete "Interface" and insert --interface--.

In Column 52, Line 9, delete "Internal" and insert --internal--.

In Column 52, Line 15, delete "Interface" and insert --interface--.

In Column 52, Line 15, delete "Indirectly" and insert --indirectly--.

In Column 52, Line 35, delete "In" and insert --in--.

In Column 52, Lines 51-52, delete "Incorporated" and insert --incorporated--.

In Column 52, Line 54, delete "Interface" and insert --interface--.

In Column 52, Line 62, delete "Interface" and insert --interface--.

In Column 52, Line 65, delete "Interlock" and insert --interlock--.

In Column 52, Line 65, delete "Interface" and insert --interface--.

In Column 53, Line 38, delete "Improve" and insert --improve--.

In Column 53, Line 46, delete "Inwardly" and insert --inwardly--.

In Column 54, Line 1, delete "Increased" and insert --increased--.

In Column 54, Line 20, delete "Interface" and insert --interface--.

In Column 54, Line 30, delete "Illustrates" and insert --illustrates--.

In Column 54, Line 36, delete "Inwardly" and insert --inwardly--.

In Column 55, Line 25, delete "Improve" and insert --improve--.

In Column 55, Line 35, delete "Illustrated" and insert --illustrated--.

In Column 56, Line 14, delete "Increase" and insert --increase--.

In Column 56, Line 19, delete "Increase" and insert --increase--.

In Column 56, Line 40, delete "Interface" and insert --interface--.

In Column 56, Line 49, delete "Interface" and insert --interface--.

In Column 56, Line 57, delete "Inwardly" and insert --inwardly--.

CERTIFICATE OF CORRECTION (continued)
U.S. Pat. No. 12,048,814 B2

In Column 57, Line 5, delete "Improvements" and insert --improvements--.

In Column 57, Line 12 (Approx.), delete "Interface" and insert --interface--.

In Column 57, Line 22, delete "Inelastic" and insert --inelastic--.

In Column 57, Line 33, delete "Interface" and insert --interface--.

In Column 58, Line 20, delete "Inflexible" and insert --inflexible--.

In Column 58, Line 21, delete "Include" and insert --include--.

In Column 58, Line 31, delete "Interface," and insert --interface,--.

In Column 58, Line 51, delete "Inflatable" and insert --inflatable--.

In Column 58, Line 54, delete "Inflated" and insert --inflated--.

In Column 59, Line 12, delete "Internal" and insert --internal--.

In Column 59, Line 13, delete "Internal" and insert --internal--.

In Column 59, Line 15, delete "Internal" and insert --internal--.

In Column 59, Line 24, delete "Inserted" and insert --inserted--.

In Column 59, Line 59, delete "Inwardly" and insert --inwardly--.

In Column 60, Line 20, delete "Is/are" and insert --is/are--.

In Column 60, Line 30, delete "Is/are" and insert --is/are--.

In Column 61, Line 5, delete "Inhibit" and insert --inhibit--.

In Column 61, Line 21, delete "Increasing" and insert --increasing--.

In Column 61, Line 26, delete "Interface" and insert --interface--.

In Column 62, Line 28, delete "Initially" and insert --initially--.

In Column 62, Line 53, delete "Interface" and insert --interface--.

In Column 62, Line 63, delete "In" and insert --in--.

In Column 63, Line 23, delete "Interface" and insert --interface--.

In Column 63, Line 26, delete "Interface" and insert --interface--.

In Column 63, Line 38, delete "Interface" and insert --interface--.

In Column 64, Line 11, delete "Intended" and insert --intended--.

In Column 64, Line 33, delete "Including" and insert --including--.

In Column 65, Line 9, delete "It" and insert --it--.

In Column 65, Line 42, delete "Inwards" and insert --inwards--.

In Column 65, Line 55, delete "Isolated" and insert --isolated--.

In Column 65, Line 65, delete "Indicated" and insert --indicated--.

In Column 66, Line 1, delete "Indicated" and insert --indicated--.

In Column 66, Line 2, delete "Isolates" and insert --isolates--.

In Column 66, Line 10, delete "Include" and insert --include--.

In Column 66, Line 40, delete "Interface" and insert --interface--.

In Column 66, Line 45, delete "Interface" and insert --interface--.

In Column 67, Line 1, delete "Increasing" and insert --increasing--.

In Column 67, Line 7, delete "Illustrated" and insert --illustrated--.

In Column 67, Line 16, delete "Improved" and insert --improved--.

In Column 67, Line 22, delete "Is Itself" and insert --is itself--.

In Column 67, Line 32, delete "Integrated" and insert --integrated--.

In Column 67, Line 49, delete "Illustrate" and insert --illustrate--.

In Column 68, Line 1, delete "Integrated" and insert --integrated--.

In Column 68, Line 4, delete "Interface" and insert --interface--.

In Column 68, Line 8, delete "Interface" and insert --interface--.

In Column 68, Line 10, delete "Interface," and insert --interface,--.

In Column 68, Line 31, delete "Itself," and insert --itself,--.

In Column 68, Line 51, delete "Interface." and insert --interface.--

In Column 68, Line 66, delete "Itself" and insert --itself--.

In Column 69, Line 5, delete "Into" and insert --into--.

In Column 69, Line 7, delete "Interface Itself)." and insert --interface itself).--.

In Column 69, Line 21, delete "Isolated" and insert --isolated--.

In Column 69, Line 43, delete "Intended" and insert --intended--.

In Column 69, Line 49, delete "Illustrated" and insert --illustrated--.

In Column 69, Lines 60-61, delete "Interface" and insert --interface--.

In Column 70, Line 20, delete "Include" and insert --include--.

In Column 70, Line 36, delete "Inwards" and insert --inwards--.

In Column 71, Line 7, delete "Improved" and insert --improved--.

In Column 71, Line 34, delete "Increased" and insert --increased--.

In Column 71, Line 41, delete "Including" and insert --including--.

In Column 71, Line 47, delete "Increased" and insert --increased--.

In Column 71, Line 48, delete "Improve" and insert --improve--.

In Column 71, Line 54, delete "Isolate" and insert --isolate--.

In Column 72, Line 29, delete "Isolate" and insert --isolate--.

In Column 72, Line 32, delete "Including" and insert --including--.

In Column 73, Line 35, delete "Improve" and insert --improve--.

In Column 74, Line 43, delete "Isolated" and insert --isolated--.

In Column 74, Line 63, delete "Increase" and insert --increase--.

In Column 75, Line 6, delete "Improve" and insert --improve--.

In Column 75, Line 18, delete "Illustrated)" and insert --illustrated)--.

In Column 75, Line 25, delete "Interface" and insert --interface--.

In Column 75, Line 26, delete "Infants," and insert --infants,--.

In Column 75, Line 28, delete "Infants," and insert --infants,--.

In Column 75, Line 36, delete ""Including," and insert --"including,--.

In Column 75, Line 42, delete "Instance," and insert --instance,--.

In Column 75, Line 46, delete "Intended" and insert --intended--.

In Column 76, Line 19, delete "Includes" and insert --includes--.

In Column 77, Line 3, delete "Inwards" and insert --inwards--.

In Column 77, Line 27, delete "Interface" and insert --interface--.

In Column 77, Line 49, delete "Interface" and insert --interface--.

In Column 78, Line 12, delete "Inwardly" and insert --inwardly--.

In Column 78, Line 34, delete "Interface" and insert --interface--.

In Column 78, Line 50, delete "Interface" and insert --interface--.

In Column 79, Line 60, delete "Interface" and insert --interface--.

In Column 79, Line 62, delete "Isolated" and insert --isolated--.

In Column 79, Line 64, delete "Interface" and insert --interface--.

In Column 80, Line 4, delete "Interface" and insert --interface--.

In Column 80, Line 6, delete "Interface" and insert --interface--.

In Column 80, Line 10 (Approx.), delete "Interface" and insert --interface--.

In Column 80, Line 15 (Approx.), delete "Interface" and insert --interface--.

In Column 80, Line 20, delete "Interface" and insert --interface--.

In Column 80, Line 23, delete "Interface" and insert --interface--.

In Column 80, Line 26, delete "Interconnected," and insert --interconnected,--.

In Column 80, Line 29, delete "Interface" and insert --interface--.

In Column 80, Line 32, delete "Interface" and insert --interface--.

In Column 80, Line 37, delete "Interface" and insert --interface--.

In Column 80, Line 37, delete "Items" and insert --items--.

In Column 80, Line 41, delete "Interface" and insert --interface--.

In Column 80, Line 48, delete "Interface" and insert --interface--.

In Column 80, Lines 50-51, delete "Interposed" and insert --interposed--.

In Column 80, Line 54, delete "Interface" and insert --interface--.

In Column 80, Line 58, delete "Interface" and insert --interface--.

In Column 80, Line 61, delete "Interface" and insert --interface--.

In Column 80, Line 64, delete "Interface" and insert --interface--.

In Column 81, Line 3, delete "Interface" and insert --interface--.

In Column 81, Line 4, delete "Includes" and insert --includes--.

In Column 81, Line 8, delete "Interface" and insert --interface--.

In Column 81, Line 9, delete "Includes" and insert --includes--.

In Column 81, Line 14, delete "Interface" and insert --interface--.

In Column 81, Line 18, delete "Interface" and insert --interface--.

In Column 81, Line 22, delete "Interface" and insert --interface--.

In Column 81, Line 27, delete "Interface" and insert --interface--.

In Column 81, Line 32, delete "Interface" and insert --interface--.

In Column 81, Line 37, delete "Interface" and insert --interface--.

In Column 81, Line 43, delete "Interface" and insert --interface--.

CERTIFICATE OF CORRECTION (continued)
U.S. Pat. No. 12,048,814 B2

In Column 81, Line 43, delete "Items" and insert --items--.

In Column 81, Line 48, delete "Interface" and insert --interface--.

In Column 81, Line 48, delete "Items" and insert --items--.

In Column 81, Line 51, delete "Interface" and insert --interface--.

In Column 81, Line 56, delete "Interface" and insert --interface--.

In Column 81, Line 60, delete "Interface" and insert --interface--.

In Column 81, Line 65, delete "Interface" and insert --interface--.

In Column 82, Line 17, delete "Interface" and insert --interface--.

In Column 82, Line 20, delete "Interface" and insert --interface--.

In Column 82, Line 23, delete "Interface" and insert --interface--.

In Column 82, Line 26, delete "Interface" and insert --interface--.

In Column 82, Line 29, delete "Interface" and insert --interface--.

In Column 82, Line 33, delete "Interface" and insert --interface--.

In Column 82, Line 37, delete "Interface" and insert --interface--.

In Column 82, Line 42, delete "Interface" and insert --interface--.

In Column 82, Line 47, delete "Interface" and insert --interface--.

In Column 82, Line 50, delete "Interface" and insert --interface--.

In Column 82, Line 50, delete "Items" and insert --items--.

In Column 82, Line 54, delete "Interface" and insert --interface--.

In Column 82, Line 54, delete "Items" and insert --items--.

In Column 82, Line 55, delete "Interaction" and insert --interaction--.

In Column 82, Line 59, delete "Interface" and insert --interface--.

In Column 82, Line 61, delete "Incompressible" and insert --incompressible--.

In Column 83, Line 1, delete "Interface" and insert --interface--.

In Column 83, Line 4, delete "Interface" and insert --interface--.

In Column 83, Line 4, delete "Items" and insert --items--.

In Column 83, Line 7 (Approx.), delete "Interface" and insert --interface--.

In Column 83, Line 7 (Approx.), delete "Items" and insert --items--.

In Column 83, Line 10 (Approx.), delete "Interface" and insert --interface--.

In Column 83, Line 13 (Approx.), delete "Interface" and insert --interface--.

In Column 83, Line 19, delete "Interface" and insert --interface--.

In Column 83, Line 26, delete "Interface" and insert --interface--.

In Column 83, Line 29, delete "Interface" and insert --interface--.

In Column 83, Line 32, delete "Interface" and insert --interface--.

In Column 83, Line 37, delete "Interface" and insert --interface--.

In Column 83, Line 40, delete "Interface" and insert --interface--.

In Column 83, Line 40, delete "Items" and insert --items--.

In Column 83, Line 41, delete "Includes" and insert --includes--.

In Column 83, Line 43, delete "Interface" and insert --interface--.

In Column 83, Line 49, delete "Interface" and insert --interface--.

In Column 83, Line 49, delete "Items" and insert --items--.

In Column 83, Line 51, delete "Interface" and insert --interface--.

In Column 83, Line 51, delete "Items" and insert --items--.

In Column 83, Line 53, delete "Interface" and insert --interface--.

In Column 83, Line 58, delete "Interface" and insert --interface--.

In Column 83, Line 58, delete "Items" and insert --items--.

In Column 83, Line 63, delete "Interface" and insert --interface--.

In Column 84, Line 1, delete "Interface" and insert --interface--.

In Column 84, Line 4, delete "Interface" and insert --interface--.

In Column 84, Line 8, delete "Interface" and insert --interface--.

In Column 84, Line 8, delete "Items" and insert --items--.

In Column 84, Line 12, delete "Interface" and insert --interface--.

In Column 84, Line 12, delete "Items" and insert --items--.

In Column 84, Line 15, delete "Interface" and insert --interface--.

In Column 84, Line 18, delete "Interface" and insert --interface--.

In Column 84, Line 21, delete "Interface" and insert --interface--.

In Column 84, Line 27, delete "Interface" and insert --interface--.

In Column 84, Line 27, delete "Items" and insert --items--.

In Column 84, Line 34, delete "Interface" and insert --interface--.

In Column 84, Line 34, delete "Items" and insert --items--.

In Column 84, Line 38, delete "Interface" and insert --interface--.

In Column 84, Line 41, delete "Interface" and insert --interface--.

In Column 84, Line 44, delete "Interface" and insert --interface--.

In Column 84, Line 44, delete "Items" and insert --items--.

In Column 91, Line 32, delete "Include" and insert --include--.

In the Claims

In Column 92, Claim 13, Line 44, after "1," insert --the--.